United States Patent
Itoh et al.

(10) Patent No.: US 6,723,722 B1
(45) Date of Patent: Apr. 20, 2004

(54) ACYLHYDRAZINE DERIVATIVES, THEIR PRODUCTION AND USE

(75) Inventors: Fumio Itoh, Toyonaka (JP); Hiroshi Hosono, Toyonaka (JP); Masaki Kawamura, Ikeda (JP); Keiji Kubo, Minoo (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/018,962

(22) PCT Filed: Jun. 21, 2000

(86) PCT No.: PCT/JP00/04034

§ 371 (c)(1),
(2), (4) Date: Dec. 18, 2001

(87) PCT Pub. No.: WO00/78747

PCT Pub. Date: Dec. 28, 2000

(30) Foreign Application Priority Data

| Jun. 22, 1999 | (JP) | 11-176057 |
| Sep. 20, 1999 | (JP) | 11-266280 |
| Jan. 24, 2000 | (JP) | 2000-017956 |

(51) Int. Cl.$^7$ .................. A61K 31/395; C07D 241/06; C07D 241/08
(52) U.S. Cl. .............. 514/253.01; 514/253.11; 544/364
(58) Field of Search .............. 544/364; 514/253.01, 514/253.11

(56) References Cited

U.S. PATENT DOCUMENTS

| 3,067,237 A | 12/1962 | Larsen |
| 3,124,610 A | 3/1964 | Stirling |
| 5,559,232 A | 9/1996 | Ackermann .............. 544/122 |

FOREIGN PATENT DOCUMENTS

| DE | 2602422 | 7/1977 |
| EP | 126849 A1 | 12/1984 |
| EP | 284202 | 9/1988 |
| EP | 458642 | 11/1991 |
| EP | 558961 A2 | 9/1993 |
| EP | 584694 A | 3/1994 |
| EP | 957398 | 11/1999 |
| EP | 1 048 652 A1 | 11/2000 |
| EP | 1 054 005 A1 | 11/2000 |
| GB | 992961 | 3/1965 |
| GB | 1125671 A1 | 8/1968 |
| JP | 49-41488 | 4/1974 |
| JP | 63-46450 | 2/1988 |
| JP | 2-8833 | 1/1990 |
| JP | 10-161270 | 6/1998 |
| JP | 10-339932 | 12/1998 |
| JP | 11-119373 | 4/1999 |
| JP | 11-133545 | 5/1999 |
| WO | WO 92/19605 | 11/1992 |
| WO | WO 96/10022 | 4/1996 |
| WO | WO 96/40679 | 12/1996 |
| WO | WO 98/21188 | 5/1998 |
| WO | WO 98/46582 | 10/1998 |
| WO | WO 98/54164 | 12/1998 |
| WO | WO 99/01472 | 1/1999 |
| WO | WO 99/06395 | 2/1999 |
| WO | WO 99/37304 | 7/1999 |
| WO | WO 2000/00465 | 1/2000 |

OTHER PUBLICATIONS

Grehn et al. "Multisubstituted urea derivatives of hydrazines by a flexible approach with potential application in combinatorial chemistry" Syntesys (1998) (12), pp. 1817–1821.
Chemical Abstracts vol. 111 Abstract No. 134093, Arm. Khim. Zh. (1988) 41(6), pp. 351–357.
Chemical Abstracts vol. 69 Abstract No. 96400, Collec. Czech. Chem. Commun. (1968) 33(9) pp. 3065–3067.
Kim et al. "Acyl–hydrazide derivatives of a xanthine carboxylic congerner(XCC) as selective antagonists at human A2B adenosine receptor" Drug Dev. Res. (1999) 47(4) pp. 178–188.
Duffy et al. "Design and synthesis of diaminopyrrolidine inhibitors of human osteoclast cathepsin K" Bioorg Med. Chem. Lett. (1999) 9(14) pp. 1907–1910.
Chemical Abstracts vol. 126 Abstract No. 8639.
Obrecht et al. "A novel synthesis of (R)–and (S)–α–Alkylated aspartic and glutamic acids: α–alkylated aspartic succinides as new type of β–turn type II and III'mimetics" Tetrahdron (1995) 51(40) pp. 10883–10990.
Chemical Abstracts, vol 110 Abstract No. 39341, Liebigs Ann. Chem (1988) (12) pp. 1127–1133.

(List continued on next page.)

Primary Examiner—Richard L. Raymond
(74) Attorney, Agent, or Firm—Mark Chao; Elaine M. Ramesh

(57) ABSTRACT

Novel acylhydrazine derivatives exhibiting an inhibitory activity against activated blood coagulation factor X, which are compounds of general formula (I)

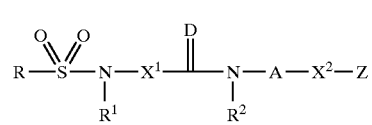

or salts thereof, wherein R is an optionally substituted hydrocarbon group or an optionally substituted heterocyclic group; $R^1$ and $R^2$ are each hydrogen or optionally substituted hydrocarbyl, or alternatively $R^1$ and $R^2$ or the substituent of $X^1$ and $R^2$ may be united to form an optionally substituted ring; $X^1$ and $X^2$ are each free valency, optionally substituted alkylene, or optionally substituted imino; D is oxygen or sulfur; A is —N($R^3$)—Y— or —N=Y—, $R^3$ is hydrogen, optionally substituted hydrocarbyl, or acyl; Y is an optionally substituted chain hydrocarbon group or an optionally substituted cyclic group; and Z is (1) optionally substituted amino, (2) optionally substituted imidoyl, or (3) an optionally substituted nitrogenous heterocycle group.

24 Claims, No Drawings

OTHER PUBLICATIONS

Chemical Abstracts, vol 106 Abstract No. 188558, Med Sci Res (1987) 15 (1) pp27–28.

Fridinger et al. "Bioactive conformation of luteinizing hormone–releasing hormone: evidence from a conformational analog" Science (1980) 210(4470) pp. 656–658.

Barraclough et al., "Synthesis of hexahydrocyclopent–imidazol–2–(1H)–one derivatives displaying selective DP–receptor antagonist properties" Bioorg. Med. Chem. (1996) 4(1) pp 81–90.

Leff et al. "Classification of platelet and vascular prostaglandin D2(DP) receptors: estimation of affinities and relative efficacies for a series of novel bicyclic ligands" Br. J. Pharmacol. (1992) 106(4) pp 996–1003.

Chemical Abstracts, vol. 110 Abstract No. 129192, Brj. J. Pharmacol. (1989) 96(2) pp. 291–300.

Mongea et al. "Synthesis of 3–amino–5H–pyrimido[5,4–B] Indol–4–one Derivatives" J. Heterocycl. chem. (1987) 24(2) pp. 437–439.

Mohamed et al., "Synthesis and Biological activity of some 3–heterocyclyl–4–hydroxy–6–methyl–2 1H)–quinolones" Indian. J. Chem. Sect. B: Org. Chem. Incl. Med. Chem. (1995) 34B(1) pp. 21–26.

Lobanov et al. "Strucutre of condensation products of α–amino acid hydrazides with carbonyl compounds" Zh. Org. Khim. (1978) 14(5) pp. 1086–1092.

Chemical Abstracts, vol. 65, col. 19175 Par. h.

Chemical Abstracts, vol. 65, col. 9015 Par. e.

Chemical Abstracts, vol. 64, col. 807 Par. c.

Chemical Abstracts, vol. 61, col. 8212 Par. e.

Chemical Abstracts, vol. 60, col. 4105 Par. f.

Chemical Abstracts, vol. 58, col. 2504 Par. f.

Chemical Abstracts, vol. 56, col. 5880 Par. g.

Chemical Abstracts, vol. 55, col. 23394 Par. b.

Chemical Abstracts, vol. 55, col. 13351 Par. b.

Chemical Abstracts, vol. 51, col. 9002 Par. e.

Ouf A.A. Abou et al. "Synthesis of N4 (alpha–Thiophene Sulphonyl) Semicarbazides and Semicarbazones" J. Drug Res. Egypt 5(No. 1): 127–134 (1977).

ACYLHYDRAZINE DERIVATIVES, THEIR PRODUCTION AND USE

This application is the National Phase filing of International Patent Application No. PCT/JP00/04034, filed Jun. 21, 2000.

TECHNICAL FIELD

The present invention relates to novel acyl hydrazine derivatives which inhibit activated coagulation factor X (FXa) to exhibit anti-coagulative effect and which are useful as pharmaceuticals, as well as their production and use.

BACKGROUND ART

It is important to inhibit the formation of a thrombus in preventing and treating cardiac infarction, cerebral thrombosis and the like, and various anti-thombotic agents such as anti-thrombin agents and platelet aggregation inhibitors have been developed. Nevertheless, platelet aggregation inhibitors as well as anti-thrombin agents have bleeding side effects and problems in their safety, since these agents posses a platelet aggregation-inhibiting activity in combination with anticoagulative effect. On the other hand, FXa inhibitors specifically inhibit on a coagulation factor, and thus are useful as anticoagulant.

So far, compounds having FXa-inhibiting effects are disclosed for example in JP-A-7-112970, JP-A-5-208946, WO-96/16940, WO96/40679 and WO 96/10022, as well as Journal of Medicinal Chemistry, Vol.41, page 3357 (1998), etc.

Since such compounds having FXa-inhibiting effects described above do not have sufficient FXa-inhibiting effects and, in particular, do not exhibit sufficient activities when given orally, therefore, they have not been successful in giving any practically satisfactory pharmaceutical effects.

DISCLOSURE OF THE INVENTION

The invention provides novel acylhydrazine derivatives which specifically inhibit FXa, which are capable of being given orally and which are useful as a pharmaceutical capable of being used safely in preventing and treating a disease associated with thrombus or infarction.

The present inventors made an effort and finally was successful for the first time to synthesis a compound characterized chemically by the presence of a two nitrogen atoms [nitrogen atom in —n($R^2$)—; and nitrogen atom in —n($R^3$)— or —N═] adjacent to a carbonyl group and the presence of an optionally substituted amino group, an optionally substituted imidoyl group or an optionally substituted nitrogen-containing heterocyclic group at its terminal, i.e., a compound represented by Formula:

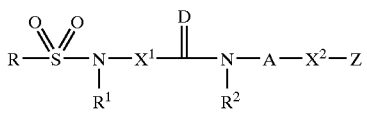

(I)

wherein R is an optionally substituted hydrocarbon group or an optionally substituted heterocyclic group, each of $R^1$ and $R^2$ is a hydrogen atom or an optionally substituted hydrocarbon group, or $R^1$ and $R^2$ or a substituent on $X^1$ and $R^2$ are bound to each other to form an optionally substituted ring, each of $X^1$ and $X^2$ is a bond, an optionally substituted alkylene group or an optionally substituted imino group, D is an oxygen atom or a sulfur atom, A is —N($R^3$)—Y— or —N═Y—, $R^3$ is a hydrogen atom, an optionally substituted hydrocarbon group or an acyl group, Y is an optionally substituted linear hydrocarbon group or an optionally substituted cyclic group, Z is (1) an optionally substituted amino group, (2) an optionally substituted imidoyl group or (3) an optionally substituted nitrogen-containing heterocyclic group or a salt thereof (hereinafter sometimes referred to as Compound (I)), and discovered that this compound exhibits an unexpectedly excellent FXa inhibiting effect due to its particular chemical structure, and thus can safely be given orally as a prophylactic and therapeutic agent for a disease associated with a thrombus or an infarction, thus establishing the invention.

Accordingly, the invention relates to:

(1) a Compound (I);
(2) a prodrug of a compound according to Section (1) described above or a salt thereof;
(3) a compound according to Section (1) described above wherein R is an optionally substituted hydrocarbon group;
(4) a compound according to Section (1) described above wherein R is an optionally substituted heterocyclic group;
(5) a compound according to Section (1) described above wherein R is a halogen atom or an aryl group optionally substituted by a $C_{2-4}$ alkenyl;
(6) a compound according to Section (1) described above wherein R is a naphthyl group optionally substituted by a halogen atom;
(7) a compound according to Section (1) described above wherein R is a benzopyranyl group optionally substituted by a halogen atom;
(8) a compound according to Section (1) described above wherein $R^1$ and $R^2$ are bound to each other and taken together with —N—$X^1$—CD—N— to form a group represented by Formula:

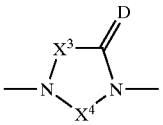

wherein $X^3$ is an optionally substituted $C_{1-2}$ alkylene, $X^4$ is an optionally substituted $C_{1-3}$ alkylene and D is an oxygen atom or a sulfur atom;
(9) a compound according to Section (1) described above wherein $R^1$ and $R^2$ are bound to each other and taken together with —N—$X^1$—CD—N— to form a group represented by Formula:

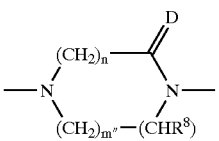

wherein n is 1 or 2, m″ is 1 or 2, $R^8$ is a hydrogen atom, an optionally substituted hydroxyl group, an optionally substituted mercapto group, a nitro group, a cyano group, an optionally substituted amino group, an optionally substituted lower alkyl group, an optionally substituted lower alkoxy group, an optionally esterified carboxyl group, an optionally substituted carbamoyl group, an optionally substituted thiocarbamoyl group or an optionally substituted sulfamoyl group (preferably, a hydrogen atom, an optionally substituted lower alkyl group, a cyano group, an optionally esterified carboxyl group, an optionally substituted carbamoyl group or an optionally substituted thiocarbamoyl group), and D is an oxygen atom or a sulfur atom;

(10) a compound according to Section (1) described above wherein $R^1$ and $R^2$ are bound to each other and taken together with —N—$X^1$—CD—N— to form a group represented by Formula:

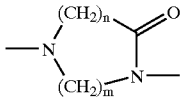

wherein n is 1 or 2 and m is 2 or 3.

(11) a compound according to Section (10) described above wherein n=1 and m=2;

(12) a compound according to Section (1) described above wherein a substituent on $X^1$ and $R^2$ are bound to each other and a divalent group represented by —$X^1$—CD—N($R^2$)— is a group represented by Formula:

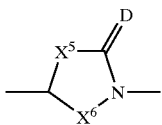

wherein $X^5$ is a bond or an optionally substituted methylene, $X^6$ is an optionally substituted $C_{2-3}$ alkylene and D is an oxygen atom or a sulfur atom;

(13) a compound according to Section (1) described above wherein a substituent on $X^1$ and $R^2$ are bound to each other and a divalent group represented by —$X^1$—CD—N($R^2$)— is a group represented by Formula:

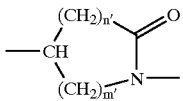

wherein n' is 0 or 1 and m' is 2 or 3;

(14) a compound according to Section (13) described above wherein n'=0 and m'=2;

(15) a compound according to Section (1) described above wherein each of $R^1$ and $R^2$ is a hydrogen atom or an optionally substituted lower alkyl;

(16) a compound according to Section (1) described above wherein an optionally substituted imino group is a group represented by Formula —N($R^4$)— wherein $R^4$ is a hydrogen atom, an optionally substituted hydrocarbon group or an acyl group;

(17) a compound according to Section (1) described above wherein $X^1$ is methylene;

(18) a compound according to Section (1) described above wherein $X^2$ is a bond;

(19) a compound according to Section (1) described above wherein $R^3$ is a hydrogen atom, an optionally substituted lower alkyl group, formyl or an optionally substituted lower alkanoyl group;

(20) a compound according to Section (1) described above wherein $R^3$ is a hydrogen atom or an optionally substituted lower alkyl group;

(21) a compound according to Section (1) described above wherein Y is an optionally substituted cyclic hydrocarbon group;

(22) a compound according to Section (1) described above wherein A is —N($R^3$)—Y— and Y is an optionally substituted phenylene;

(23) a compound according to Section (1) described above wherein Y is an optionally substituted heterocyclic group;

(24) a compound according to Section (1) described above wherein Y is an optionally substituted piperidine residue;

(25) a compound according to Section (1) described above wherein Z is an optionally substituted nitrogen-containing heterocyclic group;

(26) a compound according to Section (1) described above wherein D is an oxygen atom;

(27) a compound selected from the group consisting of 4-(7-chloro-2H-benzopyran-3-sulfonyl)-1-[1-(4-pyridyl)piperidin-4-ylamino]-2-piperazinone, 4-(6-chloronaphthalene-2-sulfonyl)-1-[1-(4-pyridyl)piperidin-4-ylamino]-2-piperazinone, 4-(6-bromonaphthalene-2-sulfonyl)-1-[1-(4-pyridyl)piperidin-4-ylamino]-2-piperazinone, 4-(7-bromo-2H-benzopyran-3-sulfonyl)-1-[1-(4-pyridyl)piperidin-4-yl]amino}-2-piperazinone, 4-(6-chloronaphthalene-2-sulfonyl)-1-{methyl[1-(4-pyridyl)piperidin-4-yl]amino}-2-piperazinone, 4-(6-bromonaphthalene-2-sulfonyl)-1-{methyl[1-(4-pyridyl)piperidin-4-yl]amino}-2-piperazinone, 4-(7-bromo-2H-benzopyran-3-sulfonyl)-1-{methyl[1-(4-pyridyl)piperidin-4-yl]amino}-2-piperazinone, 4-(6-chloronaphthalene-2-sulfonyl)-1-{methyl[1-(4-pyridyl)piperidin-4-yl]amino}-2-piperazinone, 4-(6-chloronaphthalene-2-sulfonyl)-1-{methyl[1-(2-methyl-4-pyridyl)piperidin-4-yl]amino}-2-piperazinone, {[4-(6-chloronaphthalene-2-sulfonyl)-2-oxo-1-piperazinyl][1-(2-methyl-4-pyridyl)-4-piperidinyl]amino}acetic acid, 4-(6-chloronaphthalene-2-sulfonyl)-1-{[1-(4-pyridyl)-4-piperidinyl]amino}-6-oxo-2-piperazinecarboxylic acid, 4-(6-chloronaphthalene-2-sulfonyl)-1-{methyl[1-(4-pyridyl)-4-piperidinyl]amino}-6-oxo-2-piperazinecarboxylic acid, 4-(6-chloronaphthalene-2-sulfonyl)-1-{methyl[1-(4-pyridyl)-4-piperidinyl]amino}-6-oxo-2-piperazinecarboxamide, 4-(6-chloronaphthalene-2-sulfonyl)-1-{methyl[1-(2-methyl-4-pyridyl)-4-piperidinyl]amino}-6-oxo-2-piperazinecarboxamide, 4-(6-chloronaphthalene-2-sulfonyl)-6-hydroxymethyl-1-{methyl[1-(4-pyridyl)-4-piperidinyl]amino}-2-piperazinone, 6-aminomethyl-4-(6-chloronaphthalene-2-sulfonyl)-1-{methyl[1-(4-pyridyl)-4-piperidinyl]amino}-2-piperazinone, 6-acetylaminomethyl-4-(6-chloronaphthalene-2-sulfonyl)-1-{methyl[1-(4-pyridyl)-4-piperidinyl]amino}-2-piperazinone, 4-(6-chloronaphthalene-2-sulfonyl)-1-{[1-(4-pyridyl)-4-piperidinyl]amino}-6-oxo-2-piperazineacetic acid and 4-(6-chloronaphthalene-2-sulfonyl)-1-{[1-(2-methyl-4-pyridyl)-4-piperidinyl]amino}-6-oxo-2-piperazineacetic acid as well as a salt thereof;

(28) a prodrug of a compound according to Section (27) described above or a salt thereof;

(29) a pharmaceutical composition comprising a compound according to Section (1) described above or a salt thereof;

(30) a composition according to Section (29) described above which is an anticoagulant;

(31) a composition according to Section (29) described above which is an activated coagulation factor X inhibitor;

(32) a composition according to Section (29) described above which is a prophylactic and therapeutic agent for cardiac infarction, cerebral thrombosis or deep vein thrombosis;

(33) a method for producing a compound according to Section (1) described above or a salt thereof comprising: reacting a compound represented by Formula (II) $RSO_2Q$ wherein Q is a leaving group and other symbols are defined as described in Section (1) described above or a salt thereof with a compound represented by Formula (III):

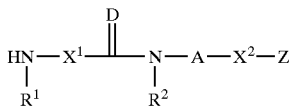 (III)

wherein the symbols are defined as described in Section (1) described above or a salt thereof; or,
reacting a compound represented by Formula (IV):

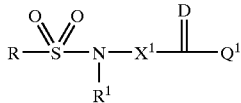 (IV)

wherein $Q^1$ is a leaving group and other symbols are defined as described in Section (1) described above or a salt thereof with a compound represented by Formula (V):

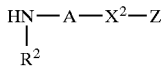 (V)

wherein the symbols are defined as described in Section (1) described above or a salt thereof; or,
reacting a compound represented by Formnula (VI):

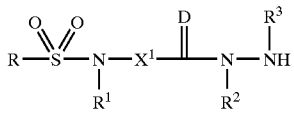 (VI)

wherein the symbols are defined as described in Section (1) described above or a salt thereof with a compound represented by Formula (VII):

$A^1$—$X^2$—Z (VII)

wherein $A^1$ is $Q^1$—Y— or O=Y—, $Q^1$ is a leaving group and other symbols are defined as described in Section (1) described above or a salt thereof; or, reacting a compound represented by Formula (VIII):

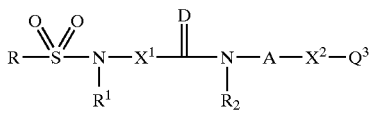 (VIII)

wherein $Q^3$ is a hydrogen atom or a leaving group and other symbols are defined as described in Section (1) described above or a salt thereof with a compound represented by Formula (IX):

$Q^4$—Z (IX)

wherein $Q^4$ is a hydrogen atom or a leaving group and other symbols are defined as described in Section (1) described above or a salt thereof;

(34) a compound represented by Formula:

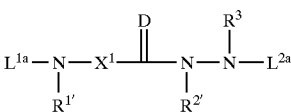

wherein each of $L^{1a}$ and $L^{2a}$ is a hydrogen atom or an amino-protecting group, $R^{1'}$ and $R^{2'}$ are bound to each other to form an optionally substituted ring, or $R^{1'}$ is a hydrogen atom or an optionally substituted hydrocarbon group and a substituent of $X^1$ and $R^{2'}$ are bound to each other to form an optionally substituted ring, and other symbols are defined as described in Section (1) described above or a salt thereof;

(35) a compound according to Section (34) described above wherein $R^{1'}$ and $R^{2'}$ are bound to each other and taken together with —N—$X^1$—CD—N— to form a group represented by Formula:

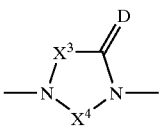

wherein $X^3$ is an o ptionally substituted $C_{1-2}$ alkylene, $X^4$ is an optionally substituted $C_{1-3}$ alkylene and D is an oxygen atom or a sulfur atom;

(36) a compound according to Section (34) described above 34 wherein $R^1$ and $R^2$ are bound to each other and taken together with —N—$X^1$—CD—N— to form a group represented by Formula:

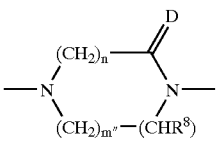

wherein n is 1 or 2, m''' is 1 or 2, $R^8$ is a hydrogen atom, an optionally substituted hydroxyl group, an optionally substituted mercapto group, a nitro group, a cyano group, an optionally substituted amino group, an optionally substituted lower alkyl group, an optionally substituted lower alkoxy group, an optionally esterified carboxyl group, an optionally substituted carbamoyl group, an optionally substituted thiocarbamoyl group or an optionally substituted sulfamoyl group (preferably, a hydrogen atom, an optionally substituted lower alkyl group, a cyano group, an optionally esterified carboxyl group, an optionally substituted carbamoyl group or an optionally substituted thiocarbamoyl group), and D is an oxygen atom or a sulfur atom;

(37) a compound according to Section (34) described above wherein $R^{1'}$ and $R^{2'}$ are bound to each other and taken together with —N—$X^1$—CD—N— to form a group represented by Formula:

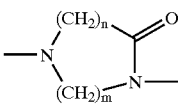

wherein n is 1 or 2 and m is 2 or 3;
(38) a compound according to Section (37) described above wherein n=1 and m=2;
(39) a compound according to Section (34) described above wherein a substituent on $X^1$ and $R^{2'}$ are bound to each other and a divalent group represented by —X$^1$—CD—N(R$^{2'}$)— is a group represented by Formula:

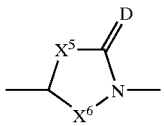

wherein X$^5$ is a bond or an optionally substituted methylene, X$^6$ is an optionally substituted C$_{2-3}$ alkylene and D is an oxygen atom or a sulfur atom;

(40) a compound according to Section (34) described above wherein a substituent on X$^1$ and R$^{2'}$ are bound to each other and a divalent group represented by —X$^1$—CD—N(R$^{2'}$)— is a group represented by Formula:

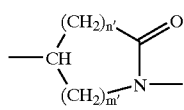

wherein n' is 0 or 1 and m' is 2 or 3;

(41) a compound according to Section (40) described above wherein n'=0 and m'=2;

(42) an enzyme inhibiting agent or a receptor Hmodulating agent containing a compound comprising as its moiety a divalent group represented by Formula:

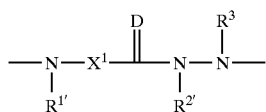

wherein R$^{1'}$ and R$^{2'}$ are bound to each other to form an optionally substituted ring, or R$^{1'}$ is a hydrogen atom or an optionally substituted hydrocarbon group and a substituent of X$^1$ and R$^{2'}$ are bound to each other to form an optionally substituted ring, and other symbols are defined as described in Section (1) described above or a salt thereof;

(43) an agent according to Section (42) described above which is an activated coagulation factor X inhibitor;

(44) an agent according to Section (42) described above which is a prophylactic and therapeutic agent for cardiac infarction, cerebral thrombosis or deep vein thrombosis;

(45) a method for inhibiting a blood coagulation in mammals comprising administering an effective amount of a compound according to Section (1) described above or a salt thereof to said mammals;

(46) a method for inhibiting an activated coagulation factor X in mammals comprising administering an effective amount of a compound according to Section (1) Adescribed above or a salt thereof to said mammals;

(47) a method for preventing and treating cardiac infarction, cerebral thrombosis or deep vein thrombosis in mammals comprising administering an effective amount of a compound according to Section (1) described above 1 or a salt thereof to said mammals;

(48) a use of a compound according to Section (1) described above or a salt thereof for producing a pharmaceutical for inhibiting a blood coagulation;

(49) a use of a compound according to Section (1) described above or a salt thereof for producing a pharmaceutical for inhibiting an activated coagulation factor X;

(50) a use of a compound according to Section (1) described above or a salt thereof for producing a pharmaceutical for preventing and treating cardiac infarction, cerebral thrombosis or deep vein thrombosis; and the like.

In the formulae described above, R is an optionally substituted hydrocarbon group or an optionally substituted heterocyclic group.

A hydrocarbon group in "optionally substituted hydrocarbon group" represented by R may for example be an aliphatic linear hydrocarbon group, an alicyclic hydrocarbon group and an aryl group, with an aryl group being preferred.

"Aliphatic linear hydrocarbon group" as an example of a hydrocarbon group may for example be a straight or branched aliphatic hydrocarbon group such as an alkyl group, an alkenyl group and an alkynyl group.

An alkyl group mentioned here may for example be a C$_{1-10}$ alkyl group such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like (preferably a C$_{1-6}$ alkyl and the like).

An alkenyl group may for example be a C$_{2-6}$ alkenyl group such as vinyl, allyl, isopropenyl, 2-methyl, allyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

An alkynyl group may for example be a C$_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

"Alicyclic hydrocarbon group" as an example of a hydrocarbon group may for example be a saturated or unsaturated alicyclic hydrocarbon group such as a cycloalkyl group, a cycloalkenyl group, a cycloalkadienyl group and the like.

"Cyloalkyl group" mentioned here may for example be a C$_{3-9}$ cycloalkyl group such as cyclopropyl, cyclobutyl, cyclopentyl, cyclohexyl, cycloheptyl, cyclooctyl, cyclononyl and the like.

"Cycloalkenyl group" may for example be a C$_{3-9}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, 1-cyclohexen-1-yl, 1-cyclohepten-1-yl and the like.

"Cycloalkadienyl group" may for example be a C$_{4-6}$ cycloalkadienyl group such as 2,4-cyclopentadien-1-yl, 2,4-cyclohexadien-1-yl, 2,5-cyclohexadien-1-yl and the like.

"Aryl group" as an example of a hydrocarbon group may for example be a monocyclic or fused polycyclic aromatic hydrocarbon group such as phenyl, naphthyl, anthryl, phenanthryl, acenaphthylenyl and the like, with phenyl, 1-naphthyl and 2-naphthyl being preferred especially.

An example of a hydrocarbon group may also be a bicyclic or tricyclic hydrocarbon group resulted from a condensation of two to three groups (preferably 2 or more types of the groups) which may be same or different and selected from the group consisting of the alicyclic hydrocarbon groups and the aromatic hydrocarbon groups described above such as 1,2-dihydronaphthyl, 1,2,3,4-tetrahydronaphthyl, indenyl, dihydrobenzocycloheptenyl, fluorenyl and the like.

A heterocyclic group in "optionally substituted heterocyclic group" represented by R may for example be an aromatic heterocyclic group, a saturated or unsaturated non-aromatic heterocyclic group (aliphatic heterocyclic group) containing, as an atom constituting a ring system (ring atom), at least one (preferably 1 to 4, more preferably 1 to 2) atom of 1 to 3 species (preferably 1 to 2 species) of the heteroatoms selected from oxygen, sulfur and nitrogen atoms.

"Aromatic heterocyclic group" may for example be a 5- to 6-membered aromatic monocyclic heterocyclic group such as an aromatic monocyclic heterocyclic group (for example, furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) and a 8- to 12-membered aromatic fused heterocyclic group such as an aromatic fused heterocyclic group (for example, benzofuranyl, isobenzofuranyl, benzo[b] thienyl, indolyl, isoindolyl, 1H-indazolyl, benzindazolyl, benzokisazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, puteridinyl, carbazolyl, α-carbolinyl, β-carbolinyl, γ-carbolinyl, acridinyl, phenoxazinyl, phenothiazinyl, phenazinyl, phenoxathiynyl, thianthrenyl, phenathridinyl, phenathrolinyl, indolidinyl, pyrrolo[1,2-b]pyridazinyl, pyrrazolo[1,5-a]pyridyl, imidazo[1,2-a]pyridyl, imidazo[1,5-a]pyridyl, imidazo[1,2-b]pyridazinyl, imidazo[1,2-a] pyrimidinyl, 1,2,4-triazolo[4,3-a]pyridyl, 1,2,4-triazolo[4,3-b]pyridazinyl and the like) and the like (preferably a heterocyclic ring formed by a condensation of a 5- to 6-membered aromatic monocyclic heterocyclic group described above with a benzene ring, or a heterocyclic ring formed by a condensation of two same or different heterocyclic rings of 5- to 6-membered aromatic monocyclic heterocyclic groups described above, more preferably a heterocyclic ring formed by a condensation of a 5- to 6-membered aromatic monocyclic heterocyclic group described above, particularly, benzofuranyl, benzopyranyl, benzo[b]thienyl and the like).

"Non-aromatic heterocyclic group" may for example be a 3- to 8-membered (preferred 5- to 6-membered) saturated or non-saturated (preferably saturated) non-aromatic heterocyclic group (aliphatic heterocyclic group) such as oxylanyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl and the like, as well as a non-aromatic heterocyclic group formed as a result of a saturation of a part or all of the double bonds of an aromatic monocyclic heterocyclic group or an aromatic fused heterocyclic group described above such as 1,2,3,4-tetrahydroquiolyl, 1,2,3,4-tetrahydroisoquinolyl and the like.

A substituent on "optionally substituted hydrocarbon group" and "optionally substituted heterocyclic group" represented by R may for example be an optionally substituted alkyl group, an optionally substituted alkenyl group, an optionally substituted alkynyl group, an optionally substituted aryl group, an optionally substituted cycloalkyl group, an optionally substituted cycloalkenyl group, an optionally substituted heterocyclic group, an optionally substituted amino group, an optionally substituted imidoyl group (for example a group represented by Formula —C(U')=N—U wherein each of U and U' is a hydrogen atom or a substituent (U is preferably a hydrogen atom)), an optionally substituted amidino group (for example a group represented by Formula —C(NT'T")=N—T wherein each of T, T' and T" is a hydrogen atom or a substituent (T is preferably a hydrogen atom)), an optionally substituted hydroxyl group, an optionally substituted thiol group, an optionally esterified carboxyl group, an optionally substituted carbamoyl group, an optionally substituted thiocarbamoyl group, an optionally substituted sulfamoyl group, a halogen atom (for example, fluorine, chlorine, iodine and the like, preferably chlorine, bromine and the like), a cyano group, a nitro group, a sulfonic acid-derived acyl group, a carboxylic acid-derived acyl group and the like, and any of these substituent may occur 1 to 5 times (preferably 1 to 3 times) in any possible positions. It may also possible. that "optionally substituted hydrocarbon group" and "optionally substituted heterocyclic group" represented by have oxo groups, and when R is benzopyranyl then R may form benzo-α-pyronyl, benzo-γ-pyronyl and the like.

An aryl group in "optionally substituted aryl group" as a substituent may for example be a $C_{6-14}$ aryl group such as phenyl, naphthyl, anthryl, phenanthryl, acenaphthylenyl and the like. A substituent on an aryl group mentioned here may for example be a lower alkoxy group (for example a $C_{1-6}$ alkoxy group such as methoxy, ethoxy), a halogen atom (for example fluorine, chlorine, bromine and iodine), a lower alkyl group (such as a $C_{1-6}$ alkyl group such as methyl, ethyl and propyl), a lower alkenyl group (for example a $C_{2-6}$ alkenyl group such as vinyl and allyl), a lower alkynyl group (for example a $C_{2-6}$ alkynyl group such as ethynyl and propargyl), an optionally substituted amino group, an optionally substituted hydroxyl group, a cyano group, an optionally substituted amidino group, a carboxyl group, a lower alkoxycarbonyl group (for example a $C_{1-6}$ alkoxycarbonyl group such as methoxycarbonyl and ethoxycarbonyl), an optionally substituted carbamoyl group (for example a carbamoyl group which may be substituted by a $C_{1-6}$ alkoxy or acyl group (for example, formyl, $C_{2-6}$ alkanoyl, benzoyl, an optionally halogenated $C_{1-6}$ alkoxy-carbonyl, an optionally halogenated $C_{1-6}$ alkyl-sulfonyl, benzenesulfonyl group)) and the like, and any of these substituent may occur 1 to 3 times in any possible positions. "Optionally substituted amino group", "optionally substituted hydroxyl group" and "optionally substituted amidino group" as substituents are similar to "optionally substituted amino group", "optionally substituted hydroxyl group" and "optionally substituted amidino group" as substituents which may be possessed by "optionally substituted hydrocarbon group" and "optionally substituted heterocyclic group" represented by R.

A cycloalkyl group in "optionally substituted cycloalkyl group" as a substituent may for example be a $C_{3-7}$ cycloalkyl group such as cyclopropyl, cyclobutyl, cyclopentyl, cyclohexyl and cycloheptyl. A substituent on a cycloalkyl group mentioned here may be similar to those of a substituent on "optionally substituted aryl group" described above and may occur similar times.

A cycloalkenyl group in "optionally substituted cycloalkenyl group" as a substituent may for example be a $C_{3-6}$ cycloalkenyl group such as cyclopropenyl, cyclobutenyl, cyclopentenyl and cyclohexenyl, and a substituent on an optionally substituted cycloalkenyl group mentioned here may be similar to those of a substituent on "optionally substituted aryl group" described above and may occur similar times.

An alkyl group in "optionally substituted alkyl group" as a substituent may for example be a $C_{1-6}$ alkyl group such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and the like. A substituent on an alkyl group mentioned here may be similar to those of a substituent on "optionally substituted aryl group" described above and may occur similar times.

An alkenyl group in "optionally substituted alkenyl group" as a substituent may for example be a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like. A substituent on an alkenyl group mentioned here may be similar to those of a substituent on "optionally substituted aryl group" described above and may occur similar times.

An alkynyl group in "optionally substituted alkynyl group" as a substituent may for example be a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. A substituent on an alkynyl group mentioned here may be similar to those of a substituent on "optionally substituted aryl group" described above and may occur similar times.

A heterocyclic group in "optionally substituted heterocyclic group" as a substituent may for example be an aromatic heterocyclic group, a saturated or unsaturated non-aromatic heterocyclic group (aliphatic heterocyclic group) containing as an atom constituting a ring system (ring atom) at least one (preferably 1 to 4, more preferably 1 to 2) atom of 1 to 3 species (preferably 1 to 2 species) of the heteroatoms selected from oxygen, sulfur and nitrogen atoms. "Aromatic heterocyclic group" may for example be a 5- to 6-membered aromatic monocyclic heterocyclic group such as an aromatic monocyclic heterocyclic group (for example, furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) and a 8- to 12-membered aromatic fused heterocyclic group such as an aromatic fused heterocyclic group (for example, benzofuranyl, isobenzofuranyl, benzo[b]thienyl, indolyl, isoindolyl, 1H-indazolyl, benzimidazolyl, benzoxazolyl, 1,2-benzoisooxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, puteridinyl, carbazolyl, α-carbolinyl, β-carbolinyl, γ-carbolinyl, acridinyl, phenoxazinyl, phenothiazinyl, phenazinyl, phenoxathinyl, , thianthrenyl, phenathridinyl, phenathrolinyl, indolidinyl, pyrrolo[1,2-b]pyridazinyl, pyrrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like) and the like (preferably a heterocyclic ring formed by a condensation of a 5- to 6-membered aromatic monocyclic heterocyclic group described above with a benzene ring, or a heterocyclic ring formed by a condensation of two same or different heterocyclic rings of 5- to 6-membered aromatic monocyclic heterocyclic groups described above).

"Non-aromatic heterocyclic group" may for example be a 3- to 8-membered (preferred 5- to 6-membered) saturated or non-saturated (preferably saturated) non-aromatic heterocyclic group (aliphatic heterocyclic group) such as oxylanyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like, as well as a non-aromatic heterocyclic group formed as a result of a saturation of a part or all of the double bonds of an aromatic monocyclic heterocyclic group or an aromatic fused heterocyclic group described above such as 1,2,3,4-tetrahydroquinolyl, 1,2,3,4-tetrahydroisoquinolyl and the like.

A substituent which may be possessed by "optionally substituted heterocyclic group" as a substituent may for example be a lower alkyl group (for example a $C_{1-5}$ alkyl group such as methyl, ethyl and propyl), a lower alkenyl group (for example a $C_{2-5}$ alkenyl group such as vinyl and allyl), a lower alkynyl group (for example a $C_{2-6}$ alkynyl group such as ethynyl and propargyl), an acyl group (for example a $C_{1-6}$ alkanoyl group such as formyl, acetyl, propyl and pivaloyl and benzoyl), an optionally substituted amino group, an optionally substituted hydroxyl group, a halogen atom (for example, fluorine, chlorine, bromine, iodine, preferably chlorine, bromine), an optionally substituted imidoyl group, an optionally substituted amidino group and the like.

"Optionally substituted amino group", "optionally substituted hydroxyl group", "optionally substituted imidoyl group" and "optionally substituted amidino group" which may be possessed by "optionally substituted heterocyclic group" as a substituent may for example be those similar to "optionally substituted amino group", "optionally substituted hydroxyl group", "optionally substituted imidoyl group" and "optionally substituted amidino group" which may be possessed by "optionally substituted hydrocarbon group" and "optionally substituted heterocyclic group" represented by R.

A substituent on "optionally substituted amino group", "optionally substituted imidoyl group", "optionally substituted amidino group", "optionally substituted hydroxy group" and "optionally substituted thiol group" as substituents which may be possessed by "optionally substituted hydrocarbon group" and "optionally substituted heterocyclic group" represented by R may for example a lower alkyl group (for example a $C_{1-6}$ alkyl group such as methyl, ethyl, propyl, isopropyl, butyl, isobutyl, t-butyl, pentyl, hexyl) which may be substituted by a substituent selected from a halogen atom (for example fluorine, chlorine, bromine, iodine) and an optionally halogenated $C_{1-6}$ alkoxy group (for example methoxy, ethoxy, trifluoromethoxy, 2,2,2-trifluoroethoxy, trichloromethoxy, 2,2,2-trichloroethoxy), an acyl group (a $C_{1-6}$ alkanoyl (for example formyl, acetyl, propionyl, pivaloyl), benzoyl), an optionally halogenated $C_{1-6}$ alkoxy-carbonyl (for example, methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl), an optionally halogenated $C_{1-6}$ alkyl-sulfonyl, benzenesulfonyl), a heterocyclic group (those similar to "heterocyclic group" in "optionally substituted heterocyclic group" represented by R, preferably pyridyl, more preferably 4-pyridyl), and "amino group" in "optionally substituted amino group" as a substituent may be substituted by an optionally substituted imidoyl group (for example a $C_{1-6}$ alkylimidoyl (for example formyl imidoyl, acetylimidoyl), a $C_{1-6}$ alkoxyimidoyl, a $C_{1-6}$ alkylthioimidoyl, amidino) and an amino group which may be substituted by 1 to 2 $C_{1-6}$ alkyls, or two substituents are taken together with a nitrogen atom to form a cyclic amino group, and in such case such cyclic amino group may for example be a 3- to 8-membered (preferably 5- to 6-membered) cyclic amino group such as 1-azetidinyl; 1-pyrrolidinyl; piperidino; thiomorpholino; morpholino; 1-piperazinyl; 1-piperazinyl; which may have in its 4-position a lower alkyl group (for example a $C_{1-6}$ alkyl group such as methyl, ethyl, propyl, isopropyl, butyl, t-butyl, pentyl, hexyl), an aralkyl group (for example a $C_{7-10}$ aralkyl group such as benzyl and phenethyl) and an aryl group (for example a $C_{6-10}$ aryl group such as phenyl, 1-naphthyl, 2-naphthyl); 1-pyrrolyl; and 1-imidazolyl.

"Optionally substituted carbamoyl group" may for example be a unsubstituted carbamoyl as well as an N-monosubstituted carbamoyl group and an N,N-disubstituted carbamoyl group.

"N-Monosubstituted carbamoyl group" means a carbamoyl group having one substituent on a nitrogen atom, and such substituent may for example be a lower alkyl group (for example a $C_{1-6}$ alkyl group such as methyl, ethyl, propyl, isopropyl, butyl, isobutyl, t-butyl, pentyl, hexyl), a lower alkenyl group (for example a $C_{2-6}$ alkenyl group such as vinyl, allyl, isopropenyl, propenyl, butenyl, pentenyl, hexenyl), a cycloalkyl group (for example a $C_{3-6}$ cycloalkyl group such as cyclopropyl, cyclobutyl, cyclopentyl, cyclohexyl), an aryl group (for example a $C_{6-10}$ aryl group such as phenyl, 1-naphthyl and 2-naphthyl), an aralkyl group (for example a $C_{7-10}$ aralkyl group such as benzyl and phenethyl, preferably a phenyl-$C_{1-4}$ alkyl group), an arylalkenyl group (for example a $C_{8-10}$ arylalkenyl group such as cinnamyl, preferably a phenyl-$C_{2-4}$ alkenyl group), a heterocyclic group (for example those similar to "heterocyclic ring" as a substituent on "optionally substituted hydrocarbon group" represented by R described above) and the like. Each of such lower alkyl group, a lower alkenyl group, a cycloalkyl group, an aryl group, an aralkyl group, an arylalkenyl group and a heterocyclic group may have a substituent, and such substituent may for example be a hydroxyl group, an optionally substituted amino group [such amino group may have as its substituents one or two groups selected from a lower alkyl group (for example a $C_{1-6}$ alkyl group such as methyl, ethyl, propyl, isopropyl, butyl, isobutyl, t-butyl, pentyl, hexyl), an acyl group (for example a $C_{1-6}$ alkanoyl group such as formyl, acetyl, propionyl and pivaloyl as well as benzoyl), a carboxyl group, a $C_{1-6}$ alkoxy-carbonyl group and the like], a halogen atom (for example fluorine, chlorine, bromine, iodine), a nitro group, a cyano group, a carboxyl group, a $C_{1-6}$ alkoxy-carbonyl group, a lower alkyl group which may be substituted by 1 to 5 halogen atoms (for example, fluorine, chlorine, bromine, iodine), a lower alkylthio group which may be substituted by 1 to 5 halogen atoms (for example, fluorine, chlorine, bromine, iodine), a lower alkoxy group which may be substituted by 1 to 5 halogen atoms (for example, fluorine, chlorine, bromine, iodine) and the like. A lower alkyl group mentioned above may for example be a $C_{1-6}$ alkyl group such as methyl, ethyl, n-propyl, isopropyl, n-butyl, isobutyl, sec-butyl, tert-butyl, pentyl and hexyl, with methyl and ethyl being preferred. A lower alkylthio group mentioned above may for example be a $C_{1-6}$ alkylthio group such as methylthio, ethylthio, n-propylthio, isopropylthio, n-butylthio, isobutylthio, sec-butylthio, tert-butylthio, pentylthio and hexylthio, with methylthio and ethylthio being preferred. A lower aikoxy group mentioned above may for example be a $C_{1-6}$ alkoxy group such as methoxy, ethoxy, n-propoxy, isopropoxy, n-butoxy, isobutoxy, sec-butoxy, tert-butoxy, with methoxy and ethoxy being preferred. Any of these substituent may be same or different and occurs preferably 1 or 2 to 3 times (preferably 1 or 2 times).

"N,N-Disubstituted carbamoyl group" means a carbamoyl group having two substituents on a nitrogen atom, and an example of one of these substituents is similar to a substituent on "N-monosubstituted carbamoyl group" described above, and an example of the other may for example be a lower alkyl group (for example a $C_{1-6}$ alkyl group such as methyl, ethyl, propyl, isopropyl, butyl, t-butyl, pentyl, hexyl), a $C_{3-6}$ cycloalkyl group (for example cyclopropyl, cyclobutyl, cyclopentyl, cyclohexyl), a $C_{7-10}$ aralkyl group (for example benzyl, phenethyl, preferably a phenyl-$C_{1-4}$ alkyl group). Alternatively, two substituents may be taken together with a nitrogen atom to form a cyclic amino group, and in such case a cyclic aminocarbamoyl group may for example be a 3- to 8-membered (preferably 5- to 6-membered) cyclic amino-carbonyl such as 1-azetidinylcarbonyl, 1-pyrrolidinylcarbonyl, piperidinocarbonyl as well as piperidinylcarbonyl which may have in its 4-position a lower alkyl group (for example a $C_{1-6}$ alkyl group such as methyl, ethyl, propyl, isopropyl, butyl, t-butyl, pentyl, hexyl), an aralkyl group (for example a $C_{7-10}$ aralkyl group such as benzyl and phenethyl), an aryl group (for example a $C_{6-10}$ aryl group such as phenyl, 1-naphthyl, 2-naphthyl), a hydroxyl group, a $C_{1-6}$ alkoxyl group, a carboxyl group, a $C_{1-6}$ alkoxy-carbonyl group and the like, morpholinocarbonyl, thiomorpholinocarbonyl whose sulfur atom may be oxidized, 1-piperazinylcarbonyl as well as 1-piperazinylcarbonyl which may have in its 4-position a lower alkyl group (for example a $C_{1-6}$ alkyl group such as methyl, ethyl, propyl, isopropyl, butyl, t-butyl, pentyl, hexyl), an aralkyl group (for example a $C_{7-10}$ aralkyl group such as benzyl and phenethyl), an aryl group (for example a $C_{6-10}$ aryl group such as phenyl, 1-naphthyl, 2-naphthyl) and the like.

A substituent on "optionally substituted thiocarbamoyl group" and "optionally substituted sulfamoyl group" may for example be a substituent on "optionally substituted carbamoyl group" described above.

An optionally esterified carboxyl group may for example be a free carboxyl group as well as a lower alkoxycarbonyl group, an aryloxycarbonyl group, an aralkyloxycarbonyl group and the like.

"Lower alkoxycarbonyl group" may for example be a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl and neopentyloxycarbonyl, which a $C_{1-3}$ alkoxycarbonyl group such as methoxycarbonyl, ethoxycarbonyl and propoxycarbonyl being preferred.

"Aryloxycarbonyl group" may for example be a $C_{7-12}$ aryloxy-carbonyl group such as phenoxycarbonyl, 1-naphthoxycarbpnyl, 2-naphthoxycarbonyl and the like.

"Aralkyloxycarbonyl group" may for example be a $C_{7-10}$ aralkyloxy-carbonyl group such as benzyloxycarbonyl and phenethyloxycarbony (preferably a $C_{6-10}$ aryl-$C_{1-4}$ alkoxycarbonyl).

Each of such "aryloxycarbonyl group" and "aralkoxycarbonyl group" may have a substituent, and such substituent may be similar to those of a substituent on an aryl group and an aralkyl group as the examples of a substituent on an N-monosubstituted carbamoyl group described above and may occur similar times.

"Sulfonic acid-derived acyl group" as a substituent may for example be a sulfonyl bound to a substituent occurring one time on a nitrogen atom of "N-monosubstituted carbamoyl group" described above, and is preferably an acyl such as a $C_{1-6}$ alkylsulfonyl including methanesulfonyl and ethanesulfonyl. "Carboxylic acid-derived acyl group" as a substituent may for example be a carbonyl bound to a substituent occurring one time on a nitrogen atom of "N-monosubstituted carbamoyl group" described above, and is preferably an acyl such as a $C_{1-6}$ alkanoyl such as formyl, acetyl, propionyl and pivaloyl as well as benzoyl.

R is preferably an optionally substituted hydrocarbon group, especially, an aryl group which may be substituted by a halogen atom or a $C_{2-4}$ alkenyl (preferably a $C_{6-14}$ aryl group, such as phenyl and 2-naphthyl, which may be substituted by a halogen atom or a $C_{2-4}$ alkenyl group, more preferably naphthyl which may be substituted by a halogen atom, most preferably 2-naphthyl having a halogen atom in its 6-position).

It is also preferable that R is an optionally substituted heterocyclic group, especially a heterocyclic group which may be substituted by a halogen atom (preferably, benzofuranyl group, benzopyranyl group, more preferably benzopyranyl group).

In Formula shown above, "optionally substituted hydrocarbon group" represented by $R^1$ and $R^2$ or $R^{1'}$ may for example be one similar to "optionally substituted hydrocarbon group" represented by R, with an optionally substituted lower ($C_{1-4}$) alkyl group being preferred.

It is also possible that $R^1$ and $R^2$ are bound to each other to form a ring, and $R^1$ and $R^2$ are bound to each other and taken together with —N—$X^1$—CD—N— to form "optionally substituted divalent nitrogen-containing heterocyclic group".

Such "divalent nitrogen-containing heterocyclic group" in "optionally substituted divalent nitrogen-containing heterocyclic group" is a divalent 5- to 8-membered nitrogen-containing heterocyclic group containing two or 3 nitrogen atoms, in addition to carbon atoms, as its atoms constituting a ring system (ring atoms) (preferably a divalent 5- to 8-membered nitrogen-containing heterocyclic group comprising carbon atoms and two nitrogen atoms).

While such "divalent nitrogen-containing heterocyclic group" has an oxo group or a thioxo group on a carbon atom adjacent to the nitrogen atom to which a substituent represented by $R^2$ is bound and forms a "divalent 5- to 8-membered nitrogen-containing cyclic amide group", such "divalent 5- to 8-membered nitrogen-containing cyclic amide group" may for example be 2-oxoimidazolidine-1,3-diyl, 2-oxoimidazolone-1,3-diyl, 2-oxopiperazine-1,4-diyl, 2-oxo-1,2,3,4-tetrahydropyrazine-1,4-diyl, 2-oxohomopiperazine-1,4-diyl, 5-oxohomopiperazine-1,4-diyl, 2-oxo-1,4-diazacyclooctane-1,4-diyl, 5-oxo-1,4-diazacyclooctane-1,4-diyl, 2-oxo-1,5-diazacyclooctane-1,5-diyl, 5-oxo-2,3-dehydrohomopiperazine-1,4-diyl, 3-oxo-1,2,4-triazacyclohexane-1,4-diyl, 3-oxo-1,2,3,4-tetrahydro-1,2,4"triaziyne-1,4-diyl, 6-oxo-1,2,4-triazacyclohexane-1,4-diyl and the like.

A substituent on "divalent nitrogen-containing heterocyclic group" in "optionally substituted divalent nitrogen-containing heterocyclic group" described above, in addition to one oxo group or thioxo group, may for example be an optionally substituted hydroxyl group, an optionally substituted mercapto group, a halogen atom (for example, chlorine, bromine, iodine), a nitro group, a cyano group, an oxo group, an optionally substituted amino group, an optionally substituted lower alkyl group, an optionally substituted lower alkylidene group, an optionally substituted lower aralkylidene group, a lower alkoxy group which may be substituted by 1 to 5 halogen atoms (for example, fluorine, chlorine, bromine, iodine), an optionally esterified carboxyl group, an optionally substituted carbamoyl group, an optionally substituted thiocarbamoyl group, an optionally substituted sulfamoyl group (preferably, an optionally substituted lower alkyl group, an optionally esterified carboxyl group, an optionally substituted carbamoyl group and the like), and any of these substituents may occur 1 to 3 times (preferably 1 to 2 times) in any possible positions.

While a substituent on "optionally substituted amino group" mentioned here may for example be 1 to 2 optionally substituted alkyl groups, an optionally substituted carbamoyl group, an optionally substituted thiocarbamoyl group, an optionally substituted sulfamnoyl group, an optionally esterified carboxyl group, a sulfonic acid-derived acyl group and a carboxylic acid-derived acyl group, "optionally substituted alkyl group", "optionally substituted carbamoyl group", "optionally substituted thiocarbamoyl group", "optionally substituted sulfamoyl group", "optionally esterified carboxyl group", "sulfonic acid-derived acyl group" and "carboxylic acid-derived acyl group" mentioned here may for example be those similar to "optionally substituted alkyl group", "optionally substituted carbamoyl group", "optionally su bst ituted thiocarbamoyl group", "optionally substituted sulfamoyl group", "optionally esterified carboxyl group", "sulfonic acid-derived acyl group" and "carboxylic acid-derived acyl group" as substituents on "optionally substituted hydrocarbon group" represented by R described above, and a preferred example of "optionally substituted amino group" is an amino group which may have 1 to 2 substituents selected from (1) a lower ($C_{1-6}$)alkylgroup such as methyl, ethyl, n-propyl, isopropyl, n-butyl, isobutyl, sec-butyl and t-butyl, (2) a mono- or di-lower ($C_{1-6}$) alkylcarbamoyl group, (3) a ($C_{1-6}$)alkylsulfonyl group such as methanesulfonyl and ethanesulfonyl, (4) a ($C_{1-6}$)alkanoyl such as formyl, acetyl, propionyl and pivaloyl, and (5) benzoyl.

A lower alkyl group in "optionally substituted lower alkyl group" may for example be a $C_{1-6}$ alkyl group such as methyl, ethyl, n-propyl, isopropyl, n-butyl, isobutyl, sec-butyl, tert-butyl and the like, with methyl and ethyl being preferred especially. Its substituent may for example be a halogen atom (for example, fluorine, chlorine, bromine and iodine), an amino group which may be substituted by a $C_{1-6}$ alkyl or acyl group (e.g., formyl, $C_{2-6}$ alkanoyl, benzoyl, an optionally halogenated $C_{1-6}$ alkoxy-carbonyl, an optionally halogenated $C_{1-6}$ alkyl-sulfonyl, benzenesulfonyl), a carboxyl group, a $C_{1-6}$ alkoxy-carbonyl group, a carbamoyl group which may be substituted by a $C_{1-6}$ alkyl or acyl group (e.g., formyl, $C_{2-6}$ alkanoyl, benzoyl, an optionally halogenated $C_{1-6}$ alkoxy-carbonyl, an optionally halogenated $C_{1-5}$ alkyl-sulfonyl, benzenesulfonyl), a hydroxyl group, a $C_{6-10}$ aryl, a $C_{6-10}$ aryloxy, a $C_{6-10}$ aryl-$C_{1-4}$ alkoxy and the like, and any of these substituents may occur 1 to 5 times (preferably 1 to 2 times) in any possible positions.

"Optionally substituted lower alkylidene group" may for example be a $C_{1-6}$ alkylidene such as methylidene and ethylidene, and its substituent may for example be a halogen atom (for example, fluorine, chlorine, bromine and iodine), an amino group, a carboxyl group and a hydroxyl group, and any of these substituents may occur 1 to 5 times (preferably 1 to 2 times) in any possible positions.

"Optionally substituted lower aralkylidene group" may for example be a $C_{6-10}$ aryl-$C_{1-4}$ alkylidene such as benzylidene, and its substituent may for example be a halogen atom (for example, fluorine, chlorine, bromine and iodine), an amino group, a carboxyl group and a hydroxyl group, and any of these substituents may occur 1 to 5 times (preferably 1 to 2 times) in any possible positions.

A lower alkoxy group in "lower alkoxy group which may be substituted by a halogen and the like" may for example be a $C_{1-6}$ alkoxy group such as methoxy, ethoxy, n-propoxy, isopropoxy, n-butoxy, isobutoxy, sec-butoxy, tert-butoxy, with methoxy and ethoxy being preferred especially. Such lower alkoxy group may have a substituent similar to "lower alkyl group" in "optionally substituted lower alkyl group" which may be possessed as a substituent by "optionally substituted divalent nitrogen-containing heterocyclic group" described above.

"Optionally esterified carboxyl group" may for example be one similar to an optionally esterified carboxyl group as a substituent on "optionally substituted hydrocarbon group" represented by R described above.

"Optionally substituted carbamoyl group", "optionally substituted thiocarbamoyl group" and "optionally substituted sulfamoyl group" may for example be those similar to an optionally substituted carbamoyl group, an optionally substituted thiocarbamoyl group and an optionally substituted sulfamoyl group as substituents on "optionally substituted hydrocarbon group" represented by R described above.

A substituent which may be possessed by "hydroxyl group" and "mercapto group" in "optionally substituted hydroxyl group" and "optionally substituted mercapto group" as substituents which may be possessed by "divalent nitrogen-containing heterocyclic group" described above may for example be an optionally substituted lower alkyl group, an optionally esterified carboxyl group, an optionally substituted carbamoyl group, an optionally substituted thiocarbamoyl group, an optionally substituted sulfamoyl group, a sulfonic acid-derived acyl group, a carboxylic group-derived acyl group and the like. Such lower alkyl group may for example be a $C_{1-6}$ alkyl group such as methyl, ethyl, n-propyl, isopropyl, n-butyl, isobutyl, sec-butyl, tert-butyl, pentyl and hexyl, and a substituent which may be possessed by this lower alkyl group may for example be a halogen atom (for example, fluorine, chlorine, bromine and iodine), an optionally substituted aryl group [for example phenyl or naphthyl which may be substituted by a halogen atom (for example, fluorine, chlorine, bromine and iodine), a lower alkyl group (e.g., a $C_{1-6}$ alkyl group such as methyl, ethyl, n-propyl, isopropyl, n-butyl, isobutyl, sec-butyl, tert-butyl, pentyl and hexyl), a lower alkoxy group (e.g., $C_{1-6}$ alkoxy group such as methoxy, ethoxy, n-propoxy, isopropoxy, n-butoxy, isobutoxy, sec-butoxy and tert-butoxy) and the like], an optionally substituted hydroxyl group (e.g., one similar to an optionally substituted hydroxyl group as a substituent on "optionally substituted hydrocarbon group" represented by R described above"), an optionally substituted thiol group (e.g., one similar to an optionally substituted thiol group as a substituent on "optionally substituted hydrocarbon group" represented by R described above"), an optionally substituted amino group (e.g., one similar to an optionally substituted amino group as a substituent on "optionally substituted hydrocarbon group" represented by R described above"), an optionally esterified carboxyl group (e.g., one similar to an optionally esterified carboxyl group as a substituent on "optionally substituted hydrocarbon group" represented by R described above") and the like. In "optionally substituted mercapto group", a sulfur atom may be oxidized, and may have a structure represented for example by S(O)k wherein k is an integer of 0 to 2.

"Optionally esterified carboxyl group", "optionally substituted carbamoyl group", "optionally substituted thiocarbamoyl group", "optionally substituted sulfamoyl group", "sulfonic acid-derived acyl group" and "carboxylic group-derived acyl group" as substituents which may be possessed by "hydroxyl group" and "mercapto group" in "optionally substituted hydroxyl group" and "optionally substituted mercapto group" as substituents which may be possessed by "divalent nitrogen-containing heterocyclic group" described above may for example be those similar to "optionally esterified carboxyl group", "optionally substituted carbamoyl group", "optionally substituted thiocarbamoyl group", "optionally substituted sulfamoyl group", "sulfonic acid-derived acyl group" and "carboxylic group-derived acyl group" as substituents on "optionally substituted hydrocarbon group" represented by R described above.

A preferred "divalent nitrogen-containing heterocyclic group" described above may for example be a group represented by Formula:

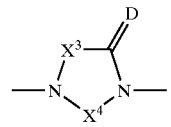

wherein $X^3$ is an optionally substituted $C_{1-2}$ alkylene, $X^4$ is an optionally substituted $C_{1-3}$ alkylene and D is an oxygen atom or a sulfur atom, and more preferably a group represented by Formula:

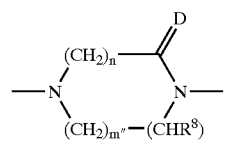

wherein n is 1 or 2, m" is 1 or 2, $R^8$ is a hydrogen atom, an optionally substituted hydroxyl group, an optionally substituted mercapto group, a nitro group, a cyano group, an optionally substituted amino group, an optionally substituted lower alkyl group, an optionally substituted lower alkoxy group, an optionally esterified carboxyl group, an optionally substituted carbamoyl group, an optionally substituted thiocarbamoyl group or an optionally substituted sulfamoyl group (preferably, a hydrogen atom, an optionally substituted lower alkyl group, a cyano group, an optionally esterified carboxyl group, an optionally substituted carbamoyl group or an optionally substituted thiocarbamoyl group), and D is an oxygen atom or a sulfur atom.

"$C_{1-2}$ Alkylene" in "optionally substituted $C_{1-2}$ alkylene" represented by $X^3$ may for example be a straight alkylene such as methylene and ethylene, and such "$C_{1-2}$ alkylene" may have a group similar to a substituent which may be possessed by "divalent nitrogen-containing heterocyclic group" in "optionally substituted divalent nitrogen-containing heterocyclic group" described above. "$C_{1-3}$ Alkylene" in "optionally substituted $C_{1-3}$ alkylene represented by $X^4$ may for example be a straight alkylene such as methylene, ethylene and propylene, and such "$C_{1-3}$ alkylene" may have a group similar to a substituent which may be possessed by "divalent nitrogen-containing heterocyclic group" in "optionally substituted divalent nitrogen-containing heterocyclic group" described above.

In the formula described above, "optionally substituted hydroxyl group", "optionally substituted mercapto group", "nitro group", "cyano group", "optionally substituted amino group", "optionally substituted lower alkyl group", "optionally substituted lower alkoxy group", "optionally esterified carboxyl group", "optionally substituted carbamoyl group", "optionally substituted thiocarbamoyl group" and "optionally substituted sulfamoyl group" may for example those similar to "optionally substituted hydroxyl group", "optionally substituted mercapto group", "nitro group", "cyano group", "optionally substituted amino group", "optionally substituted lower alkyl group", "optionally substituted lower alkoxy group", "optionally esterified carboxyl group", "optionally substituted carbamoyl group", "optionally substituted thiocarbamoyl group" and "optionally substituted sulfamoyl group" which may be possessed as substituents by "divalent nitrogen-containing heterocyclic group" in "optionally substituted divalent nitrogen-containing heterocyclic group" described above.

"Divalent nitrogen-containing heterocyclic group" described above is preferably a group represented by Formula:

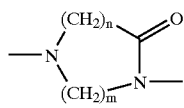

wherein n is 1 or 2 and m is 2 or 3.

In the formula shown above, m is preferably 2, and n is preferably 1.

Most preferably, "divalent nitrogen-containing heterocyclic group" described above is 2-oxopiperazine-1,4-diyl.

It is also possible that a substituent on $X^1$ and $R^2$ are bound to each other and a divalent group represented by —$X^1$—CD—N($R^2$)— forms "optionally substituted divalent nitrogen-containing heterocyclic group". "Divalent nitrogen-containing heterocyclic group" in this "optionally substituted divalent nitrogen-containing heterocyclic group" may for example be a divalent 5- to 8-membered nitrogen-containing heterocyclic group containing 1 or 3 nitrogen atoms, in addition to carbon atoms, as its atoms constituting a ring system (ring atoms) (preferably a divalent 5- to 7-membered nitrogen-containing heterocyclic group comprising carbon atoms and one nitrogen atom).

While such "divalent nitrogen-containing heterocyclic group" has an oxo group or a thioxo group -on a carbon atom adjacent to the nitrogen atom to which a substituent represented by $R^2$ is bound and forms a "divalent 5- to 8-membered nitrogen-containing cyclic amide group", a substituent on "divalent nitrogen-containing heterocyclic group" in such "optionally substituted divalent nitrogen-containing heterocyclic group" may for example be one similar to a substituent which may be possessed by "divalent nitrogen-containing heterocyclic group" in "optionally substituted divalent nitrogen-containing heterocyclic group" formed by binding $R^1$ and $R^2$ to each other.

"Divalent nitrogen-containing heterocyclic group" formed by binding a substituent on $X^1$ and $R^2$ to each other may for example be "optionally substituted divalent nitrogen-containing heterocyclic group" which may be a group represented by Formula:

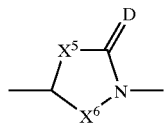

wherein $X^5$ is a bond or an optionally substituted methylene, $X^6$ is an optionally substituted $C_{2-3}$ alkylene and D is an oxygen atom or a sulfur atom.

"Methylene" represented by $X^5$ shown here may have a group similar to a substituent which may be possessed by "divalent nitrogen-containing heterocyclic group" in "optionally substituted divalent nitrogen-containing heterocyclic group" described above. "$C_{2-3}$ Alkylene" in "optionally substituted $C_{2-3}$ alkylene" represented by $X^6$ may for example be a straight alkylene such as ethylene and propylene, and such "$C_{2-3}$ alkylene" may have a group similar to a substituent which may be possessed by "divalent nitrogen-containing heterocyclic group" in "optionally substituted divalent nitrogen-containing heterocyclic group" described above.

Among those listed above, a group represented by Formula:

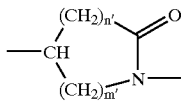

wherein n' is 0 or 1 and m' is 2 or 3 is preferred.

In the formula shown above, m' is preferably 2, and n' is preferably 0.

Most preferably, "divalent nitrogen-containing heterocyclic group" described above is 2-pyrrolidone-1,3-diyl.

"Alkylene group" in "optionally substituted alkylene group" represented by $X^1$ and $X^2$ may for example be a straight lower ($C_{1-6}$) alkylene such as methylene, ethylene, propylene, butylene and pentylene, with a $C_{1-4}$ alkylene such as methylene and ethylene being preferred. A substituent on "alkylene group" may for example be an optionally substituted lower alkyl group [one similar to "optionally substituted lower alkyl group" as a substituent on "optionally substituted divalent nitrogen-containing heterocyclic group" described above, preferably, a lower alkyl group (for example a $C_{1-6}$ alkyl such as methyl, ethyl, n-propyl, isopropyl, n-butyl, isobutyl, sec-butyl, tert-butyl)], an optionally substituted carbamoyl group [one similar to "optionally substituted carbamoyl group" as a substituent on "optionally substituted divalent nitrogen-containing heterocyclic group" described above, preferably, a carbamoyl group, a N-monolower($C_{1-6}$) alkylcarbamoyl group, N,N-dilower($C_{1-6}$) alkylcarbamoyl group and the like], a cyano group, a halogen atom (for example, fluorine, chlorine, bromine, iodine), a hydroxyl group, an optionally esterified carboxyl group (such as one similar to "optionally esterified carboxyl group" as a substituent on "optionally substituted hydrocarbon group" represented by R) and the like, and any of these substituent may occur 1 to 3 times in any possible positions.

"Optionally substituted imino group" represented by $X^1$ and $X^2$ may for example be a group represented by Formula —N($R^4$)— wherein $R^4$ denotes a hydrogen atom or a substituent, and this $R^4$ is preferably a hydrogen atom, an optionally substituted hydrocarbon group, an acyl group (preferably a hydrogen atom, an optionally substituted hydrocarbon group) and the like.

In the formula shown above, "optionally substituted hydrocarbon group" represented by $R^4$ may for example be one similar to "optionally substituted hydrocarbon group" represented by R.

In the formula shown above, "acyl group" represented by $R^1$ may be one similar to "sulfonic acid-derived acyl group" and "carboxylic acid-derived acyl group" as substituents on "optionally substituted hydrocarbon group" represented by R described above, it is preferably formyl, an optionally substituted lower ($C_{2-5}$)alkanoyl group and the like, with a lower ($C_{2-5}$)alkanoyl group being more preferred.

In the formula shown above, $X^1$ is preferably methylene and $X^2$ is preferably a bond.

In the formula shown above, D is an oxygen atom or a sulfur atom (preferably an oxygen atom).

In the formula shown above, A is —N($R^3$)—Y— or —N=Y—, $R^3$ is a hydrogen atom, an optionally substituted hydrocarbon group or an acyl group, and Y is an optionally substituted linear hydrocarbon group or an optionally substituted cyclic group.

While "optionally substituted hydrocarbon group" represented by $R^3$ may for example be one similar to "optionally substituted hydrocarbon group" represented by R and "acyl group" represented by $R^3$ may for example be one similar to "sulfonic acid-derived acyl group" and "carboxylic acid-derived acyl group" as substituents on "optionally substituted hydrocarbon group" represented by R described above, $R^3$ is preferably a hydrogen atom, an optionally substituted lower $(C_{1-4})$alkyl group, formyl, an optionally substituted lower $(C_{2-5})$alkanoyl group and the like, and more preferably hydrogen atom, an optionally substituted lower $(C_{1-4})$ alkyl group and the like.

"Linear hydrocarbon group" in "optionally substituted linear hydrocarbon group" represented by Y may for example be a divalent or trivalent group formed by removing 1 to 2 hydrogen atoms from one carbon atom in "straight or branched (preferably straight) aliphatic hydrocarbon group" as "optionally substituted hydrocarbon group" represented by R, and is typically an optionally substituted $C_{1-6}$ alkylene group (such as one similar to "optionally substituted alkylene group" represented by $X^1$ and $X^2$ described above), a group represented by Formula =CH—$(CH_2)_k$— wherein k is an integer of 0 to 5 which may have a substituent on any carbon atom, and the like.

A substituent which may be possessed by "linear hydrocarbon group" as "optionally substituted linear hydrocarbon group" represented by Y may for example be an optionally substituted lower alkyl group [one similar to "optionally substituted lower alkyl group" as a substituent on "optionally substituted divalent nitrogen-containing heterocyclic group" described above, preferably, a lower alkyl group (for example a $C_{1-6}$ alkyl such as methyl, ethyl, n-propyl, isopropyl, n-butyl, isobutyl, sec-butyl, tert-butyl)], an optionally substituted carbamoyl group [one similar to "optionally substituted carbamoyl group" as a substituent on "optionally substituted divalent nitrogen-containing heterocyclic group" described above, preferably, a carbamoyl group, a N-monolower$(C_{1-6})$alkylcarbamoyl group, N,N-dilower$(C_{1-6})$alkylcarbamoyl group and the like], a cyano group, a halogen atom (for example, fluorine, chlorine, bromine, iodine), a hydroxyl group, an optionally esterified carboxyl group (such as one similar to "optionally esterified carboxyl group" as a substituent on "optionally substituted hydrocarbon group" represented by R) and the like, and any of these substituent may occur 1 to 3 times in any possible positions.

"Linear hydrocarbon group" in "optionally substituted linear hydrocarbon group" (preferably an optionally substituted $C_{1-6}$ alkylene group) represented by Y may undergo a substitution of any methylene group by an oxo group to form a carbonyl group, and may typically be a group represented by Formula —(C=O)—$CH_2$— formed as a result of a substitution of a methylene group in —$CH_2$—$CH_2$— by an oxo group.

A substituent on "optionally substituted cyclic group" represented by Y is one similar to a substituent on "divalent nitrogen-containing heterocyclic group" described above.

"Cyclic group" in "optionally substituted cyclic group" represented by Y may for example be a divalent or trivalent cyclic hydrocarbon group or heterocyclic group (preferably heterocyclic group". "Hydrocarbon group" as "cyclic group" in "optionally substituted cyclic group" represented by Y may for example be a saturated or unsaturated, cyclic, divalent or trivalent hydrocarbon group.

A saturated cyclic divalent hydrocarbon group mentioned here may for example be a group obtained by removing one hydrogen atom in any position (preferably on a different carbon atom, more preferably on the farthest carbon atom) of a cycloalkyl group (for example, a $C_{3-9}$ cycloalkyl such as cyclopropyl, cyclobutyl, cyclopentyl, cyclohexyl, cycloheptyl, cyclooctyl and cyclononyl, preferably a $C_{5-7}$ cycloalkyl, more preferably cyclohexyl) (for example, a $C_{5-7}$ cycloalkylene, preferably, 1,4-cyclohexylene).

An unsaturated cyclic divalent hydrocarbon group mentioned here may for example be a group obtained by removing one hydrogen atom in any position (preferably on a different carbon atom, more preferably on the farthest carbon atom) of a cycloalkenyl group (for example, a $C_{3-6}$ cycloalkenyl group such as 2-cyclopenten-2-yl, 3-cyclopenten-1-yl, 2-cyclohexen-1-yl, 3-cyclohexen-1-yl, 1-cyclobuten-1-yl and 1-cyclopenten-1-yl), a cycloalkadienyl group (for example, a $C_{4-6}$ cycloalkadienyl group such as 2,4-cyclopentadien-1-yl, 2,4-cyclohexadien-1-yl and 2,5-cyclohexadien-1-yl), an aryl group (for example, a $C_{6-10}$ aryl group such as phenyl and naphthyl, preferably phenyl), with phenylene being preferred and 1,4-phenylene being particularly preferred.

Such "divalent hydrocarbon group" is preferably a $C_{5-7}$ cycloalkylene (preferably 1,4-cyclohexylene), phenylene (preferably 1,4-phenylene) and the like.

"Saturated or unsaturated cyclic trivalent hydrocarbon group" mentioned here may for example be a group formed by removing one hydrogen atom on any carbon atom in which "saturated or unsaturated cyclic divalent hydrocarbon group" mentioned here has a bond.

"Divalent heterocyclic group" as "cyclic group" in "optionally substituted cyclic group" represented by Y may for example be a 5- to 6-membered divalent aromatic heterocyclic group, saturated or unsaturated non-aromatic heterocyclic group (aliphatic heterocyclic group) containing at least one (preferably 1 to 3, more preferably 1 to 2) atom of 1 to 3 species (preferably 1 to 2 species) of the heteroatoms selected from oxygen, sulfur and nitrogen atoms as an atom constituting a ring system (ring atom) in addition to carbon atoms.

"Divalent aromatic heterocyclic group" may for example be a divalent group obtained by removing 2 hydrogen atoms from 2 different ring atoms of a 5-membered aromatic heterocyclic group such as thiophene, pyrrole, oxazole, isooxazole, thiazole, isothiazole, imidazole, pyrazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole and 1,2,4-triazole and also of a 6-membered aromatic heterocyclic group such as pyridine, :2 pyridazine, pyrimidine, 1,2,4-triazine and 1,3,5-triazine.

"Divalent non-aromatic heterocyclic group" may for example be a 5- to 6-membered saturated or unsaturated (preferably saturated) non-aromatic heterocyclic group (aliphatic heterocyclic group) such as pyrrolidine, tetrahydrofuran, piperidine, tetrahydropyran, morpholin, thiomorpholin and piperazine.

"Trivalent heterocyclic group" as "cyclic group" of "optionally substituted cyclic group" represented by Y may for example be a group formed by adding one bond to any atom in which "divalent non-aromatic heterocyclic group" described above has a bond.

Y is preferably an optionally substituted phenylene, an optionally substituted piperidine and the like.

In the formula shown above, A is preferably a group represented by Formula:

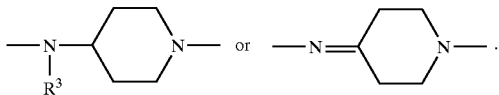

Z is (1) an optionally substituted amino group, (2) an optionally substituted imidoyl group or (3) an optionally substituted nitrogen-containing heterocyclic group.

A substituent on "optionally substituted amino group represented by Z may for example be one similar to "optionally substituted hydrocarbon group" and "optionally substituted heterocyclic group" represented by R described above or two such substituents are taken together with a nitrogen atom to form a cyclic amino group, and in such case such cyclic amino group may for example be a 3- to 8-membered (preferably 5- to 6-membered) cyclic amino group such as 1-azetidinyl, 1-pyrrolidinyl, piperidino, morpholino, 1-piperazinyl as well as 1-piperazinyl which may have in its 4-position a lower alkyl group (for example a $C_{1-6}$ alkyl group such as methyl, ethyl, propyl, isopropyl, butyl, t-butyl, pentyl, hexyl), an aralkyl group (for example a $C_{7-10}$ aralkyl group such as benzyl and phenethyl) and an aryl group (for example a $C_{6-10}$ aryl group such as phenyl, 1-naphthyl, 2-naphthyl), and such cyclic amino group may have a substituent similar to those of a substituent on bkoptionally substituted hydrocarbon group" represented by R described above which may occur similar times.

Also when "optionally substituted hydrocarbon * group" as a substituent on "amino group which may be substituted by an optionally substituted hydrocarbon group" represented by Z contains "optionally substituted imino group" in its a-position, then "optionally substituted amino group" represented by Z forms an amino group substituted by "optionally substituted imidoyl group" represented below by Z, and a group represented by Formula —N(R")—C(R')=N—R'" wherein R" is a hydrogen bond or an optionally substituted hydrocarbon group, R'" is a hydrogen atom, an optionally substituted hydroxyl group, an optionally substituted hydrocarbon group or a carboxylic acid-derived acyl group, R' is a hydrogen atom, an optionally substituted hydrocarbon group, a carboxylic acid-derived acyl group, an optionally substituted amino group, an optionally substituted mercapto group or an optionally substituted hydroxyl group is included in "optionally substituted amino group" represented by Z. Also when $R^1$ is a mercapto group or a hydroxyl group and R" is a hydrogen atom in "optionally substituted imidoyl group", such "optionally substituted imidoyl group" may each be a group represented by Formula —C(=O)—$NH_2$ or —C(=S)—$NH_2$.

In the formula shown above, "optionally substituted hydrocarbon group" represented by R'", R' and R" may for example be one similar to "optionally substituted hydrocarbon group" represented by R described above, "carboxylic acid-derived acyl group" represented by R'" and R' may for example be one similar to "carboxylic acid-derived acyl group" as a substituent which may be possessed by "optionally substituted hydrocarbon group" represented by R described above, "optionally substituted hydroxyl group" represented by R' may for example be one similar to "optionally substituted hydroxyl group" as a substituent which may be possessed by "optionally substituted hydrocarbon group" represented by R described above, "optionally substituted amino group" represented by R' may for example be one similar to "optionally substituted amino group" as a substituent which may be possessed by "optionally substituted hydrocarbon group" represented by R described above or an amino group which may have 1 to 2 "optionally substituted hydrocarbon groups" represented by R described above. A compound represented by Formula (I) wherein R'" is a carboxylic acid-derived acyl group is useful as a prodrug for a compound in which R'" is a hydrogen atom.

While "carboxylic acid-derived acyl group" represented by R'" may for example be one similar to "carboxylic acid-derived acyl group" as a substituent which may be possessed by "optionally substituted hydrocarbon group" represented by R described above, "carboxylic acid-derived acyl group" represented by R may be an optionally esterified carboxyl group such as a group represented by Formula-COOR"" wherein R"" is an optionally substituted hydrocarbon group.

"Optionally substituted hydrocarbon group" represented by R"" may for example be one similar to "optionally substituted hydrocarbon group" represented by R described above.

A preferred example of "hydrocarbon group" in "optionally substituted hydrocarbon group" represented by R"" is $C_{1-6}$ alkyl, $C_{2-6}$ alkenyl, $C_{3-6}$ cycloalkyl, $C_{6-10}$ aryl, $C_{6-10}$ aryl-$C_{1-4}$ alkyl and the like. A substituent which may be possessed by such "hydrocarbon group" may for example be similar to a substituent which may be possessed by "optionally substituted hydrocarbon group" represented by $R^1$ described above and may occur similar times.

A group represented by Formula —COOR"" may for example be a $C_{1-6}$ alkoxy-carbonyl group (e.g., methoxycarbonyl, ethoxycarbonyl, isopropoxycarbonyl), a $C_{1-6}$ alkanoyloxy-$C_{1-6}$ alkoxy-carbonyl group (e.g., pivaloyloxymethoxycarbonyl, 1-(acetoxy)ethoxycarbonyl, acetoxy-tert-butoxycarbonyl), a $C_{1-6}$ alkoxy-carbonyloxy-$C_{1-6}$ alkoxy-carbonyl group (e.g., ethoxycarbonyloxymethoxycarbonyl), a 5-$C_{1-4}$ alkyl-2-oxo-dioxolen-4-yl-$C_{1-6}$ alkoxy-carbonyl group (e.g., 5-methyl-2-oxo-dioxolen-4-ylmethoxycaronyl) and the like.

More typically, "optionally substituted amino group" represented by Formula Z may for example be an amino group, a mono- or di-lower ($C_{1-6}$)alkylamino group which may further be substituted by a $C_{6-10}$ aryl group (preferably phenyl) (for example, methylamino, ethylamino, benzylamino, dimethylamino, diethylamino, diisobutylamino, diisopropylamino, N-ethyl-t-butylamino, benzylmethylamino), a group represented by Formula —N(R")—C(R')=N—R'" wherein R" is a hydrogen atom or an optionally substituted hydrocarbon group (preferably a hydrogen atom or a lower ($C_{1-6}$)alkyl group), R'" is a hydrogen atom, an optionally substituted hydroxyl group, an optionally substituted hydrocarbon group or a carboxylic acid-derived acyl group (preferably a hydrogen atom or a carboxylic acid-derived acyl group), R' is a hydrogen atom, an optionally substituted hydrocarbon group, an optionally substituted amino group, an optionally substituted mercapto group or an optionally substituted hydroxyl group (preferably a hydrogen atom, a lower ($C_{1-6}$)alkyl group, an amino group or a mono- or di-lower ($C_{1-6}$)alkylamino group (for example, a guanidino group, a formimidoylamino group, an acetoimidoylamino group), a 5- to 6-membered cyclic amino group (for example piperidino group) and the like. "Optionally substituted imidoyl group" represented by Z may for example be a group represented by Formula —C(R')=N—R'" wherein each symbol is defined as described above.

When R' mentioned here represents an optionally substituted amino group (preferably, amino, methylamino, ethylamino, propylamino, dimethylamino, diethylamino, hydrazino, piperidino, piperazino, morpholino, thiomorpholino), then "optionally substituted imidoyl group" represented by Z forms an optionally substituted amidino group. Such optionally substituted amidino group may typically be an amidino group which may be substituted by one to two lower ($C_{1-6}$)alkyl groups, lower ($C_{1-6}$) alkanoyl groups, benzoyl groups and the like (for example, amidino, N-methylamidino, N-ethylamidino, N-propylamidino, N,N'-dimethylamidino, N,N'-diethylamidino, N-methyl-N'-diethylamidino, N-formylamidino, N-acetylamidino) and the like. A preferred example of R'" described above is hydrogen, a lower alkyl group (for example a $C_{1-6}$ alkyl group such as methyl, ethyl, propyl, isopropyl, butyl, isobutyl), an acyl group (for example a $C_{1-6}$ alkanoyl such as formyl, acetyl, propionyl, pivaloyl); benzoyl; a $C_{1-8}$ alkoxycarbonyl group such as methoxycarbonyl, ethoxycarbonyl, propoxycarbonyl, isopropoxycarbonyl, butoxycarbonyl, isobutoxycarbonyl; a $C_{7-10}$ aralkyloxycarbonyl such as benzyloxycarbonyl, phenethyloxycarbonyl; a hydroxyl group and the like, while a preferred example of R' is hydrogen, a lower alkyl group (for example a $C_{1-6}$ alkyl group such as methyl, ethyl, propyl, isopropyl, butyl, isobutyl), an optionally substituted amino group (for example an amino group which may be substituted by one or two, same or different lower alkyl groups (for example a $C_{1-6}$ alkyl group such as methyl, ethyl, propyl, isopropyl, butyl, isobutyl) or an acyl group (for example a $C_{1-6}$ alkanoyl such as formyl, acetyl, propionyl, pivaloyl, benzoyl), a hydrazino group, a 5- to 6-membered cyclic amino group (for example, piperidino, thiomorpholino, morpholino, piperazino), a hydroxyl group, a lower alkoxy group (for example, a $C_{1-6}$ alkoxy group such as methoxy, ethoxy, propoxy, isopropoxy, butoxy, isobutoxy), a mercapto group, a lower alkylthio group (for example, a $C_{1-6}$ alkylthio group such as methylthio, ethylthio, propylthio, isopropylthio, butylthio, isobutylthio) and the like.

In the formula shown above, R'" is preferably hydrogen.

In the formula shown above, R' is preferably hydrogen, a lower alkyl group or an optionally substituted amino group, with a lower alkyl group or an optionally substituted amino group being more preferred and an optionally substituted amino group (preferably amino which may be substituted by a $C_{1-4}$ alkyl) being particularly preferred.

"Nitrogen-containing heterocyclic group" in "optionally substituted nitrogen-containing heterocyclic group" represented by Z may for example be an aromatic nitrogen-containing heterocyclic group and saturated or unsaturated non-aromatic nitrogen-containing heterocyclic group (aliphatic heterocyclic group) which contains at least one (preferably 1 to 3) nitrogen atom as an atom constituting a ring system (ring atom) in addition to carbon atoms, and which may also contain 1 to 3 heteroatoms selected from oxygen and sulfur atoms.

"Aromatic nitrogen-containing heterocyclic group" may for example be an aromatic monocyclic nitrogen-containing heterocyclic group such as pyrrolyl, oxazolyl, isooxazolyl, thiazolyl, isothiazolyl, imidazolyl (1H-imidazol-1-yl, 1H-imidazol-4-yl and the like), pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl (1,2,4-triazolyl-1-yl, 1,2,4-triazolyl-4-yl and the like), tetrazolyl, pyridyl (2-, 3- or 4-pyridyl), pyridazinyl, pyrimidinyl and pyrazinyl, triazinyl as well as an N-oxide form thereof, with a 5-to 6-membered aromatic monocyclic nitrogen-containing heterocyclic group being preferred and imidazolyl and pyridyl being particularly preferred.

A preferred pyridyl is 4-pyridyl which may have a substituent (e.g., an optionally substituted lower alkyl group) in its 2-position.

"Non-aromatic nitrogen-containing heterocyclic group" may for example be a partially reduced form of "aromatic nitrogen-containing heterocyclic group" described above (e.g., imidazolinyl, tetrahydropyrimidinyl), as well as azetidinyl, pyrrolidinyl, piperidyl (2-, 3- or 4-piperidyl), morpholinyl, thiomorpholinyl, piperazinyl (1-piperazinyl and the like), homopiperazinyl and the like, with a 5- to 6-membered non-aromatic monocyclic nitrogen-containing heterocyclic group being preferred.

A substituent on "nitrogen-containing heterocyclic group" represented by Z is one similar to a substituent on "heterocyclic group" represented by R described above. A nitrogen atom which is a constituent of a nitrogen-containing heterocyclic group may be oxidized. It is also possible that the substituents on "nitrogen-containing heterocyclic group" represented by Z are bound to each other to form a ring (e.g., a benzene ring).

Z is preferably an optionally substituted nitrogen-containing heterocyclic group, with an optionally substituted aromatic nitrogen-containing heterocyclic group being particularly preferred.

Compound (I) is preferably 4-(7-chloro-2H-benzopyran-3-sulfonyl)-1-[1-(4-pyridyl)piperidin-4-ylamino]-2-piperazinone, 4-(6-chloronaphthalene-2-sulfonyl)-1-[1-(4-pyridyl)piperidin-4-ylamino]-2-piperazinone, 4-(6-bromonaphthalene-2-sulfonyl)-1-[1-(4-pyridyl)piperidin-4-ylamino]-2-piperazinone, 4-(7-bromo-2H-benzopyran-3-sulfonyl)-1-[1-(4-pyridyl)piperidin-4-ylamino]-2-piperazinone, 4-(6-chloronaphthalene-2-sulfonyl)-1-{methyl[1-(4-pyridyl)piperidin-4-yl]amino}-2-piperazinone, 4-(6-bromonaphthalene-2-sulfonyl)-1-{methyl[1-(4-pyridyl)piperidin-4-yl]amino}-2-piperazinone, 4-(7-bromo-2H-benzopyran-3-sulfonyl)-1-{methyl[1-(4-pyridyl)piperidin-4-yl]amino}-2-piperazinone, 4-(6-chloronaphthalene-2-sulfonyl)-1-{ethyl[1-(4-pyridyl)piperidin-4-yl]amino}-2-piperazinone, 4-(6-chloronaphthalene-2-sulfonyl)-1-{methyl[1-(2-methyl-4-pyridyl)piperidin-4-yl]amino}-2-piperazinone, {[4-(6-chloronaphthalene-2-sulfonyl)-2-oxo-1-piperazinyl][1-(2-methyl-4-pyridyl)-4-piperidinyl]amino}acetic acid, 4-(6-chloronaphthalene-2-sulfonyl)-1-{[1-(4-pyridyl)-4-piperidinyl]amino}-6-oxo-2-piperazinecarboxylic acid, 4-(6-chloronaphthalene-2-sulfonyl)-1-{methyl[1-(4-pyridyl)-4-piperidinyl]amino}-6-oxo-2-piperazinecarboxylic acid, 4-(6-chloronaphthalene-2-sulfonyl)-1-{methyl[1-(4-pyridyl)-4-piperidinyl]amino}-6-oxo-2-piperazinecarboxamide, 4-(6-chloronaphthalene-2-sulfonyl)-1-{methyl[1-(2-methyl-4-pyridyl)-4-piperidinyl]amino}-6-oxo-2-piperazinecarboxamide, 4-(6-chloronaphthalene-2-sulfonyl)-6-hydroxymethyl-1-{methyl[1-(4-pyridyl)-4-piperidinyl]amino}-2-piperazinone, 6-aminomethyl-4-(6-chloronaphthalene-2-sulfonyl)-1-{methyl[1-(4-pyridyl)-4-piperidinyl]amino}-2-piperazinone, 6-acetylaminomethyl-4-(6-chloronaphthalene-2-sulfonyl)-1-{methyl[1-(4-pyridyl)-4-piperidinyl]amino}-2-piperazinone, 4-(6-chloronaphthalene-2-sulfonyl)-1-{[1-(4-pyridyl)-4-piperidinyl]amino}-6-oxo-2-piperazineacetic acid and 4-(6-chloronaphthalene-2-sulfonyl)-1-{[1-(2-methyl-4-pyridyl)-4-piperidinyl]amino}-6-oxo-2-piperazineacetic acid as well as a salt thereof.

A prodrug for Compound (I) means a compound which is converted into Compound (I) by a reaction with an enzyme or a gastric acid under an in vivo physiological condition, i.e. a compound which undergoes an enzymatic oxidation or reduction to form Compound (I) and a compound which is hydrolyzed by a gastric acid to form Compound (I). A prodrug for Compound (I) may for example be a compound resulting from an acylation, an alkylation or a phosporylation of an amino group of Compound (I) (for example, a compound resulting from eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation of an amino acid of Compound (I)), a compound resulting from an acylation, an alkylation, a phosphorylation and a boration of a hydroxyl group of Compound (I) (for example a compound resulting from acetylation, palmitoylation, propanoylation, pivaloylation, succinylation, fumarylation, alanylation, dimethylaminomethylcarbonylation of a hydroxyl group of Compound (I)), or a compound resulting from an esterification or an amidation of a carboxyl group of Compound (I) (for example a compound resulting from ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxclen-4-yl)methyl esterification, cyclohexyloxycarbonylethyl esterification, methylamidation of a carboxyl group of Compound (I)) and the like. Any of these compounds can be produced from Compound (I) by a method known per se.

A prodrug for Compound (I) may also be a compound which is changed into Compound (I) under a physiological condition described in "IYAKUHIN NO KAIHATSU (Pharmaceutical development)", Vol.7, Molecular design, p163-198, HIROKAWA SHOTEN, 1990.

A salt of Compound (I) may for example be a pharmaceutically acceptable salt such as an acid addition salt with acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like, a metal salt with sodium, potassium, magnesium, calcium and the like, an organic. salt with trimethylamine, triethylamine, pyridine, picolin, N-methylpyrrolidine, N-methylpiperidine, N-methylmorpholine and the like.

Compound (I) or a salt thereof can be produced for example by Processes A to D described below. Each compound shown in the following methods may form a salt as long as the reaction is not affected adversely, and such salt may for example be one similar to a salt of Compound (I).

Process A

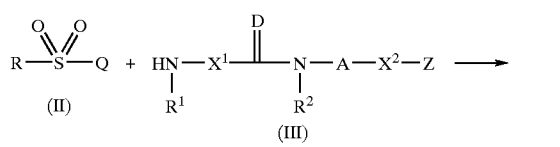

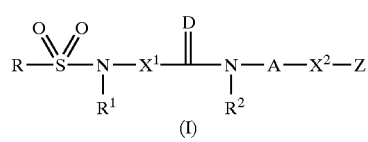

Process B

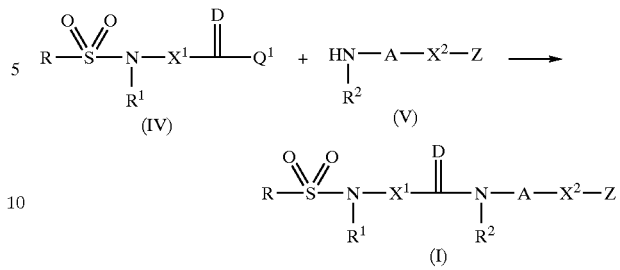

Process C

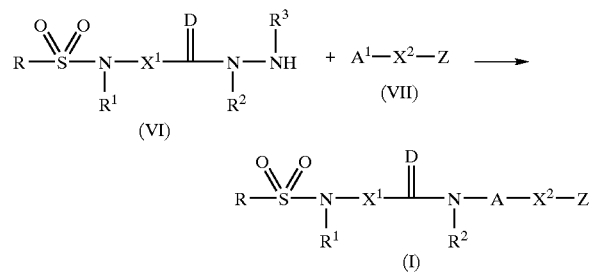

Process D

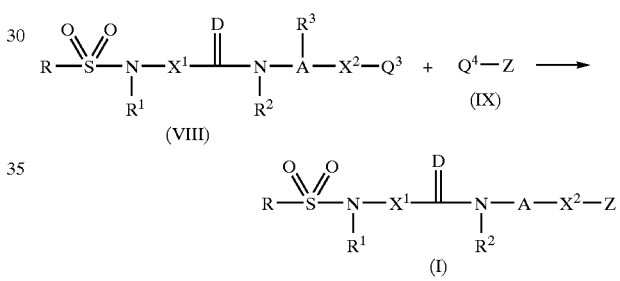

Process A

Compound (II) represented by Formula RSO$_2$Q (II) wherein Q is a leaving group and other symbols are defined as described above or a salt thereof is reacted with Compound (III) represented by Formula (III):

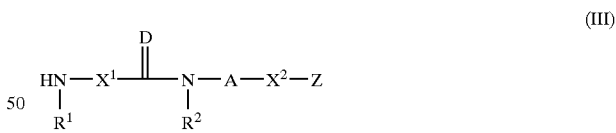

wherein the symbols are defined as described above or a salt thereof to form Compound (I).

In Formula (II) shown above, Q is a leaving group. A leaving group represented by Q may for example be a halogen atom (e.g., fluorine, chlorine, bromine, iodine) or a group which forms a reactive derivative of a sulfonic acid (e.g., sulfonic anhydride, activated sulfonyl amide, (e.g., 1,2,4-triazolide, imidazolide), a quaternary amine sulfonyl form (e.g., methylpyrrolidinium salt), bissulfonyl imide (e.g., N-phenylbissulfonyl imide) and the like).

This process is performed by reacting Compound (II) or a salt thereof with Compound (III) or a salt thereof, and a salt of Compound (II) or Compound (III) may for example be an acid addition salt with an acid which forms an acid addition salt with Compound (I) described above.

This reaction is performed generally in a solvent, and a solvent by which the reaction is not affected adversely is selected appropriately. Such solvent may for example be an alcohol such as methanol, ethanol, propanol, isopropanol, butanol and tert-butanol, an ether such as dioxane, tetrahydrofuran, diethyl ether, tert-butylmethyl ether, diisopropyl ether and ethylene glycol-dimethyl ether, an ester such as ethyl formate, ethyl acetate and n-butyl acetate, a halogenated hydrocarbon such as dichloromethane, chloroform, carbon tetrachloride, trichloroethylene and 1,2-dichloroethane, a hydrocarbon such as n-hexane, benzene and toluene, an amide such as formamide, N,N-dimethylformamide and N,N-dimethylacetamide, a ketone such as acetone, methylethyl ketone and methylisobutyl ketone, a nitrile such as acetonitrile and propionitrile as well as dimethylsulfoxide, sulfolane, hexamethyl phosphoramide, water and the like, which may be employed alone or in combination with each other as a solvent mixture.

This reaction may be conducted also in the presence of a base if necessary, and such base may for example be an inorganic base such as lithium hydroxide, potassium hydroxide, sodium hydroxide, sodium carbonate, potassium carbonate and sodium hydrogen carbonate as well as a tertiary amine such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine and N-methylmorpholine.

The reaction employs about 1 to about 5 moles, preferably about 1 to about 3 moles of Compound (II) per mole of Compound (III).

The reaction temperature is about −80° C. to about 100° C., preferably about −50° C. to about 80° C.

The reaction time may vary depending on the type of Compound (II) or Compound (III), the type of the solvent and the reaction temperature, and is usually about 1 minutes to about 72 hours, preferably about 15 minutes to about 24 hours.

Process B

Compound (IV) represented by Formula (IV):

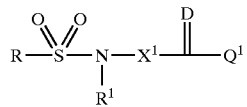

(IV)

wherein $Q^1$ is a leaving group (for example, a halogen atom (e.g., fluorine, chlorine, bromine, iodine), a group which forms a free carboxylic acid, a salt thereof (inorganic or organic salt) or a reactive derivative thereof (e.g., acid halide, ester, acid azide, acid anhydride, mixed acid anhydride, active amide, active ester, active thioester) such as a hydroxyl group) and other symbols are defined as described above is reacted with Compound (V) represented by Formula (V):

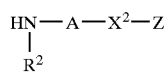

(V)

wherein the symbols are defined as described above to form Compound (I).

This process is performed by reacting Compound (V) or a salt thereof with a free acid (IV) or a salt thereof (inorganic or organic salt) or a reactive derivative thereof (for example, acid halide, ester, acid azide, acid anhydride, mixed acid anhydride, active amide, active ester, active thioester). A salt of Compound (V) may for example be an acid addition salt with an acid which forms an acid addition salt with Compound (I) described above.

An inorganic salt employed as Compound (IV) may for example be an alkaline metal salt (for example, sodium salt and potassium salt), an alkaline earth metal (for example, calcium salt), while an organic salt employed may for example be a trimethylamine salt, a triethylamine salt, tert-butyldimehtylamine salt, a dibenzylmethylamine salt, a benzyldimethylamine salt, an N,N-dimethylaniline salt, a pyridine salt and a quinoline salt. An acid halide may for example be an acid chloride and acid bromide, an ester may for example be a lower alkyl ester such as methyl and ethyl esters, a mixed acid anhydride may for example be a mono $C_{1-4}$ alkyl-carbonic acid mixed anhydride (for example, a mixed acid anhydride of a free acid (IV) with monomethyl carbonic acid, monoethyl carbonic acid, monoisopropyl carbonic acid, monoisobutyl carbonic acid, mono tert-butyl carbonic acid, monobenzyl carbonic acid, mono (p-nitrobenzyl)carbonic acid and monoallyl carbonic acid), a $C_{1-6}$ aliphatic carboxylic acid mixed anhydride (for example a mixed acid anhydride of a free acid (IV) with acetic acid, cyanoacetic acid, propionic. acid, butyric acid, isobutyric acid, valeric acid, isovaleric acid, pivalic acid, trifluoroacetic acid, trichloroacetic acid and acetoacetic acid), a $C_{7-11}$ aromatic carboxylic acid mixed anhydride (for example, a mixed acid anhydride of a free acid (IV) with benzoic acid, p-toluic acid and p-chlorobenzoic acid), an organic sulfonic acid mixed anhydride (for example, with methanesulfonic acid, ethanesulfonic acid, benzenesulfonic acid and p-toluenesulfonic acid), and an active amide may for example be an amide with a nitrogen-containing heterocyclic compound (for example, an acid amide of a free acid (IV) with pyrazole, imidazole and benzotriazole, and such nitrogen-containing heterocyclic compound may be substituted by a $C_{1-6}$ alkyl (for example, methyl, ethyl, isopropyl, butyl, isobutyl, sec-butyl, tert-butyl), a $C_{1-6}$ alkoxy (for example, methoxy, ethoxy, propoxy, isopropoxy, butoxy, tert-butoxy), a halogen atom (for example, fluorine, chlorine, bromine), oxo, thioxo, a $C_{1-6}$ alkylthio (for example, methylthio, ethylthio, propylthio, butylthio) and the like).

An active ester may for example be an organic phosphate (for example, an ester such as diethoxyphosphate and diphenoxyphosphate) as well as p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1- hbydroxy-1H-2-pyridone ester and the like. An active thioester may for example be an ester with an aromatic heterocyclic thiol compound [such heterocyclic ring may be substituted by a $C_{1-6}$ alkyl (for example, methyl, ethyl, isopropyl, butyl, isobutyl, sec-butyl, tert-butyl), a $C_{1-6}$ alkoxy (for example, methoxy, ethoxy, propoxy, isopropoxy, butoxy, tert-butoxy), a halogen atom (for example, fluorine, chlorine, bromine), a $C_{1-6}$ alkylthio (for example, methylthio, ethylthio, propylthio, butylthio) and the like], such as 2-pyridylthiol ester and 2-benzothiazolylthiol ester.

This reaction is performed generally in a solvent optionally in the presence of a base or a condensing agent (for example, carbodiimides (DCC, WSC, DIC and the like), a phosphate derivative (for example, diethyl cyanophosphate, DPPA, BOP-Cl)). Such solvent and base may be those described above in Process A.

The reaction employs about 1 to about 5 moles, preferably about 1 to about 2 moles of Compound (V) per mole of Compound (IV).

The reaction temperature is about −50° C. to about 150° C., preferably about −20° C. to about 100° C.

The reaction time may vary depending on the types of Compound (IV) or Compound (V), the types of the solvent and the base and the reaction temperature, and is usually about 1 minutes to about 100 hours, preferably about 15 minutes to about 48 hours.

Process C

Compound (VI) represented by Formula (VI):

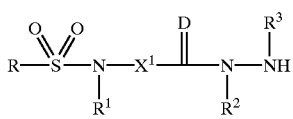 (VI)

wherein the symbols are defined as described above or a salt thereof is reacted with a compound represented by Formula (VII) :$A^1$—$X^2$—Z wherein $A^1$ is $Q^2$—Y— or O=Y— and $Q^2$ is a leaving group (e.g., a halogen atom, a group represented by Formula:$R^5$—$SO_2$—O— wherein $R^5$ is a lower alkyl group which may be substituted by a halogen atom or a phenyl group which may have a substituent) and other symbols are defined as described above or a salt thereof to form Compound (I) or a salt thereof.

This process is performed by reacting Compound (VI) with Compound (VII).

In Formula (VII) shown above, a halogen atom represented by $Q^2$ may for example be chlorine, bromine and iodine.

In the formula shown above, a lower alkyl group which may be substituted by a halogen atom represented by $R^5$ may for example be a $C_{1-6}$ alkyl group such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl, with a $C_{1-4}$ alkyl such as methyl, ethyl, propyl, isopropyl, butyl and isobutyl being preferred. A lower alkyl group substituted by a halogen atom (for example, fluorine, chlorine, bromine and iodine) represented by $R^5$ may for example be trichloromehtyl and trifluoromethyl.

A substituent on a phenyl group represented by $R^5$ may for example be a lower alkyl group (similar to a lower alkyl group represented by $R^5$ described above), a lower alkoxy group (for example, a $C_{1-6}$ alkoxy group such as methoxy, ethoxy, propoxy, isopropoxy and butoxy), a halogen atom (for example, fluorine, chlorine, bromine and iodine), a nitro group, a cyano group and a carboxyl group.

A reaction in this method is performed generally in a solvent, and a solvent by which the reaction is not affected adversely is selected appropriately. Such solvent may for example be an alcohol such as methanol, ethanol, propanol, isopropanol, butanol and tert-butanol, an ether such as dioxane, tetrahydrofuran, diethyl ether, tert-butylmethyl ether, diisopropyl ether and ethylene glycol-dimethyl ether, an ester such as ethyl formate, ethyl acetate and n-butyl acetate, a halogenated hydrocarbon such as dichloromethane, chloroform, carbon tetrachloride, trichloroethylene and 1,2-dichloroethane, a hydrocarbon such as n-hexane, benzene and toluene, an amide such as formamide, N,N-dimethylformamide and N,N-dimethylacetamide, a nitrile such as acetonitrile and propionitrile as well as dimethylsulfoxide, sulfolane, hexamethyl phosphoramide, water and the like, which may be employed alone or in combination with each other as a solvent mixture.

This reaction may be conducted also in the presence of a base if necessary, and such base may for example be an alkaline metal hydride such as potassium hydride and sodium hydride, a metal alkoxide having 1 to 6 carbon atoms such as lithium ethoxide, lithium t-butoxide, sodium methoxide, sodium ethoxide and carboxyl t-butoxide, an inorganic base such as lithium hydroxide, potassium hydroxide, sodium hydroxide, sodium carbonate, potassium carbonate and sodium hydrogen carbonate as well as a tertiary amine such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine and N-methylmorpholine.

The reaction employs about 1 to about 100 moles, preferably about 1 to about 50 moles of Compound (VII) per mole of Compound (VI).

The reaction temperature is about −30° C. to about 250° C., preferably about −10° C. to about 20° C.

The reaction time may vary depending on the types of Compound (VI) or Compound (VII), the type of the solvent and the reaction temperature, and is usually about 1 minutes to about 72 hours, preferably about 15 minutes to about 24 hours.

Alternatively, Compound (VI) or a salt thereof is reacted with Compound (VII) having an oxo group or a salt thereof to form Compound (I) whose substituent A has a double bond, which is then subjected to a reductive amination to form Compound (I) whose substituent A has a single bond or a salt thereof.

A reducing agent employed in this reductive alkylation may for example be a metal hydrogen complex such as lithium aluminum hydride, trimethoxylithium aluminum hydride, tri-t-butoxylithium aluminum hydride, sodium aluminum hydride, sodium triethoxyaluminum hydride, sodium borohydride, sodium trimethoxyborohydride, sodium cyanoborohydride, sodium triacetoxy bodohydride, lithium borohydride, lithium cyanoborohydride and lithium triethylborohydride, as well as triethylsilane. A catalytic hydrogenation employing a catalyst may also be employed. Such catalyst may for example be a palladium catalyst such as palladium black, palladium carbon, palladium-silica gel and palladium-barium sulfate, a platinum catalyst such as platinum oxide, platinum carbon and platinum black, a rhodium catalyst such as rhodium carbon and rhodium alumina, a ruthenium catalyst such as ruthenium oxide and ruthenium carbon as well as a Raney nickel, each of which is subjected to a reaction under a hydrogen atmosphere. The amount of a catalyst to be employed per mole of Compound (I) ranges from about 0.001 to about 2 moles, preferably about 0.001 to about 1 mole. While this catalytic hydrogenation is conducted generally under an atmospheric pressure, it may be conducted also under pressure if necessary. Such pressure is usually about 1 to about 150 atms, preferably about 1 to about 100 atms.

This reaction is performed generally in a solvent, and a solvent by which the reaction is not affected adversely is selected appropriately. Such solvent may for example be an alcohol such as methanol, ethanol, propanol, isopropanol, butanol and tert-butanol, an ether such as dioxane, tetrahydrofuran, diethyl ether, tert-butylmethyl ether, diisopropyl ether and ethylene glycol-dimethyl ether, an ester such as ethyl formate, ethyl acetate and n-butyl acetate, a halogenated hydrocarbon such as dichloromethane, chloroform, carbon tetrachloride, trichloroethylene and 1,2-dichloroethane, a hydrocarbon such as n-hexane, benzene and toluene, an amide such as formamide, N,N-dimethylformamide and N,N-dimethylacetamide, an organic acid such as formic acid, acetic acid and trifluoroacetic acid as well as dimethylsulfoxide, sulfolane, hexamethyl phosphoramide, water and the like, which may be employed alone or in combination with each other as a solvent mixture.

This reaction may be conducted also in the presence of an acid if necessary, and such acid may for example be a mineral acid such as hydrochloric acid, hydrobromic acid, sulfuric acid, phosphoric acid and perchloric acid, a sulfonic acid such as methanesulfonic acid, ethanesulfonic acid, benzenesulfonic acid, toluenesulfonic acid and camphorsulfonic acid, an organic acid such as formic acid, acetic acid, propionic acid and trifluoroacetic acid. The amount of such acid to be employed per mole of Compound (I) ranges from about 0.01 to about 20 moles, preferably about 0.1 to about 10 moles.

The reaction temperature is about −30° C. to about 150° C., preferably about −10° C. to about 120° C.

The reaction time may vary depending on the type of Compound (I), the type of the solvent and the reaction temperature, and is usually about 10 minutes to about 72 hours, preferably about 15 minutes to about 48 hours.

Among the compounds represented by Formula (VI), a compound whose $R^3$ is an acyl group is a novel compound, and useful as an intermediate for synthesizing a compound represented by Formula (I) or a salt thereof.

Process D

Compound (VIII) represented by Formula (VIII):

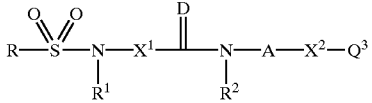

(VIII)

wherein $Q^3$ is a leaving group (for example a hydrogen atom when being bound to a nitrogen atom in Y or $X^2$, a halogen atom, a moiety capable of cross-coupling (for example, a substituent and being bound via boron, tin, magnesium and the like), a group represented by Formula: $R^6$—$SO_2$—O wherein $R^6$ is a lower alkyl group which may be substituted by a halogen atom or a phenyl group which may have a substituent when being bound to a carbon atom in Y or $X^2$) and other symbols are defined as described above or a salt thereof is reacted with Compound (IX) represented by Formula Z—$Q^4$ (IX) wherein $Q^4$ is a leaving group (a halogen atom, a group represented by Formula $R^7$—$SO_2$—O— wherein $R^7$ is a lower alkyl group which may be substituted by a halogen atom or a phenyl group which may have a substituent, a moiety capable of cross-coupling and being bound via boron, tin, magnesium and the like) when Z is not an optionally substituted amino group, or $Q^4$ is a hydrogen atom when Z is an optionally substituted amino group and other symbols are defined as described above or a salt thereof to form Compound (I).

In the formula shown above, a halogen atom represented by $Q^3$ may for example be chlorine, bromine and iodine. Each of $R^6$ and $R^7$ s a lower alkyl group which may be substituted by a halogen atom or a phenyl group which may have a substituent. A lower alkyl group represented by $R^6$ and $R^7$ may for example be methyl, ethyl, propyl, isopropyl, butyl, isobutyl, sec-butyl, tert-butyl, pentyl, isopentyl, neopentyl and hexyl, with methyl, ethyl, propyl, isopropyl and butyl being preferred. A halogen atom may for example be fluorine, chlorine, bromine and iodine, which may occur 1 to 9 times, preferably 1 to 5 times in any substitutable positions. A substituent on a phenyl group which may have a substituent may for example be a lower alkyl group (for example a $C_{1-6}$ alkyl group such as methyl, ethyl, propyl and butyl), a lower alkoxy group (e.g., A $C_{1-6}$ alkoxy group such as methoxy, ethoxy, propoxy and butoxy), a halogen atom (e.g., fluorine, chlorine, bromine and iodine), a nitro group, a cyano group and a carboxyl group.

This process optionally employs a metal catalyst to promote a reaction. Such metal catalyst may for example be a palladium compound [e.g., palladium acetate, tetrakis(triphenylphosphine)palladium, bis(triphenylphosphine)palladium chloride, dichlorobis(triethylphosphine)palladium, tris(dibenzylideneacetone)dipalladium-2,2'-bis(diphenylphosphino)-1,1'-binaphthyl], a nickel compound [e.g., tetrakis(triphenylphosphine)nickel, bis(triethylphosphine)nickel chloride, bis(triphenylphosphine)nickel chloride], a rhodium compound [e.g., tri(triphenylphosphine)rhodium chloride], with a palladium compound being preferred. The amount of such catalyst per mole of Compound (VIII) ranges from about 1 to 0.000001 moles, preferably about 0.1 to 0.00001 moles.

This reaction may be performed also in a sealed tube.

Compound (I) whose Z is an optionally substituted amidino group can be produced by reacting Compound (VIII) whose $Q^3$ is a cyano group or a salt thereof with a lower alcohol to form an iminoether and then reacting with an amine.

A lower alcohol may for example be a $C_{1-4}$ alcohol such as methanol, ethanol, 1-propanol, 2-propanol, 1-butanol and 2-butanol.

This reaction is performed usually in a solvent. Such solvent may be one exemplified in Process A, and an alocohol itself may serve also as a solvent.

This reaction is performed usually in the presence of acid (e.g., an inorganic acid such as hydrochloric acid, hydrobromic acid, sulfuric acid and phosphoric acid, an organic acid such as methanesulfonic acid, toluenesulfonic acid, trifluoromethanesulfonic acid, acetic acid and trifluoroacetic acid) and a base (e.g., potassium methoxide, sodium methoxide, sodium ethoxide, potassium t-butoxide). Each of these acids and bases may be used in an amount ranging from a catalytic amount (about 0.001 moles) to a large excess.

The reaction temperature is about −50° C. to about 150° C., preferably about −20° C. to about 100° C.

The reaction time may vary depending on the type of Compound (III) and the types of the acid, the base and the solvent, and is usually about 30 minutes to about 240 hours, preferably about 1 hour to about 120 hours.

An iminoether is reacted with an amine (e.g., ammonia; a primary amine such as methylamine, ethylamine and propylamine; a secondary amine such as dimethylamine, diethylamine, methylethylamine, di-n-propylamine, pyrrolidine, piperidine, morpholine, piperazine and 1-methylpiperazine; an aromatic amine such as aniline and N-methylaniline) to form Compound (I).

While this reaction is performed usually in a solvent and such solvent may be any solvent as long as the reaction is not affected adversely, a solvent exemplified in Process A is employed preferably. Alternatively, an amine itself may serve also as a solvent.

The reaction temperature is about −20° C. to about 200° C., preferably about −10° C. to about 150° C.

The reaction time may vary depending on the types of the iminoether, the amine and the solvent, and is usually about 30 minutes to about 240 hours, preferably about 1 hour to about 120 hours. This reaction may be performed also in a sealed tube.

Any of starting Compounds (III), (IV), (VI) and (VIII) employed in Processes A to D described above can be produced by a method known per se or an analogous method.

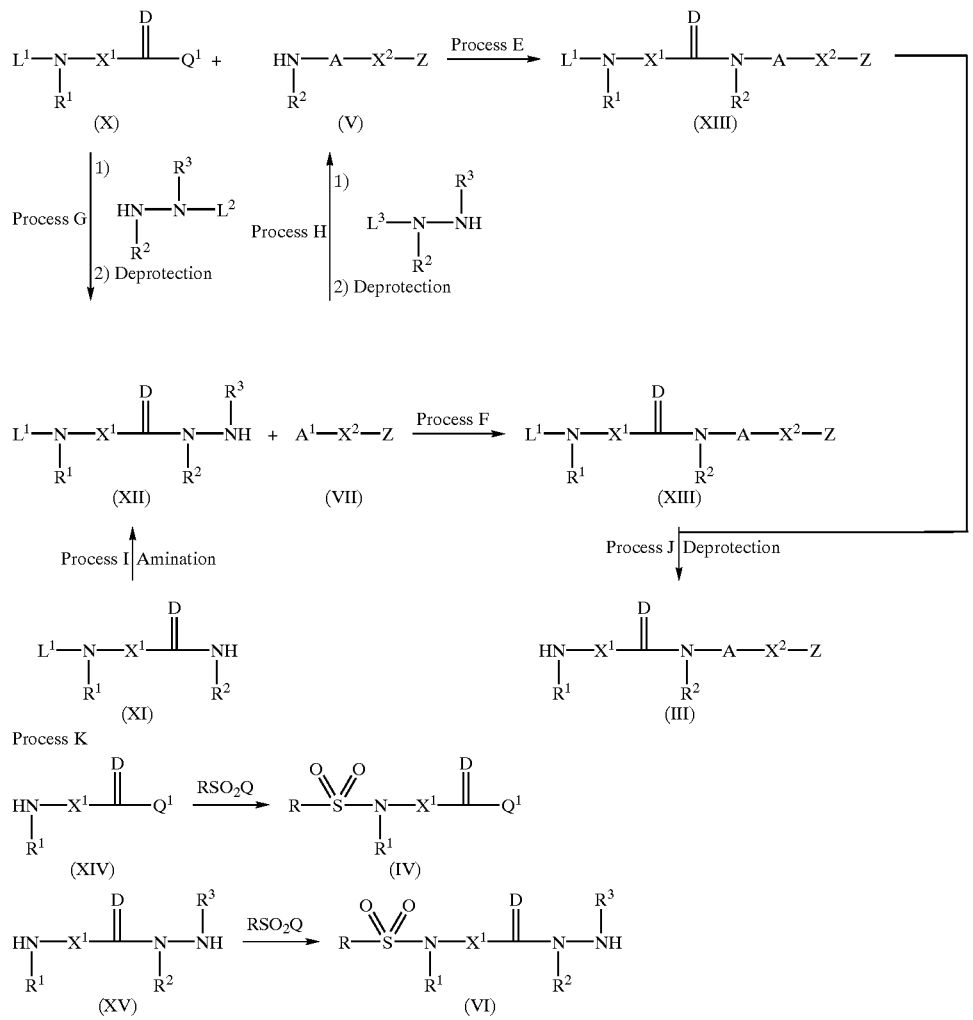

Process E

Compound (X) represented by Formula (X):

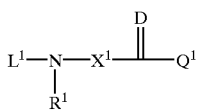

(X)

wherein $L^1$ is a protecting group for an amino group, and other symbols are defined as described above or a salt thereof is reacted with Compound (V) represented by Formula (V):

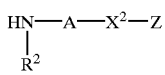

(V)

wherein each symbol is defined as described above or a salt thereof to form Compound (XIII) represented by Formula (XIII):

(XIII)

$$L^1-N(R^1)-X^1-\overset{D}{\underset{\|}{C}}-N(R^2)-A-X^2-Z$$

wherein each symbol is defined as described above.

In Formulae (X) and (XIII), a protective group represented by L1 may for example be a formyl group, a $C_{1-6}$ alkyl-carbonyl group (for example, acetyl, ethylcarbonyl), a $C_{1-6}$ alkyl-sulfonyl group, a tert-butyloxycarbonyl group, a benzyloxycarbonyl group, an allyloxycarbonyl group, a fluorenylmethyloxycarbonyl group, an arylcarbonyl group (for example, phenylcarbonyl, naphthylcarbonyl), an arylsulfonyl group (for example, phenrylsulfonyl, naphthylsulfonyl), a $C_{1-6}$ alkyloxy-carbonyl group (for example, methoxycarbonyl, ethoxycarbonyl), a $C_{7-10}$ aralkyl-carbonyl group (for example, benzylcarbonyl), a methyl group, an aralkyl group (for example, benzyl, diphenylmethyl, trimethyl group) and the like. Each of these groups may be substituted by 1 to 3 halogen atoms (for example, fluorine, chlorine, bromine), nitro groups and the like.

This reaction employs the reactive derivative, the reaction condition, the reaction solvent and the reaction time which are similar or analogous to those in the reaction between Compound (IV) and Compound (V) in Process B described above.

Process F

Compound (XII) represented by Formula (XII):

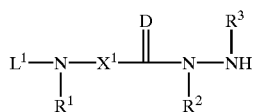
(XII)

wherein $L^1$ is a protecting group for an amino group, and other symbols are defined as described above or a salt thereof is reacted with Compound (VII) represented by Formula (VII):

(VII)

wherein each symbol is defined as described above or a salt thereof to form Compound (XIII) represented by Formula (XIII):

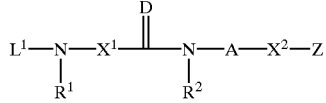
(XIII)

wherein each symbol is defined as described above.

This reaction employs the reactive derivative, the reaction condition, the reaction solvent and the reaction time which are similar or analogous to those in the reaction between Compound (VI) and Compound (VII) in Process C described above.

Proess G

Compound (X) represented by Formula (X):

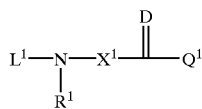
(X)

wherein each symbol is defined as described above or a salt thereof is reacted with a hydrazine derivative represented by Formula:

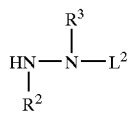

wherein $L^2$ is a protecting group for an amino group, and other symbols are defined as described above or a salt thereof and then the protecting group of the amino group in the hydrazine is deprotected selectively to form Compound (XII) represented by Formula (XII):

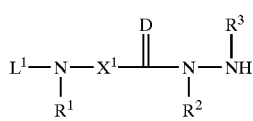
(XII)

wherein each symbol is defined as described above or a salt thereof.

This reaction employs the reactive derivative, the reaction condition, the reaction solvent and the reaction time which are similar or analogous to those in the reaction between Compound (IV) and Compound (V) in Process B described above.

In order to deprotect the protective group of an amino group in the hydrazine, a method per se or a method analogous thereto is employed, for example by using an acid, a base, a reduction, an ultraviolet, palladium acetate and the like.

Process H

Compound (VII) represented by Formula (VII):

(VII)

wherein each symbol is defined as described above or a salt thereof is reacted with a hydrazine derivative represented by Formula:

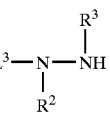

wherein $L^3$ is a protecting group for an amino group, and other symbols are defined as described above or a salt thereof and then the protecting group of the amino group is deprotected to form Compound (V) represented by Formula (V):

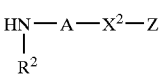
(V)

wherein each symbol is defined as described above or a salt thereof.

This reaction employs the reactive derivative, the reaction condition, the reaction solvent and the reaction time which are similar or analogous to those in the reaction between Compound (VI) and Compound (VII) in Process C described above.

In order to deprotect the protective group of an amino group, a method per se or a method analogous thereto is employed, for example by using an acid, a base, a reduction, an ultraviolet, palladium acetate and the like.

Process I

An amide nitrogen atom in Compound (XI) represented by Formula (XI):

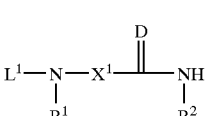
(XI)

wherein each symbol is defined as described above is aminated to produce Compound (XII) represented by Formula (XII):

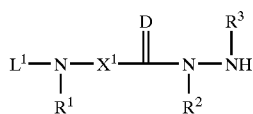

(XII)

wherein each symbol is defined as described above or a salt thereof.

An aminating agent employed preferably in this amination may for example be an O-acylhydroxylamine such as O-diphenylphosphinyl hydroxylamine, hydroxylamine O-sulfate, O-(2,4,6-trimethylbenzenesulfonyl) hydroxylamine and the like.

This reaction is conducted usually in the presence of a base. Preferable base may for example be an alkaline metal hydride such as sodium hydride and potassium hydride, an alkaline metal hydroxide such as lithium hydroxide, sodium hydroxide and potassium hydroxide, an alkaline earth metal hydroxide such as magnesium hydroxide and calcium hydroxide, an alkaline metal carbonate such as sodium carbonate and potassium carbonate, an inorganic base of an alkaline metal hydrogen carbonate such as sodium hydrogen carbonate and potassium hydrogen carbonate, an alkaline metal alcholate such as sodium methylate, sodium ethylate, potassium methylate and tert-butoxypotassium, an organic base such as trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2] octane and 1,8-diazabicyclo[5.4.0]-7-undecene, a lithium salt such as methyllithium, n-butyllithium, sec-butyllithium and tert-butyllithium as well as a lithium amide such as lithium diisopropylamide.

This reaction is conducted generally in a solvent. Such solvent may be one exemplified in Process A described above.

While the reaction employs a base in an amount of about 1 to 10 moles, preferably about 1 to about 20 moles per mole of Compound (XI), the base itself may sometimes serve as a solvent.

The reaction temperature is about –100° C. to about 200° C., preferably about –78° C. to about 100° C.

The reaction time may vary depending on the types of Compound (XI), the aminating agent, the base and the solvent as well as the reaction temperature, and is usually about 1 hour to about 200 hours, preferably about 5 minutes to about 100 hours.

Process J

An amino protecting group in Compound (XIII) represented by Formula (XI):

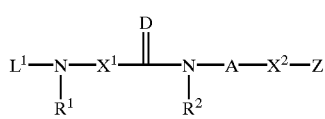

(XIII)

wherein each symbol is defined as described above or a salt thereof is deprotected to produce Compound (III) represented by Formula (III):

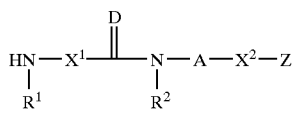

(III)

wherein each symbol is defined as described above or a salt thereof.

In order to deprotect the protective group of an amino group, a method per se or a method analogous thereto is employed, for example by using an acid, a base, a reduction, an ultraviolet, palladium acetate and the like.

Process K

Compound (XIX) and Compound (XV) represented by Formula (XIV):

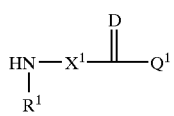

(XIV)

or Formula (XV):

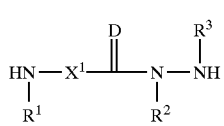

(XV)

wherein each symbol is defined as described above or a salt thereof is sulfonylated by a compound represented by Formula R—SO$_2$Q wherein each symbol is defined as described above to form Compound (IV) and Compound (VI) represented by Formula (IV):

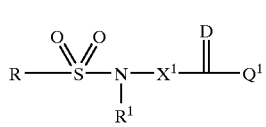

(IV)

or Formula (VI):

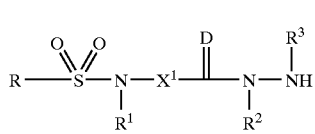

(VI)

wherein each symbol is defined as described above or a salt thereof, respectively.

Process L

Compound (VIII) represented by Formula (VIII):

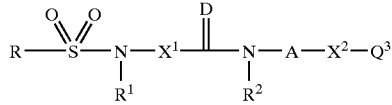

(VIII)

wherein each symbol is defined as described above or a salt thereof can be produced using Compound (II) with Compound (XVI), Compound (IV) with Compound (XVII) and Compound (VI) with Compound (XVIII) by the procedures described in Processes A, B and C, respectively.

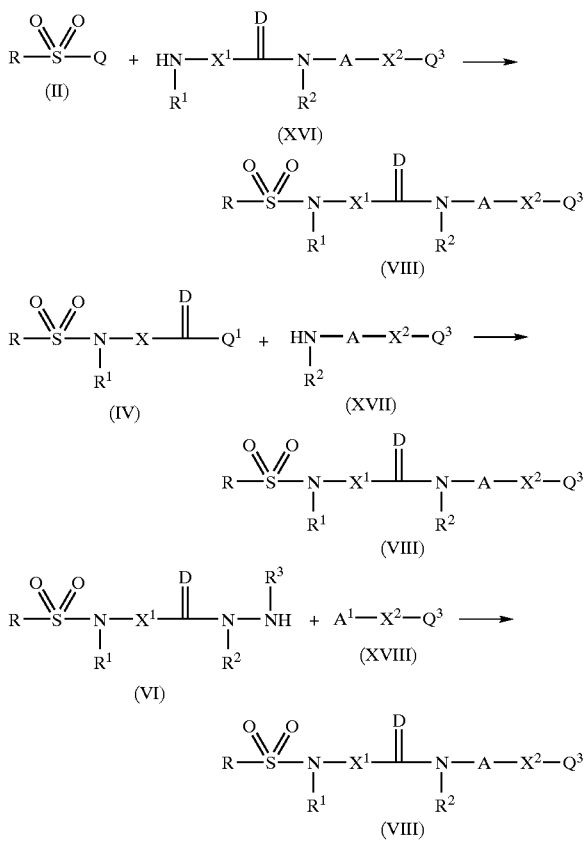

In Process G described above, a compound obtained before a deprotection step, which is represented by Formula:

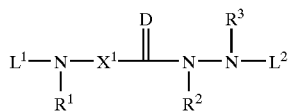

wherein each of $L^1$ and $L^2$ is a protecting group for an amino group and other symbols are defined as described above or a salt thereof and a compound obtained by subjecting it to an appropriate deprotection step or a salt thereof is encompassed by a compound represented by Formula:

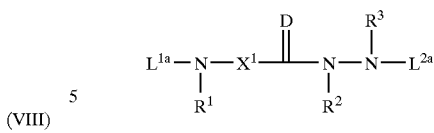

wherein each of $L^{1a}$ and $L^{2a}$ is a hydrogen atom or a protecting group for an amino group and other symbols are defined as described above or a salt thereof, among which a compound represented by Formula:

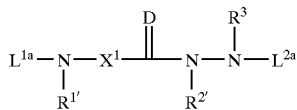

wherein each of $L^{1a}$ and $L^{2a}$ is a hydrogen atom or a protecting group for an amino group and $R^{1'}$ and $R^{2'}$ are bound to each other to form an optionally substituted ring, or, $R^{1'}$ is an hydrogen atom or an optionally substituted hydrocarbon group and a substituent on $X^1$ and $R^{2'}$ are bound to each other to form an optionally substituted ring and other symbols are defined as described above or a salt thereof is a novel compound and useful as an intermediate for synthesizing a compound represented by Formula (I) or a salt thereof.

In the formula shown above, a protecting group for an amino group represented by $L^{1a}$ and $L^{2a}$ may for example be similar to a protecting group for an amino group represented by $L^1$, and may also be "sulfonic acid-derived acyl group" or "carboxylic acid-derived acyl group" as a substituent on "optionally substituted hydrocarbon group" and "optionally substituted heterocyclic group" represented by R. It is preferable that one of $L^{1a}$ and $L^{2a}$ is not a hydrogen, and it is more preferable that $L^{1a}$ is a protecting group for an amino group while $L^{2a}$ is a hydrogen atom.

Such intermediate is preferably a compound in which $R^{1'}$ and $R^{2'}$ are bound to each other and taken together with —N—$X^1$—CD—N— to form a group represented by Formula:

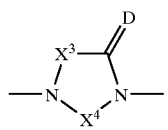

wherein $X^3$ is an optionally substituted $C_{1-2}$ alkylene, $X^4$ is an optionally substituted $C_{1-3}$ alkylene and D is an oxygen atom or a sulfur atom, more preferably a compound in which $R^{1'}$ and $R^{2'}$ are bound to each other and taken together with —N—$X^1$—CD—N— to form a group represented by Formula:

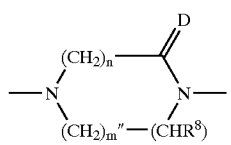

wherein n is 1 or 2, m" is 1 or 2, $R^8$ is a hydrogen atom, an optionally substituted hydroxyl group, an optionally substituted mercapto group, a nitro group, a cyano group, an optionally substituted amino group, an optionally substituted lower alkyl group, an optionally substituted lower alkoxy group, an optionally esterified carboxyl group, an optionally substituted carbamoyl group, an optionally substituted thiocarbamoyl group or an optionally substituted sulfamoyl group (preferably, a hydrogen atom, an optionally substituted lower alkyl group, a cyano group, an optionally esterified carboxyl group, an optionally substituted carbamoyl group or an optionally substituted thiocarbamoyl group), and D is an oxygen atom or a sulfur atom, and particularly a compound in which $R^{1'}$ and $R^{2'}$ are bound to each other and taken together with —N—$X^1$—CD—N— to form a group represented by Formula:

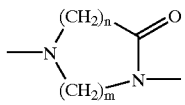

wherein n is 1 or 2 and m is 2 or 3 (more preferably n=1 and m=2).

Such synthetic intermediate may also be a compound in which a substituent on $X^1$ and $R^2$ are bound to each other and a divalent group represented by —$X^1$—CD—N($R^2$)— is a group represented by Formula:

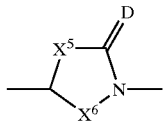

wherein $X^5$ is a bond or an optionally substituted methylene, $X^6$ is an optionally substituted $C_{2-3}$ alkylene and D is an oxygen atom or a sulfur atom, more preferably a compound in which a substituent on $X^1$ and $R^2$ are bound to each other and a divalent group represented by —$X^1$—CD—N($R^2$)— is a group represented by Formula:

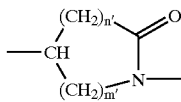

wherein n' is 0 or 1 and m' is 2 or 3 (more preferably n'=0 and m'=2).

Any of starting Compounds (II), (III), (IV), (V), (VI), (VII), (VIII), (IX), (X), (XI), (XII), (XIV) (XV), (XVI), (XVII) and (XVIII) employed in Processes A to L described above can be produced by a method known per se or an analogous method.

When a compound obtained by each reaction according to the invention is in a free form, then it can be converted into a salt in accordance with a standard method, and when it is obtained in the form of a salt, then it can be converted into a free form or other salts.

Compound (I) thus obtained can be isolated and purified from a reaction mixture by a method known per se such as extraction, concentration, neutralization, filtration, recrystallization, column chromatography, thin layer chromatography and the like.

A salt of Compound (I) can be produced by adding an inorganic or organic acid to Compound (I) by a method known per se.

When Compound (I) can exist as a stereoisomer, any of such individual isomers and mixtures thereof are encompassed in the scope of the invention, and any of such isomers can exclusively be produced if necessary.

It is also possible that Compound (I) or a salt thereof is a hydrate, and both of a hydrate and an anhydride are included in the invention.

A compound comprising as its moiety a divalent group represented by Formula:

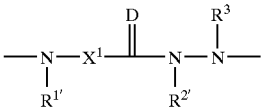

wherein $R^{1'}$ and $R^{2'}$ are bound to each other to form an optionally substituted ring, or $R^{1'}$ is a hydrogen atom or an optionally substituted hydrocarbon group and a substituent of $X^1$ and $R^{2'}$ are bound to each other to form an optionally substituted ring, and other symbols are defined as described above or a salt thereof (including Compound (I); preferably a compound comprising as its moiety a divalent group represented by Formula:

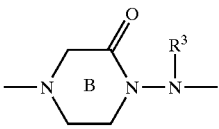

wherein B is an optionally substituted piperazinone ring and $R^3$ is defined as described above or a salt thereof, a compound comprising as its moiety a divalent group represented by Formula:

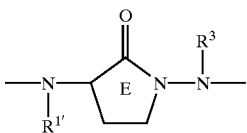

wherein Ring E is an optionally substituted pyrrolidone ring and $R^3$ is defined as described above or a salt thereof, and the like) has an effect mimicking any of various peptides (including proteins) (especially an effect mimicking a peptide at the site on which said peptide exerts its physiological effect), and accordingly it is useful as an enzyme inhibitor, a receptor regulator (e.g., receptor antagonist, receptor agonist), an ion channel regulator (e.g., ion channel blocker, ion channel opener) and the like. Thus, it is possible to inhibit the formation of an enzyme-substrate complex by means of mimicking an enzyme's catalytic site and/or a substrate's binding site, and a use as an agonist or antagonist of a receptor is also possible by means of mimicking a receptor's ligand.

Such enzyme inhibitors may for example be activated coagulation factor inhibitors such as activated coagulation factor X inhibitors, thrombin inhibitors and activated coagulation factor VII inhibitors, plasmin inhibitors, kallikrein inhibitors, nitrogen monooxide synthetase inhibitors, HIV reverse transcriptase inhibitors, HIV protease inhibitors, farnesyl protein transferase inhibitors, various matrix metalloprdtease inhibitors, tyrosine phosphatase inhibitors, cyclin-dependent kinase inhibitors, protein tyrosine kinase inhibitors, various protein kinase inhibitors, telomerase inhibitors, cathepsin inhibitors, elastase inhibitors, phosphodiesterase inhibitors, various serine protease inhibitors, interleukin-1β converting enzyme inhibitors, various cysteine protease inhibitors and the like, while receptor regulators may for example be antagonists and agonists of receptors including-fibrinogen receptors such as glycoprotein (GP) IIb/IIIa, integrins (vitronectin receptors), thrombin receptors, orphan receptors, intranuclear receptors, adrenaline receptors, histamine receptors, angiotensin II receptors, endoserine receptors, leukotriene receptors, thromboxanthine receptors, chemokine receptors, opioid receptors, adenosin receptors, tachykinin receptors such as substance P or neurokinins, bradykinin receptors, prostaglandin receptors, dopamine receptors, serotonin receptors, adrenocorticotropic hormone releasing factor (CRF) receptors, LH-RH receptors, somatostatin receptors, glucagon receptors, various G protein-conjugated receptors, insulin-like growth factor receptors (IGF), and receptors of various growth factors such as epithelial growth factors (EGF), fibrocyte growth factors (FGF), platelet-derived growth factors (PDGF), hepatocyte growth factors (HGF), vascular endothelium growth factors (VEGF), transformation growth factors (TGF), nerve growth factors (NGF) and tumor necrosis factors (TNF), erythropoietin (EPO), thrombopoietin (TPO), receptors of various stimulating factors such as granulocyte colony stimulating factor (G-CSF), granulocyte-macrophage colony stimulating factor (GM-CSF) and macrophage colony stimulating factor (M-CSF), receptors of various cytokines such as interleukin-1, interleukin-6 and interleukin-8 as well as hormone receptors, and ion channel regulators may for example be antagonists and agonists of ion channels for calcium, potassium and chlorine.

Each of Intermediates (XIX) and (XXVIII) which is useful especially as a backbone mimicking a peptide in designing the molecules of such enzyme inhibitors, receptor regulators (e.g., receptor antagonists, receptor agonists) and ion channel regulators (e.g., ion channel blockers and ion channel openers) can be synthesized for example by the methods described in Sections [1] to [6] or the methods described in Sections [7] to [9] described below.

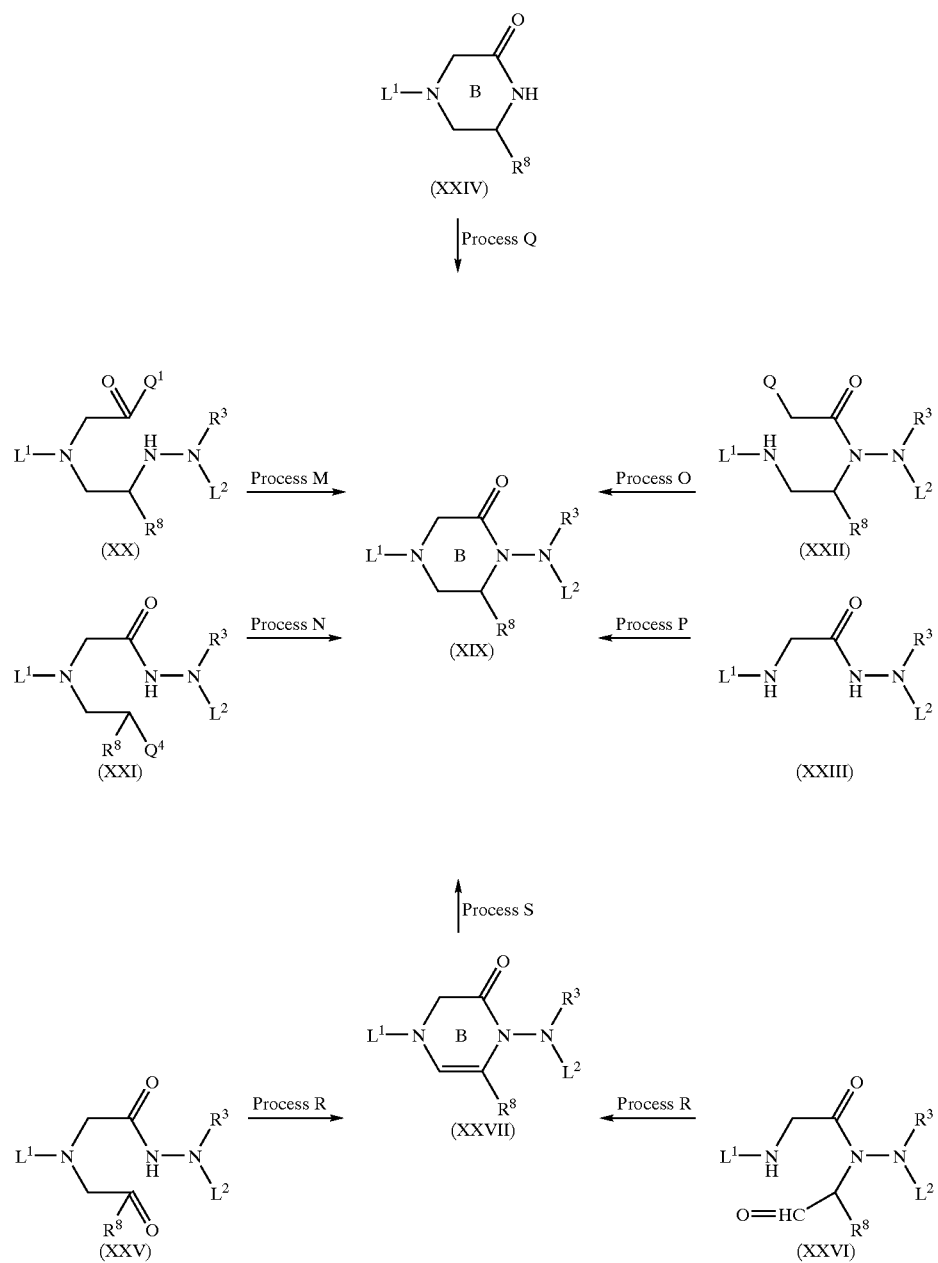

-continued

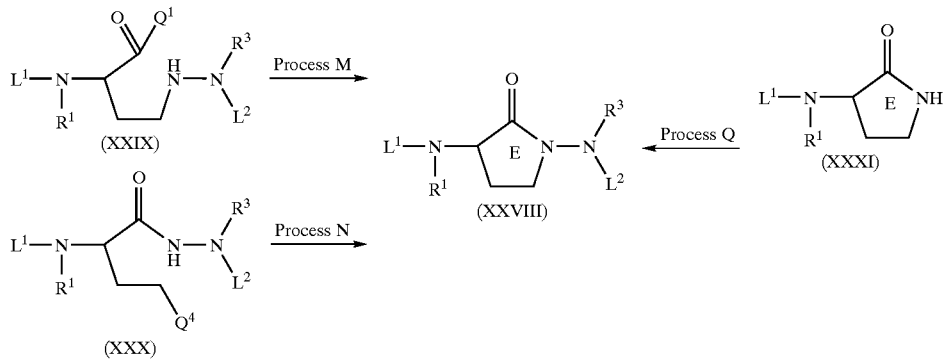

wherein each symbols is defined as described above. Methods for producing Compound (XIX)

[1] Process M: A synthesis can be effected by subjecting a hydrazine compound (XX) to an intramolecular acylation. Usually, a solvent which is not involved in the reaction is employed, and a condensation with a carboxylic acid is effected preferably in the presence of a condensing agent. It is also possible to perform a reaction in the presence of a base or acid catalyst.

[2] Process N: A synthesis can be effected by means of a ring closure reaction of an acid hydrazide compound (XXI). When $Q^4$ is a leaving group, the reaction is performed preferably in the presence of a base. It is also possible that $Q^4$ is a hydroxyl group, and in such case a synthesis can be effected by Mitsunobu reaction. When $Q^4$ together with $R^8$ forms a conjugated double bond, a synthesis can readily be effected by performing a conjugate addition reaction in the presence of a base catalyst.

[3] Process O: A synthesis can be effected by performing a ring closure reaction in the presence of a base.

[4] Process P: A synthesis can be effected by performing a reaction of an amino acid hydrazide compound (XXIII) in the presence of a base with 1,2-dibromaethane (instead of the bromo moiety, a leaving group such as iodo or trifluoromethanesulfonyloxy may be present.).

[5] Process Q: A synthesis can be effected by subjecting a piperazinone compound (XXIV) to an amination reaction for example in the presence of a base such as sodium hydride using an aminating agent such as O-diphenylphosphinyl hydroxylamine.

[6] Process R: Compound (XXVII) can be synthesized by subjecting a carbonyl compound (XXV) or (XXVI) or an acetal-protected form to a ring closure reaction in the presence of an acid catalyst. Subsequently, Compound (XXVII) is hydrogenated in accordance with Process S, whereby synthesizing Compound (XIX). Methods for producing Compound (XXVIII)

[7] Process M: A synthesis can be effected by subjecting a hydrazine compound (XXIX) to an intramolecular acylation. Usually, a solvent which is not involved in the reaction is employed, and a condensation with a carboxylic acid is effected preferably in the presence of a condensing agent. It is also possible to perform a reaction in the presence of a base or acid catalyst.

[8] Process N: A synthesis can be effected by means of a ring closure reaction of an acid hydrazide compound (XXX). When $Q^4$ is a leaving group (for example, dimethylsulfonium group, bromine, iodine, various sulfonyloy group), the reaction is performed preferably in the presence of a base. It is also possible that $Q^4$ is a hydroxyl group, and in such case a synthesis can be effected by Mitsunobu reaction.

[5] Process Q: A synthesis can be effected by subjecting a pyrrolidinone compound (XXXI) to an amination reaction for example in the presence of a base such as sodium hydride using an aminating agent such as O-diphenylphosphinyl hydroxylamine.

Since Compound (I) according to the invention or a salt thereof has a low toxicity and is safe and it inhibits an FXa and has an anticoagulative effect, it is useful in preventing or treating a disease such as those listed below in animals especially in mammals (for example, human, monkey, cat, pig, horse, cattle, mouse, rat, guinea pig, dog, rabbit), and is preferred especially when being used in preventing or treating an atrial fibrillation-induced cerebral infarction and deep vein thrombosis.

Brain:
Atrial fibrillation-induced cerebral infarction, acute ischemic apoplexy, acute cerebral thrombosis, cerebrovascular spasm after subarachnoid hemorrhage, Alzheimer's disease, transient cerebral ischemic attack (TIA), mixed dementia, cerebrovascular/multi-infarct dementia Heart:
Acute cardiac infarction, sequela of myocardial infarction, unstable angina, angina pectris, vascular reocclusion and restenosis after coronary intervention such as stenting, PTCA (percutaneous transluminal coronary angioplasty) and atherectomy Peripheral organs: Deep vein thrombosis, peripheral blood disease, adult respiratory distress syndrome, chronic renal disease (for example, diabetic nephrosis, chronic glomerulonephritis, IgA nephrosis), diabetic circulatory disorder, pain, neuropathy Others:
Dialysis-induced thrombocytopenia, thrombocytopenia after major surgery, arterial sclerosis, cancer metastasis, systemic inflammatory response syndrome (SIRS) or pancreatitis- or cancer-related disseminated intravascular coagulation (DIC), implant rejection, implant organ protection or improvement, shock- or DIC-related various organ failures (for example, pulmonary insufficiency, hepatic insufficiency, renal insufficiency, cardiac insufficiency)

Compound (I) of the invention or a salt thereof can orally or parenterally be administered as it is or in combination with a pharmaceutically acceptable carrier.

A formulation containing Compound (I) or a salt thereof can be given orally in a dosage form such as tablets (including sugar-coated tablets and film-coated tablets), pills, granules, powders, capsules (including soft capsules), syrups, emulsions and suspensions, while it can be given parenterally in a dosage form such as injection, infusion and dripping formulations as well as suppositories.

While the amount of Compound (I) or a salt thereof in a formulation of the invention may vary depending on the form of the formulation, it is usually 2 to 85% by weight, preferably 5 to 70% by weight based on the entire amount of the formulation.

A method for formulating Compound (I) or a salt thereof into a dosage form described above, a known method employed generally in the art can be applied. Also for producing a dosage form described above, appropriate amounts of appropriate additives employed usually in the pharmaceutical field such as excipients, binders, disintegrants, lubricants, sweeteners, surfactants, suspending agents, emulsifiers and the like can be incorporated.

For example, Compound (I) or a salt can be formulated into a tablet by incorporating an excipient, a binder, a disintegrant, a lubricant and the like, while it can be formulated into a pill or a granule by incorporating an excipient, a binder, a disintegrant and the like. It can be formulated also into a powder or a capsule by incorporating an excipient, into a syrup by incorporating a sweetener, into an emulsion or a suspension by incorporating a suspending agent, a surfactant, an emulsifier and the like.

An excipient may for example be lactose, sugar, glucose, starch, sucrose, microcrystalline cellulose, licorice powder, mannitol, sodium hydrogen carbonate, calcium phosphate, calcium sulfate and the like.

A binder may for example be 5 to 10% by weight starch glue, 10 to 20% by weight gum arabic or gelatin, 1 to 5% by weight tragacanth gum, carboxymethyl cellulose, sodium alginate, glycerin and the like.

A disintegrant may for example be a starch, calcium carbonate and the like.

A lubricant may for example be magnesium stearate, stearic acid, calcium stearate, purified talc and the like.

A sweetener may for example be glucose, fructose, inverted sugar, sorbitol, xylitol, glycerin, syrups simplex and the like.

A surfactant may for example be sodium laurylsulfate, polysorbate 80, sorbitan monofatty ester, polyoxyl stearate 40 and the like.

A suspending agent may for example be gum arabic, sodium alginate, sodium carboxymethyl cellulose, methyl cellulose, bentonite and the like.

An emulsified may for example be gum arabic, tragacanth gum, gelatin, polysorbate 80 and the like.

Also for formulating Compound (I) or a salt thereof into a dosage form described above, appropriate amounts of appropriate additives employed usually in the pharmaceutical field such as colorants, preservatives, flavors, seasonings, stabilizers, thickening agents and the like can be incorporated if necessary.

A formulation according to the invention containing Compound (I) or a salt thereof is stable and has a low toxicity, and can be used safely. Its daily dose may vary depending on the condition and the body weight of the patient, the type of the compound and the administration route, and is usually about 1 to 1000 mg as an active ingredient (Compound (I) or a salt thereof) per day in an adult weighing about 60 kg when given orally to a patient having a thrombosis, preferably about 3 to 300 mg, more preferably about 10 to 200 mg, which can be given at once, or divided into two or 3 dosages.

When Compound (I) of the invention or a salt thereof is given parenterally, it is given usually in a liquid formulation (for example, injection formulation). In such case, a single dosage may vary depending on the target organ, the condition and the administration mode, and is usually about 0.01 mg to about 100 mg per kg body weight when given in an injection formulation, preferably about 0.01 to about 50 mg, more preferably about 0.01 to about 20 mg, which is given conveniently via an intravenous injection. In addition to the intravenous injection formulation, a subcutaneous injection formulation, an intradermal injection formulation, an intramuscular injection formulation and a dripping injection formulation may also included in the injection formulation, and an iontophoresis percutaneous formulation is included in a sustained release formulation. Any of such injection formulations can be prepared by a method known per se, i.e., by dissolving, suspending or emulsifying Compound (I) of the invention or a salt thereof in an aseptic aqueous or oily liquid. An aqueous liquid for an injection may for example be a physiological saline and an isotonic solution containing glucose or other auxiliary agents (for example, D-sorbitol, D-mannitol, sodium chloride and the like), which may be used in combination with a suitable solubilizing aid such as an alcohol (for example, ethanol), a polyalcohol (for example, propylene glycol, polyethylene glycol), a nonionic surfactant (for example, polysorbate 80, HCO-50) and the like. An oily liquid may for example be a sesame oil and a soybean oil, which may be used in combination with a solubilizing aid such as benzyl benzoate and benzyl alcohol. Those which may also be incorporated are a buffering agent (for example, phosphate buffer and sodium acetate buffer), an analgesic (for example, benzalkonium chloride and procaine hydrochloride), a stabilizer (for example, human serum albumin and polyethylene glycol), a preservative (for example, benzyl alcohol and phenol) and the like. An injection formulation thus prepared is contained usually in an ampule.

A formulation of the invention may appropriately be used in combination with a thrombolytic agent (for example, TPA, heparin and urokinase), an Alzheimer treating agent (for example, Avan and Calan), a cholesterol treating agent (for example, HMG-CoA reductase inhibitor such as simvastatin and pravastatin), a TG reducing agent (for example, clofibrate), an AII antagonist (for example, blopress), an antiplatelet agent (for example, aspirin), a Ca antagonist (for example, calslot and amlodipine) and the like, and an appropriate amount of any of these agents may be incorporated.

BEST MODE FOR CARYYING OUT THE INVENTION

The present invention is further detailed in the following Reference Examples, Examples, Formulation Examples and Experiments, which serve only as examples and are not intended to restrict the invention and can be modified without departing the scope of the invention.

An elution of a column chromatography in Reference Examples and Examples was conducted with observing by a TLC (thin layer chromatography). In the observation of a TLC, a TLC plate employed was a 60F254 manufactured by Merck and a development was performed using a solvent which was employed as an eluent in a column chromatography, while an UV detector was used for a detection. The silica gel packed in the column was kiesel gel 60 (70 to 230 mesh) manufactured by Merck. An NMR spectrum was determined by a spectrometer model Varian Gemini 200 using tetramethylsilane as an internal or external standard and the data were represented as total δ values in ppm. An IR spectrum was determined by a Shimadzu spectrometer model FTZR-8200. A figure in a bracket indicated in conjunction with a mixed solvent is a volume ratio of the constituent solvents. A % value indicated in conjunction with a solution is an amount in gram contained in 100 ml of the solution. The following abbreviations are employed in Reference Examples and Examples.

s: singlet
d: doublet
t: triplet
q: quartet
dd: double doublet
m: multiplet
br: broad
brs: broad singlet
J: coupling constant
WSC: water-soluble carbodiimide
THF: tetrahydrofuran
DMF: dimethylformamide
DMSO: dimethylsulfoxide
HOBt: 1-hydroxybenzotriazole

EXAMPLES

Reference Example 1

4-(tert-Butoxycarbonyl)-2-piperazinone

To a mixture of 2-piperazinone (3.00 g) in acetonitrile (50 ml) was added dropwise di-tert-butyl dicarbonate (7.20 g) and the mixture was stirred at room temperature for 2 hours. After concentrating the reaction mixture under reduced pressure, crystals precipitated were washed with ether to obtain the title compound (4.77) g as colorless crystals.

$^1$H-NMR (CDCl$_3$) δ: 1.48 (9H, s), 3.33–3.43 (2H, m), 3.64 (2H, t, J=5.3 Hz), 4.09 (2H, s), 6.40–6.70 (1H, br).

IR (KBr): 1696, 1667, 1400, 1341, 1130 cm$^{-1}$.

Reference Example 2

4-Benzyloxycarbonyl-2-piperazinone

A mixture of 2-piperazinone (10 g), benzyl chlorocarbonate (20.5 g) and sodium carbonate (31.8 g) in ethyl acetate (200 ml) and water (200 ml) was stirred at room temperature for 2 hours. The organic phase was separated, washed with brine, dried (MgSO$_2$) and concentrated. The obtained crystals were collected by filtration, washed with ethyl acetate—ether and dried to obtain the title compound (18.5 g) as colorless crystals.

$^1$H-NMR (CDCl$_3$) δ: 3.35–3.47 (2H, m), 3.71 (2H, t, J=5.4 Hz), 4.17 (2H, s), 6.22–6.42 (1H, br), 7.37 (5H, s).

IR (KBr): 1711, 1663, 1412, 1337, 1287 cm$^{-1}$.

Reference Example 3

4-Benzyloxycarbonyl-1,2,3,4-tetrahydropyradin-2-one

To a solution of N-benzyloxycarbonyl glycine (10.5 g) and 2,2-diethoxyethylamine (7.33 g) in acetonitrile (50 ml), WSC (10.5 g) was added with cooling on ice and the mixture was stirred at room temperature for 2 hours. The reaction mixture was concentrated and the residue was combined with ethyl acetate and dilute hydrochloric acid. The organic phase was separated, washed successively with saturated aqueous sodium bicarbonate and brine, dried (MgSO$_2$) and then concentrated. The residue was combined with p-toluenesulfonic acid (951 mg) and toluene (150 ml), and heated under reflux for 30 minutes. After allowing to cool, the reaction mixture was combined with ethyl acetate, washed successively with saturated aqueous sodium bicarbonate and brine, dried (MgSO$_2$) and then concentrated. The crystals obtained were collected by filtration, washed with ether, dried to obtain the title compound (7.37 g) as colorless crystals.

$^1$H-NMR (CDCl$_3$) δ: 4.30 (2H, s), 5.22 (2H, s), 5.50–5.68 (1H, m), 6.29–6.48 (1H, m), 7.38 (5H, s), 7.50–8.00 (1H, br).

IR (KBr): 1698, 1649, 1410, 1321, 1107, 957, 760 cm$^{-1}$.

Reference Example 4

4-Benzyloxycarbonyl-1-(tert-butoxycarbonylamino)-2-oxo-1,2,3,4-tetrahydropyrazine Process 1

A solution of tert-butoxycarbonylhydrazine (3.96 g) and N-benzyloxycarbonyl-N-(2,2-diethoxyethyl) glycine (9.76 g) in acetonitrile (100 ml) was treated with WSC (5.75 g) and stirred at room temperature for 15 hours. The reaction mixture was concentrated to obtain a residue, which was partitioned between ethyl acetate and water, and then the organic phase was washed with water, aqueous sodium bicarbonate, aqueous solution of citric acid and brine, dried and then concentrated. The residue obtained was dissolved in toluene (200 ml), combined with p-toluenesulfonic acid hydrate (285 mg) and then stirred at 100° C. for 90 minutes. The reaction mixture was washed with saturated aqueous sodium bicarbonate and brine, dried and then concentrated. The residue thus obtained was purified by a column chromatography on a silica gel (hexane:ethyl acetate=3:2) to obtain 4-benzyloxycarbonyl-1-(tert-butoxycarbonylamino)-2-oxo-1,2,3,4-tetrahydropyrazine (1.84 g) as a colorless oil.

Process 2

A mixture of tert-butoxycarbonylhydrazine (53 g), bromoacetoaldehyde dimethyl acetal (63.88 g), potassium carbonate (52 g) and potassium iodide (62.7 g) in DMF (350 ml) was stirred at 70° C. for 15 hours. Any insolubles were filtered off and the filtrate was combined with N-benzyloxycarbonyl glycine (79 g), HOBt (58 g) and WSC (87 g), and then stirred at room temperature for 15 hours. The reaction mixture was concentrated to obtain a residue, which was then partitioned between ethyl acetate and water, and the organic phase was washed with water, aqueous sodium bicarbonate, aqueous solution of citric acid and brine, dried and concentrated. The residue thus obtained was dissolved in toluene (1200 ml) and treated with p-toluenesulfonic acid hydrate (16.4 g) in 4 portions at an interval of 30 minutes, and stirred at 100° C. for 10 hours. The reaction mixture was washed with saturated aqueous sodium bicarbonate and brine, dried and concentrated. The residue thus obtained was purified by a column chromatography on a silica gel (hexane:ethyl acetate=3:1) to obtain 4-benzyloxycarbonyl-1-(tert-butoxycarbonylamino)-2-oxo-1,2,3,4-tetrahydropyrazine (19.36 g) as a colorless oil.

$^1$H-NMR (CDCl$_3$) δ: 1.48 (9H, s), 4.44 (2H, s), 5.21 (2H, s), 5.70 (1H, m), 6.38 (1H, m), 6.66 (1H, brs), 7.37 (5H, s).

IR (KBr): 3281, 1705, 1421, 1400, 1368, 1346, 1248, 161 cm$^{-1}$.

Reference Example 5

1-(tert-Butoxycarbonylamino)-4-(6-chloronaphthalene-2-sulfonyl)-2-piperazine

Process 1

A solution of 4-benzyloxycarbonyl-1-(tert-butoxycarbonylamino)-2-oxo-1,2,3,4-tetrahydropyrazine (1.8 g) and 10% Pd/C (300 mg) in methanol (40 ml) was stirred at room temperature for 15 hours under a hydrogen atmosphere. The catalyst was filtered off and the reaction mixture was concentrated to obtain 1-(tert-butoxycarbonylamino)-2-piperazinone as a colorless oil.

¹H-NMR (CDCl₃) δ: 1.49 (9H, s), 3.18 (2H, t, J=5.6 Hz), 3.61 (2H, s), 3.63 (2H, t, J=5.6 Hz), 6.78 (1H, brs).

The resultant solution of 1-(tert-butoxycarbonylamino)-2-piperazinone in ethyl acetate (20 ml) and a 10% aqueous solution of sodium carbonate (20 ml) was treated at 0° C. with 6-chloronaphthalene-2-sulfonyl chloride (1.36 g) and stirred at room temperature for 30 minutes. The organic phase was separated, washed with brine, dried and concentrated. The residue thus obtained was purified by a column chromatography on a silica gel (hexane:ethyl acetate=1:2) to obtain 1-(tert-butoxycarbonylamino)-4-(6-chloronaphthalene-2-sulfonyl)-2-piperazinone (848 mg) as a colorless amorphous solid.

Process 2

A solution of 2,2-dimethoxyethylamine (3 g) and triethylamine (4.318 g) in tetrahydrofuran (120 ml) was treated portionwise at 0° C. with 6-chloronaphthalene-2-sulfonyl chloride (7.45 g) and stirred at 0° C. for 30 minutes. The reaction mixture was combined with water and ethyl acetate to separate the organic phase, which was washed with an aqueous solution of citric acid and brine, dried and concentrated to obtain N-(2,2-dimethoxyethyl)-6-chloro-2-naphthalenesulfonamide as a colorless oil.

¹H-NMR (CDCl₃) δ: 3.09 (2H, t, J=5.6 Hz), 3.31 (6H, s), 4.35 (1H, t, J=5.6 Hz), 4.76 (1H, m), 7.56 (1H, dd, J=2.0, 8.8 Hz), 7.80–7.95 (4H, m), 8.41 (1H, s).

N-(2,2-Dimethoxyethyl)-6-chloro-2-naphthalenesulfonamide was dissolved in DMF (100 ml) and combined with sodium hydride (1.16 g, in oil), cooled to 0° C., treated dropwise with a solution of ethyl bromoacetate (4.843 g) in tetrahydrofuran (15 ml) and then stirred at room temperature for 3 hours. The reaction mixture was concentrated and the residue was dissolved in ethyl acetate, washed with water, aqueous sodium bicarbonate and brine, dried and concentrated to obtain N-(2,2-dimethoxyethyl)-N-(6-chloro-2-naphthalenesulfonyl)glycine ethyl ester as a colorless oil.

¹H-NMR (CDCl₃) δ: 1.10 (3H, t, J=7.0 Hz), 3.37 (6H, s), 3.38 (2H, d, J=5.4 Hz), 3.99 (2H, q, J=7.0 Hz), 4.28 (2H, s), 4.50 (1H, t, J=5.4 Hz), 7.55 (1H, dd, J=1.8, 8.8 Hz), 7.80–7.95 (4H, m), 8.40 (1H, s).

N-(6-chloro-2-naphthalenesulfonyl)-N-(2,2-dimethoxyethyl)glycine ethyl ester was combined with acetone (100 ml) and 4N hydrochloric acid (50 ml) and stirred at 50° C. for 2 hours. Acetone was distilled off and the mixture was extracted with ethyl acetate, and then the organic phase was washed with water and brine, and then concentrated. The residue was dissolved in ethanol (70 ml), combined with tert-butyl carbazate (3.76 g) and then stirred at 70° C. for 2 hours. The crystals formed were collected by filtration and washed with diisopropyl ether to obtain N-[2-(tert-butoxycarbonylhydrazono)ethyl]-N-(6-chloro-2-naphthalenesulfonyl)glycine ethyl ester (10.89 g) as colorless crystals.

¹H-NMR (CDCl₃) δ: 1.16 (3H, t, J=7.0 Hz), 1.48 (9H, s), 3.95–4.15 (6H, m), 7.18 (1H, t, J=5.4 Hz), 7.56 (1H, dd, J=2.0, 8.8 Hz), 7.80–8.00 (5H, m), 8.42 (1H, s).

A suspension of N-[2-(tert-butoxycarbonylhydrazono)ethyl]-N-(6-chloro-2-naphthalenesulfonyl)glycine ethyl ester (10.85 g) and acetic acid (2.60 g) in methanol (50 ml) and tetrahydrofuran (50 ml) was treated portionwise at 0° C. with sodium cyanoborohydride (2.11 g) and then stirred at room temperature for 3 days. The reaction mixture was concentrated and the residue was combined with ethyl acetate, washed with aqueous sodium bicarbonate and brine and concentrated to obtain the title compound (9.86 g) as colorless crystals.

¹H-NMR (CDCl₃) δ: 1.43 (9H, s), 3.51 (2H, m), 3.72 (2H, m), 3.88 (2H, s), 6.63 (1H, brs), 7.60 (1H, dd, J=1.8, 8.8 Hz), 7.78 (1H, dd, J=1.8, 8.8 Hz), 7.88–7.98 (3H, m), 8.35 (1H, s).

Reference Example 6

1-(tert-Butoxycarbonylamino)-4-(7-chloro-2H-benzopyran-3-sulfonyl)-2-piperazinone A solution of 4-benzyloxycarbonyl-1-(tert-butoxycarbonylamino)-2-oxo-1,2,3,4-tetrahydropirazine (2.93 g) and 10% Pd/C (600 mg) in methanol (40 ml) was stirred at room temperature for 15 hours under a hydrogen atmosphere. The catalyst was filtered off and the reaction mixture was concentrated to obtain 1-(tert-butoxycarbonylamino)-2-piperazinone as a colorless oil.

A solution of the resultant 1-(tert-butoxycarbonylamino)-2-piperazinone and diisopropylethylamine (1.31 g) in dichloromethane (30 ml) was treated portionwise with 7-chloro-4H-4-oxobenzopyran-3-sulfonyl chloride (2.36 g) with cooling on ice, and stirred at room temperature for 1 hour. The reaction mixture was washed with water and brine, dried and concentrated. The residue was dissolved in methanol (50 ml) and treated with sodium borohydride (320 mg) with cooling on ice, and then stirred at room temperature for 1 hour. The reaction mixture was concentrated and the residue was combined with an aqueous solution of potassium hydrogen sulfate, extracted with ethyl acetate. The extract was washed with aqueous sodium bicarbonate and brine, dried over sodium sulfate and concentrated. The residue was dissolved in dichloromethane (50 ml), combined with triethylamine (5.126 g), and treated with methanesulfonyl chloride (1.938 g) at 0° C., and stirred at room temperature for 1 hour. The reaction mixture was washed with aqueous sodium bicarbonate, an aqueous solution of citric acid and brine, dried and concentrated. The residue was purified by a column chromatography on a silica gel (hexane:ethyl acetate 1:1) to obtain 1-(tert-butoxycarbonylamin)-4-(7-chloro-2H-benzopyran-3-sulfonyl)-2-piperazinone (1.456 g) as a colorless solid.

¹H-NMR (CDCl₃) δ: 1.47 (9H, s), 3.60–3.80 (4H, m), 4.01 (2H, s), 4.90 (2H, d, J=1.2 Hz), 6.69 (1H, brs), 6.93 (1H, d, J=1.8 Hz), 7.00 (1H, dd, J=1.8, 8.2 Hz), 7.14 (1H, d, J=8.2 Hz), 7.30 (1H, d, J=1.2 Hz).

Reference Example 7

1-(tert-Butoxycarbonylamino)-4-(4-vinylphenylsulfonyl)-2-piperazinone

Except for using 4-vinylphenylsulfonyl chloride instead of 6-chloronaphthalene-2-sulfonyl chloride and starting from 4-benzyloxycarbonyl-1-(tert-butoxycarbonylamino)-2-oxo-1,2,3,4-tetrahydropirazine (2.5 g), the process similar to that in Reference Example 5 was employed to obtain the title compound (2.12 g) as a colorless amorphous material.

¹H-NMR (CDCl₃) δ: 1.45 (9H, s), 3.43 (2H, t, J=5.4 Hz), 3.71 (2H, t, J=5.4 Hz), 3.81 (2H, s), 5.48 (1H, d, J=11.0 Hz), 5.91 (1H, d, J=17.6 Hz), 6.68 (1H, brs), 6.77 (1H, dd, J=11.0, 17.6 Hz), 7.57 (2H, d, J=8.4 Hz), 7.75 (2H, d, J=8.4 Hz).

Reference Example 8

1-(4-Pyridyl)-4-piperidone

A mixture of 1,4-dioxa-8-azaspiro[4.5]decane (150 g), 4-chloropyridine hydrochloride (190 g) and triethylamine (320 g) in ethanol (800 ml) was reacted in a sealed tube at 150° C. for 15 hours. The reaction mixture was concentrated to obtain a residue, which was made alkaline by an addition of a 6N aqueous solution of sodium hydroxide, and then extracted with dichloromethane. After drying and concentrating, the resultant residue was triturated from hexane, collected by filtration and then dried to obtain 8-(4-pyridyl)-1,4-dioxa-8-azaspiro[4.5]decane (172 g) as a pale yellow solid.

$^1$H-NMR (CDCl$_3$) δ: 1.78 (4H, m), 3.51 (4H, m), 4.00 (4H, s), 6.68 (2H, d, J=6.6 Hz), 8.25 (2H, d, J=6.6 Hz).

A solution of 8-(4-pyridyl)-1,4-dioxa-8-azaspiro[4.5]decane (172 g) in acetone (700 ml) was combined with 4N hydrochloric acid (700 ml) and stirred at 50° C. for 20 minutes. Acetone was distilled off, and the residue was made alkaline by an addition of an aqueous solution of sodium hydroxide, and then extracted with dichloromethane. After drying and concentrating, the resultant residue was crystallized from ether, collected by filtration and dried to obtain the title compound (119 g) as a pale yellow solid.

$^1$H-NMR (CDCl$_3$) δ: 2.57 (4H, t, J=6.0 Hz), 3.75 (4H, t, J=6.0 Hz), 6.72 (2H, d, J=6.2 Hz), 8.33 (2H, d, J=6.2 Hz).

Reference Example 9

1-Amino-4-benzyloxycarbonyl-2-piperazinone 4-(Benzyloxycarbonyl)-2-piperazinone (4.685 g) was dissolved in DMF (170 ml) and combined with sodium hydride (800 mg, in oil) with cooling on ice. After stirring at room temperature for 30 minutes, O-diphenylphosphinyl hydroxylamine (4.896 g) was added and the mixture was stirred at 50° C. for 15 hours. The reaction mixture was concentrated under reduced pressure, and the residue was combined with aqueous sodium bicarbonate and extracted with dichloromethane. The extract was dried and concentrated to obtain the title compound 1-amino-4-benzyloxycarbonyl-2-piperazinone (4.8 g) as a colorless oil.

$^1$H-NMR (CDCl$_3$) δ: 3.56 (2H, t, J=5.4 Hz), 3.79 (2H, t, J=5.4 Hz), 4.22 (2H, s), 4.46 (2H, brs), 5.15 (2H, s), 7.36 (5H, s).

Reference Example 10

4-Benzyloxycarbonyl-1-[1-(tert-butoxycarbonyl)-4-piperidinylamino]-2-piperazinone A solution of 1-amino-4-benzyloxycarbonyl-2-piperazinone (2.49 g) and 1-(tert-butoxycarbonyl)-4-piperidone (1.99 g) in ethanol (40 ml) was dehydrated using a Soxlet extractor packed with molecular sieves 4A while refluxing for 15 hours. The reaction mixture was concentrated to obtain a crude 4-benzyloxycarbonyl-1-[1-(tert-butoxycarbonyl)-4-piperidinylideneamino]-2-piperazinone as an oil.

$^1$H-NMR (CDCl$_3$) δ: 1.47 (9H, s), 2.26 (2H, m), 2.53 (2H, m), 3.50–3.90 (8H, m), 4.23 (2H, s), 5.17 (2H, s), 7.37 (5H, s).

The resultant 4-benzyloxycarbonyl-1-{[1-(tert-butoxycarbonyl)-4-piperidinylidene]amino}-2-piperazinone was dissolved in methanol (40 ml), combined with acetic acid (1.2 g) with cooling on ice, followed by sodium cyanoborohydride (943 mg), and then stirred at room temperature for 30 minutes. The reaction mixture was concentrated, and the residue was dissolved in ethyl acetate, washed with aqueous sodium bicarbonate and brine, dried, concentrated and purified by a column chromatography (ethyl acetate) to obtain 4-benzyloxycarbonyl-1-[1-(tert-butoxycarbonyl)-4-piperidinylamino]-2-piperazinone (3.7 g) as a colorless amorphous material.

$^1$H-NMR (CDCl$_3$) δ: 1.36 (2H, m), 1.45 (9H, s), 1.75 (2H, m), 2.78 (2H, m), 3.08 (1H, m), 3.52 (2H, m), 3.76 (2H, m), 4.05 (214, m), 4.21 (2H, s), 5.16 (3H, s), 7.36 (5H, s).

Reference Example 11

1-[1-(tert-Butoxycarbonyl)-4-piperidinylamino]-4-(6-chloronaphthalene-2-sulfonyl)-2-piperazinone A solution of 4-benzyloxycarbonyl-1-[1-(tert-butoxycarbonyl)-4-piperidinylamino]-2-piperazinone (3.7 g) and 10% Pd/C (800 mg) in methanol (150 ml) was stirred at room temperature for 15 hours under a hydrogen atmosphere. The catalyst was filtered off and the reaction mixture was concentrated to obtain 1-[1-(tert-butoxycarbonyl)-4-piperidinylamino]-2-piperazinone.

A solution of the resultant 1-[1-(tert-butoxycarbonyl)-4-piperidinylamino]-2-piperazinone in ethyl acetate (30 ml) and a 10% aqueous solution of sodium carbonate (30 ml) was combined at 0° C. with 6-chloronaphthalene-2-sulfonyl chloride (2.24 g) and stirred at room temperature for 30 minutes, and then the organic phase was separated, washed with brine, dried and concentrated. The residue thus obtained was purified by a column chromatography on a silica gel (hexane:ethyl acetate=1:2) to obtain 1-[1-(tert-Butoxycarbonyl)-4-piperidinylamino]-4-(6-chloronaphthalene-2-sulfonyl)-2-piperazinone (3.55 g) as a colorless amorphous material.

$^1$H-NMR (CDCl$_3$) δ: 1.17 (2H, m), 1.45 (9H, s), 1.60 (2H, m), 1.86 (1H, m), 2.50–2.75 (4H, m), 2.94 (2H, m), 3.28 (2H, m), 3.40–3.60 (4H, m), 3.86 (2H, s), 4.08 (2H, m), 7.14–7.27 (3H, m), 7.34 (1H, s).

Reference Example 12

4-Benzyloxycarbonyl-1-[1-(4-pyridyl)-4-piperidinylamino]-2-piperazinone

A solution of 1-amino-4-benzyloxycarbonyl-2-piperazinone (21.92 g) and 1-(4-pyridyl)-4-piperidone (15.51 g) in ethanol (500 ml) was dehydrated using a Soxlet extractor packed with molecular sieves 4A while refluxing for 24 hours. The reaction mixture was concentrated to obtain a residue, which was dissolved in methanol (300 ml) and combined with acetic acid (18.26 g) with cooling on ice followed by sodium cycanoborohydride (7.16 g) and then stirred at 0° C. for 3 hours. The reaction mixture was concentrated, and the residue was combined with a 1N aqueous solution of sodium hydroxide, and extracted with methylene chloride. The extract was washed with water and brine, dried and concentrated to obtain 4-benzyloxycarbonyl-1-[1-(4-pyridyl)-4-piperidinylamino]-2-piperazinone (25.29 g) as a pale yellow amorphous material.

$^1$H-NMR (CDCl$_3$) δ: 1.43–1.61 (2H, m), 1.93–2.02 (2H, m), 3.14–3.40 (3H, m), 3.53–3.58 (2H, m), 3.76–3.81 (2H, m), 3.96–4.03 (2H, m), 4.22 (2H, s), 5.16 (2H, s), 5.20–5.40 (1H, br), 6.86 (2H, d, J=7.2 Hz), 7.37 (H, s), 8.11 (2H, d, J=7.2 Hz).

IR (KBr): 2934, 2317, 1696, 1645, 1601, 1539, 1418 cm$^{-1}$.

Reference Example 13

1-[1-(4-Pyridyl)-4-piperidinylamino]-2-piperazinone Trihydrochloride

A solution of 4-benzyloxycarbonyl-1-[1-(4-pyridyl)-4-piperidinylamino]-2-piperazinone (25.29 g) and an a 4N solution of hydrochloric acid in ethyl acetate (15.5 ml) in methanol (300 ml) was combined with 10% Pd/C (50% hydrated, 5.00 g) and stirred at room temperature for 15 hours under a hydrogen atmosphere. The catalyst was filtered off, and the reaction mixture was concentrated. The residue was dissolved in ethanol (300 ml), and combined with a 4N solution of hydrochloric acid in ethyl acetate (31 ml). The crystals precipitated were collected by filtration and dried to obtain 1-[1-(4-pyridyl)-4-piperidinylamino]-2-piperazinone trihydrochloride (20.16 g) as colorless crystals.

$^1$H-NMR (DMSO-$d_6$) δ: 1.32–1.47 (2H, m), 1.0–1.99 (2H, m), 3.22–3.46 (5H, m), 3.68–3.75 (4H, m), 4.09–4.16 (2H, m), 7.22 (2H, d, J=7.4 Hz), 7.38 (2H, brs), 8.03–8.21 (2H, m), 10.25 (2H, brs), 13.80 (1H, brs).

Reference Example 14

4-Benzyloxycarbonyl-1-{methyl[1-(tert-butoxycarbonyl)-4-piperidinyl]amino}-2-piperazinone A mixture of 4-benzyloxycarbonyl-1-[1-(tert-butoxycarbonyl)-4-piperidinylamino]-2-piperazinone (9.00 g), potassium carbonate (3.46 g) and methyl iodide (29.81 g) in DMF (100 ml) was stirred at 50° C. overnight. The reaction mixture was concentrated under reduced pressure, and the residue was combined with water (200 ml) and extracted with a mixture of ethyl acetate and tetrahydrofuran (1:1, 120 ml×3). The extract was washed with water and brine, dried and concentrated. The residue was crystallized from diisopropyl ether to obtain the title compound (8.55 g) as colorless crystals.

$^1$H-NMR (CDCl$_3$) δ: 1.12–1.30 (2H, m), 1.45 (9H, s), 1.60–1.85 (2H, m), 2.68–2.79 (2H, m), 2.79 (3H, s), 3.25–3.60 (3H, m), 3.67–3.72 (2H, m), 4.02–4.12 (2H, m), 4.12 (2H, s), 5.16 (2H, s), 7.36 (5H, s).

IR (KBr): 2930, 1694, 1669, 1427 cm$^{-1}$.

Reference Example 15

4-Benzyloxycarbonyl-1-{methyl[1-(4-pyridyl)-4-piperidinyl]amino}-2-piperazinone

A solution of 4-benzyloxycarbonyl-1-{methyl[1-(tert-butoxycarbonyl)-4-piperidinyl]amino}-2-piperazinone (8.49 g) in trifluoroacetic acid (20 ml) was stirred at room temperature for 1 hour. The reaction mixture was concentrated under reduced pressure, and a mixture of the resultant residue, 4-chloropyridine hydrochloride (4.35 g) and triethylamine (11.54 g) in ethanol (180 ml) was reacted in a sealed tube at 150° C. for 18 hours. The reaction mixture was concentrated, and the residue was made alkaline by adding a saturated aqueous solution of sodium hydrogen carbonate, and then extracted with dichloromethane. The extract was washed with water and brine, dried, and concentrated to obtain a residue, which was purified by a column chromatography on a silica gel (dichloromethane: 10% aqueous ammonia-containing methanol=20:1) to obtain the title compound (2.23 g) as a pale yellow amorphous material.

$^1$H-NMR (CDCl$_3$) δ: 1.30–1.55 (2H, m), 1.70–2.05 (2H, m), 2.82 (3H, s), 2.82–2.96 (2H, m), 3.25–3.65 (3H, m), 3.68–3.73 (2H, m), 3.81–3.87 (2H, m), 4.14 (2H, s), 5.16 (2H, s), 6.65 (2H, d, J=6.8 Hz), 7.37 (5H, s), 8.25 (2H, d, J=6.8 Hz).

IR (KBr): 2953, 2878, 1705, 1667, 1597, 1512, 1414 cm$^{-1}$.

Reference Example 16

1-{Methyl[1-(4-pyridyl)-4-piperidinyl]amino}-2-piperazinone Dihydrochloride

A solution of 4-benzyloxycarbonyl-1-{methyl[1-(4-pyridyl)-4-piperidinyl]amino}-2-piperazinone (2.22 g) and a 4N solution of hydrochloric acid in ethyl acetate (2.6 ml) in methanol (50 ml) was combined with 10% Pd/C (50% hydrated, 0.44 g) and stirred at room temperature for 5 hours under a hydrogen atmosphere. The catalyst was filtered off and the reaction mixture was concentrated to obtain the title compound. (2.13 g) as a yellow amorphous material.

$^1$H-NMR (DMSO-$d_6$) δ: 1.12–1.50 (2H, br), 1.88–2.10 (2H, br), 2.73 (3H, s), 3.17–3.80 (9H, m), 4.15–4.21 (2H, m), 7.21 (2H, d, J=7.2 Hz), 8.21 (2H, brs), 10.00–10.35 (2H, br), 13.70–13.90 (1H, br).

Reference Example 17

4-(7-Bromo-4H-4-oxobenzopyran-3-sulfonyl)-1-[1-(tert-butoxycarbonyl)-4-piperidinylamino]-2-piperazinone A solution of 4-benzyloxycarbonyl-1-[1-(tert-butoxycarbonyl)-4-piperidinylamino]-2-piperazinone (3.19 g) and 10% Pd/C (0.64 g) in methanol (50 ml) was stirred at room temperature for 15 hours under a hydrogen atmosphere. The catalyst was filtered off, and the reaction mixture was concentrated to obtain 1-[1-(tert-butoxycarbonyl)-4-piperidinylamino]-2-piperazinone (1.93 g) as a colorless oil.

A solution of the resultant 1-[1-(tert-butoxycarbonyl)-4-piperidinylamino]-2-piperazinone (193 g) and N-ethyldiisopropylamine (1.27 g) in dichloromethane (60 ml) was treated portionwise with 7-bromo-4H-4-oxobenzopyran-3-sulfonyl chloride (2.33 g) with cooling on ice, and stirred for 2 hours. The reaction mixture was washed with water and brine, dried and concentrated to obtain a residue, which was purified by a column chromatography on a silica gel (hexane:ethyl acetate=1:5), and crystallized from ethyl acetate to obtain the title compound (1.60 g) as colorless crystals.

$^1$H-NMR (CDCl$_3$) δ: 1.21–1.39 (2H, m), 1.45 (9H, s), 1.70–1.76 (2H, m), 2.70–2.81 (2H, m), 3.00–3.20 (1H, m), 3.57–3.62 (2H, m), 3.80–3.85 (2H, m), 3.98–4.04 (2H, m), 4.14 (2H, s), 5.00–5.25 (1H, br), 7.65 (1H, dd, J=8.4, 1.6 Hz), 7.78 (1H, d, J=1.6 Hz), 8.08 (1H, d, J=8.4 Hz), 8.66 (1H, s).

IR (KBr): 2926, 1669, 1653, 1607, 1557, 1472, 1456, 1442 cm$^{-1}$.

Reference Example 18

4-(7-Bromo-2H-benzopyran-3-sulfonyl)-1-[1-(tert-butoxycarbonyl)-4-piperidinylamino]-2-piperazinone 4-(7-Bromo-4H-4-oxobenzopyran-3-sulfonyl)-1-[1-(tert-butoxycarbonyl)-4-piperidinylamino]-2-piperazinone (1.53 g) was suspended in methanol (25 ml) and tetrahydrofuran (25 ml) and treated with sodium borohydride (148 mg) with cooling on ice and stirred at room temperature for 1 hour. The reaction mixture was concentrated, and the residue was combined with ethyl acetate, washed with aqueous sodium bicarbonate and brine, and then dried over magnesium sulfate. The solvent was concentrated to obtain a residue, which was dissolved in dichloromethane (200 ml), combined with triethylamine (0.98 g) followed by methanesulfonyl chloride (0.33 g) at 0° C., and then stirred at room temperature for 3 hours. The reaction mixture was washed with water and brine, dried and concentrated to obtain a residue, which was crystallized from diethyl ether to obtain the title compound (1.03 g) as colorless crystals.

$^1$H-NMR (CDCl$_3$) δ: 1.22–1.41 (2H, m), 1.45 (9H, s), 1.72–1.79 (2H, m), 2.72–2.83 (2H, m), 3.05–3.19 (1H, m), 3.56–3.65 (4H, m), 3.95 (2H, s), 4.00–4.07 (2H, m), 4.87

(2H, s), 5.13 (1H, d, J=4.6 Hz), 7.06 (1H, d, J=8.0 Hz), 7.09 (1H, d, J=1.8 Hz), 7.16 (1H, dd, J=8.0, 1.8 Hz), 7.28 (1H, s).
IR (KBr): 2920, 1686, 1655, 1597, 1480, 1420 cm$^{-1}$.

Reference Example 19

4-(7-Bromo-2H-benzopyran-3-sulfonyl)-1-(4-piperidinylaminol-2-piperazinone

A solution of 4-(7-bromo-2H-benzopyran-3-sulfonyl)-1-[1-(tert-butoxycarbonyl)-4-piperidinylamino]-2-piperazinone (980 mg) in tetrahydrofuran (20 ml) was treated dropwise with a 4N solution of hydrochloric acid in ethyl acetate (2.6 ml) and stirred at room temperature for 2 hours. The reaction mixture was concentrated, and the residue was combined with water and a 1N aqueous solution of sodium hydroxide, extracted with dichloromethane, washed with brine and dried over magnesium sulfate. The solvent was concentrated to obtain a residue, which was crystallized from diisopropyl ether to obtain the title compound (616 mg) as colorless crystals.

$^1$H-NMR (DMSO-d$_6$) δ: 1.05–1.22 (2H, m), 1.63–1.69 (2H, m), 2.35–2.45 (2H, m), 2.88–3.05 (3H, m), 3.25–3.57 (7H, m), 3.84 (2H, s), 4.98 (2H, s), 5.47 (1H, d, J=4.8 Hz), 7.19 (1H, d, J=1.8 Hz), 7.25 (1H, dd, J=8.0, 1.8 Hz), 7.40 (1H, d, J=8.0 Hz), 7.48 (1H, s).

Reference Example 20

2-[1-(tert-Butoxycarbonyl)-4-piperidinyl]-N-[4-(6-chloronaphthalene-2-sulfonyl)-2-oxo-1-piperazinyl]acetamide A solution of 1-(tert-butoxycarbonyl)-4-piperidinylacetic acid (440 mg), 1-amino-4-benzyloxycarbonyl-2-piperazinone (541 mg), triethylamine (273 mg) and HOBt (333 mg) in DMF (30 ml) was combined with WSC (518 mg) and stirred at room temperature for 15 hours. The reaction mixture was concentrated to obtain a residue, which was partitioned between ethyl acetate and water, and the organic phase was washed with water, aqueous sodium bicarbonate, an aqueous solution of citric acid and brine, dried and concentrated to obtain N-(4-benzyloxycarbonyl-2-oxo-1-piperazinyl)-2-[1-(tert-butoxycarbonyl)-4-piperidinyl]acetamide (840 mg).

$^1$H-NMR (CDCl$_3$) δ: 1.18 (2H, m), 1.45 (9H, s), 1.73 (2H, m), 2.00 (1H, m), 2.17 (2H, d, J=7.0 Hz), 2.71 (2H, m), 3.67 (2H, m), 3.87 (2H, m), 4.10 (2H, m), 4.28 (2H, s), 5.16 (2H, s), 7.36 (5H, s), 7.76 (1H, br).

A solution of N-(4-benzyloxycarbonyl-2-oxo-1-piperazinyl)-2-[1-(tert-butoxycarbonyl)-4-piperidinyl]acetamide (840 mg) and 10% Pd/C (500 mg) in methanol (35 ml) was stirred at room temperature for 15 hours under a hydrogen atmosphere. The catalyst was filtered off and the reaction mixture was concentrated to obtain N-(2-oxo-1-piperazinyl)-2-[1-(tert-butoxycarbonyl)-4-piperidinyl]acetamide as a colorless syrup. A solution of the resultant 2-[1-(tert-butoxycarbonyl)-4-piperidinyl]-N-(2-oxo-1-piperazinyl)acetamide in ethyl acetate (40 ml) and a 10% aqueous solution of sodium carbonate (40 ml) was combined at 0° C. with 6-chloronaphthalene-2-sulfonyl chloride (470 mg) and stirred at room temperature for 30 minutes. The organic phase was separated, washed with brine, dried and concentrated to obtain a residue, which was purified by a column chromatography on a silica gel (ethyl acetate) and crystallized from ethyl acetate to obtain the title compound (420 mg) as colorless crystals.

$^1$H-NMR (CDCl$_3$) δ: 1.15 (2H, m), 1.44 (9H, s), 1.71 (2H, m), 1.94 (1H, m), 2.10–2.25 (2H, m), 2.67 (2H, m), 3.54 (2H, m), 3.72 (2H, m), 3.89 (2H, s), 4.07 (2H, m), 7.52 (1H, s), 7.61 (1H, dd, J=2.0, 8.8 Hz), 7.79 (1H, dd, J=1.8, 8.8 Hz), 7.90–8.00 (3H, m), 8.36 (1H, s).

Reference Example 21

4-(6-Chloronaphthalene-2-sulfonyl)-1-[methyl(4-piperidinyl)amino]-2-piperazinone hydrochloride A suspension of 1-{[1-(tert-butoxycarbonyl)piperidinyl]methylamino}-4-(6-chloronaphthalene-2-sulfonyl)-2-piperazinone (10.42 g) in methanol (40 ml) was combined with a 4N solution of hydrochloric acid in ethyl acetate (20 ml) and stirred at room temperature for 5 hours. The reaction mixture was combined with ethyl acetate (50 ml) and the crystals precipitated were collected by filtration, dried to obtain the title compound (9.21 g) as colorless crystals.

$^1$H-NMR (DMSO-d$_6$) δ: 1.20–1.42 (2H, m), 1.60–1.90 (2H, m), 2.50 (3H, s), 2.60–2.90 (3H, m), 2.98–3.52 (7H, m), 3.70 (2H, s), 7.74 (1H, dd, J=8.8, 2.0 Hz), 7.90 (1H, dd, J=8.8, 2.0 Hz), 8.19 (1H, d, J=8.8 Hz), 8.27–8.31 (2H, m), 8.31–8.65 (3H, m).

Reference Example 22 tert-Butyl 3-methyl-5-oxo-1-piperazinecarboxylate

A mixture of 2-amino-1-propanol (5.0 g) and sodium carbonate (21.2 g) in ethyl acetate (50 ml) and water (50 ml) was treated dropwise with Z-chloride (9.5 ml) and stirred at room temperature for 1 hour. The organic phase was separated, washed with saturated brine, dried (MgSO$_2$) and concentrated under reduced pressure. The crystals thus obtained were collected by filtration, washed with ethyl acetate-ether, dried to obtain benzyl (2-hydroxy-1-methylethyl) carbamate (11.0 g) as colorless crystals.

$^1$H-NMR (CDCl$_3$) δ: 1.17 (3H, d, J=6.6 Hz), 2.27–2.47 (1H, m), 3.42–3.73 (2H, m), 3.73–3.95 (1H, m), 4.80–5.03 (1H, m), 5.10 (2H, s), 7.26–7.45 (5H,m).

IR (KBr): 3316, 1688, 1539, 1267, 1046 cm$^{-1}$.

A solution of oxalyl chloride (3.5 ml) in methylene chloride (64 ml) was cooled to −78° C. under a nitrogen atmosphere and treated dropwise with a solution of dimethyl sulfoxide (6.4 ml) in methylene chloride (32 ml) over 1 hour. While cooling at −78° C., a solution of benzyl (2-hydroxy-1-methylethyl) carbamate (6.4 g) in methylene chloride (64 ml) was added dropwise over 1 hour, and the mixture was stirred at −65 to −55° C. for 1 hour, cooled again to −78° C., and combined with triethylamine (17 ml). The reaction mixture was warmed to room temperature, combined with a saturated aqueous solution of ammonium chloride, and extracted with methylene chloride. The organic phase was washed with saturated brine and dried over anhydrous sodium sulfate, and the solvent was distilled off under reduced pressure to obtain benzyl (1-methyl-2-oxoethyl) carbamate as a yellow oil. Then this substance in a mixture with glycine ethyl ester hydrochloride (4.7 g) and acetic acid (3.6 ml) in methanol (120 ml) was combined with sodium cyanoborohydride (3.8 g) and stirred at room temperature for 1 hour. The solvent was distilled off under reduced pressure, and the residue was diluted with ethyl acetate and washed with saturated aqueous sodium bicarbonate. The organic phase was dried over magnesium sulfate and concentrated under reduced pressure. The residue was purified by a column chromatography on a silica gel (ethyl acetate:methanol=10:1) to obtain ethyl 2-[[2-[[(benzyloxy)carbonyl]amino]propyl]amino]acetate (4.9 g) as a pale yellow oil.

¹H-NMR (CDCl₃) δ: 1.00–1.40 (6H, m), 2.20–2.80 (3H, m), 3.25–3.50 (1H, m), 3.63–3.95 (1H, m), 4.02–4.30 (2H, m), 4.90–5.50 (4H, m), 7.10–7.50 (5H, m).

A mixture of ethyl 2-[[2-[[(benzyloxy)carbonyl]amino]propyl]amino]acetate (1.9 g) and sodium carbonate (1.4 g) in ethyl acetate (20 ml) and water (20 ml) was treated dropwise with di-tert-butyl dicarbonate (1.6 ml) and stirred at room temperature for 2 hours. The organic phase was separated, washed with saturated brine, dried (MgSO₂) and concentrated under reduced pressure. The residue was purified by a column chromatography on a silica gel (hexane:ethyl acetate=3:2) to obtain ethyl 2-[[2-[[(benzyloxy)carbonyl]amino]propyl](tert-butoxycarbonyl)amino]acetate (2.3 g) as a colorless oil.

¹H-NMR (CDCl₃) δ: 1.18 (3H, t, J=6.6 Hz), 1.26 (3H, t, J=7.0 Hz), 1.40, 1.46 (total 9H, s for each), 3.05–3.65 (2H, m), 3.70–4.00 (3H, m), 4.17 (2H, q, J=7.0 Hz), 5.08 (2H, s), 5.25–5.45 (1H, m), 7.25–7.45 (5H, m).

A solution of ethyl 2-[[2-[[(benzyloxy)carbonyl]amino]propyl](tert-butoxycarbonyl)amino]acetate (2.3 g) and 10% Pd/C (0.23 g) in methanol (46 ml) was stirred at room temperature for 1 hour under a hydrogen atmosphere. The catalyst was filtered off and the filtrate was stirred at 50° C. for 1 hour, concentrated under reduced pressure to obtain the title compound (1.1 g) as a colorless non-crystalline powder.

¹H-NMR (CDCl₃) δ: 1.21 (3H, d, J=6.6 Hz), 1.47 (9H, s), 2.80–3.15 (1H, m), 3.50–3.75 (1H, m), 3.75–4.10 (1H, m), 3.90 (1H, d, J=18.6 Hz), 4.24 (1H, d, J=18.6 Hz), 6.25–6.60 (1H, m).

IR (KBr): 2976, 1696, 1682, 1335, 1246, 1175 cm⁻¹.

Reference Example 23 tert-Butyl 3-methyl-5-oxo-4-[[1-(4-pyridinyl)-4-piperidinyl]amino]-1-piperazinecarboxylate tert-Butyl 3-methyl-5-oxo-1-piperazinecarboxylate (1.1 g) was dissolved in DMF (20 ml) and treated with sodium hydride (0.25 g, in oil) with cooling on ice. After stirring at 50° C. for 1 hour, O-diphenylphosphinyl hydroxylamine (1.3 g) was added and the mixture was stirred at 50° C. for 15 hours. The reaction mixture was concentrated under reduced pressure, and the residue was combined with aqueous sodium bicarbonate and extracted with dichloromethane. The extract was dried and concentrated to obtain tert-butyl 4-amino-3-methyl-5-oxo-1-piperazinecarboxylate as a yellow oil.

A solution of this material and 1-(4-pyridinyl)-4-piperidone (0.91 g) in ethanol (23 ml) was dehydrated using a Soxlet extractor packed with molecular sieves 4A while refluxing for 15 hours. The reaction mixture was concentrated to obtain a residue, which was dissolved in methanol (20 ml) and combined with acetic acid (0.61 ml) with cooling on ice followed by sodium cyanoborohydride (0.65 g) and then stirred at room temperature for 30 minutes. The reaction mixture was concentrated, and the residue was dissolved in ethyl acetate, and washed with brine, dried, concentrated and purified by a column chromatography on a basic silica gel (NH-DM1020, FUJI SILICIA CHEMICAL, ethyl acetate) to obtain the title compound (1.2 g) as a colorless crystalline powder.

¹H-NMR (CDCl₃) δ: 1.26 (3H, d, J=6.6 Hz), 1.48 (9H, s), 1.35–1.60 (2H, m), 1.78–1.97 (2H, m), 2.82–3.03 (2H, m), 3.10–3.33 (1H, m), 3.35–3.70 (2H, m), 3.73–4.03 (4H, m), 4.15–4.45 (1H, m), 4.90 (1H, d, J=4.4 Hz), 6.65 (2H, d, J=6.6 Hz), 8.25 (2H, d, J=6.6 Hz).

Reference Example 24

1-(tert-Butyl) 3-Methyl 5-oxo-1,3-Piperazinecarboxylate

A mixture of N-Z-DL-asparagine (30 g) (z=benzyloxycarbonyl] in dimethylformamide (200 ml) and water (200 ml) was combined with [bis(trifluoroacetoxy)iodo) benzene (72.7 g). The mixture was stirred at room temperature for 1 hour, combined with pyridine (18.3 ml) and then stirred further for 12 hours. The reaction mixture was concentrated under reduced pressure, and the residue was partitioned between a 5N aqueous solution of sodium hydroxide and diethyl ether, and the aqueous phase was combined with tetrahydrofuran (100 ml) and di-tert-butyl dicarbonate (28.6 ml). After stirring at room temperature for 1 hour followed by drying over magnesium sulfate, the mixture was concentrated under reduced pressure. Then a mixture of the resultant residue and potassium carbonate (23.4 g) in dimethylformamide (150 ml) was combined with iodomethane (10.5 ml) and stirred at room temperature for 1 hour. After completion of the reaction, the reaction mixture was diluted with ethyl acetate and washed with water. The organic phase was washed with saturated brine, dried (MgSO₂) and concentrated under reduced pressure. The residue was crystallized from hexane/ethyl acetate to obtain methyl 2-[[(benzyloxy)carbonyl]amino]-3-[(tert-butoxycarbonyl)amino]propanoate (24 g) as a colorless crystalline powder.

¹H-NMR (CDCl₃) δ: 1.42 (9H, s), 3.55 (2H, t, J=5.2 Hz), 3.76 (3H, s), 4.32–4.48 (1H, m), 4.70–4.95 (1H, m), 5.12 (2H, s), 5.67–5.88 (1H, m), 7.28–7.43 (5H, m).

IR (KBr): 1715, 1520, 1254, 1167 cm⁻¹.

A solution of methyl 2-[[(benzyloxy)carbonyl]amino]-3-[(tert-butoxycarbonyl)amino]propanoate (4.3 g) in toluene (20 ml) was treated dropwise with trifluoroacetic acid (20 ml) and stirred at room temperature for 1 hour, and concentrated under reduced pressure. The residue was crystallized from ethyl acetate to obtain methyl 3-amino-2-[[(benzyloxy)carbonyl)amino]propanoate trifluoroacetate (4.4 g).

¹H-NMR (CD₃OD) δ: 3.12–3.52 (2H, m), 3.76 (3H, s), 4.40–4.58 (1H, m), 5.13 (2H, s), 7.23–7.45 (5H, m).

A mixture of methyl 3-amino-2-([(benzyloxy)carbonyl]amino]propanoate trifluoroacetate (8.9 g) and triethylamine (30.6 ml) in dimethylformamide (89 ml) was treated by a slow dropwise addition of a solution of ethyl chloroacetate (7.8 ml) in dimethylformamide (20 ml). After stirring at room temperature for 12 hours, triethylamine (20.4 ml) was added again, and the mixture was treated by a slow dropwise addition of a solution of ethyl chloroacetate (5.2 ml) in dimethylformamide (15 ml) and stirred at room temperature for further 6 hours. The system was partitioned between water and ethyl acetate and the organic phase was washed with saturated brine, dried (MgSO₂) and concentrated under reduced pressure. The residue was purified by a column chromatography on a silica gel (hexane:ethyl acetate=1:4) to obtain methyl 2-[[(benzyloxy)carbonyl]amino]-3-((2-ethoxy-2-oxoethyl)amino]propanoate (6.6 g) as a colorless oil.

¹H-NMR (CD₃OD) δ: 1.27 (3H, t, J=7.4 Hz), 2.96 (1H, dd, J=4.6, 12.6 Hz), 3.12 (1H, dd, J=4.8, 12.6 Hz), 3.37 (2H, s), 3.77 (3H, s), 4.18 (2H, q, J=7.4 Hz), 4.35–4.48 (1H, m), 5.13 (2H, s), 5.72–5.87 (1H, m), 7.28–7.42 (5H, m).

IR (KBr): 3331, 2953, 1728, 1526, 1209 cm⁻¹.

A mixture of methyl 2-[[(benzyloxy)carbonyl]amino]-3-[(2-ethoxy-2-oxoethyl)amino]propanoate (6.6 g) and sodium hydrogen carbonate (3.3 g) in ethyl acetate (66 ml) and water (66 ml) was treated dropwise with di-tert-butyl dicarbonate (4.9 ml), and stirred at room temperature for 2 hours. The organic phase was separated, washed with saturated brine, dried (MgSO₂) and concentrated under reduced pressure. The residue was purified by a column chromatography on a silica gel (hexane:ethyl acetate=3:2) to obtain methyl 2-[[(benzyloxy)carbonyl]amino]-3-[(tert-butoxycarbonyl)(2-ethoxy-2-oxoethyl)amino]propanoate (8.4 g) as a colorless oil.

$^1$H-NMR (CDCl$_3$) δ: 1.26 (3H, t, J=7.0 Hz), 1.39, 1.44 (total 9H, s for each), 3.46–4.02 (7H, m), 4.17 (2H, q, J=7.0 Hz), 4.14–4.62 (1H, m), 5.02–5.20 (2H, m), 5.74–6.18 (1H, m), 7.20–7.40 (5H, m).

A solution of methyl 2-[[(benzyloxy)carbonyl]amino]-3-[(tert-butoxycarbonyl)(2-ethoxy-2-oxoethyl)amino]propanoate (8.4 g) and 10% Pd/C (0.84 g) in methanol (84 ml) was stirred at room temperature for 1 hour under a hydrogen atmosphere. The catalyst was filtered off, and the filtrate was combined with triethylamine (10.6 ml) and stirred at 50° C. further for 1 hour. The solvent was distilled off under reduced pressure, and the residue was crystallized from hexane/ethyl acetate to obtain the title compound (4.5 g) as a colorless crystalline powder.

$^1$H-NMR (CDCl$_3$) δ: 1.47 (9H, s), 3.81 (3H, s), 3.55–4.25 (5H, m), 6.62–6.78 (5H, m).

IR (KBr): 1748, 1694, 1424, 1248, 1148 cm$^{-1}$.

Reference Example 25

1-(tert-Butyl) 3-Methyl 5-oxo-4-[[1-(4-Pyridinyl)-4-piperidinyl]amino]-1,3-piperazinedicarboxylate 1-(tert-Butyl) 3-methyl 5-oxo-1,3-piperazinedicarboxylate (4.5 g) was dissolved in DMF (90 ml) and combined with sodium hydride (0.84 g, in oil) with cooling on ice. After stirring at 50° C. for 1 hour, O-diphenylphosphinyl hydroxylamine (4.5 g) was added and the mixture was stirred at room temperature for 2 hours. The reaction mixture was concentrated under reduced pressure, and the residue was combined with aqueous sodium bicarbonate and extracted with dichloromethane. The extract was dried and concentrated to obtain 1-(tert-butyl) 3-methyl 4-amino-5-oxo-1,3-piperazinedicarboxylate as a yellow oil. A solution of this material and 1-(4-pyridinyl)-4-piperidone (3.1 g) in ethanol (90 ml) was dehydrated using a Soxlet extractor packed with molecular sieves 4A while refluxing for 15 hours. The reaction mixture was concentrated to obtain a residue, which was dissolved in methanol (90 ml) and combined with acetic acid (2.1 ml) with cooling on ice, followed by sodium cycanoborohydride (2.2 g) and then stirred at room temperature for 2 hours. The reaction mixture was concentrated, and the residue was dissolved in ethyl acetate, washed with aqueous sodium bicarbonate, dried, concentrated and purified by a column chromatography on a basic silica gel (ethyl acetate:methanol=20:1) to obtain the title compound (3.8 g) as a pale yellow non-crystalline powder.

$^1$H-NMR (CDCl$_3$) δ: 1.20–1.60 (2H, m), 1.45 (9H, s), 1.70–1.98 (2H, m), 2.80–3.05 (2H, m), 3.13–4.60 (8H, m), 3.76 (3H, s), 5.03 (1H, d, J=3.8 Hz), 6.64 (2H, d, J=6.6 Hz), 8.25 (2H, d, J=6.6 Hz).

IR (KBr): 2980, 1748, 1698, 1672, 1597, 1397, 1246, 1136 cm$^{-1}$.

Reference Example 26

(3S)-1,3-bis(tert-Butoxycarbonylamino)-2-pyrrolidone

A solution of Boc-L-methionine (9.972 g) [Boc:tert-butoxycarbonyl] and tert-butyl carbazate (5.29 g) in acetonitrile (100 ml) was combined with WSC (9.202 g) and stirred at room temperature for 5 hours. The reaction mixture was concentrated and the resultant residue was combined with ethyl acetate and water, and the organic phase was washed with water, aqueous sodium bicarbonate and brine, dried and concentrated to obtain tert-butyl 2-(Boc-L-methionyl)-1-hydrazine carboxylate as a colorless oil.

$^1$H-NMR (CDCl$_3$) δ: 1.45 (9H, s), 1.47 (9H, s), 1.90–2.20 (5H, m), 2.64 (2H, m), 4.35 (1H, m), 5.18 (1H, brd, J=8.8 Hz), 6.44 (1H, brs), 8.08 (1H, brs).

A solution of the resultant tert-butyl 2-(Boc-L-methionyl)-1-hydrazine carboxylate in acetone (20 ml) was combined with methyl iodide (17 ml, 240 mmol) and stirred at room temperature overnight. The reaction mixture was concentrated, and the resultant residue was triturated from ether, collected by filtration, washed with ether and dried to obtain tert-butyl 2-(Boc-L-methionyl)-1-hydrazine carboxylate methylsulfonium iodide (19.14 g) as a colorless solid.

A solution of tert-butyl 2-(Boc-L-methionyl)-1-hydrazine carboxylate methylsulfonium iodide (18 g) in DMF (200 ml) was combined with sodium hydride (3.93 g, in oil) with cooling on ice, and then stirred at room temperature for 3 hours. The reaction mixture was combined with ice-water, and extracted with ethyl acetate, and the organic phase was washed with water and brine, dried and concentrated to obtain a residue, which was triturated from isopropyl ether/hexane (1/1) solution, collected by filtration, washed with isopropyl ether/hexane (1/1) solution and dried to obtain the title compound (5.7 g) as a colorless solid.

$^1$H-NMR (CDCl$_3$) δ: 1.45 (9H, s), 1.47 (9H, s), 2.00 (1H, m), 2.62 (1H, m), 3.40–3.70 (2H, m), 4.23 (1H, m), 5.13 (1H, brs), 6.65 (1H, brs).

IR (KBr): 3289, 1713, 1699, m 1505, 1368, 1250, 1167 cm$^{-1}$.

$[α]_D$=+5.1° (c=0.993, CHCl$_3$).

Reference Example 27

(3S)-1,3-bis(tert-Butoxycarbonylamino)-2-pyrrolidone

Similarly to Reference Example 26, a synthesis was performed starting from 2-(Boc-D-methionine).

$[a]_D$=−5.30 (c=1.006, CHCl$_3$)

Reference Example 28

(3S)-1-Amino-3-(6-chloronaphthalene-2-sulfonylamino)-2-pyrrolidone

A solution of (3S)-1,3-bis(tert-butoxycarbonylamino)-2-pyrrolidone (1.0 g) in methanol (10 ml) was combined with a 4N solution of hydrochloric acid in ethyl acetate (10 ml) and stirred at room temperature for 30 minutes. The reaction mixture was concentrated, and the resultant residue was combined with dichloromethane (30 ml) and triethylamine (1.6 g), followed by 6-chloronaphthalene-2-sulfonyl chloride (830 mg) at 0° C., and stirred at room temperature for 1 hour. The reaction mixture was combined with an aqueous solution of sodium carbonate, extracted with dichloromethane, dried and concentrated. The resultant residue was washed with ether to obtain the title compound as a colorless solid.

$^1$H-NMR (CDCl$_3$) δ: 2.05 (1H, m), 2.50 (1H, m), 3.35–3.55 (2H, m), 3.83 (1H, t, J=9.0 Hz), 4.08 (2H, s), 7.55 (1H, dd, J=2.0, 8.8 Hz), 7.80–8.05 (4H, m), 8.46 (1H, s).

IR (KBr): 3059 (br), 1703, 1329, 1159, 1136, 1080 cm$^{-1}$.

Reference Example 29

(3S)-3-(tert-Butoxycarbonylamino)-1-[1-(4-pyridyl)-4-piperidinylamino]-2-pyrrolidone A solution of (3S)-1,3-bis(tert-butoxycarbonylamino)-2-pyrrolidone (3.15 g) in methanol (10 ml) was combined with a 4N solution of hydrochloric acid in ethyl acetate (20 ml) and stirred at room temperature for 30 minutes. The reaction mixture was concentrated, and the resultant residue was combined with dichloromethane (30 ml) and triethylamine (6.06 g), and then with di-tert-butyl dicarbonate (2.62 g) at 0° C. and stirred at room temperature for 1 hour. The reaction mixture was combined with an aqueous solution of sodium carbonate, extracted with dichloromethane, dried and concentrated. The residue obtained was washed with hexane to obtain (3S)-1-amino-3-(tert-butoxycarbonylamino)-2-pyrrolidone (1.89 g) as a colorless solid.

$^1$H-NMR (CDCl$_3$) δ: 1.45 (9H, s), 1.91 (1H, m), 2.60 (1H, m), 3.40–3.55 (2H, m), 4.13 (2H, s), 4.19 (1H, t, J=9.0 Hz), 5.08 (1H, brs).

IR (KBr): 3300, 1694, 1169 cm$^{-1}$.

A solution of (3S)-1-amino-3-(tert-butoxycarbonylamino)-2-pyrrolidone (1.84 g) and 1-(4-pyridyl)-4-piperidone (1.51 g) in ethanol (30 ml) was dehydrated using a Soxlet extractor packed with molecular sieves 4A while refluxing for 15 hours. The reaction mixture was concentrated to obtain (3S)-3-(tert-butoxycarbonylamino)-1-[1-(4-pyridyl)-4-piperidinylideneamino]-2-pyrrolidone (3.57 g) as a syrup.

$^1$H-NMR (CDCl$_3$) δ: 1.46 (9H, s), 2.10 (1H, m), 2.40–2.70 (5H, m), 3.45–3.80 (6H, m), 4.17 (1H, m), 5.08 (1H, br), 6.68 (2H, d, J=6.6 Hz), 8.30 (2H, d, J=6.6 Hz).

IR (KBr): 1690, 159.7, 1514 cm$^{-1}$.

(3S)-3-(tert-Butoxycarbonylamino)-1-[1-(4-pyridyl)-4-piperidinylideneamino]-2-pyrrolidone (3.57 g) was dissolved in methanol (40 ml), combined with acetic acid (2.05 g) with cooling on ice, followed by sodium cyanoborohydride (807 mg) and stirred at room temperature for 30 minutes. The reaction mixture was concentrated, and the residue was combined with an aqueous solution of sodium hydroxide, extracted with dichloromethane, dried, concentrated, and purified by a column chromatography (dichloromethane: 10% aqueous ammonia-containing methanol=20:1) to obtain the title compound (2.56 g) as a colorless amorphous material.

$^1$H-NMR (CDCl$_3$) δ: 1.45 (9H, s), 1.51 (2H, m), 1.93 (2H, m), 2.03 (1H, m), 2.61 (1H, m), 2.95 (2H, m), 3.28 (1H, m), 3.40–3.50 (2H, m), 4.19 (1H, m), 4.55 (1H, br), 5.14 (1H, brs), 6.66 (2H, d, J=6.6 Hz), 8.24 (2H, d, J=6.6 Hz).

IR (KBr): 1694, 1599, 1514, 1366, 1289, 1250, 1233, 1167 cm$^{-1}$.

Reference Example 30

1-(tert-Butyl) 3-Methyl 4-[[1-(2-methyl-4-pyridinyl)-4-piperidinyl]amino-5-oxo-1,3-piperazine dicarboxylate 1-(tert-Butyl) 3-methyl 5-oxo-1,3-piperazinedicarboxylate (3.15 g) was dissolved in DMF (63 ml) and combined with sodium hydride (0.59 g, in oil) with cooling on ice. The mixture was stirred at 50° C. for 1 hour and then cooled to room temperature, combined with O-diphenylphosphinyl hydroxylamine (3.13 g), and stirred at room temperature for 2 hours. The reaction mixture was concentrated under reduced pressure, and the residue was combined with aqueous sodium bicarbonate and extracted with dichloromethane. The extract was dried and concentrated to obtain 1-(tert-butyl) 3-methyl 4-amino-5-oxo-1,3-piperazine dicarboxylate as a yellow oil. A mixture of this material and 1-(2-methyl-4-pyridinyl)-4-piperidone (2.3 g) in ethanol (63 ml) was dehydrated using a Soxlet extractor packed with molecular sieves 4A while refluxing for 15 hours. The reaction mixture was concentrated, and the residue was dissolved in methanol (63 ml), combined with acetic acid (1.45 ml) with cooling on ice, followed by sodium cyanoborohydride (1.53 g), and then stirred at room temperature for 2 hours. The reaction mixture was concentrated, and the residue was dissolved in ethyl acetate, washed with aqueous sodium bicarbonate and brine, dried, concentrated and purified by a column chromatography on a basic silica gel (ethyl acetate:methanol=20:1) to obtain the title compound (3.4 g) as a pale yellow non-crystalline powder.

$^1$H-NMR (CDCl$_3$) δ: 1.36–1.66 (2H, m), 1.44 (9H, s), 1.86–2.14 (2H, m), 2.56 (3H, s), 3.10–4.66 (13H, m), 5.02 (1H, d, J=3.6 Hz), 6.69 (1H, d, J=2.6 Hz), 6.85 (1H, dd, J=2.6, 7.4 Hz), 7.89 (1H, d, J=7.4 Hz).

Reference Example 31

4-Chloro-2-chloromethylpyridine Hydrochloride

A solution of 4-chloro-2-hydroxymethylpyridine (430 mg), thionyl chloride (0.43 ml) and DMF (1 drop) in chloroform (20 ml) was heated under reflux for 2 hours. The reaction mixture was concentrated to obtain the title compound (0.44 g) as a tan powder.

$^1$H-NMR (CDCl$_3$) δ: 4.95 (2H, s), 7.57 (1H, dd, J=2.0, 5.8 Hz), 7.81 (1H, d, J=1.8 Hz), 8.59 (1H, d, J=5.8 Hz).

Reference Example 32

4-Chloro-2-methoxymethylpyridine

A mixture of 4-chloro-2-chloromethylpyridine hydrochloride (0.43 g), sodium methoxide (1.11 g) and methanol (15 ml) was stirred at room temperature for 10 hours and at 70° C. for 7 hours. The reaction mixture was concentrated, and the residue was combined with water and methylene chloride, and the organic phase was separated. After washing with saturated aqueous sodium bicarbonate followed by drying and concentrating, a title compound (0.28 g) was obtained as a tan oil.

$^1$H-NMR (CDCl$_3$) δ: 3.49 (3H, s), 4.57 (2H, s), 7.20 (1H, dd, J=2.0. 5.2 Hz), 7.46–7.47 (1H, m), 8.45 (1H, d, J=5.6 Hz).

Reference Example 33

4-Chloro-2-ethoxymethylpyridine

Similarly to Reference Example 32 but using sodium ethoxide (1.09 g) instead of sodium methoxide and ethanol instead of methanol, the title compound (550 mg) was obtained as a tan oil.

$^1$H-NMR (CDCl$_3$) δ: 1.30 (3H, t, J=6.9 Hz), 3.64 (2H, q, J=7.0 Hz), 4.62 (2H, s), 7.20 (1H, dd, J=1.9, 5.4 Hz), 7.49 (1H, d, J=1.8 Hz), 8.44 (1H, d, J=5.4 Hz).

Reference Example 34

4-Chloro-2-dimethylaminomethylpyridine

Similarly to Reference Example 32 but using a 50% aqueous solution of dimethylamine (1.44 g) instead of sodium methoxide, the title compound (530 mg) was obtained as a tan oil.

$^1$H-NMR (CDCl$_3$) δ: 2.30 (6H, s), 3.58 (2H, s), 7.19 (1H, dd, J=2.0, 5.2 Hz), 7.46 (1H, d, J=.1.8 Hz), 8.45 (1H, d, J=5.4 Hz).

Reference Example 35

4-Chloro-2-aminomethylpyridine

Similarly to Reference Example 32 but using a 25% aqueous solution of ammonia (30 ml) instead of sodium methoxide, the title compound (1.22 g) was obtained as a tan oil.

$^1$H-NMR (CDCl$_3$) δ: 1.79 (2H, br), 3.96 (1H, s), 3.98 (1H, s), 7.16–7.21 (1H, m), 7.37 (1H, dd, J=2.0, 9.8 Hz), 8.45 (1H, d, J=5.2 Hz).

Reference Example 36

4-Chloro-2-racetylaminomethylpyridine

A solution of 4-chloro-2-aminomethylpyridine (0.57 g) and acetic anhydride (1.5 ml) in THF (10 ml) was stirred at room temperature for 14 hours and at 50° C. for 4 hours. The reaction mixture was concentrated, and the resultant residue was partitioned between saturated aqueous sodium bicarbonate and water, and the organic phase was washed with brine, dried and concentrated. The resultant residue was purified by a column chromatography on a silica gel (ethyl acetate:methanol=20:1) to obtain the title compound (190 mg) as a yellow solid.

$^1$H-NMR (CDCl$_3$) δ: 2.09 (3H, s), 4.54 (1H, d, J=5.2 Hz), 6.60 (1H, br), 7.17–7.28 (2H, m), 8.43 (1H, d, J=5.6 Hz).

Reference Example 37

4-Chloro-2-(1-hydroxy-1-methylethyl)pyridine

A 1.5 M solution of methyllithium in diethyl ether (6.0 ml) dissolved in diethyl ether (15 ml) was treated dropwise with a solution of 4-chloropyridine-2-carboxylic acid in diethyl ether (15 ml) under an argon atmosphere, and stirred at room temperature for 2 hours. The reaction mixture was diluted with a saturated solution of ammonium chloride and diethyl ether, and the organic phase was washed with brine, dried and concentrated. The resultant residue was purified by a column chromatography on a silica gel (ethyl acetate:methanol=20:1) to obtain the title compound (459 mg) as a tan oil.

$^1$H-NMR (CDCl$_3$) δ: 1.54 (6H, s), 4.56 (1H, s), 7.21 (1H, dd, J=1.9, 5.5 Hz), 7.41 (1H, d, J=1.4 Hz), 8.42 (1H, d, J=5.6 Hz).

Reference Example 38

Methyl 6-Methylpyridine-2-carboxylate N-oxide

A mixture of methyl 6-methylpyridine-2-carboxylate hydrochloride (5.8 g) and m-chloroperbenzoic acid (15.24 g) in dichloromethane (200 ml) was stirred at room temperature for 20 hours and 50° C. for 6 hours. After adding a small amount of sodium sulfite at 0° C., an aqueous solution of potassium carbonate was added to make the solution basic. The mixture was extracted with dichloromethane, and the organic phase was dried and concentrated. The resultant residue was purified by a column chromatography on a silica gel (ethyl acetate:hexane=5:1 to ethyl acetate:methanol=20:1) to obtain the title compound (2.29 g) as a tan oil.

$^1$H-NMR (CDCl$_3$) δ: 2.54 (3H, s), 4.01 (3H, s), 7.20 (1H, t, J=7.6 Hz), 7.35 (1H, dd, J=2.2, 8.0 Hz), 7.44 (1H, dd, J=2.2, 7.6 Hz).

Reference Example 39

Ethyl 4-Chloro-6-methylpyridine-2-carboxylate

A mixture of methyl 6-methylpyridine-2-carboxylate N-oxide (2.29 g), a 4N solution of hydrogen chloride in ethyl acetate (5 ml) and ethyl acetate (15 ml) was stirred at room temperature for 30 minutes. The reaction mixture was concentrated and the resultant residue was combined with phosphorus oxychloride (17.90 g), and stirred at 90° C. for 2 hours with heating. The reaction mixture was concentrated, and the resultant residue was diluted with ice-water and then combined with an aqueous solution of potassium carbonate to make the solution basic. The mixture was extracted with dichloromethane, and the organic phase was dried and concentrated. A solution of the residue obtained and triethylamine (5 ml) in ethanol (50) was heated under reflux for 10 hours. The reaction mixture was concentrated, and the residue was combined with water and ethyl acetate, and the organic phase was isolated, dried and concentrated to obtain the title compound (1.74 g) as a tan oil.

$^1$H-NMR (CDCl$_3$) δ: 1.44 (3H, t, J=7.2 Hz), 2.65 (3H, s), 4.47 (2H, q, J=7.1 Hz), 7.35 (1H, d, J=1.4 Hz), 7.94 (1H, d, J=1.8 Hz).

Reference Example 40

4-Chloro-2-hydroxymethyl-6-methylpyridine

A solution of ethyl 4-chloro-6-methylpyridine-2-carboxylate (0.80 g) in methanol (30 ml) was treated at room temperature portionwise with sodium borohydride (1.51 g) and the reaction mixture was heated under reflux for 2 hours. The reaction mixture was concentrated and the resultant residue was combined with water and ethyl acetate, and the organic phase was isolated, dried and concentrated to obtain the title compound (0.60 g) as a tan powder.

$^1$H-NMR (CDCl$_3$) δ: 2.54 (3H, s), 3.62 (1H, br), 4.70 (2H, s), 7.09 (2H, s).

Reference Example 41

2-(4-Chloro-2-pyridinyl)acetamide

A solution of 4-chloro-2-methylpyridine (1.28 g) in diethyl ether (15 ml) was treated at −70° C. dropwise with a 2M lithium diisopropylamide heptane/THF solution (6.0 ml) and stirred at −70° C. for 30 minutes. The mixture was treated dropwise also with diethyl carbonate (1.45 ml) at −70° C., and stirred at −70° C. for 1 hour. The reaction mixture was allowed to warm to room temperature, and combined with aqueous sodium bicarbonate and dichloromethane, and the organic phase was isolated, dried and concentrated. A mixture of the resultant residue and a 13% solution of ammonia in methanol (5 ml) was stirred at 75° C. for 7 hours. The reaction mixture was concentrated, and the resultant residue was triturated from diethylether to obtain the title compound (0.47 g) as a tan powder.

$^1$H-NMR (CDCl$_3$) δ: 3.73 (2H, s), 5.46 (1H, br), 7.06 (1H, br), 7.23–7.26 (1H, m), 7.32 (1H, d, J=2.0 Hz), 8.47 (1H, d, J=5.2 Hz).

Reference Example 42

1-(2-Hydroxymethyl-4-pyridyl)-4-piperidone

Similarly to Reference Example 8 but using 4-chloro-2-hydroxymethylpyridine (3.14 g) instead of 4-chloropydirine hydrochloride, the title compound (3.11 g) was obtained as a tan powder.

$^1$H-NMR (CDCl$_3$) δ: 2.57 (4H, t, J=6.1 Hz), 3.76 (4H, t, J=6.3 Hz), 4.68 (2H, s), 6.62–6.67 (2H, m), 8.27 (1H, d, J=5.4 Hz).

Reference Example 43

1-(tert-Butyl) 3-Methyl 5-oxo-4-[[1-(2-Hydroxymethyl-4-pyridinyl)-4-piperidinyl]amino]-1,3-piperazinedicarboxylate

Similarly to Reference Example 25 but using 1-(2-hydroxymethyl-4-pyridyl)-4-piperidone (1.51 g) instead of 1-(4-pyridinyl)-4-piperidone, the title compound (1.23 g) was obtained as a pale yellow non-crystalline powder.

$^1$H-NMR (CDCl$_3$) δ: 1.45 (9H, s), 1.84–1.90 (2H, m), 2.33 (3H, m), 2.89–3.01 (2H, m), 3.23–3.49 (3H, m), 3.76 (3H, s), .3.81–3.93 (3H, m), 4.15–4.27 (2H, m), 4.44–4.53 (2H, m), 4.63 (2H, m), 5.02 (1H, d, J=3.6 Hz), 6.57–6.59 (2H, m), 8.20 (1H, d, J=6.4, 2.2 Hz)

Reference Example 44

1-(2-Methyl-4-pyridyl)-4-piperidone

A mixture of piperidone hydrochloride hydrate (68.98 g), 4-chloro-2-picolin (47.7 g) and sodium acetate (36.8 g) in acetic acid (500 ml) was refluxed for 15 hours and then the reaction mixture was concentrated, and the resultant residue was dissolved in water, combined with potassium hydroxide to make alkaline, and then extracted with dichloromethane, dried and concentrated. The residue obtained was purified by a column chromatography on a silica gel (dichloromethane: 10% aqueous ammonia-containing methanol=30:1) to obtain the title compound (59.1 g) as a pale yellow oil.

$^1$H-NMR (CDCl$_3$) δ: 2.48 (3H, s), 2.56 (4H, t, J=6.2 Hz), 3.73 (4H, t, J=6.2 Hz), 6.54–6.60 (2H, m), 8.22 (1H, d, J=5.8 Hz).

Reference Example 45

Methyl 1-(tert-Butoxycarbonylamino)-4-[(6-chloro-2-naphthyl)sulfonyl]-6-oxo-2-piperazineacetate

A mixture of (6-chloro-naphthalene-2-sulfonyl)glycine tert-butyl ester (17.79 g), methyl 4-bromocrotonate (13.426 g) and potassium carbonate (8.28 g) in DMF (150 ml) was stirred at 50° C. for 1 hour. The reaction mixture was concentrated, and the residue was dissolved in ethyl acetate, washed with water and brine, dried and concentrated to obtain a residue, which was crystallized from ether to obtain methyl 4-[(tert-butoxycarbonylmethyl)(6-chloro-naphthalene-2-sulfonyl)amino]-2-butenoate (25.13 g) as colorless crystals.

$^1$H-NMR (CDCl$_3$) δ: 1.30 (9H, s), 3.71 (3H, s), 3.99 (2H, s), 4.14 (2H, dd, J=1.4, 5.4 Hz), 5.96 (1H, dt, J=17.8, 1.4 Hz), 6.81 (1H, dt, J=17.8, 5.4 Hz), 7.55 (1H, dd, J=8.8, 2.2 Hz), 7.80–7.95 (4H, m), 8.39 (1H, s).

A solution of methyl 4-[(tert-butoxycarbonylmethyl)(6-chloro-naphthalene-2-sulfonyl)amino]-2-butenoate (22.7 g) in toluene (30 ml) was combined with trifluoroacetic acid (30 ml) and stirred at room temperature for 1.5 hours. The reaction mixture was concentrated and the resultant residue was crystallized from ether-hexane to obtain methyl 4-[carboxymethyl(6-chloro-naphthalene-2-sulfonyl)amino]-2-butenate (19.35 g) as colorless crystals.

$^1$H-NMR (CDCl$_3$) δ: 3.71 (3H, s), 4.09 (2H, s), 4.12 (2H, d, J=5.8 Hz), 5.94 (1H, d, J=15.8 Hz), 6.75 (1H, dt, J=15.8, 5.8 Hz), 7.57 (1H, dd, J=8.8, 2.0 Hz), 7.75–7.95 (4H, m), 8.40 (1H, s)

A solution of methyl 4-[carboxymethyl(6-chloro-naphthalene-2-sulfonyl)amino]-2-butenate (796 mg), tert-butyl carbazate (265 mg) and HOBt (367 mg) in acetonitrile (20 ml) was combined with WSC (575 mg) and stirred at room temperature for 15 hours. The reaction mixture was concentrated and the residue was dissolved in ethyl acetate, washed with water and brine, dried, concentrated to obtain a residue, which was then crystallized from ether-hexane to obtain methyl 4-[[2-(N'-tert-butoxycarbonylhydrazino)-2-oxoethyl](6-chloro-naphthalene-2-sulfonyl)amino]-2-butenoate (1.05 g) as colorless crystals.

$^1$H-NMR (CDCl$_3$) δ: 1.47 (9H, s), 3.66 (3H, s), 3.95 (2H, s), 4.16 (2H, d, J=6.2 Hz), 5.91 (1H, d, J=15.8 Hz), 6.42 (1H, brs), 6.67 (1H, dt, J=15.8, 6.2 Hz), 7.58 (1H, dd, J=8.8, 1.8 Hz), 7.77–7.95 (4H, m), 8.12 (1H, brs), 8.41 (1H, s).

A solution of methyl 4-[[2-(N'-tert-butoxycarbonylhydrazino)-2-oxoethyl](6-chloro-naphthalene-2-sulfonyl)amino]-2-butenoate (500 mg) in THF (25 ml) was combined with potassium t-butoxide (22 mg) and stirred at 70° C. for 15 hours. The reaction mixture was concentrated and the residue was dissolved in ethyl acetate, washed with water and brine, dried and concentrated to obtain the title compound (500 mg) as a colorless amorphous material.

$^1$H-NMR (CDCl$_3$) δ: 1.43 (9H, s), 2.79 (1H, dd, J=16.4, 4.8 Hz), 2.92 (1H, dd, J=16.4, 8.4 Hz), 3.15 (1H, dd, J=12.4, 3.2 Hz), 3.49 (1H, d, J=16.6 Hz), 3.73 (3H, s), 3.92 (1H, brd, J=12.4 Hz), 4.11 (1H, m), 4.22 (1H, d, J=16.6 Hz), 6.57 (1H, brs), 7.61 (1H, dd, J=8.8, 1.8 Hz), 7.77 (1H, dd, J=8.8, 1.8 Hz), 7.90–8.00 (3H, m), 8.34 (1H, s).

IR (KBr): 1738, 1682, 1370, 1350, 1242, 1165 cm$^{-1}$.

Reference Example 46

Methyl 1-Amino-4-[(6-chloro-2-naphthyl)sulfonyl]-6-oxo-2-piperazineacetate

Methyl 1-(tert-butoxycarbonylamino)-4-[(6-chloro-2-naphthyl)sulfonyl]-6-oxo-2-piperazineacetate (500 mg) was combined with a 4N solution of hydrochloric acid in ethyl acetate (10 ml) and stirred at room temperature for 3 hours. The reaction mixture was concentrated and the residue was combined with an aqueous solution of sodium hydrogen carbonate, extracted with dichloromethane, dried and concentrated to obtain the title compound (373 mg) as a colorless solid.

$^1$H-NMR (CDCl$_3$) δ: 2.80 (1H, dd, J=16.4, 8.4 Hz), 2.93 (1H, dd, J=16.4, 6.0 Hz), 3.07 (1H, dd, J=12.4, 3.2 Hz), 3.47 (1H, d, J=16.2 Hz), 3.72 (3H, s), 3.85 (1H, m), 3.99 (1H, m), 4.15 (1H, dd, J=16.2, 1.6 Hz), 4.20 (2H, brs), 7.61 (1H, dd, J=8.8, 1.8 Hz), 7.78 (1H, dd, J=8.8, 1.8 Hz), 7.90–8.00 (3H, m), 8.34 (1H, s).

Reference Example 47

Methyl 1-(tert-Butoxycarbonylamino)-6-oxo-4-(4-vinylbenzenesulfonyl)-2-piperazineacetate

Similarly to Reference Example 45 and starting from 4-vinylbenzenesulfonyl glycine tert-butyl ester, the title compound was obtained as colorless crystals.

$^1$H-NMR (CDCl$_3$) δ: 1.44 (9H, s), 2.70–3.00 (2H, m), 3.09 (1H, dd, J=12.8, 3.2 Hz), 3.42 (1H, d, J=16.4 Hz), 3.74 (3H, s), 3.79 (1H, m), 4.05–4.20 (2H, m), 5.48 (1H, d, J=11.0 Hz), 5.92 (1H, d, J=17.6 Hz), 6.60 (1H, brs), 6.77 (1H, dd, J=17.6, 11.0 Hz), 7.57 (2H, d, J=8.6 Hz), 7.73 (2H, d, J=8.6 Hz).

Reference Example 48

Methyl 1-Amino-6-oxo-4-(4-vinylbenzenesulfonyl)-2-piperazineacetate

Similarly to Reference Example 46 and starting from methyl 1-(tert-butoxycarbonylamino)-6-oxo-4-(4- vinylbenzenesulfonyl)-2-piperazineacetate (11.66 g), the title compound (8.89 g) as a colorless syrup was obtained.

$^1$H-NMR (CDCl$_3$) δ: 2.70–3.00 (2H, m), 3.02 (1H, dd, J=12.8, 3.8 Hz), 3.41 (1H, d, J=16.0 Hz), 3.73 (3H, s), 3.75 (1H, m), 3.93–4.20 (2H, m), 4.22 (2H, s), 5.48 (1H, d, J=11.0 Hz), 5.91 (1H, d, J=17.6 Hz), 6.76 (1H, dd, J=17.6, 11.0 Hz), 7.57 (2H, d, J=8.4 Hz), 7.73 (2H, d, J=8.4 Hz).

Example 1

6-Chloro-N-methyl-N-(2-{2-[1-(4-pyridyl)-4-piperidinyl]hydrazino}-2-oxoethyl)-2-naphthalenesulfonamide A solution of 1-(4-pyridyl)-4-piperidone (3.52 g) and hydrazine hydrate (1.25 q) in ethanol (50 ml) was stirred at room temperature for 15 hours. The reaction mixture was concentrated and the residue obtained was crystallized from ether to obtain [1-(4-pyridyl)-4-piperidinylidene]hydrazine (3.51 g) as colorless crystals.

$^1$H-NMR (CDCl$_3$) δ: 2.50 (2H, t, J=6.2 Hz), 2.61 (2H, t, J=6.2 Hz), 3.54 (2H, t, J=6.2 Hz), 3.62 (2H, t, J=6.2 Hz), 4.98 (2H, br), 6.60 (2H, d, J=6.6 Hz), 8.26 (2H, d, J=6.6 Hz).

A solution of [1-(4-pyridyl)-4-piperidinylidene]hydrazine (1.90 g) and 1-(tert-butoxycarbonyl)sarcosine (1.90 g) in DMF (40 ml) was combined with WSC (2.30 g) and stirred at room temperature for 15 hours. The reaction mixture was concentrated and the residue obtained was combined with aqueous sodium bicarbonate, extracted with ethyl acetate, dried and concentrated to obtain a residue, which was purified by a column chromatography on a silica gel (dichloromethane: 10% aqueous ammonia-containing methanol=30:1) to obtain 1-[(tert-butoxycarbonyl)sarcosinyl]-2-[1-(4-pyridyl)-4-piperidinylidene]hydrazine (1.0 g) as an oil.

$^1$H-NMR (CDCl$_3$) δ: 1.48 (9H, s), 2.45–2.80 (4H, m), 2.90–3.00 (3H, m), 3.50–3.70 (4H, m), 3.90 (2H ×3/5, s), 4.30 (2H ×1/5, s), 4.36 (2H ×1/5, s), 6.62 (2H, d, J=6.6 Hz), 8.29 (2H, d, J=6.6 Hz).

The resultant 1-[(tert-butoxycarbonyl)sarcosinyl]-2-[1-(4-pyridyl)-4-piperidinylidene]hydrazine (1.0 g) was dissolved in methanol (20 ml) and treated with acetic acid (665 mg) with cooling on ice, followed by sodium cyanoborohydride (261 mg) and stirred at room temperature for 30 minutes. The reaction mixture was concentrated and the residue was dissolved in dichloromethane, washed with aqueous sodium bicarbonate and brine, dried and concentrated to obtain 1-[(tert-butoxycarbonyl)sarcosinyl]-2-[1-(4-pyridyl)-4-piperidinyl]hydrazine (1.0 g) as a colorless oil.

$^1$H-NMR (CDCl$_3$) δ: 1.46 (2H, m), 1.47 (9H, s), 1.90 (2H, m), 2.93 (2H, m), 2.96 (3H, s), 3.11 (1H, m), 3.81 (2H, m), 3.88 (2H, s), 4.55 (1H, brs), 6.65 (2H, d, J=6.6 Hz), 7.70 (1H, br), 8.25 (2H, d, J=6.6 Hz).

1-[(tert-Butoxycarbonyl)sarcosinyl]-2-[1-(4-pyridyl)-4-piperidinyl]hydrazine (1.0 g) was combined with methanol (12 ml) and a 4N solution of hydrochloric acid in ethyl acetate (6 ml), and stirred at room temperature for 30 minutes. The reaction mixture was concentrated and the residue was combined with aqueous sodium bicarbonate, extracted with dichloromethane, dried and concentrated to obtain 1-methylaminoacetyl-2-[1-(4-pyridyl)-4-piperidinyl]hydrazine (1.04 g) as a colorless solid.

A solution of the resultant 1-methylaminoacetyl-2-[1-(4-pyridyl)-4-piperidinyl]hydrazine trihydrochloride (200 mg) in dichloromethane (15 ml and a 10% aqueous solution of sodium carbonate (15 ml) was combined at 0° C. with 6-chloronaphthalene-2-sulfonyl chloride (150 mg) and stirred at room temperature for 30 minutes. The organic phase was isolated, washed with brine, dried and concentrated. The residue obtained was purified by a column chromatography on a silica gel (dichloromethane: 10% aqueous ammonia-containing methanol=20:1) to obtain the title compound (108 mg) as colorless crystals.

$^1$H-NMR (CDCl$_3$) δ: 1.51 (2H, m), 1.94 (2H, m), 2.88 (3H, s), 2.98 (2H, m), 3.15 (1H, m), 3.74 (2H, s), 3.83 (2H, m), 4.57 (1H, brs), 6.67 (2H, d, J=6.6 Hz), 7.61 (1H, dd, J=1.8, 8.8 Hz), 7.79 (1H, dd, J=1.8, 8.8 Hz), 7.90–8.05 (4H, m), 8.26 (2H, d, J=6.6 Hz), 8.36 (1H, s).

Example 2

6-Chloro-N-methyl-N-(2-{1-methyl-(4-pyridyl)-4-piperidinyl]hydrazino}-2-oxoethyl)-2-naphthalenesulfonamide Similarly to Example 1 but using methylhydrazine instead of hydrazine hydrate, the title compound (204 mg) was obtained as colorless crystals.

$^1$H-NMR (CDCl$_3$) δ: 1.48 (2H, m), 1.83 (2H, m), 2.91 (2H, m), 2.93 (3H×4/5, s), 3.08 (3H×4/5, s), 3.21 (1H, m), 3.30 (3H×1/5, s), 3.50 (3H×1/5, s), 3.84 (2H, m), 4.02 (2H×1/5, s), 4.34 (2H×4/5, s), 6.67 (2H, d, J=6.6 Hz), 7.52 (1H, dd, J=1.8, 8.8 Hz), 7.80–7.96 (4H, m), 8.29 (2H, d, J=6.6 Hz), 8.39 (1H, s).

Example 3

4-(6-Chloronaphthalene-2-sulfonyl)-1-[1-(4-pyridyl)-4-piperidinylideneamino]-2-piperazinone 1-(tert-Butoxycarbonylamino)-4-(6-chloronaphthalene-2-sulfonyl)-2-piperazinone (575 mg) was combined with methanol (4 ml) and a 4N solution of hydrochloric-acid in ethyl acetate (4 ml) and stirred at room temperature for 30 minutes. The reaction mixture was concentrated and the residue obtained was combined with aqueous sodium bicarbonate, extracted with dichloromethane, dried and concentrated to obtain 1-amino-4-(6-chloronaphthalene-2-sulfonyl)-2-piperazinone as a colorless solid. A solution of the resultant 1-amino-4-(6-chloronaphthalene-2-sulfonyl)-2-piperazinone and 1-(4-pyridyl)-4-piperidone (237 mg) in ethanol (30 ml) was dehydrated using a Soxlet extractor packed with molecular sieves 4A while refluxing for 24 hours. The reaction mixture was concentrated and the residue was purified by a column chromatography (dichloromethane: 10% aqueous ammonia-containing methanol=20:1) and crystallized from ether to obtain the title compound (265 mg) as colorless crystals.

$^1$H-NMR (CDCl$_3$) δ: 2.21 (2H, m), 2.61 (2H, m), 3.43 (2H, m), 3.50–3.70 (6H, m), 3.88 (2H, s), 6.60 (2H, d, J=6.4 Hz), 7.62 (1H, dd, J=1.8, 8.8 Hz), 7.82 (1H, dd, J=1.8, 8.8 Hz), 7.90–8.00 (3H, m), 8.29 (2H, d, J=6.4 Hz), 8.39 (1H, s).

IR (KBr): 1651, 1597, 1346, 1161 cm$^{-1}$.

Example 4

4-(6-Chloronaphthalene-2-sulfonyl)-1-[1-(4-pyridyl)-4-piperidinylamino]-2-piperazinone A solution of 4-(6-chloronaphthalene-2-sulfonyl)-1-[1-(4-pyridyl)-4-piperidinylideneamino]-2-piperazinone (120 mg) in trifluoroacetic acid (1 ml) was combined with triethylsilane (60 mg) and stirred at 50° C. for 4 hours. The reaction mixture was concentrated and the residue was combined with an ice-cooled 1 N aqueous solution of sodium hydroxide, extracted with dichloromethane, dried and then concentrated. The residue obtained was purified by a column chromatography (dichloromethane: 10% aqueous ammonia-containing methanol=20:1) and crystallized from acetone to obtain the title compound (88 mg) as colorless crystals.

$^1$H-NMR (CDCl$_3$) δ: 1.42 (2H, m), 1.74 (2H, m), 2.85 (2H, m), 3.15 (1H, m), 3.46 (2H, m), 3.61 (2H, m), 3.78 (2H, m), 3.86 (2H, s), 5.07 (1H, brs), 6.62 (2H, d, J=6.2 Hz), 7.62 (1H, dd, J=1.8, 8.8 Hz), 7.80 (1H, dd, J=1.8, 8.8 Hz), 7.90–8.00 (3H, m), 8.24 (2H, d, J=6.2 Hz), 8.38 (1H, s).

IR (KBr): 1651, 1597, 1348, 1163 cm$^{-1}$.

Example 5

4-(7-Chloro-2H-benzopyran-3-sulfonyl)-1-[1-(4-pyridyl)-4-piperidinylideneamino]-2-piperazinone Similarly to Example 3 and starting from 1-(tert-butoxycarbonylamino)-4-(7-chloro-2H-benzopyran-3-sulfonyl)-2-piperazinone (1.45 g), the title compound (700 mg) was obtained as colorless crystals.

$^1$H-NMR (CDCl$_3$) δ: 2.40 (2H, m), 2.67 (2H, m), 3.55 (2H, m), 3.67 (2H, m), 3.71 (4H, s), 3.97 (2H, s), 4.90 (2H, s), 6.67 (2H, d, J=6.6 Hz), 6.94 (1H, d, J=2.0 Hz), 7.01 (1H, dd, J=2.0, 8.0 Hz), 7.15 (1H, d, J=8.0 Hz), 7.31 (1H, s), 8.30 (2H, d, J=6.6 Hz).

IR (KBr): 1651, 1599, 1348, 1325, 1155 cm$^{-1}$.

Example 6

4-(7-Chloro-2H-benzopyran-3-sulfonyl)-1-[1-(4-pyridyl)-4-piperidinylaminol-2-piperazinone Similarly to Example 4 and starting from 4-(7-chloro-2H-benzopyran-3-sulfonyl)-1-[1-(4-pyridyl)-4-piperidinylideneamino]-2-piperazinone (500 mg), the title compound (405 mg) was obtained as colorless crystals.

$^1$H-NMR (CDCl$_3$) δ: 1.46 (2H, m), 1.89 (2H, m), 2.91 (2H, m), 3.24 (1H, m), 3.55–3.70 (4H, m), 3.83 (2H, m), 3.96 (2H, s), 4.89 (2H, s), 5.16 (1H, brs), 6.64 (2H, d, J=6.6 Hz), 6.93 (1H, d, J=2.0 Hz), 7.00 (1H, dd, J=2.0, 8.0 Hz), 7.14 (1, d, J=8.0 Hz), 7.30 (1H, s), 8.25 (2H, d, J=6.6 Hz).

Example 7

N-[4-(7-Chloro-2H-benzopyran-3-sulfonyl)-2-oxo-1-piperazinyl]-N-[1-(4-pyridyl)-4-piperidinyl] formamide A solution of 4-(7-chloro-2H-benzopyran-3-sulfonyl)-1-[1-(4-pyridyl)-4-piperidinylaminol-2-piperazinone (100 mg) in formic acid (4 ml) was refluxed for 15 hours. The reaction mixture was concentrated and the residue was dissolved in dichloromethane, washed with a 1N aqueous solution of sodium hydroxide, dried and concentrated. The residue obtained was crystallized from dichloromethane/ether to obtain the title compound (91 mg) as colorless crystals.

$^1$H-NMR (CDCl$_3$) δ: 1.60–2.20 (4H, m), 2.90 (2H, m), 3.60–4.10 (9H, m), 4.89 (2H×1/2, d, J=1.0 Hz), 4.91 (2H×1/2, d, J=1.0 Hz), 6.65 (2H, m), 6.92 (1H, m), 6.95–7.04 (1H, m), 7.14 (1H, ×1/2, d, J=8.4 Hz), 7.15 (1H×1/2, d, J=8.2 Hz), 7.30 (1H ×1/2, s), 7.33 (1H×1/2, s), 8.05 (1H×1/2, s), 8.22 (1H×1/2, s), 8.24–8.34 (2H, m).

IR (KBr): 1698, 1676, 1599, 1151 cm$^{-1}$.

Example 8

N-(4-(7-Chloro-2H-benzopyran-3-sulfonyl)-2-oxo-1-piperazinyl]-N-[1-(4-pyridyl)-4-piperidinyl] acetamide Hydrochloride A solution of 4-(7-chloro-2H-benzopyran-3-sulfonyl)-1-[1-(4-pyridyl)-4-piperidinylamino]-2-piperazinone (95 mg) in acetic anhydride (4 ml) was stirred at 80° C. for 10 hours. The reaction mixture was concentrated and the residue obtained was combined with a 1N aqueous solution of sodium hydroxide and extracted with dichloromethane. The organic phase was washed with aqueous sodium bicarbonate and brine, dried and concentrated to obtain N-[(7-chloro-2H-benzopyran-3-sulfonyl)-2-oxo-1-piperazinyl]-N-[1-(4-pyridyl)-4-piperidinyllacetamide. The resultant free form was dissolved in ethyl acetate, and combined with a solution of hydrochloric acid in ethyl acetate to form a precipitate, which was collected by filtration, washed with ethyl acetate, dried under reduced pressure to obtain the title compound (90 mg) as a colorless solid.

$^1$H-NMR (DMSO-d$_6$) δ: 1.60–2.20 (7H, m), 3.05–4.05 (8H, m), 4.20–4.50 (3H, m), 5.00 (2H, s), 7.00–7.20 (4H, m), 7.40–7.55 (2H, m), 8.21 (2H, d, J=6.6 Hz).

Example 9

4-(6-Chloronaphthalene-2-sulfonyl)-1-[1-(4-pyridyl)-4-piperidinylaminol-2-piperazinone Hydrochloride A suspension of 4-(6-chloronaphthalene-2-sulfonyl)-1-[1-(4-pyridyl)-4-piperidinylamino]-2-piperazinone (500 ml) in methanol (20 ml) was combined with a 4N solution of hydrochloric acid in ethyl acetate (1 ml) to effect a dissolution, and then the solution was concentrated. The residue was combined with ethanol, crystallized, filtered and dried to obtain the title compound (526 mg) as a colorless solid.

$^1$H-NMR (DMSO-d$_6$) δ: 1.10–1.30 (2H, m), 1.60–1.75 (2H, m), 3.00–3.60 (8H, m), 3.77 (2H, s), 3.90–4.05 (2H, m), 7.13 (2H, d, J=7.6 Hz), 7.76 (1H, dd, J=1.8, 8.8 Hz), 7.91 (1H, dd, J=1.8, 8.8 Hz), 8.15–8.25 (3H, m), 8.28–8.33 (2H, m), 8.61 (1H, s).

Example 10

1-[1-(4-Pyridyl)-4-piperidinylideneamino]-4-(4-vinylphenylsulfonyl)-2-piperazinone Similarly to Example 3 and starting from 1-(tert-butoxycarbonylamino)-4-(4-vinylphenylsulfonyl)-2-piperazinone (2.1 g), the title compound (1.4 g) was obtained as colorless crystals.

$^1$H-NMR (CDCl$_3$) δ: 2.29 (2H, t, J=5.8 Hz), 2.63 (2H, t, J=5.8 Hz), 3.43–3.55 (4H, m), 3.60–3.70 (4H, m), 3.81 (2H, s), 5.49 (1H, d, J=11.0 Hz), 5.93 (1H, d, J=17.6 Hz), 6.66 (2H, d, J=6.6 Hz), 6.78 (1H, dd, J=11.0, 17.6 Hz), 7.59 (2H, d, J=8.6 Hz), 7.77 (2H, d, J=8.6 Hz), 8.30 (2H, d, J=6.6 Hz).

Example 11

1-[1-(4-Pyridyl)-4-piperidinylamino]-4-(4-vinylphenylsulfonyl)-2-piperazinone

1-[1-(4-Pyridyl)-4-piperidinylideneamino]-4-(4-vinylphenylsulfonyl)-2-piperazinone (200 mg) was dissolved in methanol (10 ml), combined with acetic acid (110 mg) with cooling on ice followed by sodium cyanoborohydride (57 mg), and stirred at room temperature for 30 minutes. The reaction mixture was concentrated and the residue was dissolved in dichloromethane, washed with aqueous sodium bicarbonate and brine, dried, concentrated and purified by a column chromatography (dichloromethane: 10% aqueous ammonia-containing methanol=20:1) to obtain the title compound (150 mg) as a colorless amorphous material.

¹H-NMR (CDCl₃) δ: 1.46 (2H, m), 1.80 (2H, m), 2.88 (2H, m), 3.17 (1H, m), 3.37 (2H, m), 3.60 (2H, m), 3.80 (2H, s), 3.82 (2H, m), 5.08 (1H, d, J=4.8 Hz), 5.49 (1H, d, J=11.0 Hz), 5.92 (1H, d, J=17.6 Hz), 6.63 (2H, d, J=6.6 Hz), 6.77 (1H, dd, J=11.0, 17.6 Hz), 7.58 (2H, d, J=8.6 Hz), 7.76 (2H, d, J=8.6 Hz), 8.25 (2H, d, J=6.6 Hz).

Example 12

1-(1-Acetoimidoyl-4-piperidinylamino)-4-(6-chloronaphthalene-2-sulfonyl)-2-piperazinone Hydrochloride 1-[1-(tert-Butoxycarbonyl)-4-piperidinylamino]-4-(6-chloronaphthalene-2-sulfonyl)-2-piperazinone (300 mg) was combined with a 4N solution of hydrochloric acid in ethyl acetate (10 ml) and stirred at room temperature for 30 minutes. The reaction mixture was concentrated to obtain a crude crystal of 4-(6-chloronaphthalene-2-sulfonyl)-1-(4-piperidinylamino)-2-piperazinone hydrochloride. A solution of the resultant 4-(6-chloronaphthalene-2-sulfonyl)-1-(4-piperidinylamino)-2-piperazinone hydrochloride and triethylamine (1.16 g) in methanol (15 ml) was combined with ethyl acetoimidate (712 mg) and stirred at room temperature for 15 hours. The reaction mixture was concentrated and the residue was dissolved in dichloromethane, washed with a 1N aqueous solution of sodium hydroxide, dried and concentrated. The resultant residue was dissolved in ethyl acetate, combined with a solution of hydrochloric acid in ethyl acetate to precipitate a hydrochloride, which was collected by filtration and dried to obtain the title compound (243 mg) as a colorless solid.

¹H-NMR (DMSO-d₆) δ: 1.27 (2H, m), 1.68 (2H, m), 2.23 (3H, s), 3.00–3.23 (3H, m), 3.43 (4H, s), 3.65 (1H, m), 3.75 (2H, s), 3.91 (2H, m), 4.05 (1H, m), 7.75 (1H, dd, J=2.0, 8.8 Hz), 7.90 (1H, dd, J=2.0, 8.8 Hz), 8.19 (1H, d, J=8.8 Hz), 8.25–8.33 (2H, m), 8.60 (1H, s), 8.71 (1H, s), 9.29 (1H, s).

Example 13

1-[1-(2-Amino-4-pyrimidinyl)-4-piperidnylideneamino]-4-(6-chloronaphthalene-2-sulfonyl)-2-piperazinone Similarly to Example 3, a solution of 1-amino-4-(6-chloronaphthalene-2-sulfonyl)-2-piperazinone (320 mg) and 1-(2-amino-4-pyridinyl)-4-piperidone (173 mg) in 1-butanol (30 ml) was dehydrated using a Soxlet extractor packed with molecular sieves 4A while refluxing for 18 hours. The reaction mixture was concentrated and the residue was purified by a column chromatography (dichloromethane: 10% aqueous ammonia-containing methanol=20–1) and crystallized from ethyl acetate and ether to obtain the title compound (185 mg) as colorless crystals.

¹H-NMR (CDCl₃) δ: 2.14–2.20 (2H, m), 2.53–2.59 (2H, m), 3.50–3.70 (6H, m), 3.76–3.82 (2H, m), 3.87 (2H, s), 4.69 (2H, brs), 5.96 (1H, d, J=5.8 Hz), 7.62 (1H, dd, J=8.8, 1.8 Hz), 7.82 (1H, dd, J=8.8, 1.8 Hz), 7.91 (1H, d, J=5.8 Hz), 7.95 (1H, d, J=1.8 Hz), 7.95 (2H, d, J=8.8 Hz), 8.38 (1H, d, J=1.8 Hz).

IR (KBr): 1660, 1590, 1550, 1490, 146b, 1450 cm⁻¹.

Example 14

1-[1-(2-Amino-4-pyrimidinyl)-4-piperidinylamino]-4-(6-chloronaphthalene-2-sulfonyl)-2-piperazinone Similarly to Example 4 and starting from 1-[1-(2-amino-4-pyrimidinyl)-4-piperidinylideneamino]-4-(6-chloronaphthalene-2-sulfonyl)-2-piperazinone (120 mg), the title compound (61 mg) was obtained as colorless crystals.

¹H-NMR (CDCl₃) δ: 1.20–1.40 (2H, m), 1.68–1.78 (2H, m), 2.76–2.90 (2H, m), 3.02–3.22 (1H, m), 3.41–3.47 (2H, m), 3.57–3.62 (2H, m), 3.85 (2H, s), 4.17–4.24 (2H, m), 4.62 (2H, brs), 5.06 (1H, d, J=4.8 Hz), 5.92 (1H, d, J=6.4 Hz), 7.62 (1H, dd, J=8.8, 1.8 Hz), 7.80 (1H, dd, J=8.8, 1.8 Hz), 7.86 (1H, d, J=6.4 Hz), 7.95 (1H, d, J=1.8 Hz), 7.95 (2H, d, J=8.8 Hz), 8.37 (1H, d, J=1.8 Hz).

IR (KBr): 1655, 1588, 1549, 1495, 1449 cm⁻¹.

Example 15

4-(8-Chloro-2,3-dihydrobenzo[b]oxepine-4-sulfonyl)-1-[1-(4-pyridyl-4-piperizinylamino]-2-pioerazinone A solution of 1-[1-(4-pyridyl)-4-piperidinylamino]-2-piperazinone trihydrochloride (385 mg) obtained in Reference Example 13 in dichloromethane (15 ml) and a 10% aqueous solution of sodium carbonate (15 ml) was combined at 0° C. with 8-chloro-2,3-dihydrobenzo[b]oxepine-4-sulfonyl chloride (307 mg) and stirred at room temperature for 3 hours. The organic phase was isolated, washed with brine, dried and concentrated. The residue obtained was purified by a column chromatography on a silica gel (dichloromethane: 10% aqueous ammonia-containing methanol=15:1) and crystallized from ethanol and ether to obtain the title compound (298 mg) as colorless crystals.

¹H-NMR (CDCl₃) δ: 1.38–1.57 (2H, m), 1.82–1.97 (2H, m), 2.87–3.00 (4H, m), 3.15–3.35 (1H, m), 3.57–3.66 (4H, m), 3.82–3.89 (2H, m), 3.94 (2H, s), 4.31 (2H, t, J=4.6 Hz), 5.17 (1H, d, J=4.8 Hz), 6.66 (2H, d, J=6.6 Hz), 7.05 (1H, d, J=2.2 Hz), 7.07 (1H, dd, J=7.8, 2.2 Hz), 7.28 (1H, d, J=7.8 Hz), 7.39 (1H, s), 8.25 (2H, d, J=6.6 Hz).

IR (KBr): 3280, 2928, 1653, 1599, 1557, 1543, 1514, 1483, 1410 cm⁻¹.

Example 16

4-(6-Bromonaphthalene-2-sulfonyl)-1-[1-(4-pyridyl)-4-piperidinylamino]-2-piperazinone Similarly to Example 15 and using 6-bromonaphthalene-2-sulfonyl chloride (101 mg) instead of 8-chloro-2,3-dihydrobenzo[b]oxepine-4-sulfonyl chloride, the title compound (83 mg) was obtained as colorless crystals.

¹H-NMR (CDCl₃) δ: 1.31–1.47 (2H, m), 1.72–1.77 (2H, m), 2.76–2.89 (2H, m), 3.02–3.22 (1H, m), 3.43–3.48 (2H, m), 3.57–3.63 (2H, m), 3.70–3.80 (2H, m), 3.87 (2H, s), 5.07 (1H, d, J=4.4 Hz), 6.61 (2H, d, J=6.2 Hz), 7.75 (1H, dd, J=8.8, 1.8 Hz), 7.80 (1H, dd, J=8.8, 1.8Hz), 7.89 (1H, d, J=8.8 Hz), 7.94 (1H, d, J 8.8 Hz), 8.14 (1H, d, J=1.8 Hz), 8.25 (2H, d, J=6.2 Hz), 8.36 (1H, d, J=1.8 Hz).

IR (KBr): 2928, 1651, 1595, 1539, 1514, 1454, 1422 cm⁻¹.

Example 17

4-[2(E)-(4-Chlorophenyl)ethenesulfonyl]-1-[1-(4-pyridyl)-4-piperidinylamino]-2-piperazinone Similarly to Example 15 and using 2(E)-(4-chlorophenyl)ethenesulfonyl chloride (223 mg) instead of 8-chloro-2,3-dihydrobenzo[bloxepine-4-sulfonyl chloride, the title compound (8 mg) was obtained as colorless crystals.

¹H-NMR (CDCl₃) δ: 1.37–1.56 (2H, m), 1.84–1.91 (2H, m), 2.83–2.97 (2H, m), 3.13–3.30 (1H, m), 3.53–3.58 (2H, m), 3.63–3.68 (2H, m), 3.79–3.86 (2H, m), 3.95 (2H, s), 5.10–5.25 (1H, br), 6.66 (2H, brs), 6.67 (1H, d, J=15.4 Hz), 7.41 (2H, d, J=9.4 Hz), 7.46 (2H, d, J=9.4 Hz), 7.50 (1H, d, J=15.4 Hz), 8.25 (2H, brs).

IR (KBr): 2924, 1645, 1541, 1489, 1456, 1422 cm$^{-1}$.

Example 18

4-(5-Chloro-3-methylbenzo[b]thiophene-2-sulfonyl)-1-[1-(4-pyridyl)-4-piperidinylamino]-2-piperazinone Similarly to Example 15 and using 5-chloro-3-methylbenzo[b]thiophene-2-sulfonyl chloride (149 mg) instead of 8-chloro-2,3-dihydrobenzo[b]oxepine-4-sulfonyl chloride, the title compound (158 mg) was obtained as colorless crystals.

$^1$H-NMR (CDCl$_3$) δ: 1.34–1.51 (2H, m), 1.75–1.82 (2H, m), 2.72 (3H, s), 2.77–2.90 (2H, m), 3.10–3.28 (1H, m), 3.54–3.65 (4H, m), 3.74–3.81 (2H, m), 3.98 (2H, s), 5.11 (1H, d, J=4.8 Hz), 6.62 (2H, d, J=6.6 Hz), 7.51 (1H, dd, J=8.8, 2.2 Hz), 7.79 (1H, d, J=8.8 Hz), 7.84 (1H, d, J=2.2 Hz), 8.25 (2H, d, J=6.6 Hz).

IR (KBr): 2924, 1655, 1649, 1642, 1597, 1545, 1512, 1422 cm$^{-1}$.

Example 19

4-(6-Chloronaphthalene-2-sulfonyl)-1-[1-(4-pyridyl)-4-piperidinylamino]-2-piperazinone Similarly to Example 15 and using 6-chloronaphthalene-2-sulfonyl chloride (4.75 g) instead of 8-chloro-2,3-dihydrobenzo[b]oxepine-4-sulfonyl chloride, the title compound (5.82 g) was obtained as colorless crystals.

Example 20

4-(2-Acetamide-4-methylthiazole-5-sulfonyl)-1-(1-(4-pyridyl)-4-piperidinylamino]-2-piperazinone Similarly to Example 15 and using 2-acetamide-4-methylthiazole-5-sulfonyl chloride (105 mg) instead of 8-chloro-2,3-dihydrobenzo[b]oxepine-4-sulfonyl chloride, the title compound (58 mg) was obtained as a colorless amorphous material.

$^1$H-NMR (CDCl$_3$) δ: 1.48 (2H, m), 1.86 (2H, m), 2.32 (3H, s), 2.55 (3H, s), 2.92 (2H, m), 3.10–3.35 (2H, m), 3.52 (2H, m), 3.62 (2H, m), 3.86 (2H, m), 3.90 (2H, s), 5.20 (1H, d, J=4.4 Hz), 6.66 (2H, d, J=6.6 Hz), 8.28 (2H, d, J=6.6 Hz).

Example 21

4-(9-Chloro-2,3-dihydrobenzo[b]oxepine-4-sulfonyl)-1-[1-(4-pyridyl)-4-piperidinylamino]-2-piperazinone Similarly to Example 15 and using 9-chloro-2,3-dihydrobenzo(b]oxepine-4-sulfonyl chloride (304 mg) instead of 8-chloro-2,3-dihydrobenzo(bloxepine-4-sulfonyl chloride, the title compound (312 mg) was obtained as colorless crystals.

$^1$H-NMR (CDCl$_3$) δ: 1.38–1.57 (2H, m), 1.85–1.92 (2H, m), 2.85–2.99 (2H, m), 3.02 (2H, t, J=4.8 Hz), 3.18–3.30 (1H, m), 3.57–3.66 (4H, m), 3.81–3.88 (2H, m), 3.95 (2H, s), 4.41 (2H, t, J=4.8 Hz), 5.16 (1H, d, J=4.8 Hz), 6.65 (2H, d, J=6.6 Hz), 7.03 (1H, t, J=8.0 Hz), 7.28 (1H, dd, J=8.0, 1.8 Hz), 7.42 (1H, s), 7.45 (1H, dd, J=8.0, 1.8 Hz), 8.26 (2H, d, J=6.6 Hz).

IR (KBr): 2942, 1651, 1597, 1539, 1510, 1472, 1443, 1418 cm$^{-1}$.

Example 22

4-(5-Chlorobenzo[b]furan-2-sulfonyl)-1-(1-(4-pyridyl)-4-piperidinylamina]-2-piperazinone Similarly to Example 15 and using 5-chlorobenzo(b]furan-2-sulfonyl chloride (201 mg) instead of 8-chloro-2,3-dihydrobenzo[b]oxepine-4-sulfonyl chloride, the title compound (97 mg) was obtained as colorless crystals.

$^1$H-NMR (CDCl$_3$) δ: 1.43–1.62 (2H, m), 1.87–1.94 (2H, m), 2.87–3.02 (2H, m), 3.10–3.35 (1H, m), 3.72–3.77 (2H, m), 3.83–3.89 (2H, m), 3.97–4.02 (2H, m), 4.41 (2H, s), 5.19 (1H, d, J=4.8 Hz), 6.66 (2H, d, J=6.6 Hz), 6.89 (1H, s), 6.93 (1H, d, J=8.8 Hz), 7.08 (1H, d, J=2.2 Hz), 7.09 (1H, dd, J=8.8, 2.2 Hz), 8.26 (2H, d, J=6.6 Hz).

IR (KBr): 1640, 1601, 1514, 1476, 1449, 1416 cm$^{-1}$.

Example 23

4-(6-Chlorobenzo[b]thiophene-2-sulfonyl)-1-[1-(4-pyridyl)-4-piperidinylamino]-2-piperazinone Similarly to Example 15 and using 6-chlorobenzo[b]thiophene-2-sulfonyl chloride (294 mg) instead of 8-chloro-2,3-dihydrobenzo[b]oxepine-4-sulfonyl chloride, the title compound (321 mg) was obtained as colorless crystals.

$^1$H-NMR (CDCl$_3$) δ: 1.32–1.50 (2H, m), 1.73–1.82 (2H, m), 2.80–2.93 (2H, m), 3.05–3.22 (1H, m), 3.49–3.62 (4H, m), 3.77–3.83 (2H, m), 3.90 (2H, s), 5.07 (1H, d, J=4.8 Hz), 6.63 (2H, d, J=6.6 Hz), 7.51 (1H, dd, J=8.8, 1.8 Hz), 7.93 (1H, d, J=1.8 Hz), 8.17 (1H, d, J=8.8 Hz), 8.25 (1H, s), 8.25 (2H, d, J=6.6 Hz).

IR (KBr): 1651, 1597, 1543, 1512, 1478, 1449, 1422 cm$^{-1}$.

Example 24

4-(6-Bromonaphthalene-2-sulfonyl)-1-(1-(4-pyridyl)-4-piperidinylamino]-2-piperazinone dihydrochloride Similarly to Example 9 and starting from 4-(6-bromonaphthalene-2-sulfonyl)-1-[1-(4-pyridyl)-4-piperidinylamino]-2-piperazinone (1.10 g), the title compound (1.26 g) was obtained as a colorless solid.

$^1$H-NMR (DMSO-d$_6$) δ: 1.10–1.30 (2H, m), 1.65–1.71 (2H, m), 3.07–3.20 (3H, m), 3.39–3.50 (4H, m), 3.78 (2H, s), 3.96–4.02 (2H, m), 5.83 (2H, brs), 7.14 (2H, d, J=7.2 Hz), 7.87 (1H, dd, J=8.4, 2.2 Hz), 7.91 (1H, dd, J=8.4, 2.2 Hz), 8.18–8.25 (4H, m), 8.46 (1H, s), 8.61 (1H, s), 13.61 (1H, brs).

Example 25

4-(4-Chlorobenzenesulfonyl)-1-[1-(4-pyridyl)-4-piperidinylamino]-2-piperazinone

Similarly to Example 15 and using 4-chlorobenzenesulfonyl chloride (91 mg) instead of 8-chloro-2,3-dihydrobenzo[bloxepine-4-sulfonyl chloride, the title compound (58 mg) was obtained as colorless crystals.

$^1$H-NMR (CDCl$_3$) δ: 1.35–1.54 (2H, m), 1.80–1.85 (2H, m), 2.85–2.98 (2H, m), 3.08–3.25 (1H, m), 3.36–3.41 (2H, m), 3.58–3.63 (2H, m), 3.79 (2H, s), 3.79–3.87 (2H, m), 5.09 (1H, d, J=4.4 Hz), 6.65 (2H, d, J=6.4 Hz), 7.57 (2H, d, J=8.6 Hz), 7.75 (2H, d, J=8.6 Hz), 8.25 (2H, d, J=6.4 Hz).

IR (KBr): 2920, 1655, 1597, 1540, 1512, 1480, 1425 cm$^{-1}$.

Example 26

4-(4-Bromobenzenesulfonyl)-1-[1-(4-pyridyl)-4-piperidinylamino]-2-piperazinone

Similarly to Example 15 and using 4-bromobenzenesulfonyl chloride (112 mg) instead of 8-chloro-2,3-dihydrobenzo[b]oxepine-4-sulfonyl chloride, the title compound (74 mg) was obtained as colorless crystals.

$^1$H-NMR (CDCl$_3$) δ: 1.33–1.53 (2H, m), 1.78–1.85 (2H, m), 2.83–2.96 (2H, m), 3.05–3.28 (1H, m), 3.35–3.41 (2H, m), 3.58–3.63 (2H, m), 3.79 (2H, s), 3.79–3.86 (2H, m), 5.09 (1H, d, J=4.4 Hz), 6.64 (2H, d, J=5.8 Hz), 7.67 (2H, d, J=8.6 Hz), 7.74 (2H, d, J=8.6 Hz), 8.25 (2H, d, J=5.8Hz).

IR (KBr): 2920, 1660, 1650, 1600, 1575, 1545, 1510, 1425 cm$^{-1}$.

Example 27

4-(6-Chloro-2H-indene-2-sulfonyl)-1-[1-(4-pyridyl)-4-piperidinylamino]-2-piperazinone Similarly to Example 15 and using 6-chloro-2H-indene-2-sulfonyl chloride (249 mg) instead of 8-chloro-2,3-dihydrobenzo[b]oxepine-4-sulfonyl chloride, the title compound (14 mg) was obtained as colorless crystals.

$^1$H-NMR (CDCl$_3$) δ: 1.35–1.65 (2H, m), 1.80–1.87 (2H, m), 2.81–2.93 (2H, m), 3.10–3.30 (1H, m), 3.55–3.68 (4H, m), 3.75 (2H, s), 3.75–3.84 (2H, m), 4.07 (2H, s), 5.12–5.20 (1H, br), 6.63 (2H, d, J=6.2 Hz), 7.32–7.59 (4H, m), 8.25 (2H, d, J=6.2 Hz).

IR (KBr): 2932, 1651, 1597, 1545, 1512, 1456, 1420 cm$^{-1}$.

Example 28

4-(5-Chlorothieno[3,2-b]pyridine-2-sulfonyl)-1-[1-(4-pyridyl)-4-piperidinylamino]-2-piperazinone Similarly to Example 15 and using 5-chlorothieno[3,2-b]pyridine-2-sulfonyl chloride (203 mg) instead of 8-chloro-2,3-dihydrobenzo[b]oxepine-4-sulfonyl chloride, the title compound (107 mg) was obtained as colorless crystals.

$^1$H-NMR (CDCl$_3$) δ: 1.35–1.55 (2H, m), 1.72–1.84 (2H, m), 2.83–2.96 (2H, m), 3.10–3.30 (1H, m), 3.58–3.63 (2H, m), 3.71–3.78 (2H, m), 3.89–3.94 (2H, m), 4.16 (2H, s), 5.13 (1H, d, J=4.4 Hz), 6.64 (2H, d, J=5.4 Hz), 7.43 (1H, d, J=8.4 Hz), 8.20 (1H, dd, J=8.4, 1.0 Hz), 8.25 (2H, d, J=5.4 Hz), 8.25 (1H, d, J=1.0 Hz).

IR (KBr): 3100, 2940, 1651, 1599, 1564, 1532, 1514, 1422 cm$^{-1}$.

Example 29

4-(6-Chlorothieno[3,2-b]pyridine-2-sulfonyl)-1-[1-(4-pyridyl)-4-piperidinylamino]-2-piperazinone Similarly to Example 15 and using 6-chlorothieno[3,2-b]pyridine-2-sulfonyl chloride (240 mg) instead of 8-chloro-2,3-dihydrobenzo[b]oxepine-4-sulfonyl chloride, the title compound (176 mg) was obtained as colorless crystals.

$^1$H-NMR (CDCl$_3$) δ: 1.45–1.60 (2H, m), 1.85–1.95 (2H, m), 3.16–3.40 (3H, m), 3.46–3.64 (4H, m), 3.90 (2H, s), 3.96–4.03 (2H, m), 6.83 (2H, d, J=6.8 Hz), 7.52 (1H, d, J=8.8 Hz), 8.26 (2H, d, J=6.8 Hz), 8.32 (1H, s), 8.45 (1H, d, J=8.8 Hz).

IR (KBr): 1676, 1645, 1545, 1468, 1422 cm$^{-1}$.

Example 30

4-[2(E)-(4-Bromophenyl)ethenesulfonyl]-1-[1-(4-pyridyl)-4-piperidinylamino]-2-piperazinone Similarly to Example 15 and using 2(E)-(4-bromophenyl)ethenesulfonyl chloride (150 mg) instead of 8-chloro-2,3-dihydrobenzo[b]oxepine-4-sulfonyl chloride, the title compound (143 mg) was obtained as colorless crystals.

$^1$H-NMR (CDCl$_3$) δ: 1.51 (2H, m), 1.87 (2H, m), 2.89 (2H, m), 3.22 (1H, m), 3.58 (2H, m), 3.64 (2H, m), 3.81 (2H, m), 3.95 (2H, s), 5.15 (1H, d, J=4.6 Hz), 6.63 (2H, d, J=6.6 Hz), 6.67 (1H, d, J=15.4 Hz), 7.37 (2H, d, J=8.4 Hz), 7.48 (1H, d, J=15.4 Hz), 7.58 (2H, d, J=8.4 Hz), 8.25 (2H, d, J=6.6 Hz).

Example 31

4-[2(E)-(4-Methoxyphenyl)ethenesulfonyl]-1-[1-(4-pyridyl)-4-piperidinylamino]-2-piperazinone Similarly to Example 15 and using 2(E)-(4-methoxyphenyl)ethenesulfonyl chloride (121 mg) instead of 8-chloro-2,3-dihydrobenzo[b]oxepine-4-sulfonyl chloride, the title compound (146 mg) was obtained as colorless crystals.

$^1$H-NMR (CDCl$_3$) δ: 1.49 (2H, m), 1.86 (2H, m), 2.88 (2H, m), 3.23 (1H, m), 3.54 (2H, m), 3.64 (2H, m), 3.82 (2H, m), 3.86 (3H, s), 3.95 (2H, s), 5.16 (1H, d, J=4.6 Hz), 6.52 (1H, d, J=15.4 Hz), 6.63 (2H, d, J=6.6 Hz), 6.94 (2H, d, J=8.8 Hz), 7.46 (2H, d, J=8.8 Hz), 7.49 (1H, d, J=15.4 Hz), 8.25 (2H, d, J=6.6 Hz).

Example 32

4-[2(E)-(4-Methylphenyl)ethenesulfonyl]-1-[1-(4-pyridyl)-4-piperidinylamino]-2-piperazinone Similarly to Example 15 and using 2(E)-(4-methylphenyl)ethenesulfonyl chloride (115 mg) instead of 8-chloro-2,3-dihydrobenzo[b]oxepine-4-sulfonyl chloride, the title compound (146 mg) was obtained as colorless crystals.

$^1$H-NMR (CDCl$_3$) δ: 1.45 (2H, m), 1.86 (2H, m), 2.41 (3H, s), 2.87 (2H, m), 3.21 (1H, m), 3.55 (2H, m), 3.65 (2H, m), 3.80 (2H, m), 3.95 (2H, s), 5.16 (1H, d, J=4.8 Hz), 6.62 (1H, d, J=15.4 Hz), 6.63 (2H, d, J=6.6 Hz), 7.24 (2H, d, J=8.4 Hz), 7.41 (2H, d, J=8.4 Hz), 7.52 (1H, d, J=15.4 Hz), 8.25 (2H, d, J=6.6 Hz).

Example 33

4-[2(E)-(4-Fluorophenyl)ethenesulfonyl]-1-[1-(4-pyridyl)-4-piperidinylamino]-2-piperazinone Similarly to Example 15 and using 2(E)-(4-fluorophenyl)ethenesulfonyl chloride (115 mg) instead of 8-chloro-2,3-dihydrobenzo[b]oxepine-4-sulfonyl chloride, the title compound (144 mg) was obtained as a colorless solid.

$^1$H-NMR (CDCl$_3$) δ: 1.50 (2H, m), 1.88 (2H, m), 2.90 (2H, m), 3.22 (1H, m), 3.58 (2H, m), 3.65 (2H, m), 3.830 (2H, m), 3.95 (2H, s), 5.16 (1H, d, J=4.8 Hz), 6.55–6.90 (3H, m), 7.14 (2H, t, J=8.4 Hz), 7.46–7.60 (3H, m), 8.25 (2H, d, J=6.6 Hz).

Example 34

4-[4-(2-Ethoxyethoxy)benzenesulfonyl]-1-[1-(4-pyridyl)-4-piperidinylamino]-2-piperazinone Similarly to Example 15 and using 4-(2-ethoxyethoxy)benzenesulfonyl chloride (250 mg) instead of 8-chloro-2,3- dihydrobenzo[b]oxepine-4-sulfonyl chloride, the title compound (340 mg) was obtained as a colorless syrup.

$^1$H-NMR (CDCl$_3$) δ: 1.24 (3H, t, J=7.0 Hz), 1.45 (2H, m), 1.80 (2H, m), 2.88 (2H, s), 3.17 (1H, m), 3.32 (2H, m), 3.50–3.66 (4H, m), 3.70–3.90 (6H, m), 4.19 (2H, m), 5.09 (1H, d, J=5.2 Hz), 6.64 (2H, d, J=6.6 Hz), 7.06 (2H, d, J=8.8 Hz), 7.72 (2H, d, J=8.8 Hz), 8.24 (2H, d, J=6.6 Hz).

Example 35

4-(7-Bromo-2H-benzopyran-3-sulfonyl)-1-[1-(4-pyridyl)-4-piperidinylamino]-2-piperazinone (Method A) Similarly to Example 15 and using 7-bromo-2H-benzopyran-3-sulfonyl chloride (1.61 g) instead of 8-chloro-2,3-dihydrobenzo(b)oxepine-4-sulfonyl chloride, the title compound (1.51 g) was obtained as colorless crystals.

(Method B) A mixture of 4-(7-bromo-2H-benzopyran-3-sulfonyl)-1-(4-piperidinylamino)-2-piperazinone (471 mg), 4-chloropyridine hydrochloride (225 mg) and triethylamine (405 mg) in ethanol (20 ml) was reacted in a sealed tube at 150° C. for 18 hours. The reaction mixture was concentrated, and the residue was made alkaline by adding a saturated aqueous solution of sodium hydrogen carbonate, and then extracted with dichloromethane. The extract was washed with water and brine, dried and concentrated to obtain a residue, which was purified by a column chromatography on a silica gel (dichloromethane: 10% aqueous ammonia-containing methanol=12:1) and crystallized from a mixture of ethanol and diethyl ether to obtain the title compound (156 mg) as colorless crystals.

$^1$H-NMR (CDCl$_3$) δ: 1.38–1.58 (2H, m), 1.84–1.92 (2H, m), 2.84–2.97 (2H, m), 3.15–3.35 (1H, m), 3.60–3.67 (4H, m), 3.77–3.80 (2H, m), 3.97 (2H, s), 4.88 (2H, s), 5.16 (1H, d, J=4.8 Hz), 6.64 (2H, d, J=6.2 H), 7.07 (1H, d, J=8.0 Hz), 7.10 (1H, d, J=1.8 Hz), 7.17 (1H, dd, J=8.0, 1.8 Hz), 7.28 (1H, s), 8.26 (2H, brs).

IR (KBr): 2920, 1651, 1597, 1545, 1514, 1480, 1420 cm$^{-1}$.

Example 36

4-(7-Bromo-2H-benzopyran-3-sulfonyl)-1-[1-(4-pyridyl)-4-piperidinylamino]-2-piperazinone dihydrochloride A suspension of 4-(7-bromo-2H-benzopyran-3-sulfonyl)-1-[1-(4-pyridyl)-4-piperidinylamino]-2-piperazinone (600 mg) in methanol (20 ml) was combined with a 4N solution of hydrochloric acid in ethyl acetate (1 ml) to effect a dissolution and the solution was then concentrated. The residue was crystallized from a mixture of ethanol and ethyl acetate, filtered and dried to obtain the title compound (596 mg) as a colorless solid.

$^1$H-NMR (DMSO-d$_6$) δ: 1.25–1.43 (2H, m), 1.82–1.90 (2H, m), 3.10–3.43 (3H, m), 3.55 (4H, brs), 3.86 (2H, s), 4.20–4.60 (2H, br), 4.99 (2H, s), 7.16–7.28 (4H, m), 7.41 (1H, d, J=8.0 Hz), 7.49 (1H, s), 8.17–8.24 (2H, m), 13.42–13.62 (1H, br).

IR (KBr): 3080, 2946, 1645, 1595, 1549, 1481, 1456, 1416 cm$^{-1}$.

Example 37

1-(1-Acetoimidoyl-4-piperidinylamino)-4-(7-bromo-2H-benzopyran-3-sulfonyl)-2-piperazinone dihydrochloride A solution of 4-(7-bromo-2H-benzopyran-3-sulfonyl)-1-(4-piperidinylamino)-2-piperazinone (104 mg) and triethylamine (272 mg) in methanol (10 ml) was combined with ethyl acetoimidate hydrochloride (272 mg) and stirred at room temperature for 3 hours. The reaction mixture was concentrated and the residue was dissolved in dichloromethane, washed with a 1N aqueous solution of sodium hydroxide and brine, dried and concentrated. The residue obtained was suspended in ethyl acetate, combined with a 4N solution of hydrochloric acid in ethyl acetate to precipitate a hydrochloride, which was collected by filtration and dried to obtain the title compound (243 mg) as a colorless solid.

$^1$H-NMR (DMSO-d$_6$) δ: 1.35–1.50 (2H, m), 1.80–1.87 (2H, m), 2.26 (3H, s), 3.15–3.97 (13H, m), 4.98 (2H, s), 7.20–7.27 (2H, m), 7.41 (1H, d, J=8.2 Hz), 7.49 (1H, s), 8.64 (1H, s), 9.20 (1H, s).

IR (KBr): 3140, 1671, 1627, 1597, 1557, 1481, 1416 cm$^{-1}$.

Example 38

4-(6-Chloronaphthalene-2-sulfonyl)-1-{methyl[1-(4-pyridyl)-4-piperidinyl]amino}-2-piperazinone (Method A) A mixture of 1-{(1-(tert-butoxycarbonyl)piperidinyllamino}-4-(6-chloronaphthalene-2-sulfonyl)-2-piperazinone (1.90 g), methyl iodide (10 ml) and potassium carbonate (600 mg) in DMF (50 ml) was stirred at 50° C. for 15 hours. The reaction mixture was concentrated and the residue obtained was combined with water, extracted with ethyl acetate, dried and concentrated to obtain a residue, which was purified by a column chromatography on a silica gel (hexane:ethyl acetate=1:1) to obtain 1-1-{[1-(tert-butoxycarbonyl)piperidinyl]methylamino}-4-(6-chloronaphthalene-2-sulfonyl)-2-piperazinone (1.63 g) as a colorless amorphous material.

$^1$H-NMR (CDCl$_3$) δ: 1.22 (2H, m), 1.43 (9H, s), 1.60 (1H, m), 1.75 (1H, m), 2.69 (3H, s), 2.69 (2H, m), 3.30–3.65 (5H, m), 3.73 (2H, m), 3.99 (2H, m), 7.61 (1H, dd, J=1.8, 8.8 Hz), 7.79 (1H, dd, J=1.8, 8.8 Hz), 7.90–7.98 (3H, m), 8.35 (1H, s).

1-{[1-(tert-Butoxycarbonyl)piperidinyl]methylamino}-4-(6-chloronaphthalene-2-sulfonyl)-2-piperazinone (1.63 g) was combined with methanol (10 ml) and a 4N solution of hydrochloric acid in ethyl acetate (15 ml) and stirred at room temperature for 30 minutes. The reaction mixture was concentrated and the residue obtained was combined with 4-chloropyridine hydrochloride (950 mg), triethylamine (3.8 g) and ethanol (100 ml), and reacted in a sealed tube at 150° C. for 15 hours. The reaction mixture was concentrated and the residue was combined with a 1N aqueous solution of sodium hydroxide, extracted with dichloromethane, dried and concentrated. The residue obtained was purified by a column chromatography (dichloromethane: 10% aqueous ammonia-containing methanol=20:1) and crystallized from ether to obtain the title compound (794 mg) as colorless crystals.

(Method B) A solution of 1-{methyl[1-(4-pyridyl)-4-piperidinyl]amino}-2-piperazinone dihydrochloride (1.35 g) obtained in Reference Example 16 in dichloromethane (50 ml) and a 10% aqueous solution of sodium carbonate (50 ml) was combined at 0° C. with 6-chloronaphthalene-2-sulfonyl chloride (1.34 g) and stirred at room temperature for 1 hour. The organic phase was separated, washed with brine, dried and concentrated. The residue obtained was purified by a column chromatography on a silica gel (dichloromethane: 10% aqueous ammonia-containing methanol=20:1) and crystallized from ether to obtain the title compound (1.56 g) as colorless crystals.

(Method C) 4-(6-Chloronaphthalene-2-sulfonyl)-1-[1-(4-pyridyl)-4-piperidinylamino]-2-piperazinone (90 mg) was dissolved in a 37% aqueous solution of formaldehyde (2.9 ml) and formic acid (1.4 ml) and refluxed for 15 hours. The reaction mixture was cooled, made alkaline by adding a 1N aqueous solution of sodium hydroxide, extracted with dichloromethane, dried and concentrated. The residue obtained was purified by a column chromatography (dichloromethane: 10% aqueous ammonia-containing methanol=20:1) to obtain the title compound (38 mg) as colorless crystals.

$^1$H-NMR (CDCl$_3$) δ: 1.32 (2H, m), 1.60 (1H, m), 1.86 (1H, m), 2.71 (3H, s), 281 (2H, m), 3.30–3.90 (9H, m), 6.59 (2H, d, J=6.6 Hz), 7.62 (1H, dd, J=2.0, 8.8 Hz), 7.80 (1H, dd, J=1.8, 8.8 Hz), 7.90–8.00 (3H, m), 8.24 (2H, d, J=6.6 Hz), 8.36 (1H, s).

Example 39

4-(6-Chloronaphthalene-2-sulfonyl)-1-{methyl[1-(4-pyridyl)-4-piperidinyl]amino}-2-piperazinone Hydrochloride A suspension of 4-(6-chloronaphthalene-2-sulfonyl)-1-{methyl[1-(4-pyridyl)-4-piperidinyl]amino}-2-piperazinone (500 mg) in methanol (20 ml) was combined with a 4N solution of hydrochloric acid in ethyl acetate (1 ml) to effect a dissolution, and the solution was concentrated. The residue was crystallized from ethanol/ether, collected by filtration and dried to obtain the title compound (526 mg) as a colorless solid.

$^1$H-NMR (DMSO-d$_6$) δ: 1.14 (2H, m), 1.60 (1H, m), 1.81 (1H, m), 2.53 (3H, s), 2.95–3.60 (7H, m), 3.73 (2H, m), 3.99 (2H, m), 7.09 (2H, d, J=7.8 Hz), 7.76 (1H, dd, J=2.0, 8.8 Hz), 7.91 (1H, dd, J=1.4, 8.8 Hz), 8.15–8.35 (5H, m), 8.61 (1H, s).

Example 40

1-[(1-Acetoimidoyl-4-piperidinyl)methylamino]-4-(6-chloronaphthalene-2-sulfonyl)-2-piperazinone Hydrochloride A 4N solution of hydrochloric acid in ethyl acetate (5 ml) was added to 1-{[1-(tert-butoxycarbonyl)piperidinyl]methylamino}-4-(6-chloronaphthalene-2-sulfonyl)-2-piperazinone (106 mg) obtained by Method A in Example (38), and the mixture was stirred at room temperature for 30 minutes. The reaction mixture was concentrated and the residue obtained was dissolved in methanol (8 ml), combined with triethylamine (400 mg) and ethyl acetoimidate hydrochloride (245 mg), and stirred at room temperature overnight. The reaction mixture was concentrated and the residue was dissolved in dichloromethane, washed with a 1N aqueous solution of sodium hydroxide and brine, dried and concentrated. The residue obtained was suspended in ethyl acetate, combined with a 4N solution of hydrochloric acid in ethyl acetate to precipitate a hydrochloride, which was collected by filtration and dried to obtain the title compound (87 mg) as a colorless solid.

$^1$H-NMR (DMSO-d$_6$) δ: 1.20 (2H, m), 1.56 (1H, m), 1.80 (1H, m), 2.21 (3H, s), 2.95–3.70 (10H, m), 3.71 (2H, s), 3.93 (2H, m), 7.74 (1H, dd, J=2.0, 8.8 Hz), 7.89 (1H, d, J=8.8 Hz), 8.20 (1H, d, J=8.8 Hz), 8.25–8.32 (2H, m), 8.61 (2H, brs), 9.20 (1H, br).

Example 41

4-(6-Bromonaphthalene-2-sulfonyl)-1-{methyl[1-(4-pyridyl)-4-piperidinyl]amino{-2-piperazinone (Method A) Similarly to Method B in Example 38 and using 6-bromonaphthalene-2-sulfonyl chloride (254 mg) instead of 6-chloronaphthalene-2-sulfonyl chloride, the title compound (210 mg) was obtained as colorless crystals.

(Method B) Similarly to Method C in Example 38 and using 4-(6-bromonaphthalene-2-sulfonyl)-1-[1-(4-pyridyl)-4-piperidinylamino]-2-piperazinone (1.4 g) instead of 4-(6-chloronaphthalene-2-sulfonyl)-1-[1-(4-pyridyl)-4-piperidinylamino]-2-piperazinone, the title compound (862 mg) was obtained as colorless crystals.

$^1$H-NMR (CDCl$_3$) δ: 1.20–1.40 (2H, m), 1.85–1.95 (2H, m), 2.71 (3H, s), 2.71–2.92 (2H, m), 3.30–3.90 (9H, m), 6.59 (2H, d, J=6.6 Hz), 7.75 (1H, dd, J=8.8, 1.8 Hz), 7.81 (1H, dd, J=8.8, 1.8 Hz), 7.89 (1H, d, J=8.8 Hz), 7.94 (1H, d, J=8.8 Hz), 8.15 (1H, d, J=1.8 Hz), 8.24 (2H, d, J=6.6 Hz), 8.36 (1H, d, J=1.8 Hz).

IR (KBr): 2949, 1667, 1597, 1543, 1512, 1456, 1417 cm$^{-1}$.

Example 42

4-(7-Bromo-2H-benzopyran-3-sulfonyl)-1-{methyl[1-(4-pyridyl)-4-piperidinyl]amino}-2-piperazinone (Method A) Similarly to Method B in Example 38 and using 7-bromo-2H-benzopyran-3-sulfonyl chloride (308 mg) instead of 6-chloronaphthalene-2-sulfonyl chloride, the title compound (230 mg) was obtained as colorless crystals.

(Method B) Similarly to Method C in Example 38 and using 4-(7-bromo-2H-benzopyran-3-sulfonyl)-1-[1-(4-pyridyl)-4-piperidinylamino]-2-piperazinone (1.5 g) instead of 4-(6-chloronaphthalene-2-sulfonyl)-1-[1-(4-pyridyl)-4-piperidinylamino]-2-piperazinone, the title compound (890 mg) was obtained as colorless crystals.

$^1$H-NMR (CDCl$_3$) δ: 1.30–1.52 (2H, m), 1.80–2.00 (2H, m), 2.82 (3H, s), 2.87 (2H, m), 3.40–3.70 (5H, m), 3.79–3.87 (2H, m), 3.87 (2H, d, J=3.0 Hz), 4.88 (1H, d, J=1.2 Hz), 6.63 (2H, d, J=6.6 Hz), 7.07 (1H, d, J=8.0 Hz), 7.11 (1H, d, J=1.4 Hz), 7.17 (1H, dd, J=8.0, 1.4 Hz), 7.28 (1H, d, J=1.2H), 8.25 (2H, d, J=6.6 Hz).

IR (KBr): 2955, 1669, 1597, 1510, 1480, 1416 cm$^{-1}$.

Example 43

4-(6-Chloronaphthalene-2-sulfonyl)-1-{ethyl[1-(4-pyridyl)-4-piperidinyl]amino}-2-piperazinone (Method A) Similarly to Method A in Example 38 and using 1-[1-(tert-butoxycarbonyl)-4-piperidinylamino]-4-(6-chloronaphthalene-2-sulfonyl)-2-piperazinone (1.57 g) and ethyl iodide (4.68 g) instead of methyl iodide, the title compound (4.68 g) was obtained as colorless crystals.

(Method B) 4-(6-Chloronaphthalene-2-sulfonyl)-1-[1-(4-pyridyl)-4-piperidinylamino]-2-piperazinone (14 g) was dissolved in acetic acid (160 ml) and the reaction mixture was treated portionwise with sodium borohydride (11.36 g) while keeping the temperature at 20° C., and then stirred at room temperature for 15 hours. The reaction mixture was concentrated and the residue was made alkaline by adding an aqueous solution of sodium hydroxide, extracted with dichloromethane, dried and concentrated. The residue obtained was crystallized from ethanol to obtain the title compound (12.96 g) as colorless crystals.

$^1$H-NMR (CDCl$_3$) δ: 0.97 (3H, t, J=7.2 Hz), 1.25–1.42 (2H, m), 1.57–1.70 (1H, m), 1.90–1.95 (1H, m), 2.68–2.92 (3H, m), 3.21–3.47 (6H, m), 3.65–3.83 (4H, m), 6.59 (2H, d, J=6.2 Hz), 7.63 (1H, dd, J=8.8, 1.8 Hz), 7.81 (1H, dd, J=8.8, 1.8 Hz), 7.96 (2H, d, J=8.8 Hz), 7.96 (1H, d, J=8.8 Hz), 8.25 (2H, d, J=6.2 Hz), 8.37 (1H, d, J=1.8 Hz).

IR (KBr): 2973, 1669, 1597, 1510, 1456, 1416 cm$^{-1}$.

Example 44

4-(6-Chloronaphthalene-2-sulfonyl)-1-{n-propyl[1-(4-pyridyl)-4-piperidinyl]amino}-2-piperazinone

Similarly to Method A in Example 38 and using n-propyl iodide (1.70 g) instead of methyl iodide, the title compound (58 mg) was obtained as colorless crystals.

$^1$H-NMR (CDCl$_3$) δ: 0.84 (3H, t, J=7.4 Hz), 1.21–1.40 (4H, m), 1.55–1.70 (1H, m), 1.89–1.96 (1H, m), 2.64–2.86 (3H, m), 3.16–3.50 (6H, m), 3.67–3.90 (4H, m), 6.59 (2H, d, J=6.2 Hz), 7.63 (1H, dd, J=8.8, 2.2 Hz), 7.81 (1H, dd, J=8.8, 1.4 Hz), 7.94–7.98 (3H, m), 8.24 (2H, d, J=6.2 Hz), 8.36 (1H, s).

IR (KBr): 2924, 1667, 1595, 1539, 1507, 1450 cm$^{-1}$.

Example 45

1-{Allyl[1-(4-pyridyl)-4-piperidinyl]amino}-4-(6-chloronaphthalene-2-sulfonyl)-2-piperazinone

Similarly to Method A in Example 38 and using 1-[1-(tert-butoxycarbonyl)-4-piperidinylamino]-4-(6-chloronaphthalene-2-sulfonyl)-2-piperazinone (390 mg) and allyl bromide (2 ml) instead of methyl iodide, the title compound (69 mg) was obtained as colorless crystals.

$^1$H-NMR (CDCl$_3$) δ: 1.33 (2H, m), 1.60 (1H, m), 1.90 (1H, m), 2.75 (2H, s), 3.10–3.95 (11H, m), 5.00–5.20 (2H, m), 5.75 (1H, m), 6.58 (2H, d, J=6.6 Hz), 7.62 (1H, dd, J=1.8, 8.8 Hz), 7.79 (1H, dd, J=1.8, 8.8 Hz), 7.90–8.00 (3H, m), 8.24 (2H, d, J=6.6 Hz), 8.35 (1H, s).

Example 46

4-(6-Bromonaphthalene-2-sulfonyl)-1-{methyl[1-(4-pyridyl)-4-piperidinyl]amino}-2-piperazinone Hydrochloride

Similarly to Example 39 and using 4-(6-bromonaphthalene-2-sulfonyl)-1-{methyl[1-(4-pyridyl)-4-piperidinyl]amino}-2-piperazinone (862 mg) instead of 4-(6-chloronaphthalene-2-sulfonyl)-1-{methyl[1-(4-pyridyl)-4-piperidinyl]amino}-2-piperazinone, the title compound (920 mg) was obtained as colorless crystals.

$^1$H-NMR (DMSO-d$_6$) δ: 1.08 (2H, m), 1.63 (1H, m), 1.80 (1H, m), 2.53 (3H, s), 2.95–3.55 (7H, m), 3.73 (2H, m), 3.80–4.10 (2H, m), 7.09 (2H, d, J=7.0 Hz), 7.80–7.95 (2H, m), 8.13–8.25 (4H, m), 8.46 (1H, d, J=1.8 Hz), 8.60 (1H, s).

Example 47

4-(7-Bromo-2H-benzopyran-3-sulfonyl)-1-{methyl[1-(4-pyridyl)-4-piperidinyl]amino}-2-piperazinone Hydrochloride

Similarly to Example 39 and using 4-(7-bromo-2H-benzopyran-3-sulfonyl)-1-{methyl[1-(4-pyridyl)-4-piperidinyl]amino}-2-piperazinone instead of 4-(6-chloronaphthalene-2-sulfonyl)-1-{methyl[1-(4-pyridyl)-4-piperidinyl]amino}-2-piperazinone, the title compound was obtained as colorless crystals.

Example 48

N-[4-(6-Chloronaphthalene-2-sulfonyl)-2-oxo-1-piperazinyl]-2-[1-(4-pyridyl)-4-piperidinyl]acetamide

2-[1-(tert-Butoxycarbonyl)-4-piperidinyl]-N-[4-(6-chloronaphthalene-2-sulfonyl)-2-oxo-1-piperazinyl] acetamide (210 mg) obtained in Reference Example 20 was combined with methanol (2 ml) and a 4N solution of hydrochloric acid in ethyl acetate (5 ml) and stirred at room temperature for 30 minutes. The reaction mixture was concentrated and the residue obtained was combined with 4-chloropyridine hydrochloride (168 mg), triethylamine (452 mg) and ethanol (12 ml) and reacted in a sealed tube at 150° C. for 15 hours. The reaction mixture was concentrated and the residue was combined with a 1N aqueous solution of sodium hydroxide, extracted with dichloromethane, dried and concentrated. The residue obtained was purified by a column chromatography (dichloromethane: 10% aqueous ammonia-containing methanol=20:1) and crystallized from ether to obtain the title compound (354 mg) as colorless crystals.

$^1$H-NMR (CDCl$_3$) δ: 1.22 (2H, m), 1.83 (2H, m), 2.05 (1H, m), 2.10 (2H, s), 2.87 (2H, m), 3.54 (2H, m), 3.70 (2H, m), 3.83 (2H, m), 3.90 (2H, s), 6.57 (2H, d, J=6.4 Hz), 7.60 (1H, dd, J=1.8, 8.8 Hz), 7.78 (1H, dd, J=1.8, 8.8 Hz), 7.85–7.97 (3H, m), 8.14 (2H, d, J=6.4 Hz), 8.35 (1H, s).

Example 49

2-(1-Acetoimidoyl-4-piperidinyl)-N-[4-(6-chloronaphthalene-2-sulfonyl)-2-oxo-1-piperazinyl] acetamide Dihydrochloride

2-[1-(tert-Butoxycarbonyl)-4-piperidinyl]-N-[4-(6-chloronaphthalene-2-sulfonyl)-2-oxo-1-piperazinyl] acetamide (210 mg) obtained in Reference Example 20 was combined with methanol (2 ml) and a 4N solution of hydrochloric acid in ethyl acetate (5 ml) and stirred at room temperature for 30 minutes. The reaction mixture was concentrated and the residue obtained was dissolved in methanol (15 ml), combined with triethylamine (400 mg) and ethyl acetoimidate hydrochloride (271 mg) and stirred at room temperature overnight. The reaction mixture was concentrated and the residue was dissolved in dichloromethane, washed with a 1N aqueous solution of sodium hydroxide and brine, dried and concentrated. The residue obtained was suspended in ethyl acetate, combined with a 4N solution of hydrochloric acid in ethyl acetate to precipitate a hydrochloride, which was collected by filtration and dried to obtain the title compound (8 mg) as a colorless solid.

$^1$H-NMR (DMSO-d$_6$) δ: 1.21 (2H, m), 1.77 (2H, m), 1.90–2.10 (3H, m), 2.22 (3H, s), 3.00–4.30 (10H, m), 7.72 (1H, dd, J=1.8, 8.8 Hz), 7.87 (1H, dd, J=1.8, 8.8 Hz), 8.10–8.30 (3H, m), 8.48 (1H, s), 8.56 (1H, s), 9.06 (1H, s), 10.28 (1H, s).

Example 50

4-[(6-Chloro-2-naphthyl)sulfonyl]-6-methyl-1-[[1-(4-pyridinyl)-4-piperidinyl]amino]-2-piperazinone Dihydrochloride

A solution of tert-butyl 3-methyl-5-oxo-4-[[1-(4-pyridinyl)-4-piperidinyl]amino]-1-piperazinecarboxylate (1.1 g) in toluene (11 ml) was treated dropwise with trifluoroacetic acid (11 ml) and stirred at room temperature for 1 hour, and then concentrated under reduced pressure. The residue was dissolved in dichloromethane (11 ml) and a 10% aqueous solution of sodium carbonate (11 ml), combined at 0° C. with 6-chloronaphthalene-2-sulfonyl chloride (0.90 g) and stirred at room temperature for 3 hours. The organic phase was isolated, washed with brine, dried and concentrated. The residue thus obtained was purified by a column chromatography on a silica gel (dichloromethane: 10% aqueous ammonia-containing methanol=10:1) to obtain 4-[(6-chloro-2-naphthyl)sulfonyl]-6-methyl-1-[[1-(4-pyridinyl)-4-piperidinyl]amino]-2-piperazinone (1.1 g).

This material was dissolved in methanol (5 ml), combined with a 4N solution of hydrochloric acid in ethyl acetate (1.3 ml) and concentrated under reduced pressure. The residue was crystallized from ethyl acetate/methanol, collected by filtration and dried to obtain the title compound (1.1 g) as a colorless crystalline powder.

$^1$H-NMR (DMSO-$d_6$+$D_2O$) δ: 1.10–1.38 (2H, m), 1.23 (3H, d, J=6.4 Hz), 1.62–1.88 (2H, m), 3.00–3.70 (7H, m), 3.86 (1H, d, J=15.8 Hz), 3.90–4.12 (2H, m), 7.14 (2H, d, J=6.8 Hz), 7.75 (1H, dd, J=2.2, 8.8 Hz), 7.90 (1H, dd, J=1.8, 8.8 Hz), 8.10–8.36 (5H, m), 8.60 (1H, s).

Example 51

4-[(6-Chloro-2-naphthyl)sulfonyl]-6-methyl-1-[methyl[1-(4-pyridinyl)-4-piperidinyl]amino]-2-piperazinone 4-[(6-Chloro-2-naphthyl)sulfonyl]-6-methyl-1-[[1-(4-pyridinyl)-4-piperidinyl]amino]-2-piperazinone dihydrochloride (0.63 g) was dissolved in methylene chloride (20 ml) and saturated aqueous sodium bicarbonate (20 ml) and the phases were separated. The organic phase was dried over magnesium sulfate and concentrated under reduced pressure to obtain 4-[(6-chloro-2-naphthyl)sulfonyl]-6-methyl-1-[[1-(4-pyridinyl)-4-piperidinyl]amino]-2-piperazinone. This material was dissolved in a 37% aqueous solution of formaldehyde (8.0 ml) and formic acid (4.1 ml) and refluxed for 2 hours. The reaction mixture was cooled, made alkaline by adding a 1N aqueous solution of sodium hydroxide, extracted with dichloromethane, dried and concentrated. The residue thus obtained was purified by a column chromatography on a silica gel (ethyl acetate: methanol=10:1) to obtain the title compound (370 mg) as colorless crystals.

$^1$H-NMR (DMSO-$d_6$) δ: 0.80–1.30 (2H, m), 1.23 (3H, d, J=5.8 Hz), 1.30–1.70 (1H, m), 1.75–2.00 (1H, m), 2.35–4.00 (13H, m), 6.60–6.82 (2H, m), 7.76 (1H, dd, J=1.8, 8.8 Hz), 7.90 (1H, dd, J=1.8, 8.8 Hz), 8.11 (2H, d, J=6.2 Hz), 8.20 (1H, d, J=8.8 Hz), 8.24–8.36 (2H, m), 8.60 (1H, s).

Example 52

4-[(6-Chloro-2-naphthyl)sulfonyl]-6-methyl-1-[methyl[1-(4-pyridinyl)-4-piperidinyl]amino]-2-piperazinone Hydrochloride 4-[(6-Chloro-2-naphthyl)sulfonyl]-6-methyl-1-[methyl [1-(4-pyridinyl)-4-piperidinyl]amino]-2-piperazinone (0.34 g) was dissolved in ethanol (2 ml) and combined with a 4N solution of hydrochloric acid in ethyl acetate (0.24 ml), ethyl acetate (20 ml) and diethyl ether (30 ml). The powder precipitated was collected by filtration and dried to obtain the title compound (0.37 g) as a colorless non-crystal powder.

$^1$H-NMR (CD$_3$OD) δ: 1.15–1.50 (2H, m), 1.37 (3H, d, J=6.4 Hz), 1.60–1.90 (1H, m), 1.95–2.25 (1H, m), 2.61, 2.87 (total 3H, s for each), 2.90–4.40 (10H, m), 7.00–7.18 (2H, m), 7.66 (1H, dd, J=2.0, 8.8 Hz), 7.87 (1H, dd, J=1.8, 8.8 Hz), 8.00–8.18 (5H, m), 8.48

Example 53

Methyl 4-[(6-Chloro-2-naphthyl)sulfonyl]-6-oxo-1-[[1-(4-pyridinyl)-4-piperidinyl]amino]-2-piperazine Carboxylate Dihydrochloride A solution of 1-tert-butyl 3-methyl 5-oxo-4-[[1-(4-pyridinyl)-4-piperidinyl]amino]-1,3-piperazine dicarboxylate (0.36 g) in toluene (3.6 ml) was treated dropwise with trifluoroacetic acid (3.6 ml) and stirred at room temperature for 1 hour, and then concentrated under reduced pressure. The residue was dissolved in dichloromethane (3.6 ml) and a 10% aqueous solution of sodium carbonate (3.6 ml), combined at 0° C. with 6-chloronaphthalene-2-sulfonyl chloride (0.26 g) and stirred at room temperature for 3 hours. The organic phase was isolated, washed with brine, dried and concentrated. The residue thus obtained was purified by a column chromatography on a silica gel (dichloromethane: 10% aqueous ammonia-containing methanol=10:1) to obtain methyl 4-[(6-chloro-2-naphthyl)sulfonyl]-6-oxo-1-[[1-(4-pyridinyl)-4-piperidinyl]amino]-2-piperazinecarboxylate (0.34 g).

This material was dissolved in methanol (5 ml), combined with a 4N solution of hydrochloric acid in ethyl acetate (0.38 ml) and concentrated under reduced pressure. The residue was crystallized from ethyl acetate/methanol, collected by filtration and dried to obtain the title compound (0.12 g) as a colorless crystalline powder.

$^1$H-NMR (DMSO-$d_6$+$D_2O$) δ: 1.10–1.40 (2H, m), 1.67–1.90 (2H, m), 3.00–3.40 (4H, m), 3.60 (1H, d, J=16.2 Hz), 3.69 (3H, s), 3.87–4.14 (4H, m), 4.32–4.43 (1H, m), 7.13 (2H, d, J=7.6 Hz), 7.75 (1H, dd, J=2.2, 8.8 Hz), 7.87 (1H, dd, J=1.6, 8.8 Hz), 8.10–8.34 (5H, m), 8.60 (1H, s).

Example 54

Methyl 4-[(6-Chloro-2-naphthyl)sulfonyl]-1-[methyl [1-(4-pyridinyl)-4-piperidinyl]amino]-6-oxo-2-piperazine Carboxylate Hydrochloride Methyl 4-[(6-chloro-2-naphthyl)sulfonyl]-6-oxo-1-[[1-(4-pyridinyl)-4-piperidinyl]amino]-2-piperazinecarboxylate dihydrochloride (0.26 g) was dissolved in methylene chloride (20 ml) and saturated aqueous sodium bicarbonate (20 ml) and the phases were separated. The organic phase was dried over magnesium sulfate and concentrated under reduced pressure to obtain methyl 4-[(6-chloro-2-naphthyl)sulfonyl]-6-oxo-1-[[1-(4-pyridinyl)-4-piperidinyl]amino]-2-piperazinecarboxylate. This material was dissolved in a 37% aqueous solution of formaldehyde (3.1 ml) and formic acid (1.6 ml) and refluxed for 2 hours. The reaction mixture was cooled, made alkaline by adding a saturated aqueous sodium bicarbonate, extracted with dichloromethane, dried and concentrated. The residue thus obtained was purified by a column chromatography on a basic silica gel (ethyl acetate: methanol=10:1) to obtain methyl 4-[(6-chloro-2-naphthyl) sulfonyl]-1-[methyl[1-(4-pyridinyl)-4-piperidinyl]amino]-6-oxo-2-piperazinecarboxylate as a pale yellow oil.

This material was dissolved in methanol (2 ml), combined with a 4N solution of hydrochloric acid in ethyl acetate (0.15 ml), concentrated under reduced pressure and dried to obtain the title compound (0.15 g) as a colorless non-crystalline powder.

$^1$H-NMR (CD$_3$OD) δ: 1.20–1.50 (2H, m), 1.70–2.12 (2H, m), 2.85–3.70 (5H, m), 2.94 (3H, s), 3.74 (3H, s), 3.90–4.50 (5H, m), 7.07 (2H, d, J=7.6 Hz), 7.66 (1H, dd, J=2.2, 8.8 Hz), 7.84 (1H, dd, J=1.6, 8.8 Hz), 7.98–8.18 (5H, m), 8.47 (1H, s)

Example 55

1-(2-Chloroethyl)-4-[4-[4-(6-chloronaphthalene-2-sulfonyl)-2-oxo-1-piperazinylamino]-1-piperidinyl] pyridinium Chloride A solution of 1-amino-4-(6-chloronaphthalene-2-sulfonyl)-2-piperazinone (33.98 g) and 1-(4-pyridyl)-4- piperidone (18.50 g) in ethanol (1 L)/1,2-dichloroethane (300 ml) was dehydrated using a Soxlet extractor packed with molecular sieves 4A while refluxing for 3 days. Any insolubles were filtered off and the reaction mixture was concentrated to obtain a residue, which was dissolved in methanol (1 L), combined with acetic acid (33.82 g) while cooling on ice, followed by sodium cyanoborohydride (17.06 g) and then stirred at room temperature for 1 hour. The reaction mixture was concentrated and the residue was dissolved in dichloromethane, washed with aqueous sodium bicarbonate and brine, dried, concentrated and purified by a column chromatography on a silica gel (dichloromethane: methanol=10:1 to dichloromethane: methanol: triethylamine=40:2:1) and a column chromatography on a basic silica gel (tetrahydrofuran to methanol) to obtain the title compound (30 g) as a colorless amorphous material.

$^1$H-NMR (DMSO-$d_6$) δ: 1.14–1.20 (2H, m), 1.65–1.73 (2H, m), 2.39–2.59 (2H, m), 3.17–3.24 (3H, m), 3.43 (4H, m), 3.76 (2H, s), 4.01–4.07 (2H, m), 4.50 (2H, m), 5.61 (1H, m), 7.22 (2H, d, J=8.0 Hz), 7.75 (1H, d, J=8.8 Hz), 7.90 (1H, d, J=9.2 Hz), 8.20 (1H, d, J=9.2 Hz), 8.22–8.28 (4H, m), 8.62 (1H, s).

Example 56

N-[4-(6-Chloronaphthalene-2-sulfonyl)-2-oxo-1-piperazinyl]-1-(4-pyridyl)-4-piperidinecarboxamide A solution of 1-(4-pyridinyl)-4-piperidinecarboxylic acid (102 mg) and HOBt (153 mg) in DMF (25 ml) was combined with WSC (192 mg) at 0° C. and stirred at 0° C. for 1 hour. The reaction mixture was combined with 1-amino-4-(6-chloronaphthalene-2-sulfonyl)-2-piperazinone (170 mg) obtained in Example 3 and stirred at room temperature for 2 days. The reaction mixture was concentrated and the residue obtained was partitioned between dichloromethane and aqueous sodium bicarbonate, and the organic phase was washed with saturated aqueous sodium bicarbonate, dried and concentrated to obtain a residue, which was purified by a column chromatography on a basic silica gel (dichloromethane to dichloromethane: methanol=20:1) and crystallized from ethyl acetate/methanol to obtain the title compound (115 mg) as a white powder.

$^1$H-NMR (CDCl$_3$) δ: 1.78–1.98 (4H, m), 2.40–2.47 (1H, m), 2.86–2.98 (2H, m), 3.52–3.57 (2H, m), 3.69–3.74 (2H, m), 3.84–3.88 (4H, m), 6.62 (2H, dd, J=1.5, 5.1 Hz), 7.60 (1H, dd, J=1.8, 8.8 Hz), 7.78 (1H, dd, J=1.8, 8.6 Hz), 7.92–7.96 (3H, m), 8.02 (1H, brs), 8.22 (2H, dd, J=1.4, 5.2 Hz), 8.35 (1H, d, J=1.2 Hz).

Example 57

4-(7-Bromo-2,2-dimethyl-2H-benzopyran-3-sulfonyl)-1-[1-(4-pyridyl)-4-piperidinylamino]-2-piperazinone Similarly to Example 15 and using 7-bromo-2,2-dimethyl-2H-benzopyran-3-sulfonyl chloride (0.51 g) instead of 8-chloro-2,3-dihydrobenzo[b]oxepine-4-sulfonyl chloride, the title compound (0.36 g) was obtained as colorless crystals.

$^1$H-NMR (CDCl$_3$) δ: 1.40–1.57 (2H, m), 1.62 (6H, s), 1.86–1.94 (2H, m), 2.87–3.00 (2H, m), 3.20–3.35 (1H, m), 3.63 (4H, brs), 3.81–3.89 (2H, m), 3.96 (2H, s), 5.18 (1H, d, J=5.2 Hz), 6.65 (2H, d, J=6.6 Hz), 7.05–7.16 (3H, m), 7.38 (1H, s), 8.26 (2H, d, J=6.6 Hz).

IR (KBr): 2940, 1651, 1595, 1560, 1539, 1514, 1480, 1416 cm$^{-1}$.

Example 58

4-(7-Bromo-2,2-dimethyl-2H-benzopyran-3-sulfonyl)-1-{methyl[1-(4-pyridyl)-4-piperidinyl]amino}-2-piperazinone Similarly to Method C in Example 38 and using 4-(7-bromo-2,2-dimethyl-2H-benzopyran-3-sulfonyl-1-[1-(4-pyridyl)-4-piperidinylamino]-2-piperazinone (150 mg) instead of 4-(6-chloronaphthalene-2-sulfonyl)-1-[1-(4-pyridyl)-4-piperidinylamino]-2-piperazinone, the title compound (78 mg) was obtained as colorless crystals.

$^1$H-NMR (CDCl$_3$) δ: 1.35–1.60 (2H, m), 1.62 (6H, s), 1.80–2.00 (2H, m), 2.83 (3H, s), 2.83–2.96 (2H, m), 3.40–3.70 (5H, m), 3.80–3.95 (4H, m), 6.65 (2H, d, J=6.6 Hz), 7.05–7.16 (3H, m), 7.38 (1H, s), 8.25 (2H, d, J=6.6 Hz).

IR (KBr): 2926, 1667, 1597, 1560, 1512, 1480, 1416 cm$^{-1}$.

Example 59

4-(6-Bromonaphthalene-2-sulfonyl)-1-{ethyl[1-(4-pyridyl)-4-piperidinyl]amino}-2-piperazinone Similarly to Example 43, the title compound (226 mg) was obtained as colorless crystals.

$^1$H-NMR (CDCl$_3$) δ: 0.97 (3H, t, J=7.2 Hz), 1.28–1.46 (2H, m), 1.60–1.66 (1H, m), 1.89–1.95 (1H, m), 2.67–2.96 (3H, m), 3.21–3.46 (6H, m), 3.66–3.91 (4H, m), 6.59 (2H, d, J=6.6 Hz), 7.75 (1H, dd, J=8.8, 1.8 Hz), 7.81 (1H, dd, J=8.8, 2.0 Hz), 7.89 (1H, d, J=8.8 Hz), 7.95 (1H, d, J=8.8 Hz), 8.14 (1H, s), 8.25 (2H, d, J=6.6 Hz), 8.35 (1H, s) IR (KBr): 2969, 1667, 1595, 1510, 1454, 1416 cm$^{-1}$.

Example 60

4-(6-Chloronaphthalene-2-sulfonyl)-1-{ethyl[1-(4-pyridyl)-4-piperidinyl]amino}-2-piperazinone Hydrochloride Similarly to Example 39 and using 4-(6-chloronaphthalene-2-sulfonyl)-1-{ethyl[1-(4-pyridyl)-4-piperidinyl]amino}-2-piperazinone (2.89 g), the title compound (3.04 g) was obtained as colorless crystals.

$^1$H-NMR (DMSO-$d_6$) δ: 0.81 (3H, t, J=7.0 Hz), 1.05–1.30 (2H, m), 1.64–1.71 (1H, m), 1.86–1.92 (1H, m), 2.68–2.84 (1H, m), 2.97–3.15 (3H, m), 3.34–3.41 (6H, m), 3.79 (1H, s), 3.94–4.12 (2H, m), 7.11 (2H, d, J=7.6 Hz), 7.76 (1H, dd, J=8.8, 2.0 Hz), 7.92 (1H, dd, J=8.8, 2.0 Hz), 8.19–8.33 (4H, m), 8.63 (1H, s), 13.52 (1H, brs).

Example 61

Ethyl {[4-(6-Chloronaphthalene-2-sulfonyl)-2-oxo-1-piperazinyl][1-(4-pyridyl)-4-piperazinyl]amino}acetate A mixture of 1-[1-(tert-butoxycarbonyl)-4-piperidinylamino]-4-(6-chloronaphthalene-2-sulfonyl)-2-piperazinone (523 mg) obtained in Reference Example 11, ethyl iodoacetate (2.14 g) and potassium carbonate (166 mg) in 1-methyl-2-pyrrolidone (10 ml) was stirred at 80° C. for 40 hours under an argon atmosphere. The reaction mixture was concentrated and the residue obtained was combined with water, extracted with ethyl acetate, dried and concentrated to obtain a residue, which was purified by a column chromatography on a silica gel (hexane:acetone=2:1) to obtain ethyl {[1-(tert-butoxycarbonyl)-4-piperidinyl][4-(6-chloronaphthalene-2-sulfonyl)-2-oxo-1-piperazinyl]amino}acetate (479 mg) as colorless crystals.

¹H-NMR (CDCl₃) δ: 1.19 (3H, t, J=7.2 Hz), 1.19–1.40 (2H, m), 1.44 (9H, s), 1.57–1.80 (2H, m), 2.58–2.71 (2H, m), 3.05–3.30 (1H, br), 3.35–4.15 (12H, m), 7.61 (1H, dd, J=8.8, 1.8 Hz), 7.78 (1H, dd, J=8.8, 1.8 Hz), 7.94 (1H, d, J=1.8 Hz), 7.95 (1H, d, J=8.8 Hz), 8.34 (1H, d, J=1.8 Hz).

IR (KBr): 2980, 2920, 1746, 1688, 1454, 1420 cm⁻¹.

Thereafter, by using ethyl {[1-(tert-butoxycarbonyl)-4-piperidinyl][4-(6-chloronaphthalene-2-sulfonyl)-2-oxo-1-piperazinyl]amino}acetate (450 mg) and proceeding similarly to Method A in Example 38, the title compound (80 mg) was obtained as colorless crystals.

¹H-NMR (CDCl₃) δ: 1.20 (3H, t, J=7.2 Hz), 1.39–1.49 (2H, m), 1.60–1.67 (1H, m), 1.85–1.92 (1H, m), 2.69–2.88 (3H, m), 3.08–3.19 (1H, m), 3.50–4.13 (12H, m), 6.60 (2H, d, J=6.6 Hz), 7.62 (1H, dd, J=8.8, 1.8 Hz), 7.80 (1H, dd, J=8.8, 1.8 Hz), 7.93–7.98 (3H, m), 8.25 (2H, d. J=6.6 Hz), 8.35 (1H, s).

IR (KBr): 2940, 1744, 1653, 1595, 1541, 1348, 1165 cm⁻¹.

Example 62

4-(6-Chloronaphthalene-2-sulfonyl)-1-{methyl[1-(2,3,5,6-tetrafluoro-4-pyridyl)-4-piperidinyl]amino}-2-piperazinone 4-(6-Chloronaphthalene-2-sulfonyl)-1-[methyl(4-piperidinyl)amino]-2-piperazinone hydrochloride (236 mg) obtained in Reference Example 21 was combined with pentafluoropyridine (169 mg), triethylamine (202 mg) and DMF (8 ml) and reacted at 100° C. for 2 hours under an argon atmosphere. The reaction mixture was concentrated and the residue was combined with a 10% aqueous solution of sodium hydroxide, extracted with dichloromethane, dried and concentrated. The residue obtained was crystallized from diethyl ether to obtain the title compound (208 mg) as colorless crystals.

¹H-NMR (CDCl₃) δ: 1.35–1.50 (2H, m), 1.59–2.02 (2H, m), 2.72 (3H, s), 3.00–3.25 (2H, m), 3.35–3.75 (7H, m), 3.77 (2H, s), 7.61 (1H, dd, J=8.8, 1.8 Hz), 7.80 (1H, dd, J=8.8, 1.8 Hz), 7.93–7.97 (3H, m), 8.36 (1H, d, J=1.8 Hz).

IR (KBr): 2930, 2855, 1667, 1638, 1532, 1476, 1418 cm⁻¹.

Example 63

4-(6-Chloronaphthalene-2-sulfonyl)-1-{methyl[1-(2-methyl-4-pyridyl)-4-piperidinyl]amino}-2-piperazinone 4-(6-Chloronaphthalene-2-sulfonyl)-1-[methyl(4-piperidinyl)amino]-2-piperazinone hydrochloride (945 mg) obtained in Reference Example 21 was combined with 4-chloro-2-picoline (510 mg), triethylamine (1.21 g) and ethanol (20 ml), and reacted in a sealed tube at 150° C. for 8 hours. The reaction mixture was concentrated and the residue was combined with a 10% aqueous solution of sodium hydroxide, extracted with dichloromethane, dried and concentrated. The residue obtained was purified by a column chromatography on a silica gel (dichloromethane: 10% aqueous ammonia-containing methanol=20:1) and crystallized from ethyl acetate-ethanol to obtain the title compound (764 mg) as colorless crystals.

¹H-NMR (CDCl₃) δ: 1.25–1.45 (2H, m), 1.78–2.05 (2H, m), 2.67 (3H, s), 2.72 (3H, s), 3.05–3.17 (2H, m), 3.25–3.55 (4H, m), 3.65–4.00 (5H, m), 6.54 (1H, d, J=1.8 Hz), 6.66 (1H, dd, J=7.2, 1.8 Hz), 7.62 (1H, dd, J=8.8, 1.6 Hz), 7.80 (1H, dd, J=8.8, 1.6 Hz), 7.96 (2H, d, J=8.8 Hz), 7.96 (1H, d, J=1.6 Hz), 8.02 (1H, d, J=7.2 Hz), 8.36 (1H, s).

IR (KBr): 2894, 1642, 1611, 1541, 1456 1416 cm⁻¹.

Example 64

4-(6-Chloronaphthalene-2-sulfonyl)-1-{methyl[1-(2-methyl-4-pyridyl)-4-piperidinyl]amino}-2-piperazinone Hydrochloride Similarly to Example 39 and starting from 4-(6-chloronaphthalene-2-sulfonyl)-1-{methyl[1-(2-methyl-4-pyridyl)-4-piperidinyl]amino}-2-piperazinone(528 mg), the title compound (493 mg) was obtained as colorless crystals.

¹H-NMR (DMSO-d₆) δ: 1.28–1.46 (2H, m), 1.80–2.05 (2H, m), 2.68 (3H, s), 2.72 (3H, s), 3.06–3.19 (2H, m), 3.30–3.60 (4H, m), 3.64–4.02 (5H, m), 6.56 (1H, s), 6.63–6.68 (1H, m), 7.63 (1H, dd, J=8.8, 2.0 Hz), 7.81 (1H, dd, J=8.8, 1.8 Hz), 7.97 (2H, d, J=8.8 Hz), 7.97 (1H, d, J=2.0 Hz), 7.99–8.04 (1H, m), 8.37 (1H, s), 15.40 (1H, brs).

IR (KBr): 3054, 2921, 1642, 1611, 1541, 1456, 1418 cm⁻¹.

Example 65

4-(6-Chloronaphthalene-2-sulfonyl)-1-{[1-(2-ethyl-4-pyridyl)-4-piperidinyl]methylamino}-2-piperazinone Similarly to Example 63 and using 4-bromo-2-ethylpyridine (186 mg) instead of 4-chloro-2-picoline, the title compound (135 mg) was obtained as colorless crystals.

¹H-NMR (CDCl₃) δ: 1.23–1.40 (2H, m), 1.27 (3H, t, J=7.6 Hz), 1.55–1.70 (1H, m), 1.80–1.95 (1H, m), 2.70 (2H, q, J=7.6 Hz), 2.71 (3H, s), 2.71–2.90 (2H, m), 3.35–3.90 (9H, m), 6.45 (1H, dd, J=5.8, 2.6 Hz), 6.49 (1H, d, J=2.6 Hz), 7.62 (1H, dd, J=8.8, 2.0 Hz), 7.80 (1H, dd, J=8.8, 2.0 Hz), 7.95 (2H, d, J=8.8 Hz), 7.95 (1H, d, J=2.0 Hz), 8.18 (1H, d, J=5.8 Hz), 8.36 (1H, d, J=2.0 Hz).

IR (KBr): 2922, 1667, 1597, 1547, 1495, 1454, 1416 cm⁻¹.

Example 66

1-{[1-(2-Amino-4-pyridyl)-4-piperidinyl]methylamino}-4-(6-chloronaphthalene-2-sulfonyl)-2-piperazinone Similarly to Example 63 and using 2-amino-4-chloropyridine (129 mg) instead of 4-chloro-2-picoline, the title compound (78 mg) was obtained as colorless crystals.

¹H-NMR (CDCl₃) δ: 1.18–1.38 (2H, m), 1.55–1.90 (2H, m), 2.65–2.82 (2H, m), 2.70 (3H, s), 3.37–3.78 (9H, m), 4.26 (2H, brs), 5.79 (1H, d, J=2.2 Hz), 6.12 (1H, dd, J=6.2, 2.2 Hz), 7.62 (1H, dd, J=8.8, 2.0 Hz), 7.78 (1H, d, J=6.2 Hz), 7.81 (1H, dd, J=8.8, 2.0 Hz), 7.95 (2H, d, J=8.8 Hz), 7.96 (1H, d, J=2.0 Hz), 8.37 (1H, s).

IR (KBr): 2951, 1661, 1603, 1541, 1507, 1495, 1456, 1417 cm⁻¹.

Example 67

4-(6-Chloronaphthalene-2-sulfonyl)-1-{[1-(2-hydroxymethyl-4-pyridyl)-4-piperidinyl]methylamino}-2-piperazinone Similarly to Example 63 and using (4-chloro-2-pyridyl)methanol (287 mg) instead of 4-chloro-2-picoline, the title compound (240 mg) was obtained as colorless crystals.

¹H-NMR (CDCl₃) δ: 1.20–1.40 (2H, m), 1.56–1.78 (1H, m), 1.82–2.00 (1H, m), 2.71 (3H, s), 2.80–2.98 (2H, m), 3.32–3.88 (10H, m), 4.65 (2H, s), 6.54–6.56 (2H, m), 7.63 (1H, dd, J=8.8, 2.0 Hz), 7.81 (1H, dd, J=8.8, 2.0 Hz), 7.96 (2H, d, J=8.8 Hz), 7.96 (1H, d, J=2.0 Hz), 8.17 (1H, d, J=5.4 Hz), 8.36 (1H, d, J=2.0 Hz). IR (KBr): 2930, 1663, 1601, 1541, 1491, 1456, 1418 cm$^{-1}$.

Example 68

4-(6-Chloronaphthalene-2-sulfonyl)-1-{[1-(2-hydroxymethyl-4-pyridyl)-4-piperidinyl]methylamino}-2-piperazinone Hydrochloride

Similarly to Example 39 and starting from 4-(6-chloronaphthalene-2-sulfonyl)-1-{methyl[1-(2-hydroxymethyl-4-pyridyl)-4-piperidinyl]amino}-2-piperazinone (240 mg), the title compound (255 mg) was obtained as colorless crystals.

$^1$H-NMR (DMSO-d$_6$) δ: 1.02–1.20 (2H, m), 1.62–1.85 (2H, m), 2.54 (3H, s), 3.00–3.41 (7H, m), 3.74 (2H, s), 3.90–4.10 (2H, m), 4.61 (2H, s), 6.19 (1H, brs), 7.01–7.08 (2H, m), 7.77 (1H, dd, J=8.8, 2.0 Hz), 7.92 (1H, dd, J=8.8, 1.8 Hz), 8.11 (1H, t, J=6.0 Hz), 8.22 (1H, d, J=8.8 Hz), 8.31 (1H, d, J=2.0 Hz), 8.31 (1H, d, J=8.8 Hz), 8.63 (1H, s), 13.44 (1H, brs). IR (KBr): 3150, 1680, 1645, 1590, 1545, 1460 cm$^{-1}$.

Example 69

4-(6-Chloronaphthalene-2-sulfonyl)-1-{methyl[1-(3-methyl-4-pyridyl)-4-piperidinyl]methylamino}-2-piperazinone

Similarly to Example 63 and using 4-chloro-3-picoline hydrochloride (328 mg) instead of 4-chloro-2-picoline, the title compound (98 mg) was obtained as colorless crystals.

$^1$H-NMR (CDCl$_3$) δ: 1.36–1.55 (2H, m), 1.69–1.95 (2H, m), 2.20 (3H, s), 2.56–2.69 (2H, m), 2.73 (3H, s), 3.15–3.27 (2H, m), 3.38–3.60 (5H, m), 3.77 (2H, s), 6.72 (1H, d, J=5.6 Hz), 7.61 (1H, dd, J=8.8, 2.0 Hz), 7.80 (1H, dd, J=8.8, 1.8 Hz), 7.93–7.97 (3H, m), 8.25 (1H, s), 8.27 (1H, d, J=5.6 Hz), 8.36 (1H, s).

IR (KBr): 2953, 2922, 1667, 1588, 1493, 1456, 1418 cm$^{-1}$.

Example 70

4-(6-Chloronaphthalene-2-sulfonyl)-1-{[1-(2,3-dimethyl-4-pyridyl)-4-piperidinyl]methylamino}-2-piperazinone

Similarly to Example 63 and using 4-chloro-2,3-dimethylpyridine (283 mg) instead of 4-chloro-2-picoline, the title compound (156 mg) was obtained as colorless crystals.

$^1$H-NMR (CDCl$_3$) δ: 1.37–1.57 (2H, m), 1.68–1.76 (H, m), 1.87–1.97 (1H, m), 2.13 (3H, s), 2.49 (3H, s), 2.54–2.67 (2H, m), 2.73 (3H, s), 3.06–3.20 (2H, m), 3.36–3.56 (5H, m), 3.77 (2H, s), 6.67 (1H, d, J=6.0 Hz), 7.61 (1H, dd, J=8.8, 2.0 Hz), 7.81 (1H, dd, J=8.8, 2.0 Hz), 7.93–7.97 (3H, m), 8.19 (1H, d, J=6.0 Hz), 8.36 (1H, s).

IR (KBr): 2951, 1624, 1580, 1476, 1456, 1418 cm$^{-1}$.

Example 71

4-(6-Chloronaphthalene-2-sulfonyl)-1-{[1-(2,6-dimethyl-4-pyridyl)-4-piperidinyl]methylamino}-2-piperazinone Hydrochloride

Similarly to Example 63 and Example 39 and using 4-chloro-2,6-dimethylpyridine hydrochloride (356 mg) instead of 4-chloro-2-picoline, the title compound (187 mg) was obtained as colorless crystals.

$^1$H-NMR (DMSO-d$_6$) δ: 1.00–1.21 (2H, m), 1.60–1.90 (2H, m), 2.42 (6H, s), 2.53 (3H, s), 3.00–3.40 (4H, m), 3.73 (2H, s), 3.90–4.25 (5H, m), 6.90 (2H, s), 7.76 (1H, dd, J=8.8, 2.0 Hz), 7.92 (1H, dd, J=8.8, 1.8 Hz), 8.22 (1H, d, J=8.8 Hz), 8.29–8.33 (2H, m), 8.63 (1H, s), 13.32 (1H, brs).

IR (KBr): 3393, 2928, 1636, 1539, 1456, 1418 cm$^{-1}$.

Example 72

4-(6-Chloronaphthalene-2-sulfonyl)-1-{[1-(2-ethoxycarbonyl-4-pyridyl)-4-piperidinyl]methylamino}-2-piperazinone

Similarly to Example 63 and using methyl 4-chloropyridine-2-carboxylate hydrochloride (208 mg) instead of 4-chloro-2-picoline, the title compound (57 mg) was obtained as colorless crystals.

$^1$H-NMR (CDCl$_3$) δ: 1.21–1.40 (2H, m), 1.44 (3H, t, J=7.2 Hz), 1.60–1.72 (1H, m), 1.83–1.95 (1H, m), 2.72 (3H, s), 2.75–2.97 (2H, m), 3.32–3.62 (5H, m), 3.70–3.92 (4H, m), 4.45 (2H, q, J=7.2 Hz), 6.70 (1H, dd, J=6.0, 2.8 Hz), 7.51 (1H, d, J=2.8 Hz), 7.63 (1H, dd, J=8.8, 1.8 Hz), 7.81 (1H, dd, J=8.8, 1.8 Hz), 7.94–7.98 (3H, m), 8.35–8.37 (2H, m).

IR (KBr): 2932, 1715, 1667, 1595, 1541, 1495, 1454, 1418 cm$^{-1}$.

Example 73

4-(6-Chloronaphthalene-2-sulfonyl)-1-{[1-(2-methoxycarbonyl-4-pyridyl)-4-piperidinyl]methylamino}-2-piperazinone

Similarly to Example 63 and using methyl 4-chloropyridine-2-carboxylate hydrochloride (1.08 g) instead of 4-chloro-2-picoline and using methanol instead of ethanol, the title compound (325 mg) was obtained as colorless crystals.

$^1$H-NMR (CDCl$_3$) δ: 1.20–1.40 (2H, m), 1.58–1.75 (1H, m), 1.88–1.95 (1H, m), 2.72 (3H, s), 2.80–2.95 (2H, m), 3.39–3.62 (5H, m), 3.65–3.92 (4H, m), 3.98 (3H, s), 6.70 (1H, dd, J=6.0, 2.8 Hz), 7.51 (1H, d, J=2.8 Hz), 7.63 (1H, dd, J=8.8, 1.8 Hz), 7.81 (1H, dd, J=8.8, 1.8 Hz), 7.94–7.98 (3H, m), 8.33–8.36 (2H, m).

IR (KBr): 2926, 1725, 1669, 1597, 1543, 1497, 1456, 1420 cm$^{-1}$.

Example 74

4-(6-Chloronaphthalene-2-sulfonyl)-1-{methyl[1-(4-quinolinyl)-4-piperidinyl]amino}-2-piperazinone

4-(6-Chloronaphthalene-2-sulfonyl)-1-[methyl(4-piperidinyl)amino]-2-piperazinone hydrochloride (236 mg) obtained in Reference Example 21 was combined with 4-chloroquinoline (164 mg), 4-dimethylaminopyridine (244 mg) and xylene (15 ml), and heated under reflux for 15 hours. The reaction mixture was concentrated and the residue was combined with a 10% aqueous solution of sodium hydroxide, extracted with dichloromethane, dried and concentrated. The residue obtained was purified by a column chromatography (ethyl acetate: methanol=15:1) and crystallized from dilsopropyl ether-isopropyl alcohol to obtain the title compound (46 mg) as colorless crystals.

$^1$H-NMR (CDCl$_3$) δ: 1.53–1.73 (2H, m), 1.70–1.92 (1H, m), 1.96–2.12 (1H, m), 2.77 (3H, s), 2.90–3.10 (2H, m), 3.33–3.77 (7H, m), 3.79 (2H, d, J=4.8 Hz), 6.81 (1H, d,

J=6.0 Hz), 7.49–7.57 (1H, m), 7.61 (1H, dd, J=B.4, 2.2 Hz), 7.70–7.83 (2H, m), 7.91–7.98 (4H, m), 8.27–8.33 (1H, m), 8.37 (1H, s), 8.62 (1H, d, J=6.0 Hz).

IR (KBr): 2928, 1669, 1580, 1507, 1456, 1418 cm$^{-1}$.

Example 75

1-{[1-(2-Amino-4-pyridyl)-4-piperidinyl]methylamino}-4-(6-chloronaphthalene-2-sulfonyl)-2-piperazinone Hydrochloride Similarly to Example 39 and starting from 1-{[1-(2-amino-4-pyridyl)-4-piperidinyl]methylamino}-4-(6-chloronaphthalene-2-sulfonyl)-2-piperazinone (200 mg), the title compound (224 mg) was obtained as colorless crystals.

$^1$H-NMR (DMSO-d$_6$) δ: 1.05 (2H, m), 1.54 (1H, m), 1.75 (1H, m), 2.52 (3H, s), 2.80–3.85 (11H, m) 5.95 (1H, s), 6.44 (1H, d, J=7.2 Hz), 7.17 (2H, brs), 7.60 (1H, dd, J=5.8, 7.2 Hz), 7.76 (1H, dd, J=8.8, 1.8 Hz), 7.92 (1H, dd, J=8.8, 2.0 Hz), 8.21 (1H, d, J=8.8 Hz), 8.30 (1H, d, J=8.8 Hz), 8.31 (1H, d, J=1.8 Hz), 8.62 (1H, s), 12.25 (1H, brs).

Example 76

4-(6-Chloronaphthalene-2-sulfonyl)-1-{[1-(2-methylamino-4-pyridyl)-4-piperidinyl]methylamino}-2-piperazinone Similarly to Example 63 and using 4-chloro-2-methylaminopyridine hydrochloride (223 mg) instead of 4-chloro-2-picoline, the title compound (300 mg) was obtained as colorless crystals.

$^1$H-NMR (CDCl$_3$) δ: 1.32 (2H, m), 1.62 (1H, m), 1.84 (1H, m), 2.71 (3H, s), 2.78 (2H, m), 2.87 (3H, d, J=5.2 Hz), 3.30–3.90 (9H, m), 4.66 (1H, brq, J=5.2 Hz), 5.64 (1H, d, J=2.2 Hz), 6.07 (1H, dd, J=6.4, 2.2 Hz), 7.62 (1H, dd, J=8.8, 1.8 Hz), 7.77 (1H, d, J=6.4 Hz), 7.80 (1H, dd, J=8.8, 1.8 Hz), 7.90–8.00 (3H, m), 8.35 (1H, s)

Example 77

4-(6-Chloronaphthalene-2-sulfonyl)-1-{[1-(2-dimethylamino-4-pyridyl)-4-piperidinyl]methylamino}-2-piperazinone Similarly to Example 63 and using 4-chloro-2-dimethylaminopyridine hydrochloride (306 mg) instead of 4-chloro-2-picoline, the title compound (130 mg) was obtained as a colorless solid.

$^1$H-NMR (CDCl$_3$) δ: 1.32 (2H, m), 1.63 (1H, m), 1.86 (1H, m), 2.71 (3H, s), 2.80 (2H, m), 3.05 (6H, s), 3.30–3.85 (9H, m), 5.75 (1H, d, J=2.2 Hz), 6.06 (1H, dd, J=6.2, 2.2 Hz), 7.61 (1H, dd, J=8.8, 1.8 Hz), 7.80 (1H, dd, J=8.8, 1.8 Hz), 7.88–8.00 (4H, m), 8.35 (1H, s).

Example 78

4-(6-Chloronaphthalene-2-sulfonyl)-1-[1-(4-pyridyl)-4-piperidinylamino}-2-thioxopiperazine A solution of 4-(6-chloronaphthalene-2-sulfonyl)-1-[1-(4-pyridyl)-4-piperidinylamino}-2-piperazinone (200 mg) in pyridine (10 ml) was combined with phosphorus pentasulfide (80 mg) and stirred at 100° C. for 5 hours. The supernatant of the reaction mixture was concentrated and the residue was purified by a column chromatography on a silica gel (dichloromethane: 10% aqueous ammonia-containing methanol=20:1) to obtain the title compound (35 mg) as a colorless solid.

$^1$H-NMR (CDCl$_3$) δ: 1.51 (2H, m), 1.76 (2H, m), 2.82 (2H, m), 3.25 (1H, m), 3.58 (2H, m), 3.70–3.85 (4H, m), 4.36 (2H, s), 6.61 (2H, d, J=6.6 Hz), 6.73 (1H, d, J=6.6 Hz), 7.62 (1H, dd, J=1.8, 8.8 Hz), 7.81 (1H, dd, J=1.8, 8.8 Hz), 7.90–8.00 (3H, m), 8.26 (2H, d, J=6.6 Hz), 8.39 (1H, s).

IR (KBr): 1595, 1337, 1163 cm$^{-1}$.

Example 79

4-(6-Chloronaphthalene-2-sulfonyl)-1-{[1-(4-pyridyl)-4-piperidinyl](2,2,2-trifluoroethyl)amino}-2-piperazinone Similarly to Method B in Example 43 and using 4-(6-chloronaphthalene-2-sulfonyl)-1-[1-(4-pyridyl)-4-piperidinylamino}-2-piperazinone (200 mg) and trifluoroacetic acid (5 ml) instead of acetic acid, the title compound (37 mg) was obtained as colorless crystals.

$^1$H-NMR (CDCl$_3$) δ: 1.40 (2H, m), 1.64 (1H, m), 1.87 (1H, m), 2.76 (2H, m), 3.15 (1H, m), 3.30–3.95 (9H, m), 4.04 (1H, d, J=16.4 Hz), 6.61 (2H, d, J=6.6 Hz), 7.63 (1H, dd, J=1.8, 8.8 Hz), 7.80 (1H, dd, J=1.8, 8.8 Hz), 7.90–8.00 (3H, m), 8.27 (2H, d, J=6.6 Hz), 8.37 (1H, s).

IR (KBr): 1669, 1597, 1348, 1273, 1161 cm$^{-1}$.

Example 80

4-(6-Chloronaphthalene-2-sulfonyl)-1-{(2-methoxyethyl)[1-(4-pyridyl)-4-piperidinyl]amino}-2-piperazinone Similarly to Method B in Example 43 and using 4-(6-chloronaphthalene-2-sulfonyl)-1-[1-(4-pyridyl)-4-piperidinylamino}-2-piperazinone (200 mg) and methoxyacetic acid (4 ml) instead of acetic acid, the title compound (123 mg) was obtained as colorless crystals.

$^1$H-NMR (CDCl$_3$) δ: 1.36 (2H, m), 1.60 (1H, m), 1.90 (1H, m), 2.75 (2H, m), 3.09 (1H, m), 3.24 (3H, s), 3.25–3.90 (11H, m), 3.91 (1H, d, J=17.0 Hz), 6.58 (2H, d, J=6.6 Hz), 7.62 (1H, dd, J=1.8, 8.8 Hz), 7.81 (1H, dd, J=1.8, 8.8 Hz), 7.90–8.00 (3H, m), 8.24 (2H, d, J=6.6 Hz), 8.36 (1H, s).

IR (KBr): 1663, 1595, 1348, 1165 cm$^{-1}$.

Example 81

(3S)-3-(6-Chloronaphthalene-2-sulfonylamino)-1-[1-(4-pyridyl)-4-piperidinylideneamino}-2-pyrrolidone A solution of (3S)-3-(6-chloronaphthalene-2-sulfonylamino)-2-pyrrolidone (1.84 g) and 1-(4-pyridyl)-4-piperidone (560 mg) in ethanol (50 ml) was dehydrated using a Soxlet extractor packed with molecular sieves 4A while refluxing for 15 hours. The reaction mixture was concentrated and crystallized from ethyl acetate to obtain the title compound (650 mg) as colorless crystals.

$^1$H-NMR (CDCl$_3$) δ: 2.17 (1H, m), 2.38–2.70 (5H, m), 3.40–3.80 (6H, m), 3.95 (1H, dd, J=8.4, 9.4 Hz), 6.68 (2H, d, J=6.6 Hz), 7.53 (1H, dd, J=1.8, 8.8 Hz), 7.80–8.00 (4H, m), 8.26 (2H, d, J=6.6 Hz), 8.46 (1H, s).

Example 82

(3S)-3-(6-Chloronaphthalene-2-sulfonylamino)-1-[1-(4-pyridyl)-4-piperidinylamino}-2-pyrrolidone (3S)-3-(6-Chloronaphthalene-2-sulfonylamino)-1-[1-(4-pyridyl)-4-piperidinylideneamino}-2-pyrrolidone (600 mg) was dissolved in methanol (40 ml), combined with acetic acid (761 mg) while cooling on ice, followed by sodium cyanoborohydride (300 mg) and stirred at room temperature for 30 minutes. The reaction mixture was concentrated and the residue was combined with an aqueous solution of sodium carbonate, extracted with dichloromethane, dried, concentrated and purified by a column chromatography (dichloromethane: 10% aqueous ammonia-containing methanol=20:1) and crystallized from ethyl acetate to obtain the title compound (576 mg) as colorless crystals.

$^1$H-NMR (CDCl$_3$) δ: 1.44 (2H, m), 1.82 (2H, m), 2.11 (1H, m), 2.58 (1H, m), 2.89 (2H, m), 3.17 (1H, m) 3.37–3.50 (2H, m), 3.70–3.85 (3H, m), 4.41 (1H, br), 6.62 (2H, d, J=6.6 Hz), 7.57 (1H, dd, J=2.0, 8.8 Hz), 7.90–7.96 (4H, m), 8.24 (2H, d, J=6.6 Hz), 8.46 (1H, s).

IR (KBr): 1696, 1601, 1514, 1327, 1157 cm$^{-1}$.

Example 83

(3S)-3-(6-Chloronaphthalene-2-sulfonylamino)-1-{methyl[1-(4-pyridyl)-4-piperidinyl]amino}-2-pyrrolidone (3S)-3-(6-Chloronaphthalene-2-sulfonylamino)-1-[1-(4-pyridyl)-4-piperidinylamino}-2-pyrrolidone (400 mg) was dissolved in a 37% aqueous solution of formaldehyde (11 ml) and formic acid (5 ml) and refluxed for 3 hours. The reaction mixture was cooled and made alkaline by adding an aqueous solution of sodium carbonate, extracted with dichloromethane, dried and concentrated. The residue was purified by a column chromatography (dichloromethane: 10% aqueous ammonia-containing methanol=20:1) and crystallized from dichloromethane to obtain the title compound (180 mg) as colorless crystals.

$^1$H-NMR (CDCl$_3$) δ: 1.49 (2H, m), 1.80 (2H, m), 2.10 (1H, m), 2.59 (1H, m), 2.67 (3H, s), 2.86 (2H, m), 3.17 (1H, m), 3.30–3.40 (2H, m), 3.67 (1H, dd, J=7.8, 10.4 Hz), 3.80 (2H, m), 6.61 (2H, d, J=6.6 Hz), 7.58 (1H, dd, J=1.8, 8.8 Hz), 7.90–8.00 (4H, m), 8.24 (2H, d, J=6.6 Hz), 8.46 (1H, s).

IR (KBr): 1703, 1599, 1514, 1325, 1159 cm$^{-1}$.

Example 84

(3S)-3-[6-Chloronaphthalene-2-sulfonyl)methylamino]-1-[1-(4-pyridyl)-4-piperidinylamino}-2-pyrrolidone A solution of (3S)-3-(6-chloronaphthalene-2-sulfonylamino)-1-[1-(4-pyridyl)-4-piperidinylamino}-2-pyrrolidone (150 mg) in DMF (11 ml) was combined with dimethylformaldehyde dimethyl acetal (5 ml) and stirred at 100° C. for 2 hours. The reaction mixture was concentrated and the residue was purified by a column chromatography (dichloromethane: 10% aqueous ammonia-containing methanol=20:1) to obtain the title compound (100 mg) as a colorless solid.

$^1$H-NMR (CDCl$_3$) δ: 1.47 (2H, m), 1.84 (2H, m), 2.09 (1H, m), 2.42 (1H, m), 2.80 (3H, s), 2.90 (2H, m), 3.17 (1H, m), 3.35–3.60 (2H, m), 3.81 (2H, m), 4.50 (1H, t, J=5.2 Hz), 4.90 (1H, t, J=9.0 Hz), 6.63 (2H, d, J=6.6 Hz), 7.54 (1H, dd, J=2.0, 8.8 Hz), 7.85–8.00 (4H, m), 8.25 (2H, d, J=6.6 Hz), 8.51 (1H, s).

Example 85

(3R)-3-(6-Chloronaphthalene-2-sulfonylamino)-1-[1-(4-pyridyl)-4-piperidinylamino}-2-pyrrolidone Similarly to Example 82 and using the (3R) form instead of the (3S) form, the title compound was obtained as colorless crystals.

$^1$H-NMR (CDCl$_3$) δ: 1.44 (2H, m), 1.82 (2H, m), 2.11 (1H, m), 2.58 (1H, m), 2.89 (2H, m), 3.17 (1H, m), 3.37–3.50 (2H, m), 3.70–3.85 (3H, m), 4.41 (1H, br), 6.62 (2H, d, J=6.6 Hz), 7.57 (1H, dd, J=2.0, 8.8 Hz), 7.90–7.96 (4H, m), 8.24 (2H, d, J=6.6 Hz), 8.46 (1H, s).

IR (KBr): 1682, 1599, 1514, 1329, 1159 cm$^{-1}$.

Example 86

(3S)-3-(7-Methoxynaphthalene-2-sulfonylamino)-1-[1-(4-pyridyl)-4-piperidinylamino]-2-pyrrolidone A solution of (3S)-3-(tert-butoxycarbonylamino)-1-[1-(4-pyridyl)-4-piperidinylamino]-2-pyrrolidone (220 mg) in methanol (10 ml) was combined with a 4N solution of hydrochloric acid in ethyl acetate (10 ml) and stirred at room temperature for 30 minutes. The reaction mixture was concentrated and the residue obtained was combined with dichloromethane (20 ml) and triethylamine (700 ml), followed by 7-methoxynaphthalene-2-sulfonyl chloride (150 ml) at 0° C., and then stirred at room temperature for 1 hour. The reaction mixture was combined with an aqueous solution of sodium carbonate, extracted with dichloromethane, dried, concentrated and purified by a column chromatography dichloromethane: 10% aqueous ammonia-containing methanol=20:1) to obtain the title compound (123 mg) as a colorless amorphous material.

$^1$H-NMR (CDCl$_3$) δ: 1.43 (2H, m), 1.82 (2H, m), 2.10 (1H, m), 2.52 (1H, m), 2.89 (2H, m), 3.19 (1H, m), 3.30–3.50 (2H, m), 3.70–3.90 (3H, m), 3.94 (3H, s), 4.40 (1H, br), 6.60 (2H, d, J=6.6 Hz), 7.24 (1H, d, J=2.6 Hz), 7.30 (1H, dd, J=2.6, 9.0 Hz), 7.74 (1H, dd, J=1.8, 8.4 Hz), 7.80 (1H, d, J=9.0 Hz), 7.89 (1H, d, J=8.4 Hz), 8.22 (2H, d, J=6.6 Hz), 8.36 (1H, s).

IR (KBr): 1696, 1599, 1510, 1325, 1256, 1217, 1159, 1127 cm$^{-1}$.

Example 87

1-[1-(4-Pridyl)-4-piperidinylamino]-(3S)-3-(4-vinylbenzenesulfonylamino)-2-pyrrolidone Similarly to Example 86 and using (3S)-3-(tert-butoxycarbonylamino)-1-[1-(4-pyridyl)-4-piperidinylamino]-2-pyrrolidone (220 mg) and 4-vinylbenzenesulfonyl chloride (105 mg), the title compound (179 mg) was obtained as a colorless amorphous material.

$^1$H-NMR (CDCl$_3$) δ: 1.44 (2H, m), 1.84 (2H, m), 2.10 (1H, m), 2.54 (1H, m), 2.91 (2H, m), 3.21 (1H, m), 3.38–3.50 (2H, m), 3.70–3.90 (3H, m), 4.44 (1H, br), 5.45 (1H, d, J=11.0 Hz), 5.89 (1H, d, J=17.6 Hz), 6.63 (2H, d, J=6.6 Hz), 6.76 (1H, dd, J=11.0, 17.6 Hz), 7.55 (2H, d, J=8.4 Hz), 7.88 (2H, d, J=8.4 Hz), 8.25 (2H, d, J=6.6 Hz).

IR (KBr): 1703, 1599, 1514, 1329, 1159 cm$^{-1}$.

Example 88

(3S)-3-(7-Bromo-2H-benzopyran-3-sulfonylamino)-1-[1-(4-pyridyl)-4-piperidinylamino]-2-pyrrolidone Similarly to Example 86 and using (3S)-3-(tert-butoxycarbonylamino)-1-[1-(4-pyridyl)-4-piperidinylamino]-2-pyrrolidone (220 mg) and 7-bromo-2H-benzopyran-3-sulfonyl chloride (161 mg), the title compound (87 mg) was obtained as a colorless amorphous material.

$^1$H-NMR (CDCl$_3$) δ: 1.44 (2H, m), 1.86 (2H, m), 2.07 (1H, m), 2.57 (1H, m), 2.94 (2H, m), 3.22 (1H, m), 3.35–3.55 (2H, m), 3.82 (2H, m), 4.00 (1H, dd, J=8.8, 9.8

Hz), 4.35 (1H, br), 5.06 (2H, t, J=1.5 Hz), 6.65 (2H, d, J=6.6 Hz), 6.98–7.15 (3H, m), 7.28 (1H, s), 8.24 (2H, d, J=6.6 Hz).

IR (KBr): 1701, 1597, 1481, 1323, 1155, 1065 cm$^{-1}$.

Example 89

(3S)-3-(7-Chloronaphthalene-2-sulfonylamino)-1-[1-(4-pyridyl)-4-piperidinylamino}-2-pyrrolidone Similarly to Example 86 and using (3S)-3-(tert-butoxycarbonylamino)-1-[1-(4-pyridyl)-4-piperidinylamino]-2-pyrrolidone (220 mg) and 7-chlornaphthalene-2-sulfonyl chloride (170 mg), the title compound (88 mg) was obtained as colorless crystals.

$^{1}$H-NMR (CDCl$_{3}$) δ: 1.42 (2H, m), 1.83 (2H, m), 2.11 (1H, m), 2.58 (1H, m), 2.92 (2H, m), 3.19 (1H, m), 3.30–3.50 (2H, m), 3.70–3.90 (3H, m), 4.40 (1H, br), 6.63 (2H, d, J=6.6 Hz), 7.60 (1H, dd, J=2.2, 8.8 Hz), 7.83–8.02 (4H, m), 8.24 (2H, d, J=6.6 Hz), 8.39 (1H, s).

IR (KBr): 1701, 1597, 1540, 1319, 1157 cm$^{-1}$.

Example 90

(3S)-3-(4-Chlorostyrene-β(E)-sulfonylamino)-1-[1-(4-pyridyl)-4-piperidinylamino}-2-pyrrolidone Similarly to Example 86 and using (3S)-3-(tert-butoxycarbonylamino)-1-[1-(4-pyridyl)-4-piperidinylamino]-2-pyrrolidone (220 mg) and 4-chlorostyrene-β(E)-sulfonyl chloride (150 mg), the title compound (161 mg) was obtained as a colorless amorphous material.

$^{1}$H-NMR (CDCl$_{3}$) δ: 1.45 (2H, m), 1.86 (2H, m), 2.11 (1H, m), 2.60 (1H, m), 2.98 (2H, m), 3.24 (1H, m), 3.35–3.55 (2H, m), 3.82 (2H, m), 4.02 (1H, dd, J=8.4, 9.8 Hz), 4.47 (1H, d, J=5.2 Hz), 6.63 (2H, d, J=6.6 Hz), 6.91 (1H, d, J=15.4 Hz), 7.38 (2H, d, J=8.4 Hz), 7.45 (2H, d, J=8.4 Hz), 7.48 (1H, d, J=15.4 Hz), 8.24 (2H, d, J=6.6 Hz).

IR (KBr): 1699, 1597, 1512, 1491, 1148 cm$^{-1}$.

Example 91

4-(6-Chloronaphthalene-2-sulfonyl)-1-[1-(2-methyl-4-pyridyl)-4-piperidinylamino}-2-piperazinone Similarly to Example 63 and using 4-(6-chloronaphthalene-2-sulfonyl)-1-(4-piperidinylamino)-2-piperazinone dihydrochloride (492 mg) instead of 4-(6-chloronaphthalene-2-sulfonyl)-1-[methyl(4-piperidinyl)amino]-2-piprazinone hydrochloride, the title compound (320 mg) was obtained as colorless crystals.

$^{1}$H-NMR (CDCl$_{3}$) δ: 1.25–1.38 (2H, m), 1.63–1.69 (2H, m), 2.34 (3H, s), 2.64–2.78 (2H, m), 2.95–3.08 (1H, m), 3.32–3.40 (2H, m), 3.48–3.53 (2H, m), 3.63–3.69 (2H, m), 3.76 (2H, s), 4.97 (2H, d, J=4.8 Hz), 6.34–6.40 (2H, m), 7.52 (1H, dd, J=8.8, 1.8 Hz), 7.71 (1H, dd, J=8.8, 1.8 Hz), 7.85 (1H, d, J=1.8 Hz), 7.85 (2H, d, J=8.8 Hz), 8.05 (1H, d, J=5.8 Hz), 8.27 (1H, d, J=1.8 Hz).

IR (KBr): 2930, 1655, 1599, 1540, 1495, 1453, 1425 cm$^{-1}$.

Example 92

4-(6-Chloronaphthalene-2-sulfonyl)-1-[1-(2-methyl-4-pyridyl)-4-piperidinylamino]-2-piperazinone Dihydrochloride Similarly to Example 39 and using 4-(6-chloronaphthalene-2-sulfonyl)-1-[1-(2-methyl-4-pyridyl)-4-piperidinylamino]-2-piperazinone (250 mg), the title compound (277 mg) was obtained as colorless crystals.

$^{1}$H-NMR (DMSO-d$_{6}$) δ: 1.10–1.30 (2H, m), 1.64–1.75 (2H, m), 2.44 (3H, s), 3.05–3.20 (3H, m), 3.44 (4H, s), 3.77 (2H, s), 3.94–4.01 (2H, m), 5.18 (2H, brs), 6.99–7.03 (2H, m), 7.75 (1H, dd, J=8.8, 2.0 Hz), 7.91 (1H, dd, J=8.8, 1.4 Hz), 8.06–8.13 (1H, m), 8.20 (1H, d, J=8.8 Hz), 8.28–8.32 (2H, m), 8.61 (1H, s), 13.50 (1H, brs).

IR (KBr): 3400, 2930, 1694, 1642, 1541, 1495, 1430 cm$^{-1}$.

Example 93

4-(6-Chloronaphthalene-2-sulfonyl)-1-[1-(3-pyridyl)-4-piperidinylideneamino]-2-piperazinone Similarly to Example 3, a solution of 1-amino-4-(6-chloronaphthalene-2-sulfonyl)-2-piperazinone (510 mg) and 1-(3-pyridyl)-4-piperidone (260 mg) in toluene (20 ml) was refluxed for 7 hours. The reaction mixture was cooled to room temperature, and the resultant crystal was collected by filtration to obtain the title compound (480 mg) as colorless crystals.

$^{1}$H-NMR (CDCl$_{3}$) δ: 2.25 (2H, t, J=5.9 Hz), 2.64 (2H, t, J=5.8 Hz), 3.30 (2H, t, J=5.8 Hz), 3.48–3.57 (4H, m), 3.65–3.71 (2H, m), 3.87 (2H, s), 7.16–7.18 (2H, m), 7.62 (1H, dd, J=1.8, 8.8 Hz), 7.82 (1H, dd, J=1.9, 8.8 Hz), 7.93–7.98 (3H, m), 8.11 (1H, t, J=3.0 Hz), 8.30 (1H, t, J=1.8 Hz), 8.38 (1H, d, J=1.0 Hz).

IR (KBr): 1661, 1346, 1163 cm$^{-1}$.

Example 94

4-(6-Chloronaphthalene-2-sulfonyl)-1-[1-(3-pyridyl)-4-piperidinylamino]-2-piperazinone Similarly to Example 11, 4-(6-chloronaphthalene-2-sulfonyl)-1-[1-(3-pyridyl)-4-piperidinylideneamino]-2-piperazinone (420 mg) was reduced by sodium cyanoborohydride (53 mg) to obtain the title compound (330 mg) as colorless crystals.

$^{1}$H-NMR (CDCl$_{3}$) δ: 1.41–1.60 (2H, m), 1.73–1.98 (2H, m), 2.68–2.81 (2H, m), 2.99–3.15 (1H, m), 3.45–3.50 (2H, m), 3.58–3.66 (4H, m), 3.88 (2H, s), 5.12 (1H, d, J=2.2 Hz), 7.13–7.15 (2H, m), 7.62 (1H, dd, J=2.2, 8.8 Hz), 7.81 (1H, dd, J=1.6, 8.6 Hz), 7.93–7.97 (3H, m), 8.07 (1H, t, J=2.9 Hz), 8.27 (1H, t, J=1.8 Hz), 8.37 (1H, d, J=1.6 Hz).

IR (KBr): 1651, 1346, 1163, 729, 698 cm$^{-1}$.

Example 95

4-(6-Chloronaphthalene-2-sulfonyl)-1-{methyl[1-(3-pyridyl)-4-piperidinyl]amino}-2-piperazinone Similarly to Method C in Example 38 and Method 39 and starting from 4-(6-chloronaphthalene-2-sulfonyl)-1-[1-(3-pyridyl)-4-piperidinylamino]-2-piperazinone (280 mg), the title compound (220 mg) was obtained as colorless crystals.

$^{1}$H-NMR (DMSO-d$_{6}$) δ: 1.05–1.24 (2H, m), 1.51–1.59 (1H, m), 1.73–1.80 (1H, m), 2.54 (3H, s), 2.68–2.92 (2H, m), 3.17–3.88 (9H, m), 7.73–7.80 (2H, m), 7.89–7.94 (2H, m), 8.13 (1H, d, J=4.8 Hz), 8.21 (1H, d, J=8.8 Hz), 8.26–8.36 (3H, m), 8.62 (1H, m).

IR (KBr): 1690, 1557, 1343, 1155 cm$^{-1}$.

Example 96

4-(6-Chloronaphthalene-2-sulfonyl)-1-{[1-(2-methoxymethyl-4-pyridyl)-4-piperidinyl](methyl)amino}-2-piperazinone Similarly to Example 63 and using 4-chloro-2-methoxymethylpyridine (0.27 g) instead of 4-chloro-2- picoline, the title compound (230 mg) was obtained as colorless crystals.

¹H-NMR (CDCl₃) δ: 1.33 (2H, m), 1.68 (1H, m), 1.85 (1H, m), 2.71 (3H, s), 2.81 (2H, m), 3.38–3.90 (9H, m), 3.47 (3H, s), 4.47 (2H, s), 6.50 (1H, dd, J=6.1, 2.3 Hz), 6.76 (1H, d, J=3.0 Hz), 7.63 (1H, dd, J=9.0, 2.0 Hz), 7.81 (1H, dd, J=6.6, 2.0 Hz), 7.94–7.98 (3H, m), 8.20 (1H, d, J=5.8 Hz), 8.36 (1H, m).

IR (KBr): 1667, 1599, 1449, 1348, 1163, 1105, 731, 696, 584 cm⁻¹.

Example 97

4-(6-Chloronaphthalene-2-sulfonyl)-1-{[1-(2-methoxymethyl-4-pyridyl)-4-piperidinyl](methyl)amino}-2-piperazinone Hydrochloride Similarly to Example 39 and starting from 4-(6-chloronaphthalene-2-sulfonyl)-1-{[1-(2-methoxymethyl-4-pyridyl)-4-piperidinyl](methyl)amino}-2-piperazinone (200 mg), the title compound (175 mg) was obtained as colorless crystals.

¹H-NMR (DMSO-d₆) δ: 1.10–1.15 (2H, m), 1.69–1.81 (2H, m), 2.53 (3H, s), 3.09–3.50 (7H, m), 3.72 (2H, br), 3.98–4.04 (5H, m), 4.52 (2H, s), 7.05 (1H, d, J=8.0 Hz), 7.11 (1H, s), 7.76 (1H, dd, J=9.0, 2.0 Hz), 7.92 (1H, dd, J=2.0, 8.8 Hz), 8.19–8.23 (4H, m), 8.62 (1H, s).

IR (KBr): 1644, 1541, 1456, 1346, 1319, 1161, 1136, 1105, 1078, 696, 667, 584 cm⁻¹.

Example 98

4-(6-Chloronaphthalene-2-sulfonyl)-1-{[1-(2-ethoxymethyl-4-pyridyl)-4-piperidinyl](methyl)amino}-2-piperazinone Similarly to Example 63 and using 4-chloro-2-ethoxymethylpyridine (0.55 g) instead of 4-chloro-2-picoline, the title compound (505 mg) was obtained as a tan amorphous material.

¹H-NMR (CDCl₃) δ: 1.28 (3H, t, J=7.0 Hz), 1.38 (2H, m), 1.68 (1H, m), 1.85–1.91 (1H, m), 2.71 (3H, s), 2.80 (2H, m), 3.38–3.87 (9H, m), 3.62 (2H, q, J=7.0 Hz), 4.51 (2H, s), 6.48 (1H, dd, J=6.0, 2.8 H Z), 6.79 (1H, d, J=2.6 Hz), 7.61 (1H, dd, J=8.8, 2.2 Hz), 7.81 (1H, dd, J=8.8 and 1.8 Hz), 7.93–7.97 (3H, m), 8.19 (1H, d, J=6.2 Hz), 8.36 (1H, d, J=1.2 Hz).

IR (KBr): 1669, 1599, 1456, 1348, 1163, 696 cm⁻¹.

Example 99

4-(6-Chloronaphthalene-2-sulfonyl)-1-{[1-(2-dimethylaminomethyl-4-pyridyl)-4-piperidinyl](methyl)amino}-2-piperazinone Similarly to Example 63 and using 4-chloro-2-dimethylaminomethylpyridine (530 mg) instead of 4-chloro-2-picoline, the title compound (640 mg) was obtained as a tan amorphous material.

¹H-NMR (CDCl₃) δ: 1.30–1.39 (2H, m), 1.61 (1H, m), 1.84 (1H, m), 2.28 (6H, s), 2.71 (3H, s), 2.80 (2H, m), 3.38–3.86 (13H, m), 6.48 (1H, dd, J=6.1, 2.7 Hz), 6.76 (1H, d, J=2.6 Hz), 7.62 (1H, dd, J=8.8 and 2.2 Hz), 7.81 (1H, dd, J=1.7 and 8.7 Hz), 7.93–7.98 (3H, m), 8.19 (1H, d, J=5.8 Hz), 8.36 (1H, d, J=1.2 Hz).

IR (KBr): 1667, 1597, 1456, 1348, 1163, 1003, 733, 696 cm⁻¹.

Example 100

1-{[1-(2-Acetylaminomethyl-4-pyridyl)-4-piperidinyl](methyl)amino}-4-(6-chloronaphthalene-2-sulfonyl)-2-piperazinone Similarly to Example 63 and using 2-acetylaminomethyl-4-chloropyridine (185 mg) instead of 4-chloro-2-picoline, the title compound (230 mg) was obtained as a tan powder.

¹H-NMR (CDCl₃) δ: 1.30 (2H, m), 1.63 (1H, br), 1.86 (1H, br), 2.05 (3H, s), 2.71 (3H, s), 2.80 (2H, br), 3.38–3.77 (9H, m), 4.40 (2H, d, J=4.8 Hz), 6.50–6.55 (2H, m), 6.74 (1H, m), 7.63 (1H, dd, J=1.8, 8.8 Hz), 7.81 (1H, dd, J=1.8, 9.2 Hz), 7.93–7.98 (3H, m), 8.16 (1H, d, J=5.8 Hz), 8.37 (1H, m).

IR (KBr): 1665, 1599, 1348, 1163, 698, 667, 586 cm⁻¹.

Example 101

4-(6-Chloronaphthalene-2-sulfonyl)-1-{[1-(2-(1-hydroxy-1-methylethyl)-4-pyridyl)-4-piperidinyl](methyl)amino}-2-piperazinone Similarly to Example 63 and using 4-chloro-2-(1-hydroxy-1-methylethyl)pyridine (257 mg) instead of 4-chloro-2-picoline, the title compound (220 mg) was obtained as a tan amorphous material.

¹H-NMR (CDCl₃) δ: 1.30–1.96 (4H, m), 1.50 (6H, s), 2.72 (3H, s), 2.77–2.89 (2H, m), 3.37–3.84 (9H, m), 5.18 (1H, br), 6.51 (1H, dd, J=2.4 and 6.0 Hz), 6.65 (1H, d, J=2.2 Hz), 7.62 (1H, dd, J=2.0, 8.8 Hz), 7.80 (1H, dd, J=1.6, 8.6 Hz), 7.93–7.97 (3H, m), 8.16 (1H, d, J=5.8 Hz), 8.36 (1H, d, J=1.6 Hz).

IR (KBr): 1667, 1599, 1493, 1456, 1348, 1319, 1163, 1136, 1078, 993, 964, 729, 696, 667, 584 cm⁻¹.

Example 102

4-(6-Chloronaphthalene-2-sulfonyl)-1-{[1-(2-hydroxymethyl-6-methyl-4-pyridyl)-4-piperidinyl](methyl)amino}-2-piperazinone Similarly to Example 63 and using 4-chloro-2-hydroxymethy-6-methylpyridine (236 mg) instead of 4-chloro-2-picoline, the title compound (240 mg) was obtained as a tan powder.

¹H-NMR (CDCl₃) δ: 1.26–1.33 (2H, m), 1.70 (1H, m), 1.84 (1H, m), 2.43 (3H, s), 2.71 (3H, s), 2.71–2.87 (2H, m), 3.37–3.85 (10H, m), 4.59 (2H, s), 6.39 (2H, s), 7.63 (1H, dd, J=2.0, 8.8 Hz), 7.80 (1H, dd, J=8.8, 1.8 Hz), 7.93–7.98 (3H, m), 8.36 (1H, s).

IR (KBr): 1667, 1601, 1456, 1348, 1163, 1078, 731, 698 cm⁻¹.

Example 103

1-{[1-(2-Carbamoylmethyl-4-pyridyl)-4-piperidinyl](methyl)amino}-4-(6-chloronaphthalene-2-sulfonyl)-2-piperazinone Hydrochloride Similarly to Example 63 and Example 39 and using 2-(4-chloro-2-pyridinyl)acetamide (188 mg) instead of 4-chloro-2-picoline, the title compound (105 mg) was obtained as a tan powder.

¹H-NMR (CDCl₃) δ: 1.14 (2H, m), 1.64 (1H, m), 1.82 (1H, m), 2.55 (3H, s), 3.11–4.05 (13H, m), 7.02 (1H, d, J=7.0 Hz), 7.09 (1H, s), 7.29 (1H, s), 7.74–7.79 (2H, m), 7.92 (1H, d, J=8.4 Hz), 8.12–8.33 (4H, m), 8.62 (1H, s).

IR (KBr): 1645, 1541, 1346, 1161, 698, 584 cm⁻¹.

Example 104

Methyl 4-[(6-Chloro-2-naphthyl)sulfonyl]-1-{[1-(2-hydroxymethyl-4-pyridinyl)-4-piperidinyl]amino}-6-oxo-2-piperazinecarboxylate Dihydrochioride Similarly to Example 53 and using 1-(tert-butyl)3-methyl4-[[1-(2-hydroxymethyl-4-pyridinyl)-4-piperidinyl]

amino]-5-oxo-1,3-piperazinedicarboxylate (0.15 g) instead of 1-(tert-butyl) 3-methyl 5-oxo-4-[[1-(4-pyridinyl)-4-piperidinyl]amino]-1,3-piperazine dicarboxylate, the title compound (0.13 g) was obtained as a colorless crystalline powder.

$^1$H-NMR (DMSO-d$_6$) δ: 1.17–1.23 (2H, m), 1.78 (2H, m), 3.11–3.33 (4H, m), 3.55–3.64 (3H, m), 3.69 (3H, s), 3.93–4.00 (4H, m), 4.37 (1H, m), 4.58 (2H, s), 7.04–7.07 (2H, m), 7.75 (1H, dd, J=2.2, 8.8 Hz), 7.88 (1H, dd, J=1.8, 8.8 Hz), 8.07 (1H, t, J=6.2 Hz), 8.19 (1H, d, J=8.8 Hz), 8.28 (1H, s), 8.30 (1H, d, J=9.0 H), 8.61 (1H, s).

IR (KBr): 1748, 1669, 1645, 1539, 1348, 1240, 1163, 1130, 1078 cm$^{-1}$.

Example 105

Methyl 4-[(6-Chloro-2-naphthyl)sulfonyl)-1-[[1-(2-hydroxymethyl-4-pyridinyl)-4-piperidinyl](methyl)amino]-6-oxo-2-piperazinecarboxylate Dihydrochloride Similarly to Example 54 and using methyl 4-[(6-chloro-2-naphthyl)sulfonyl)-1-[[1-(2-hydroxymethyl-4-pyridinyl)-4-piperidinyl]amino]-6-oxo-2-piperazinecarboxylate (0.19 g) instead of methyl 4-[(6-chloro-2-naphthyl)sulfonyl)-6-oxo-1-[[1-(4-pyridinyl)-4-piperidinyl]amino]-2-piperazinecarboxylate dihydrochloride, the title compound (0.12 g) was obtained as a colorless non-crystalline powder.

$^1$H-NMR (DMSO-d$_6$) δ: 1.14–1.30 (2H, m), 1.77–1.99 (2H, m), 2.86 (3H, s), 2.97–3.24 (4H, m), 3.44–3.60 (2H, m), 3.71 (3H, s), 3.89–4.17 (4H, m), 4.30 (1H, s), 4.57 (2H, s), 7.02–7.06 (2H, m), 7.75 (1H, dd, J=2.0, 8.6 Hz), 7.87 (1H, dd, J=1.8, 8.6 Hz), 8.08 (1H, m), 8.19 (1H, d, J=9.2 Hz), 8.28 (1H, s), 8.30 (1H, d, J=9.0 Hz), 8.60 (1H, s).

IR (KBr): 1748, 1669, 1645, 1539, 1454, 1404, 1348, 1331, 1240, 1217, 1184, 1161, 1080, 964, 748, 592 cm$^{-1}$.

Example 106

(+)-Methyl 4-[(6-Chloro-2-naphthyl)sulfonyl)-1-[methyl[1-(4-pyridinyl)-4-piperidinyl]amino]-6-oxo-2-piperazinecarboxylate Hydrochloride Methyl 4-[(6-chloro-2-naphthyl)sulfonyl)-1-[methyl[1-(4-pyridinyl)-4-piperidinyl]amino]-6-oxo-2-piperazinecarboxylate hydrochloride obtained in Example 54 was subjected to an optical resolution using a chiral column (CHIRALPAK AD 50 mm ID×500 mm L) (mobile phase: hexane/ethanol=2/8, flow rate: 70 ml/min, retention time: 19.42 minutes) and the intended fraction was concentrated. The material obtained was dissolved in a small amount of ethanol, combined with 4N hydrochloric acid/ethyl acetate, concentrated and dried to obtain the title compound showing a (+) optical rotation as a pale yellow powder (>99.9% ee).

Example 107

(−)-Methyl 4-[(6-Chloro-2-naphthyl)sulfonyl)-1-[methyl[1-(4-pyridinyl)-4-piperidinyl]amino]-6-oxo-2-piperazinecarboxylate Hydrochloride Methyl 4-[(6-chloro-2-naphthyl)sulfonyl)-1-[methyl[1-(4-pyridinyl)-4-piperidinyl]amino]-6-oxo-2-piperazinecarboxylate hydrochloride obtained in Example 54 was subjected to an optical resolution using a chiral column (CHIRALPAK AD 50 mm ID×500 mm L) (mobile phase: hexane/ethanol=2/8, flow rate: 70 ml/min, retention time: 25.90 minutes) and the intended fraction was concentrated. The material obtained was dissolved in a small amount of ethanol, combined with 4N hydrochloric acid/ethyl acetate, concentrated and dried to obtain the title compound showing a (−) optical rotation as a pale yellow powder (99.4% ee).

Example 108

(+)-Methyl 4-[(6-Chloro-2-naphthyl)sulfonyl)-6-oxo-1-[[1-(4-pyridinyl)-4-piperidinyl]amino]-2-piperazinecarboxylate Dihydrochloride 4-[(6-Chloro-2-naphthyl)sulfonyl)-6-oxo-1-[[1-(4-pyridinyl)-4-piperidinyl]amino]-2-piperazinecarboxylate obtained in Example 53 was subjected to an optical resolution using a chiral column (CHIRALPAK AD 50 mm ID×500 mm L) (mobile phase: hexane/ethanol=1/9, flow rate: 100 ml/min, retention time: 27.95 minutes) and the intended fraction was concentrated. The material obtained was dissolved in a small amount of ethanol, combined with 4N hydrochloric acid/ethyl acetate, concentrated and dried to obtain the title compound showing a (+) optical rotation as a pale yellow powder (>99.9% ee).

Example 109

(−)-Methyl 4-[(6-Chloro-2-naphthyl)sulfonyl)-6-oxo-1-[[1-(4-pyridinyl)-4-piperidinyl]amino]-2-piperazinecarboxylate Dihydrochloride 4-[(6-Chloro-2-naphthyl)sulfonyl)-6-oxo-1-[[1-(4-pyridinyl)-4-piperidinyl]amino]-2-piperazinecarboxylate obtained in Example 53 was subjected to an optical resolution using a chiral column (CHIRALPAK AD 50 mm ID×500 mm L) (mobile phase: hexane/ethanol=1/9, flow rate: 100 ml/min, retention time: 69.39 minutes) and the intended fraction was concentrated. The material obtained was dissolved in a small amount of ethanol, combined with 4N hydrochloric acid/ethyl acetate, concentrated and dried to obtain the title compound showing a (−) optical rotation as a pale yellow powder (>99.9% ee).

Example 110

4-[(6-Chloro-2-naphthyl)sulfonyl)-1-[methyl[1-(4-pyridinyl)-4-piperidinyl]amino]-6-oxo-2-piperazinecarboxylic Acid A mixture of methyl 4-[(6-chloro-2-naphthyl)sulfonyl)-1-[methyl[1-(4-pyridinyl)-4-piperidinyl]amino]-6-oxo-2-piperazinecarboxylate hydrochloride (0.3 g) obtained in Example 54, a 2N aqueous solution of sodium hydroxide (1.1 ml) and methanol (6.0 ml) was stirred at 40° C. for 30 minutes. The reaction mixture was cooled, and then the reaction system was adjusted at pH5 with 1N hydrochloric acid, and then concentrated under reduced pressure. The residue was purified on a CHP-20 column (water→1% 1N hydrochloric acid-containing 30% aqueous solution of acetonitrile) to obtain the title compound (0.28 g) as a colorless powder.

$^1$H-NMR (CD$_3$OD) δ: 1.18–1.50 (2H, m), 1.68–1.88 (1H, m), 1.90–2.12 (1H, m), 2.57 and 2.95 (total 3H, s for each), 2.86–3.36 (3H, m), 3.40–3.64 (2H, m), 3.96–4.30 (5H, m), 7.06 (2H, d, J=7.6 Hz), 7.66 (1H, dd, J=2.0, 8.6 Hz), 7.85 (1H, dd, J=2.0, 8.6 Hz), 7.98–8.18 (5H, m), 8.48 (1H, s).

Example 111

4-[(6-Chloro-2-naphthyl)sulfonyl]-6-hydroxymethyl-1-[methyl[1-(4-pyridinyl)-4-piperidinyl]amino]-2-piperazinone Hydrochloride A solution of methyl 4-[(6-chloro-2-naphthyl)sulfonyl)-1-[methyl[1-(4-pyridinyl)-4-piperidinyl]amino]-6-oxo-2- piperazinecarboxylate hydrochloride (0.3 g) in methanol (20 ml) was treated with 3 portions of lithium borohydride (1.14 g) with stirring at 0° C. After completion of the reaction, the reaction system was adjusted at pH 4 with a 10% hydrochloric acid/methanol solution, and then concentrated under reduced pressure. The residue was partitioned between methylene chloride and saturated aqueous sodium bicarbonate, and the organic phase was dried over magnesium sulfate, and then concentrated under reduced pressure. The residue was purified on a CHP-20 column (water→1% 1N hydrochloric acid-containing 30% aqueous solution of acetonitrile) to obtain the title compound (0.12 g) as a colorless powder.

$^1$H-NMR (CD$_3$OD) δ: 1.20–1.50 (2H, m), 1.66–1.86 (1H, m), 2.00–2.14 (1H, m), 2.63 and 2.86 (total 3H, s for each), 2.94–3.26 (3H, m), 3.28–4.36 (9H, m), 7.00–7.18 (2H, m), 7.66 (1H, dd, J=2.0, 8.8 Hz), 7.88 (1H, dd, J=2.0, 8.8 Hz), 7.98–8.20 (5H, m), 8.49 (1H, s).

Example 112

4-[(6-Chloro-2-naphthyl)sulfonyl)-1-[methyl[1-(4-pyridinyl)-4-piperidinyl]amino]-6-oxo-2-piperazinecarboxamide Hydrochloride Methyl 4-[(6-chloro-2-naphthyl)sulfonyl)-1-[methyl[1-(4-pyridinyl)-4-piperidinyl]amino]-6-oxo-2-piperazinecarboxylate hydrochloride (0.3 g) obtained in Example 54 and 13% ammonia/methanol solution (3.5 ml) were heated in a sealed tube at 90° C. for 2 days. The reaction system was cooled, and concentrated under reduced pressure. The residue was purified on a CHP-20 column (water→1% 1N hydrochloric acid-containing 30% aqueous solution of acetonitrile) to obtain the title compound (0.11 g) as a colorless powder.

$^1$H-NMR (CD$_3$OD) δ: 1.18–1.54 (2H, m), 1.70–1.90 (1H, m), 1.92–2.12 (1H, m), 2.54 and 2.88 (total 3H, s for each), 2.98–3.26 (2H, m), 3.36–4.34 (8H, m), 7.08 (2H, d, J=7.8 Hz), 7.66 (1H, dd, J=1.8, 8.8 Hz), 7.85 (1H, dd, J=1.8, 8.8 Hz), 7.98–8.18 (5H, m), 8.48 (1H, s).

Example 113

6-(Aminomethyl)-4-[(6-chloro-2-naphthyl)sulfonyl]-1-[methyl[1-(4-pyridinyl)-4-piperidinyl]amino]-2-piperazinone Dihydrochloride A mixture of triphenylphosphine (0.49 g), phthalimide (0.29 g) and methylene chloride (15 ml) was combined with diethyl azodicarboxylate (0.29 ml) with stirring at 0° C., and stirred for 10 minutes. This solution was combined, at 0° C. with stirring, with a solution of 4-[(6-chloro-2-naphthyl)sulfonyl]-6-(hydoxymethyl)-1-[methyl[1-(4-pyridinyl)-4-piperidinyl]amino]-2-piperazinone hydrochloride (0.27 g) in methylene chloride (10 ml) and stirred at room temperature for 1 hour. The reaction mixture was washed with saturated aqueous sodium bicarbonate, dried, and concentrated under reduced pressure. The residue was purified by a column chromatography on a silica gel (dichloromethane: 10% aqueous ammonia-containing methanol=10:1) to obtain 2-[(4-[(6-chloro-2-naphthyl)sulfonyl]-1-[methyl[1-(4-pyridinyl)-4-piperidinyl]amino]-6-oxo-2-piperazinyl)methyl]-1H-isoindole-1,3(2H)-dione (0.28 g) as a pale yellow powder.

$^1$H-NMR (CDCl$_3$) δ: 1.20–2.10 (4H, m), 2.60–3.00 (5H, m), 3.10–4.40 (10H, m), 6.59 (2H, d, J=6.6 Hz), 7.62 (1H, dd, J=2.0, 8.8 Hz), 7.70–8.02 (8H, m), 8.23 (2H, d, J=5.8 Hz), 8.34 (1H, s).

A mixture of this substance with hydrazine monohydrate (0.072 ml) and ethanol (8.4 ml) was heated under reflux for 3 hours. The reaction mixture was cooled and any insolubles were filtered off, and the filtrate was concentrated under reduced pressure. The residue was purified by a column chromatography on a silica gel (dichloromethane: 10% aqueous ammonia-containing methanol=10:1) and converted into a hydrochloride using 4 N hydrochloric acid/ethyl acetate, whereby obtaining the title compound (0.17 g) as a pale yellow powder.

$^1$H-NMR (CD$_3$OD) δ: 1.20–1.60 (2H, m), 1.70–1.95 (1H, m), 2.00–2.30 (1H, m), 2.70 and 2.93 (total 3H, s for each), 2.80–4.40 (12H, m), 7.04–7.22 (2H, m), 7.68 (1H, dd, J=2.0, 8.8 Hz), 7.90 (1H, dd, J=1.8, 8.8 Hz), 8.00–8.24 (5H, m), 8.53 (1H, s).

Example 114

N-[[4-[(6-Chloro-2-naphthyl)sulfonyl]-1-[methyl[1-(4-pyridinyl)-4-piperidinyl]amino]-6-oxo-2-piperazinyl]methyl]acetamide Dihydrochloride A mixture of 6-(aminomethyl)-4-[(6-chloro-2-naphthyl)sulfonyl]-1-[methyl[1-(4-pyridinyl)-4-piperidinyl]amino]-2-piperazinone dihydrochloride (0.14 g) obtained in Example 113, triethylamine (0.16 ml) and methylene chloride (3 ml) was combined with acetic anhydride (0.043 ml) with stirring at room temperature and then stirred for 24 hours. The reaction mixture was concentrated under reduced pressure, and the residue was purified on a CHP-20 column (water→1% 1N hydrochloric acid-containing 30% aqueous solution of acetonitrile) to obtain the title compound (0.12 g) as a colorless powder.

$^1$H-NMR (CD$_3$OD) δ: 1.20–1.58 (2H, m), 1.58–2.27 (2H, m), 2.02 (3H, s), 2.65 and 2.90 (total 3H, s for each), 2.90–4.40 (12H, m), 6.96–7.22 (2H, br), 7.66 (1H, d, J=8.2 Hz), 7.88 (1H, d, J=8.2 Hz), 7.98–8.22 (5H, m), 8.50 (1H, s).

Example 115

N-[[4-[(6-Chloro-2-naphthyl)sulfonyl]-1-[methyl[1-(4-pyridinyl)-4-piperidinyl]amino]-6-oxo-2-piperazinyl]methyl](trifluoro)methanesulfonamide Hydrochloride A mixture of 6-(aminomethyl)-4-[(6-chloro-2-naphthyl)sulfonyl]-1-[methyl[1-(4-pyridinyl)-4-piperidinyl]amino]-2-piperazinone dihydrochloride (0.11 g) obtained in Example 113, 2,6-lutidine (0.19 ml), 4-dimethylaminopyridine (5 mg) and methylene chloride (6 ml) was combined with trifluoromethanesulfonic anhydride (0.10 ml) with stirring at −30° C., and then stirred for 1 hour. The reaction mixture was washed with water, dried over magnesium sulfate, and then concentrated under reduced pressure. The residue was purified by a column chromatography on a silica gel (dichloromethane: 10% aqueous ammonia-containing methanol=10:1) to obtain the title compound (40 mg) as a pale yellow powder.

$^1$H-NMR (CD$_3$OD) δ: 1.16–1.55 (2H, m), 1.60–1.90 (1H, m), 1.95–2.22 (1H, m), 2.63 and 2.87 (total 3H, s for each), 3.00–4.40 (12H, m), 6.98–7.20 (2H, m), 7.67 (1H, dd, J=2.2, 8.8 Hz), 7.89 (1H, dd, J=1.6, 8.8 Hz), 7.96–8.20 (5H, m), 8.51 (1H, s).

Example 116

4-[(6-Chloro-2-naphthyl)sulfonyl]-1-[methyl[1-(4-pyridinyl)-4-piperidinyl]amino]-6-(4-morpholinylcarbonyl)-2-piperazinone Hydrochloride A mixture of 4-[(6-chloro-2-naphthyl)sulfonyl]-1-[methyl[1-(4-pyridinyl)-4-piperidinyl]amino]-6-oxo-2- piperazinecarboxylic acid (0.22 g) obtained in Example 110, morpholine (0.048 g) and 1-hydroxy-1H-benzotriazole monohydrate (0.085 g) in DMF (4.4 ml) was combined with WSC (0.12 g) and stirred at room temperature for 18 hours. The reaction mixture was concentrated under reduced pressure, and partitioned between saturated aqueous sodium bicarbonate and methylene chloride. The organic phase was dried over magnesium sulfate, and concentrated under reduced pressure. The residue was purified on a CHP-20 column (water→1% 1N hydrochloric acid-containing 30% aqueous solution of acetonitrile) to obtain the title compound (0.13 g) as a colorless powder.

$^1$H-NMR (CD$_3$OD) δ: 1.20–1.60 (2H, m), 1.72–2.13 (2H, m), 2.62 and 2.85 (total 3H, s for each), 2.98–4.30 (17H, m), 4.67 (1H, brs), 7.09 (2H, d, J=7.6 Hz), 7.65 (1H, dd, J=2.0, 8.8 Hz), 7.78–7.90 (1H, m), 7.98–8.18 (5H, m), 8.47 (1H, s).

Example 117

4-[(6-Chloro-2-naphthyl)sulfonyl]-6-[(4-hydroxy-1-piperidinyl)carbonyl]-1-[methyl[1-(4-pyridinyl)-4-piperidinyl]amino]-2-piperazinone Hydrochloride Similarly to Example 116 and using 4-[(6-chloro-2-naphthyl)sulfonyl)-1-[methyl[1-(4-pyridinyl)-4-piperidinyl]amino]-6-oxo-2-piperazinecarboxylic acid (0.20 g) obtained in Example 110 and 4-hydroxypiperidine (0.051 g), the title compound (0.13 g) was obtained as a yellow powder.

$^1$H-NMR (CD$_3$OD) δ: 1.20–2.15 (8H, m), 2.62 and 2.85 (total 3H, s for each), 2.95–4.30 (14H, m), 4.60–4.85 (1H, m), 6.98–7.20 (2H, m), 7.58–7.72 (1H, m), 7.74–7.92 (1H, m), 7.94–8.22 (5H, m), 8.46 (1H, s).

Example 118

4-[(6-Chloro-2-naphthyl)sulfonyl]-6-[(4-methyl-1-piperidinyl)carbonyl]-1-[methyl[1-(4-pyridinyl)-4-piperidinyl]amino]-2-piperazinone Dihydrochloride Similarly to Example 116 and using 4-[(6-chloro-2-naphthyl)sulfonyl)-1-[methyl[1-(4-pyridinyl)-4-piperidinyl]amino]-6-oxo-2-piperazinecarboxylic acid (0.18 g) obtained in Example 110 and 1-methylpiperidine (0.049 ml), the title compound (0.15 g) was obtained as a yellow powder.

$^1$H-NMR (CD$_3$OD) δ: 1.18–1.66 (2H, m), 1.74–2.14 (2H, m), 2.87 (3H, s), 2.97 (3H, s), 2.80–5.00 (18H, m), 7.10 (2H, d, J=7.4 Hz), 7.66 (1H, dd, J=1.8 , 8.8 Hz), 7.78–7.96 (1H, br), 8.00–8.22 (5H, m), 8.42–8.58 (1H, m).

Example 119

4-[(6-Chloro-2-naphthyl)sulfonyl]-N-[2-(dimethylamino)ethyl]-1-[methyl[1-(4-pyridinyl)-4-piperidinyl]amino]-6-oxo-2-piperazinecarboxamide Dihydrochloride Similarly to Example 116 and using 4-[(6-chloro-2-naphthyl)sulfonyl)-1-[methyl[1-(4-pyridinyl)-4-piperidinyl]amino]-6-oxo-2-piperazinecarboxylic acid (0.18 g) obtained in Example 110 and N,N-dimethyl ethylenediamine (0.035 ml), the title compound (0.17 g) was obtained as a pale yellow powder.

$^1$H-NMR (CD$_3$OD) δ: 1.20–1.62 (2H, m), 1.70–2.14 (2H, m), 2.89 (3H, s), 2.99 (3H, s), 3.00 (3H, s), 2.74–4.40 (14H, m), 7.08 (2H, d, J=7.0 Hz), 7.66 (1H, d, J=8.4 Hz), 7.88 (1H, d, J=8.4 Hz), 7.98–8.22 (5H, m), 8.51 (1H, s).

Example 120

Ethyl 1-[[[4-[(6-Chloro-2-naphthyl)sulfonyl]-1-[methyl[1-(4-pyridinyl)-4-piperidinyl]amino]-6-oxo-2-piperazinyl]carbonyl]amino]acetate A mixture of 4-[(6-chloro-2-naphthyl)sulfonyl)-1-[methyl[1-(4-pyridinyl)-4-piperidinyl]amino]-6-oxo-2-piperazinecarboxylic acid (0.18 g) obtained in Example 110, glycine ethyl ester hydrochloride (0.062 g), triethylamine (0.12 ml) and 1-hydroxy-1H-benzotriazole monohydride (0.068 g) in DMF (4.4 ml) was combined with WSC (0.096 g), and stirred at room temperature for 18 hours. The reaction mixture was concentrated under reduced pressure, and partitioned between saturated aqueous sodium bicarbonate and methylene chloride. The organic phase was dried over magnesium sulfate, and concentrated under reduced pressure. The residue was purified on a CHP-20 column (water→1% 1N hydrochloric acid-containing 30% aqueous solution of acetonitrile) to obtain the title compound (0.13 g) as a colorless powder.

$^1$H-NMR (CDCl$_3$) δ: 1.29 (3H, t, J=7.0 Hz), 1.00–1.44 (2H, m), 1.46–1.78 (1H, m), 1.80–2.06 (1H, m), 2.58–2.92 (5H, m), 3.24–3.90 (6H, m), 3.92–4.08 (3H, m), 4.10–4.28 (3H, m), 6.58 (2H, d, J=6.4 Hz), 7.54–7.84 (1H, m), 7.61 (1H, dd, J=2.2, 8.8 Hz), 7.78 (1H, dd, J=1.8, 8.8 Hz), 7.86–8.00 (3H, m), 8.23 (2H, d, J=6.4 Hz), 8.35 (1H, s).

Example 121

4-[(6-Chloro-2-naphthyl)sulfonyl]-N-[2-(ethylsulfanyl)ethyl]-1-[methyl[1-(4-pyridinyl)-4-piperidinyl]amino]-6-oxo-2-piperazine Carboxamide Hydrochloride Similarly to Example 120 and using 4-[(6-chloro-2-naphthyl)sulfonyl)-1-[methyl[1-(4-pyridinyl)-4-piperidinyl]amino]-6-oxo-2-piperazinecarboxylic acid (0.18 g) obtained in Example 110 and 2-(ethylthio)ethylamine hydrochloride (0.065 g), the title compound (0.16 g) was obtained as a pale yellow powder.

$^1$H-NMR (DMSO-d$_6$) δ: 0.96–1.36 (5H, m), 1.64–2.02 (2H, m), 2.76 (3H, s), 2.35–4.30 (16H, m), 7.14 (2H, d, J=7.0 Hz), 7.75 (1H, dd, J=2.2, 8.8 Hz), 7.85 (1H, d, J=8.8 Hz), 8.10–8.34 (5H, m), 8.38–8.52 (1H, m), 8.57 (1H, s).

Example 122

4-[(6-Chloro-2-naphthyl)sulfonyl]-1-[methyl[1-(4-pyridinyl)-4-piperidinyl]amino]-6-(4-thiomorpholinylcarbonyl)-2-piperazinone Hydrochloride Similarly to Example 116 and using 4-[(6-chloro-2-naphthyl)sulfonyl)-1-[methyl[1-(4-pyridinyl)-4-piperidinyl]amino]-6-oxo-2-piperazinecarboxylic acid (0.15 g) obtained in Example 110 and thiomorpholine (0.041 ml), the title compound (0.07 g) was obtained as a colorless powder.

$^1$H-NMR (CD$_3$OD) δ: 1.20–1.60 (2H, m), 1.70–2.12 (2H, m), 2.43–4.40 (2H, m), 6.98–7.18 (2H, m), 7.65 (1H, d, J=8.2 Hz), 7.84 (1H, d, J=8.4 Hz), 7.96–8.20 (5H, m), 8.47 (1H, s).

Example 123

4-[(6-Chloro-2-naphthyl)sulfonyl]-6-[(1,1-dioxide-4-thiomorpholinyl)carbonyl]-1-[methyl[1-(4-pyridinyl)-4-piperidinyl]amino]-2-piperazinone Hydrochloride Similarly to Example 120 and using 4-[(6-chloro-2-naphthyl)sulfonyl)-1-[methyl[1-(4-pyridinyl)-4-piperidinyl]amino]-6-oxo-2-piperazinecarboxylic acid (0.15 g) obtained in Example 110 and thiomorpholine 1,1-dioxide trifluoroacetate (0.101 g), the title compound (0.06 g) was obtained as a colorless powder. $^1$H-NMR (DMSO-d$_6$) δ: 1.00–1.40 (2H, m), 1.70–2.02 (2H, m), 2.74 and 2.86 (total 3H, s for each), 2.80–4.40 (18H, m), 7.12 (2H, d, J=7.4 Hz), 7.75 (1H, dd, J=2.2, 8.8 Hz), 7.87 (1H, dd, J=1.8, 8.8 Hz), 8.10–8.36 (5H, m), 8.60 (1H, s).

Example 124

4-[(6-Chloro-2-naphthyl)sulfonyl]-1-[methyl[1-(4-pyridinyl)-4-piperidinyl]amino]-6-[(1-oxode-4-thiomorpholinyl)carbonyl]-2-piperazinone Hydrochloride Similarly to Example 120 and using 4-[(6-chloro-2-naphthyl)sulfonyl)-1-[methyl[1-(4-pyridinyl)-4-piperidinyl]amino]-6-oxo-2-piperazinecarboxylic acid (0.17 g) obtained in Example 110 and thiomorpholine 1-oxide trifluoroacetate (0.107 g), the title compound (0.10 g) was obtained as a colorless powder.

$^1$H-NMR (DMSO-d$_6$) δ: 0.95–1.45 (2H, m), 1.70–2.05 (2H, m), 2.20–4.80 (21H, m), 7.13 (2H, d, J=7.2 Hz), 7.68–7.82 (1H, m), 7.82–7.94 (1H, m), 8.10–8.38 (5H, m), 8.59 (1H, s).

Example 125

2-[[[4-[(6-Chloro-2-naphthyl)sulfonyl]-1-[methyl[1-(4-pyridinyl)-4-piperidinyl]amino]-6-oxo-2-piperazinyl]carbonyl]amino]acetic Acid A mixture of ethyl 1-[[[4-[(6-chloro-2-naphthyl)sulfonyl]-1-[methyl[1-(4-pyridinyl)-4-piperidinyl]amino]-6-oxo-2-piperazinyl]carbonyl]amino]acetate (0.18 g), 1N sodium hydroxide (0.56 ml) and methanol (4.0 ml) was stirred at 40° C. for 30 minutes. The reaction mixture was cooled, and the reaction system was adjusted at pH 5 with 1N hydrochloric acid, and then concentrated under reduced pressure. The residue was purified on a CHP-20 column (water→1% conc. aqueous ammonia-containing 25% aqueous solution of acetonitrile) to obtain the title compound (0.11 g) as a colorless powder.

$^1$H-NMR (CD$_3$OD) δ: 1.20–1.62 (2H, m), 1.68–1.90 (1H, m), 1.90–2.10 (1H, m), 2.55 and 2.83 (total 3H, s for each) 2.98–4.40 (12H, m), 7.09 (2H, d, J=7.2 Hz), 7.66 (1H, dd, J=2.2, 8.8 Hz), 7.86 (1H, dd, J=1.8, 8.8 Hz), 7.98–8.18 (5H, m), 8.49 (1H, s).

Example 126

1-[[4-[(6-Chloro-2-naphthyl)sulfonyl]-1-[methyl[1-(4-pyridinyl)-4-piperidinyl]amino]-6-oxo-2-piperazinyl]carbonyl]-4-piperidinecarboxylic Acid A mixture of 4-[(6-chloro-2-naphthyl)sulfonyl)-1-[methyl[1-(4-pyridinyl)-4-piperidinyl]amino]-6-oxo-2-piperazine carboxylic acid (0.18 g) obtained in Example 110, ethyl isonicotinate (0.068 ml) and 1-hydroxy-1H-benzotriazole monohydrate (0.068 g) in DMF (4.4 ml) was combined with WSC (0.096 g) and stirred at room temperature for 18 hours. The reaction mixture was concentrated under reduced pressure, and partitioned between saturated aqueous sodium bicarbonate and methylene chloride. The organic phase was dried over magnesium sulfate and concentrated under reduced pressure. The residue was purified on a CHP-20 column (water→1% 1N hydrochloric acid-containing 30% aqueous solution of acetonitrile) to obtain ethyl 1-[[4-[(6-chloro-2-naphthyl)sulfonyl]-1-[methyl[1-(4-pyridinyl)-4-piperidinyl]amino]-6-oxo-2-piperazinyl]carbonyl]-4-piperidinecarboxylate as a colorless powder. Then a mixture of this material with 1N sodium hydroxide (1.14 ml) and methanol (4.0 ml) was stirred at 40° C. for 30 minutes. The reaction mixture was cooled, and the reaction system was adjusted at pH 5 with 1N hydrochloric acid, and concentrated under reduced pressure. The residue was purified on a CHP-20 column (water→1% conc. aqueous ammonia-containing 25% aqueous solution of acetonitrile) to obtain the title compound (0.07 g) as a colorless powder.

$^1$H-NMR (DMSO-d$_6$) δ: 0.95–2.00 (8H, m), 2.25–4.60 (18H, m), 6.71 (2H, d, J=6.2 Hz), 7.75 (1H, d, J=8.8 Hz), 7.85 (1H, d, J=8.8 Hz), 8.09 (2H, d, J=6.2 Hz), 8.18 (1H, d, J=8.8 Hz), 8.30 (2H, d, J=8.8 Hz), 8.50–8.62 (1H, br).

Example 127

Methyl 1-[[4-[(6-Chloro-2-naphthyl)sulfonyl]-1-[[1-(2-methyl-4-pyridinyl)-4-piperidinyl]amino]-6-oxo-2-piperazinecarboxylate Dihydrochloride A solution of 1-(tert-butyl)3-methyl4-[[1-(2-methyl-4-pyridinyl)-4-piperidinyl]amino]-5-oxo-1,3-piperazinedicarboxylate (3.5 g) in toluene (17.5 ml) was treated dropwise with trifluoroacetic acid (17.5 ml), stirred at room temperature for 1 hour, and then concentrated under reduced pressure. A mixture of the resultant residue and triethylamine (10.9 ml) in dichloromethane (35 ml) was combined with 6-chloronaphthalene-2-sulfonyl chloride (2.45 g) and stirred at room temperature for 1 hour. The organic phase was isolated, washed with saturated aqueous sodium bicarbonate and brine, dried and concentrated. The residue obtained was purified by a column chromatography on a silica gel (dichloromethane: 10% aqueous ammonia-containing methanol=10:1) and converted into a hydrochloride using a 4 N solution of hydrochloric acid in ethyl acetate to obtain the title compound (2.18 g) as a pale yellow powder.

$^1$H-NMR (DMSO-d$_6$+D$_2$O) δ: 1.06–1.38 (2H, m), 1.66–1.92 (2H, m), 2.42 (3H, s), 2.96–3.74 (8H, m), 3.86–4.10 (4H, m), 4.32–4.42 (1H, m), 6.94–7.08 (2H, m), 7.75 (1H, dd, J=1.8, 8.8 Hz), 7.87 (1H, dd, J=2.0, 8.8 Hz), 8.06 (1H, d, J=7.2 Hz), 8.20 (1H, d, J=8.8 Hz), 8.29 (2H, d, J=9.2 Hz), 8.59 (1H, s).

Example 128

Methyl 4-[(6-chloro-2-naphthyl)sulfonyl]-1-[methyl [1-(2-methyl-4-pyridinyl)-4-piperidinyl]amino]-6-oxo-2-piperazinecarboxylate Hydrochloride Methyl 1-[[4-[(6-chloro-2-naphthyl)sulfonyl]-1-[[1-(2-methyl-4-pyridinyl)-4-piperidinyl]amino]-6-oxo-2-piperazinecarboxylate dihydrochloride (1.94 g) obtained in Example 127 was dissolved in methylene chloride (20 ml) and saturated aqueous sodium bicarbonate (20 ml) and partitioned. The organic phase was dried over magnesium sulfate, concentrated under reduced pressure to obtain methyl 4-[(6-chloro-2-naphthyl)sulfonyl]-1-[[1-(2-methyl-4-pyridinyl)-4-piperidinyl]amino]-6-oxo-2-piperazinecarboxylate. This material was dissolved in a 37% aqueous solution of formaldehyde (25.2 ml) and formic acid (12.8 ml), and reflux for 2 hours. The reaction mixture was cooled, made alkaline by adding saturated aqueous sodium bicarbonate, extracted with dichloromethane, dried and then concentrated. The residue was purified on a CHP-20 column (water→1% 1N hydrochloric acid-containing 30% aqueous solution of acetonitrile) and converted into a hydrochloride using a 4 N solution of hydrochloric acid in ethyl acetate (0.15 ml) to obtain the title compound (1.67 g) as a colorless non-crystalline powder.

$^1$H-NMR (CD$_3$OD) δ: 1.10–1.50 (2H, m), 1.65–1.90 (1H, m), 1.92–2.12 (1H, m), 2.47 (3H, s), 2.58 and 2.93 (total 3H, s for each), 2.85–4.50 (1OH, m), 3.74 (3H, s), 6.86–7.00 (2H, m), 7.66 (1H, dd, J=2.2, 8.8 Hz), 7.84 (1H, dd, J=1.8, 8.8 Hz), 7.93 (1H, d, J=8.4 Hz), 8.02–8.18 (3H, m), 8.48 (1H, s).

Example 129

4-[(6-Chloro-2-naphthyl)sulfonyl]-1-[methyl[1-(2-methyl-4-pyridinyl)-4-piperidinyl]amino]-6-oxo-2-piperazinecarboxylic Acid A mixture of methyl 4-[(6-chloro-2-naphthyl)sulfonyl]-1-[methyl[1-(2-methyl-4-pyridinyl)-4-piperidinyl]amino]-6-oxo-2-piperazinecarboxylate hydrochloride (0.22 g) obtained in Example 128 and a 1N aqueous solution of sodium hydroxide (1.4 ml) in methanol (4.0 ml) was stirred at 40° C. for 30 minutes. The reaction mixture was cooled, and the reaction system was adjusted at pH 5 with 1N hydrochloric acid, and then concentrated under reduced pressure. The residue was purified on a CHP-20 column (water→1% conc. aqueous ammonia-containing 25% aqueous solution of acetonitrile) to obtain the title compound (0.17 g) as a colorless powder.

$^1$H-NMR (CD$_3$OD) δ: 1.15–1.60 (2H, m), 1.65–2.10 (2H, m), 2.48 (3H, s), 2.95 (3H, s), 2.85–4.40 (10H, m), 6.88–7.04 (2H, m), 7.66 (1H, dd, J=2.0, 8.8 Hz), 7.85 (1H, dd, J=1.8, 8.8 Hz), 7.88–8.00 (1H, m), 8.04–8.20 (3H, m), 8.48 (1H, s).

Example 130

Methyl 1-[[1-(2-Methyl-4-pyridinyl)-4-piperidinyl] amino]-6-oxo-4-[(4-vinylphenyl)sulfonyl]-2-piperazinecarboxylate Similarly to Example 127 and using 1-(tert-butyl)3-methyl4-[[1-(2-methyl-4-pyridinyl)-4-piperidinyl]amino]-5-oxo-1,3-piperazinedicarboxylate(0.59 g) and 4-vinylbenzenesulfonyl chloride, the title compound (0.25 g) was obtained as a pale yellow powder.

$^1$H-NMR (CDCl$_3$) δ: 1.22–1.54 (2H, m), 1.64–2.00 (2H, m), 2.44 (3H, s), 2.72–3.02 (2H, m), 3.04–3.30 (2H, m), 3.55 (1H, d, J=16.0 Hz), 3.78 (3H, s), 3.64–4.34 (5H, m), 4.96 (1H, d, J=2.8 Hz), 5.49 (1H, d, J=10.8 Hz), 5.92 (1H, d, J=17.6 Hz), 6.40–6.58 (2H, m), 6.77 (1H, dd, J=10.8, 17.6 Hz), 7.58 (2H, d, J=8.4 Hz), 7.74 (2H, d, J=8.4 Hz), 8.14 (1H, d, J=6.0 Hz).

Example 131

Methyl 1-[Methyl[1-(2-methyl-4-pyridinyl)-4-piperidinyl]amino]-6-oxo-4-[(4-vinylphenyl) sulfonyl]-2-piperazinecarboxylate Similarly to Example 128 and using methyl 1-[[1-(2-methyl-4-pyridinyl)-4-piperidinyl]amino]-6-oxo-4-[(4-vinylphenyl)sulfonyl]-2-piperazinecarboxylate (0.19 g) obtained in Example 130, the title compound (0.55 g) was obtained as colorless crystals.

$^1$H-NMR (CDCl$_3$) δ: 1.16–1.46 (2H, m), 1.55–1.75 (1H, m), 1.83–2.01 (1H, m), 2.43 (3H, s), 2.62 and 2.95 (total 3H, s for each), 2.67–2.90 (2H, m), 3.19 (1H, dd, J=3.6, 12.4 Hz), 3.36–3.65 (1H, m), 3.57 (1H, d, J=16.4 Hz), 3.78 (3H, s), 3.67–3.90 (3H, m), 3.97 (1H, d, J=16.4 Hz), 4.05–4.20 (1H, m), 5.50 (1H, d, J=10.8 Hz), 5.93 (1H, d, J=17.6 Hz), 6.40–6.58 (2H, m), 6.78 (1H, dd, J=10.8, 17.6 Hz), 7.58 (2H, d, J=8.6 Hz), 7.73 (2H, d, J=8.6 Hz), 8.14 (1H, d, J=5.8 Hz).

Example 132

4-[(6-Chloro-2-naphthyl)sulfonyl]-1-[methyl[1-(2-methyl-4-pyridinyl)-4-piperidinyl]amino]-6-oxo-2-piperazine Carboxamide Hydrochloride Similarly to Example 112 and using methyl 4-[(6-chloro-2-naphthyl)sulfonyl]-1-[methyl[1-(2-methyl-4-pyridinyl)-4-piperidinyl]amino]-6-oxo-2-piperazinecarboxylate hydrochloride (0.19 g) obtained in Example 128, the title compound (0.075 g) was obtained as a colorless powder.

$^1$H-NMR (DMSO-d$_6$+D$_2$O) δ: 0.95–1.25 (2H, m), 1.40–1.90 (2H, m), 2.28 (3H, s), 2.30–4.10 (13H, m), 6.46–6.66 (2H, m), 7.24–7.38 (1H, m), 7.48–7.68 (1H, m), 7.77 (1H, dd, J=1.8, 8.8 Hz), 7.80–7.92 (1H, m), 7.98 (1H, d, J=6.0 Hz), 8.19 (1H, d, J=8.8 Hz), 8.24–8.36 (2H, m), 8.57 (1H, s).

Example 133

4-[(6-Chloro-2-naphthyl)sulfonyl]-1-[methyl[1-(2-methyl-4-pyridinyl)-4-piperidinyl]amino]-6-[(1-oxide-4-thiomorpholinyl)carbonyl]-2-piperazinone Hydrochloride Similarly to Example 120 and using 4-[(6-chloro-2-naphthyl)sulfonyl]-1-[methyl[1-(2-methyl-4-pyridinyl)-4-piperidinyl]amino]-6-oxo-2-piperazinecarboxylic acid (0.25 g) obtained in Example 129 and thiomorpholine 1-oxide trifluoroacetate (0.132 g), the title compound (0.15 g) was obtained as a colorless powder.

$^1$H-NMR (DMSO-d$_6$) δ: 0.95–1.43 (2H, m), 1.70–2.05 (2H, m), 2.43 (3H, s), 2.25–4.80 (21H, m), 6.92–7.10 (2H, m), 7.68–7.82 (1H, m), 7.82–7.96 (1H, m), 8.02–8.14 (1H, m), 8.14–8.36 (3H, m), 8.58 (1H, s)

Example 134

1-{Methyl[1-(4-pyridinyl)-4-piperidinyl]amino}-4-(4-vinylbenzenesulfonyl)-2-piperazinone 1-{[1-(4-pyridinyl)-4-piperidinyl]amino}-4-(4-vinylbenzenesulfonyl)-2-piperazinone (180 mg) was dissolved in a 37% aqueous solution of formaldehyde (11 ml and formic acid (5 ml) and refluxed for 2 hours. The reaction mixture was cooled and made alkaline by adding an aqueous solution of sodium hydroxide, extracted with dichloromethane, dried and concentrated. The residue was purified by a column chromatography (dichloromethane: 10% aqueous ammonia-containing methanol=20:1) and crystallized from ether to obtain the title compound (139 mg, 75%) as colorless crystals.

$^1$H-NMR (CDCl$_3$) δ: 1.36 (2H, m), 1.70 (1H, m), 1.90 (1H, m), 2.73 (3H, s), 2.84 (2H, m), 3.20–3.90 (9H, m), 5.49 (1H, d, J=11.0 Hz), 5.92 (1H, d, J=17.6 Hz), 6.62 (2H, d, J=6.6 Hz), 6.78 (1H, dd, J=11.0, 17.6 Hz), 7.59 (2H, d, J=8.2 Hz), 7.76 (2H, d, J=8.2 Hz), 8.24 (2H, d, J=6.6 Hz).

IR (KBr): 1669, 1593, 1507, 1350, 1167 cm$^{-1}$.

Example 135

Methyl 4-[(6-Chloro-2-naphthyl)sulfonyl]-1-[[1-(4-pyridinyl)-4-piperidinyl]amino]-6-oxo-2-piperazineacetate A solution of methyl 1-amino-4-[(6-chloro-2-naphthyl) sulfonyl]-6-oxo-2-piperazineacetate (500 mg) obtained in Reference Example 46 and 1-(4-pyridinyl)-4-piperidinone (240 mg) in ethanol (25 ml) was heated under reflux overnight. The reaction mixture was concentrated under reduced pressure and the residue was dissolved in methanol (10 ml), combined with acetic acid (0.60 g) and sodium cyanoborohydride (120 mg) with cooling on ice, and stirred at room temperature for 2 hours. The reaction mixture was concentrated under reduced pressure, and the residue was partitioned between dichloromethane (100 ml) and saturated aqueous sodium bicarbonate (100 ml). The organic phase was washed with water and brine, dried and concentrated. The resultant residue was purified by a column chromatography on a silica gel (dichloromethane: 10% aqueous ammonia-containing methanol=20:1) to obtain the title compound (200 mg) as colorless crystals.

$^1$H-NMR (CDCl$_3$) δ: 1.43 (2H, m), 1.73 (2H, m), 2.65–3.20 (5H, m), 3.48 (1H, d, J=16.0 Hz), 3.70 (3H, s), 3.60–4.00 (3H, m), 4.16 (1H, d, J=16.0 Hz), 4.83 (1H, d, J=4.8 Hz), 6.60 (2H, d, J=6.6 Hz), 7.62 (1H, dd, J=1.8, 8.8 Hz), 7.79 (1H, dd, J=1.8, 8.8 Hz), 7.90–8.00 (3H, m), 8.23 (2H, d, J=6.6 Hz), 8.36 (1H, s).

Example 136

Methyl 4-[(6-Chloro-2-naphthyl)sulfonyl]-1-[methyl [1-(4-pyridinyl)-4-piperidinyl]amino]-6-oxo-2-piperazineacetate Similarly to Example 134 and using methyl 4-[(6-chloro-2-naphthyl)sulfonyl]-1-[[1-(4-pyridinyl)-4-piperidinyl] amino]-6-oxo-2-piperazineacetate (100 mg), the title compound (80 mg) was obtained as colorless crystals.

$^1$H-NMR (CDCl$_3$) δ: 1.57 (2H, m), 1.93 (2H, m), 2.53–2.90 (4H, m), 2.84 (3H, s), 3.09 (1H, m), 3.69 (3H, s), 3.40–4.05 (5H, m), 6.58 (2H, d, J=6.6 Hz), 7.62 (1H, dd, J=1.8, 8.8 Hz), 7.79 (1H, dd, J=1.8, 8.8 Hz), 7.90–8.00 (3H, m), 8.23 (2H, d, J=6.6 Hz), 8.35 (1H, s).

Example 137

Methyl 1-[[1-(2-Methyl-4-pyridinyl)-4-piperidinyl] amino]-6-oxo-4-(4-vinylbenzenesulfonyl)-2-piperazineacetate Similarly to Example 135 and using methyl 1-amino-6-oxo-4-(4-vinylbenzenesulfonyl)-2-piperazineacetate (1.06 g) obtained in Reference Example 48 and 1-(2-methyl-4-pyridinyl)-4-piperidinone (0.57 g), the title compound (264 mg) was obtained as a colorless solid.

$^1$H-NMR (CDCl$_3$) δ: 1.47 (2H, m), 1.84 (2H, m), 2.50 (3H, s), 2.75–3.10 (5H, m), 3.20 (1H, m), 3.43 (1H, d, J=16.0 Hz), 3.71 (3H, s), 3.70–4.20 (5H, m), 4.83 (1H, d, J=4.8 Hz), 5.50 (1H, d, J=11.0 Hz), 5.93 (1H, d, J=17.6 Hz), 6.54 (1H, d, J=2.6 Hz), 6.60 (1H, dd, J=6.6, 2.6 Hz), 6.81 (1H, dd, J=17.6, 11.0 Hz), 7.59 (2H, d, J=8.4 Hz), 7.75 (2H, d, J=8.4 Hz), 8.03 (1H, d, J=6.6 Hz).

IR (KBr): 1732, 1645, 1599, 1539, 1354, 1169 cm$^{-1}$.

Example 138

Methyl 4-[(6-Chloro-2-naphthyl)sulfonyl]-1-[[1-(2-methyl-4-pyridinyl)-4-piperidinyl]amino]-6-oxo-2-piperazineacetate A mixture of methyl 1-amino-4-[(6-chloro-2-naphthyl) sulfonyl]-6-oxo-2-piperazineacetate (1.03 g) obtained in Reference Example 46, 1-(2-methyl-4-pyridinyl)-4-piperidinone (0.48 g) and acetic acid (0.15 g) in ethanol (25 ml) was stirred at room temperature overnight. The reaction mixture was concentrated under reduced pressure and the residue was partitioned between dichloromethane (100 ml) and saturated aqueous sodium bicarbonate (100 ml). The organic phase was washed with water and brine, dried and concentrated. The resultant residue was dissolved in methanol (10 ml), combined with acetic acid (0.60 g) and sodium cyanoborohydride (0.24 g) with cooling on ice, and stirred at room temperature overnight. The reaction mixture was concentrated under reduced pressure and the residue was partitioned between dichloromethane (100 ml) and saturated aqueous sodium bicarbonate (100 ml). The organic phase was washed with water and brine, dried and concentrated. The resultant residue was purified by a column chromatography on a silica gel (dichloromethane: 10% aqueous ammonia-containing methanol=15:1) and crystallized from a mixture of ethyl acetate and diethyl ether to obtain the title compound (0.64 g) as colorless crystals.

$^1$H-NMR (CDCl$_3$) δ: 1.35–1.50 (2H, m), 1.60–1.80 (2H, m), 2.43 (3H, s), 2.69–3.20 (6H, m), 3.48 (1H, d, J=16.0 Hz), 3.78 (3H, s), 3.78–4.20 (5H, m), 4.82 (1H, d, J=4.8 Hz), 6.43–6.47 (2H, m), 7.62 (1H, dd, J=8.8, 1.6 Hz), 7.79 (1H, dd, J=8.8, 1.6 Hz), 7.93–7.97 (3H, m), 8.13 (1H, d, J=5.8 Hz), 8.35 (1H, s).

IR (KBr): 2924, 1732, 1659, 1599, 1541, 1494, 1454, 1416 cm$^{-1}$.

Example 139

Methyl 4-[(6-Chloro-2-naphthyl)sulfonyl]-1-[methyl [1-(2-methyl-4-pyridinyl)-4-piperidinyl]amino]-6-oxo-2-piperazineacetate Methyl 4-[(6-chloro-2-naphthyl)sulfonyl]-1-[[1-(2-methyl-4-pyridinyl)-4-piperidinyl]amino]-6-oxo-2-piperazineacetate (0.30 g) obtained in Example 138 was dissolved in a 37% aqueous solution of formaldehyde (6.5 ml) and formic acid (3.0 ml) and refluxed for 15 hours. The reaction mixture was cooled, made alkaline by adding a 1N aqueous solution of sodium hydroxide, extracted with dichloromethane, dried and concentrated. The residue thus obtained was crystallized from ethanol to obtain the title compound (95 mg) as colorless crystals.

$^1$H-NMR (CDCl$_3$) δ: 1.21–1.40 (2H, m), 1.53–1.65 (1H, m), 1.88–1.95 (1H, m), 2.43 (3H, s), 2.60–2.83 (4H, m), 2.84 (3H, s), 3.02–3.20 (1H, m), 3.44–4.04 (10H, m), 6.41–6.52 (2H, m), 7.62 (1H, dd, J=8.8, 1.8 z), 7.79 (1H, dd, J=8.8, 1.8 Hz), 7.94–7.98 (3H, m), 8.14 (1H, d, J=5.4 Hz), 8.35 (1H, s).

IR (KBr): 2953, 1732, 1667, 1599, 1543, 1494, 1456, 1410 cm$^{-1}$.

Example 140

4-[(6-Chloro-2-naphthyl)sulfonyl]-1-[[1-(2-methyl-4-pyridinyl)-4-piperidinyl]amino]-6-oxo-2-piperazineacetamide Methyl 4-[(6-chloro-2-naphthyl)sulfonyl]-1-[[1-(2-methyl-4-pyridinyl)-4-piperidinyl]amino]-6-oxo-2-piperazineacetate (100 mg) obtained in Example 138 and a 13% ammonia/ethanol solution (6.0 ml) were heated in a sealed tube at 90° C. for 6 hours. The reaction mixture was cooled and concentrated under reduced pressure. The residue obtained was purified by a column chromatography on a silica gel (dichloromethane: 10% aqueous ammonia-containing methanol=15:1) and crystallized from a mixture of ethyl acetate and diethyl ether to obtain the title compound (12 mg) as colorless crystals.

$^1$H-NMR (CDCl$_3$) δ: 1.26–1.57 (2H, m), 1.65–1.82 (2H, m), 2.42 (3H, s), 2.63–3.20 (6H, m), 3.40 (1H, d, J=16.2 Hz), 3.71–3.82 (2H, m), 3.95–4.08 (2H, m), 4.26 (1H, d, J=16.2 Hz), 4.89 (1H, d, J=5.2 Hz), 5.51 (1H, brs), 5.88 (1H, brs), 6.42–6.47 (2H, m), 7.62 (1H, dd, J=8.8, 1.6 Hz), 7.78 (1H, dd, J=8.8, 1.6 Hz), 7.93–7.98 (3H, m), 8.12 (1H, d, J=6.0 Hz), 8.34 (1H, s).

IR (KBr): 3281, 3196, 2924, 1667, 1651, 1601, 1539, 1495, 1454, 1416 cm$^{-1}$.

Example 141

4-[(6-Chloro-2-naphthyl)sulfonyl]-1-[[1-(2-methyl-4-pyridinyl)-4-piperidinyl]amino]-6-oxo-2-piperazineacetic Acid A mixture of methyl 4-[(6-chloro-2-naphthyl)sulfonyl]-1-[[1-(2-methyl-4-pyridinyl)-4-piperidinyl]amino]-6-oxo-2-piperazineacetate (1.17 g) obtained in Example 138 and a 2N aqueous solution of sodium hydroxide (2.0 ml) in methanol (20 ml) and 1,4-dioxane (10 m) was stirred at 40° C. for 2 hours. The reaction mixture was cooled, neutralized with 1N hydrochloric acid, and concentrated under reduced pressure. The residue was combined with saturated brine, extracted with a 10% methanol-containing dichloromethane, dried and concentrated. The residue obtained was crystallized from a mixture of ethanol and ethyl acetate to obtain the title compound (1.01 g) as colorless crystals.

$^1$H-NMR (DMSO-$d_6$) δ: 1.09–1.35 (2H, m), 1.65–1.85 (2H, m), 2.42 (3H, s), 2.50–2.79 (4H, m), 3.00–4.10 (8H, m), 5.54 (1H, brs), 7.01–7.04 (2H, m), 7.75 (1H, dd, J=8.8, 2.0 Hz), 7.90 (1H, dd, J=8.8, 2.0 Hz), 8.09 (1H, d, J=6.8 Hz), 8.20 (1H, d, J=8.8 Hz), 8.29–8.33 (1H, m), 8.61 (1H, s), 13.00–13.40 (1H, br).

IR (KBr): 3275, 3086, 2930, 1717, 1644, 1634, 1531, 1493, 1454, 1420, 1404 cm$^{-1}$.

Example 142

{[4-(6-Chloronaphthalene-2-sulfonyl)-oxo-1-piperazinyl][1-(4-pyridinyl)-4-piperidinyl]amino}acetonitrile A mixture of 1-{[1-(tert-butoxycarbonyl)piperidinyl]amino}-4-(6-chloronaphthalene-2-sulfonyl)-2-piperazinone (5.23 g) obtained in Reference Example 11, iodoacetonitrile (10.00 g) and potassium carbonate (1.66 g) in 1-methyl-2-pyrrolidinone (100 ml) was stirred at 80° C. for 15 hours under an nitrogen atmosphere and then cooled. The reaction mixture was combined with saturated aqueous sodium bicarbonate, extracted with ethyl acetate-tetrahydrofuran (1:1), dried and concentrated. The residue obtained was purified by a column chromatography on a silica gel (hexane:acetone=2:1) and crystallized from a mixture of ethyl acetate and diethyl ether to obtain {[1-(tert-butoxycarbonyl)piperidinyl][4-(6-chloronaphthalene-2-sulfonyl)-oxo-1-piperazinyl]amino}acetonitrile (0.80 g) as colorless crystals.

$^1$H-NMR (CDCl$_3$) δ: 1.18–1.38 (2H, m), 1.45 (9H, s), 1.65–1.77 (2H, m), 2.61–2.74 (2H, m), 3.50–3.74 (5H, m), 3.78 (1H, d, J=16.0 Hz), 3.99–4.14 (3H, m), 4.28 (1H, d, J=16.0 Hz), 7.61 (1H, dd, J=8.8, 1.8 Hz), 7.78 (1H, dd, J=8.8, 1.8 Hz), 7.95 (1H, d, J=1.8 Hz), 7.95 (2H, d, J=8.8 Hz), 8.35 (1H, s).

IR (KBr): 2980, 2260, 1676, 1630, 1480, 1455, 1420 cm$^{-1}$.

{[1-(tert-Butoxycarbonyl)piperidinyl][4-(6-chloronaphthalene-2-sulfonyl)-oxo-1-piperazinyl]amino}acetonitrile (765 mg) thus obtained was combined with methanol (10 ml) and a 4N solution of hydrochloric acid in ethyl acetate (3 ml), and stirred at room temperature for 15 hours. The reaction mixture was concentrated to obtain a residue, which was combined with 4-bromopyridine hydrochloride (529 mg), N-ethyldiisopropylamine (1.05 g) and ethanol (20 ml), and refluxed under an argon atmosphere for 2 days. The reaction mixture was concentrated, and the residue was combined with a 10% aqueous solution of sodium carbonate, extracted with dichloromethane, dried and concentrated. The resultant residue was purified by a column chromatography (dichloromethane: 10% aqueous ammonia-containing methanol=15:1) and crystallized from a mixture of ethyl acetate and diethyl ether to obtain the title compound (62 mg) as colorless crystals.

$^1$H-NMR (CDCl$_3$) δ: 1.33–1.48 (2H, m), 1.63–1.74 (1H, m), 1.80–1.90 (1H, m), 2.70–2.88 (2H, s), 3.54–3.92 (8H, m), 4.12 (1H, d, J=16.0 Hz), 4.31 (1H, d, J=16.0 Hz), 6.62 (2H, d, J=6.6 Hz), 7.63 (1H, dd, J=8.8, 1.8 Hz), 7.81 (1H, dd, J=8.8, 1.8 Hz), 7.94–7.99 (3H, m), 8.29 (2H, d, J=6.6 Hz), 8.37 (1H, s).

IR (KBr): 2940, 1669, 1595, 1508, 1454, 1416 cm$^{-1}$.

Example 143

Methyl {[4-(6-Chloronaphthalene-2-sulfonyl)-2-oxo-1-piperazinyl][1-(2-methyl-4-pyridinyl)-4-piperidinyl]amino}acetonitrile Similarly to Method B in Example 38 and using 6-chloronaphthalene-2-sulfonyl chloride (1.04 g), the title compound (1.05 g) was obtained as colorless crystals.

$^1$H-NMR (CDCl$_3$) δ: 1.26–1.50 (2H, m), 1.61–1.67 (1H, m), 1.82–1.90 (1H, m), 2.45 (3H, s), 2.68–2.84 (2H, m), 3.05–3.19 (1H, m), 3.50–4.12 (13H, m), 6.42–6.48 (2H, m), 7.62 (1H, dd, J=8.8, 2.0 Hz), 7.80 (1H, dd, J=8.8, 2.0 Hz), 7.93–7.98 (3H, m), 8.16 (1H, d, J=5.8 Hz), 8.36 (1H, s).

IR (KBr): 2953, 2922, 2851, 1748, 1667, 1599, 1543, 1495, 1454, 1418 cm$^{-1}$.

Example 144 tert-Butyl {[4-(6-Chloronaphthalene-2-sulfonyl)-2-oxo-1-piperazinyl][1-(2-methyl-4-pyridinyl)-4-piperidinyl]amino}acetate A mixture of 1-amino-4-(6-chloronaphthalene-2-sulfonyl)-2-piperazinone (544 mg) obtained in Example 3, tert-butyl Iodoacetate (2.14 g) and potassium carbonate (166 mg) in 1-methyl-2-pyrrolidone (10 ml) was stirred at 80° C. for 60 hours under an argon atmosphere. The reaction mixture was cooled, combined with water, extracted with dichloromethane, dried and concentrated to obtain a residue, which was purified by a column chromatography on a silica gel (hexane:acetonee=2:1) to obtain tert-butyl {[4-(6-chloronaphthalene-2-sulfonyl)-2-oxo-1-piperazinyl]amino}acetate (294 mg).

$^1$H-NMR (CDCl$_3$) δ: 1.43 (9H, s), 3.40–3.45 (2H, m), 3.46 (2H, d, J=5.8 Hz), 3.65–3.71 (2H, m), 3.82 (2H, s), 5.34 (1H, t, J=5.8 Hz), 7.61 (1H, dd, J=8.8, 1.8 Hz), 7.79 (1H, dd, J=8.8, 1.8 Hz), 7.94 (1H, d, J=1.8 Hz), 8.35 (1H, s).

IR (KBr): 2978, 1732, 1661, 1495, 1456, 1424 cm$^{-1}$.

A solution of tert-butyl {[4-(6-chloronaphthalene-2-sulfonyl)-2-oxo-1-piperazinyl]amino}acetate (250 mg) thus obtained and 1-(2-methyl-4-pyridinyl)-4-piperidinone (209 mg) in acetic acid (6 ml) was treated portionwise with sodium triacetoxyborohydride (233 mg) and stirred at room temperature for 2 days. The reaction mixture was concentrated under reduced pressure, made alkaline by adding a 1N aqueous solution of sodium hydroxide, extracted with dichloromethane, dried and concentrated. The residue obtained was purified by a column chromatography (dichloromethane: 10% aqueous ammonia-containing methanol=17:1) and crystallized from a mixture of ethyl acetate and diethyl ether to obtain the title compound (155 mg) as colorless crystals.

$^1$H-NMR (CDCl$_3$) δ: 1.26–1.47 (2H, m), 1.37 (9H, s), 1.55–1.68 (1H, m), 1.80–1.90 (1H, m), 2.44 (3H, s), 2.66–2.82 (2H, m), 3.08–3.22 (1H, m), 3.47–3.99 (10H, m), 6.43 (1H, dd, J=5.8, 2.2 Hz), 6.48 (1H, d, J=2.2 Hz), 7.61 (1H, dd, J=8.8, 1.8 Hz), 7.80 (1H, dd, J=8.8, 1.8 Hz), 7.92–7.97 (3H, m), 8.15 (1H, d, J=5.8 Hz), 8.35 (1H, s).

IR (KBr): 2932, 1740, 1667, 1599, 1543, 1495, 1454, 1418 cm$^{-1}$.

Example 145

{[4-(6-Chloronaphthalene-2-sulfonyl)-2-oxo-1-piperazinyl][1-(2-methyl-4-pyridinyl)-4-piperidinyl]amino}butyric Acid A mixture of tert-butyl {[4-(6-chloronaphthalene-2-sulfonyl)-2-oxo-1-piperazinyl][1-(2-methyl-4-pyridinyl)-4-piperidinyl]amino}acetate (135 g) obtained in Example 144 and toluene (1 ml) was combined with trifluoroacetic acid (1 ml) and stirred at room temperature for 2 hours. The reaction mixture was concentrated under reduced pressure and the residue was purified on a CHP-20 column (water→1% conc. aqueous ammonia-containing 25% aqueous solution of acetonitrile) to obtain the title compound (0.75 mg) as a colorless powder.

$^1$H-NMR (DMSO-d$_6$) δ: 0.90–1.15 (2H, m), 1.20–1.35 (1H, m), 1.60–1.85 (1H, m), 2.31 (3H, s), 2.50–2.72 (2H, m), 3.17–3.94 (11H, m), 6.48 (1H, dd, J=6.0, 2.0 Hz), 6.58 (1H, d, J=2.0 Hz), 7.76 (1H, dd, J=9.0, 1.8 Hz), 7.92 (1H, dd, J=9.0, 1.8 Hz), 8.01 (1H, d, J=6.0 Hz), 8.21 (1H, d, J=9.0 Hz), 8.28–8.32 (2H, m), 8.62 (1H, s).

IR (KBr): 3061, 2928, 1645, 1599, 1539, 1495, 1454, 1418 cm$^{-1}$.

Formulation Example 1

An FXa inhibitor (e.g., deep vein thrombosis treating agent, cardiogenic cerebral infarction treating agent, and the like) containing a compound represented by Formula (I) according to the invention or a salt thereof as an active ingredient can be produced for example by the following formulations.

1. Capsule

| | |
|---|---|
| (1) Compound obtained in Example 6 | 40 mg |
| (2) Lactose | 70 mg |
| (3) Microcrystalline cellulose | 9 mg |
| (4) Magnesium stearate | 1 mg |
| 1 Capsule | 120 mg |

Components (1), (2) and (3) and a half of (4) are mixed and granulated. Then the remainder of Component (4) was added and the entire mass is filled into gelatin capsules.

2. Tablet

| | |
|---|---|
| (1) Compound obtained in Example 6 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 Table | 120 mg |

Components (1), (2) and (3) and a 2/3 of (4) and a half of Component (5) are mixed and granulated. Then the remainders of Components (4) and (5) are added to the granule, and then compacted into tablets.

Formulation Example 2

50 mg of the compound obtained in Example 9 was dissolved in 50 ml of JP distilled water for injection, and JP distilled water for injection was further added to make 100 ml. This solution was filtered aseptically, and 1 ml aliquots of this solution were dispensed aseptically into injection vials, which were lyophilized and closed tightly.

Experiment 1

(1) Human Activated Coagulation Factor X (FXa) Inhibiting Effect

Method: A cuvette was charged with 225 μl of 0.05 M tris buffer (pH 8.3) containing 0.145 M sodium chloride and 2 mM calcium chloride, 5 μl of a sample (test compound dissolved in dimethyl sulfoxide) and 10 μl of human FXa (0.3 unit/ml), which were reacted at 37° C. for 10 minutes and then combined with 10 μl of a substrate (3 mM, S-2765) and further reacted at 37° C. for 10 minutes. hen the reaction was terminated by adding 25 μl of 50% aqueous acetic acid, and the change in the absorbance at 405 nm was determined using a spectrophotometer to calculate the concentration at which the FXa effect was inhibited by 50% (IC$_{50}$)

(2) In Vitro Clotting Time Measurement (2-1) Extrinsic Clotting Time (PT) Measurement:

A PT-test WAKO (WAKO PURE CHEMICAL) was employed together with an automatic clotting time meter (STA compact DIAGNOSTICA STAGO). 97 μl of human normal plasma (fresh human plasma, FFP, SEKISUI KAGAKU KOGYO) was combined with 3 μl of a test substance and pre-incubated at 37° C. for 4 minutes. 50 μl of the plasma described above was combined with 100 μl of rabbit brain-derived tissue thromboplastin solution and the time for the clotting was measured. The test substance was used after dissolving in dimethyl sulfoxide (DMSO). A concentration required for 2-fold prolongation of the clotting time was calculated based on the clotting time observed when DMSO was added instead of the test substance.

(2-2) Intrinsic Clotting Time (ATPP) Measurement:

A SSTA-APTT-LT (DIAGNOSTICA STAGO) was employed with together with an automatic clotting time meter (STA compact DIAGNOSTICA STAGO). 97 μl of human normal plasma (fresh human plasma, FFP, SEKISUI KAGAKU KOGYO) was combined with 3 μl of a test substance. 50 μl of the plasma was combined with 50 μl of an active partial thromboplastin solution and preincubated at 37° C. for 4 minutes. 50 μl of 20 mmol/L CaCl$_2$ was added and the time for the clotting was determined. The test substance was used after dissolving in DMSO. A concentration required for 2-fold prolongation of the clotting time was calculated based on the clotting time observed when DMSO was added instead of the test substance.

(2-3) Thrombin clotting time (TT) measurement:

An automatic clotting time meter (Biomatic B10, Sarstedt) was employed for a measurement. Human plasma-derived thrombin (Sigma) was dissolved in distilled water at 2.3 NIH unit/ml. 97 μl of human normal plasma (fresh human plasma, FFP, SEKISUI KAGAKU KOGYO) was combined with 3 μl of a test substance and pre-incubated at 37° C. for 3 minutes. 100 μl of the plasma described above was combined with 200 μl of a thrombin solution, and the time for the clotting was measured. The test substance was used after dissolving in DMSO. A concentration required for 2-fold prolongation of the clotting time was calculated based on the clotting time observed when DMSO was added instead of the test substance.

(3) Ex vivo Clotting Time Measurement (Mice)

(3-1) Intravenous Administration:

Male ICR mice (25 to 35 g, Slc) were employed. An animal received a test substance by a single administration of 5 ml/kg to a tail vein under anesthesia with pentobarbital (50 mg/kg, i.p.). 5 Minutes after the administration, 0.8 ml of the blood was taken from an abdominal aorta with a 1/10 volume of 3.8% sodium citrate (*CYTORAL*, YAMANOUCHI), and centrifuged at 3000 rpm for 15 minutes to obtain a plasma. 50 µl of the plasma described above was combined with 100 µl of rabbit brain-derived tissue thromboplastin solution and the time for the clotting was measured. The clotting time was measured using a PT-test WAKO (WAKO PURE CHEMICAL) together with an automatic clotting time meter (STA compact DIAGNOSTICA STAGO). The test substance was used after dissolving in physiological saline, and the physiological saline was given instead of the test substance in a control group. The activity of the substance is indicated as a ratio (%) of the clotting time in a treatment group based on the clotting time in the control group.

(3-2) Oral Administration:

Male ICR mice (25 to 35 g, Slc) were employed. 5 ml/kg of a test substance was given by a forcible oral administration to an animal after fasting for 12 hours or longer. 1 Hour after administration, a blood was taken from an abdominal aorta under anesthesia with pentobarbital (50 mg/kg, o.p.). The test substance was used after suspending in 0.5% methyl cellulose, and 0.5% methyl cellulose was given instead of the test substance in a control group. Otherwise, the procedure similar to that for the intravenous administration described above was employed.

(4) In vivo Antithrombotic Effect Measurement (4-1) Rat Arteriovenous Shunt Method:

A method by Umetsu et al (Thromb. Haemostas., 39, 74–73, (1978)) was employed. Male SD rats (weighing 250 to 350 g) were used under anesthesia with pentobarbital (50 mg/kg) to form a extracorporeal circulation of a polyethylene tube attached with a silk thread between the left jugular vein and the right jugular vein. In order to prevent a blood coagulation, the tube had previously been filled with a physiological saline containing heparin (50 U/ml). The blood was allowed to circulate for 15 minutes, the thrombus depositing on the silk thread during which period was weighed wet. A test substance was given orally or intravenously. When given orally, the test substance was suspended in 0.5% methyl cellulose, and given (5 ml/kg) 2 hours before initiation of the experiment to an animal while fasting. In a control group, 0.5% methyl cellulose was given instead of the test substance. When given intravenously, 1 ml/kg was given to a tail vein 5 minutes before initiating the blood circulation. The test substance was used after dissolving in physiological saline, and the physiological saline was given instead of the test substance in a control group. The activity of a test substance is indicated as a ratio (%) of the wet weight of the thrombus in a treatment group based on the wet weight in the control group.

(4-2) Rat abdominal large vein partial ligation model

Male Sprague-Dawley rats (250–400 g, NIPPON CLAIR) were employed. An abdominal large vein thrombus model was established by a modified Finkle's method (Thromb, Haemostas., 79, 431–438, 1998). An abdominal large vein was peeled off carefully under anesthesia with pentobarbital (50 mg/kg, i.p.), and the abdominal large vein was tied at the renal vein bifurcation and at 1 cm downstream thereof, between which all branches were ligated. A balloon catheter (Fogarty, 2F, Baxter) was inserted from the left femoral vein, and the region between the two ties was injured three times by means of the balloon inflated with 200 to 300 ml of air. The balloon catheter was removed, the thread tied at the renal vein bifurcation was bound together with a 26G needle, and then the needle was removed, whereby establishing a partial ligation. After 30 minutes, another thread was bound, and the thrombus formed between the two threads was isolated carefully, and its wet weight was measured using a hooded analytical balance (BP1110S, Satorius). On the other hand, 2 ml of the blood was taken from an abdominal aorta with a 1/10 volume of 3.8% sodium citrate (*CYTORAL*, YAMANOUCHI), and centrifuged at 3000 rpm for 10 minutes to obtain a platelet-poor plasma (PPP). A test substance was given orally or intravenously. When given orally, the test substance was suspended in 0.5% methyl cellulose, and given (5 ml/kg) 2 hours before initiation of the experiment to an animal while fasting. In a control group, 0.5% methyl cellulose was given instead of the test substance. When given intravenously, 1 ml/kg was given to a tail vein 5 minutes before initiating the partial ligation. The test substance was used after dissolving in physiological saline, and the physiological saline was given instead of the test substance in a control group. The activity (% inhibition of thrombus formation) of a test substance is indicated as a ratio (%) of the wet weight of the thrombus in a treatment group based on the wet weight in the control group.

(4-3) Rat Deep Vein Thrombosis (DVT) Model

Male SD rats (weighing 250 to 350 g) were employed. A polyethylene tube was inserted into the left femoral vein under anesthesia with pentobarbital (50 mg/kg, i.p.). In the polyethylene tube, a silk thread (5 cm in length) which had previously been attached to a guide wire was inserted, and a physiological saline containing heparin (50 U/ml) was filled in order to prevent a blood coagulation. After inserting the polyethylene to reach the abdominal large vein, the silk thread was placed in the abdominal large vein using the guide wire. After placing for 30 minutes, heparin (200 U/kg) was given intravenously from a tail vein. After exsanguinating by cutting a brachial artery, the abdominal region was opened and the silk thread was taken out and examined for the wet weight of the thrombus depositing on the thread (including the weight of the thread). A test substance was given at 1 ml/kg to a tail vein 5 minutes before placing the silk thread. The test substance was used after dissolving in physiological saline, and the physiological saline was given instead of the test substance in a control group. The wet weight only of the thrombus was calculated as (wet weight of thrombus depositing on silk thread)—(wet weight determined after immersing silk thread in heparinized venous blood (11.6±0.2 mg)).

Results

Table 1 shows an $IC_{50}$ value. Based on the results shown below, it is evident that the compound of the invention has an excellent FXa inhibiting effect.

TABLE 1

| Example | $IC_{50}$ (µM) |
| --- | --- |
| 6 | 0.0058 |

Industrial Applicability

Compound (I) according to the invention or a salt thereof has an excellent FXa inhibiting effect, has a less hemorrhagic side effect, is useful as an anticoagulant capable of being absorbed orally, and thus can advantageously be used for preventing and treating various diseases attributable to a thrombus or infarction.

What is claimed is:
1. A compound represented by Formula:

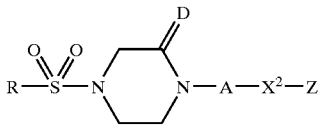

wherein R is an optionally substituted hydrocarbon group, an optionally substituted heterocyclic group, or an optionally substituted group represented by the formula

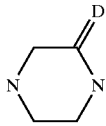

where $X^2$ is a bond, an optionally substituted alkylene group or an optionally substituted imino group, D is an oxygen atom or a sulfur atom, A is —N($R^3$)—Y— or —N=Y—, $R^3$ is a hydrogen atom, an optionally substituted hydrocarbon group or an acyl group, Y is an optionally substituted linear hydrocarbon group or an optionally substituted cyclic group, Z is (1) an optionally substituted amino group, (2) an optionally substituted imidoyl group or (3) an optionally substituted nitrogen-containing heterocyclic group or a salt thereof.

2. The compound according to claim 1 wherein R is an optionally substituted hydrocarbon group.

3. The compound according to claim 1 wherein R is an optionally substituted heterocyclic group.

4. The compound according to claim 1 wherein R is a halogen atom or an aryl group optionally substituted by a $C_{2-4}$ alkenyl.

5. The compound according to claim 1 wherein R is a naphthyl group optionally substituted by a halogen atom.

6. The compound according to claim 1 wherein R is a benzopyranyl group optionally substituted by a halogen atom.

7. The compound according to claim 1 wherein the optionally substituted group represented by the formula

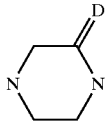

is a group represented by the formula

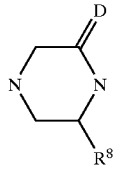

wherein $R^8$ is a hydrogen atom, an optionally substituted hydroxyl group, an optionally substituted mercapto group, a nitro group, a cyano group, an optionally substituted amino group, an optionally substituted lower alkyl group, an optionally substituted lower alkoxy group, an optionally esterified carboxyl group, an optionally substituted carbamoyl group, an optionally substituted thiocarbamoyl group or an optionally substituted sulfamoyl group, and D is an oxygen atom or a sulfur atom.

8. The compound according to claim 7 wherein $R^8$ is a hydrogen atom.

9. The compound according to claim 1 wherein an optionally substituted imino group is a group represented by Formula —N($R^4$)— wherein $R^4$ is a hydrogen atom, an optionally substituted hydrocarbon group or an acyl group.

10. The compound according to claim 1 wherein $X^2$ is a bond.

11. The compound according to claim 1 wherein $R^3$ is a hydrogen atom, an optionally substituted lower alkyl group, formyl or an optionally substituted lower alkanoyl group.

12. The compound according to claim 1 wherein $R^3$ is a hydrogen atom or an optionally substituted lower alkyl group.

13. The compound according to claim 1 wherein Y is an optionally substituted cyclic hydrocarbon group.

14. The compound according to claim 1 wherein A is —N($R^3$)—Y— and Y is an optionally substituted phenylene.

15. The compound according to claim 1 wherein Y is an optionally substituted heterocyclic group.

16. The compound according to claim 1 wherein Y is an optionally substituted piperidine residue.

17. The compound according to claim 1 wherein Z is an optionally substituted nitrogen-containing heterocyclic group.

18. The compound according to claim 1 wherein D is an oxygen atom.

19. A compound selected from the group consisting of 4-(7-chloro-2H-benzopyran-3-sulfonyl)-1-[1-(4-pyridyl)piperidin-4-ylamino]-2-piperazinone, 4-(6-chloronaphthalene-2-sulfonyl)-1-[1-(4-pyridyl)piperidin-4-ylamino]-2-piperazinone, 4-(6-bromonaphthalene-2-sulfonyl)-1-[1-(4-pyridyl)piperidin-4-ylamino]-2-piperazinone, 4-(7-bromo-2H-benzopyran-3-sulfonyl)-1-[1-(4-pyridyl)piperidin-4-ylamino]-2-piperazinone, 4-(6-chloronaphthalene-2-sulfonyl)-1-{methyl[1-(4-pyridyl)piperidin-4-yl]amino}-2-piperazinone, 4-(6-bromonaphthalene-2-sulfonyl)-1-{methyl[1-(4-pyridyl)piperidin-4-yl]amino}-2-piperazinone, 4-(7-bromo-2H-benzopyran-3-sulfonyl)-1-{methyl[1-(4-pyridyl)piperidin-4-yl]amino}-2-piperazinone, 4-(6-chloronaphthalene-2-sulfonyl)-1-{ethyl[1-(4-pyridyl)piperidin-4-yl]amino}-2-piperazinone, 4-(6-chloronaphthalene-2-sulfonyl)-1-{methyl[1-(2-methyl-4-pyridyl)piperidin-4-yl]amino}-2-piperazinone, {[4-(6-chloronaphthalene-2-sulfonyl)-2-oxo-1-piperazinyl][1-(2-methyl-4-pyridyl)-4-piperidinyl]amino}acetic acid, 4-(6-chloronaphthalene-2-sulfonyl)-1-{[1-(4-pyridyl)-4-piperidinyl]amino}-6-oxo-2-piperazinecarboxylic acid, 4-(6-chloronaphthalene-2-sulfonyl)-1-{methyl[1-(4-pyridyl)-4-piperidinyl]amino}-6-oxo-2-piperazinecarboxylic acid, 4-(6-chloronaphthalene-2-sulfonyl)-1-{methyl[1-(4-pyridyl)-4-piperidinyl]amino}-6-oxo-2-piperazinecarboxamide, 4-(6-chloronaphthalene-2-sulfonyl)-1-{methyl[1-(2-methyl-4-pyridyl)-4-piperidinyl]amino}-6-oxo-2-piperazinecarboxamide, 4-(6-chloronaphthalene-2-sulfonyl)-6-hydroxymethyl-1-{methyl[1-(4-pyridyl)-4-piperidinyl]amino}-2-piperazinone, 6-aminomethyl-4-(6-chloronaphthalene-2-sulfonyl)-1-{methyl[1-(4-pyridyl)-4-piperidinyl]amino}-2- piperazinone, 6-acetylaminomethyl-4-(6-chloronaphthalene-2-sulfonyl)-1-{methyl[1-(4-pyridyl)-4-piperidinyl]amino}-2-piperazinone, 4-(6-chloronaphthalene-2-sulfonyl)-1-{[1-(4-pyridyl)-4-piperidinyl]amino}-6-oxo-2-piperazineacetic acid and 4-(6-chloronaphthalene-2-sulfonyl)-1-{[1-(2-methyl-4-pyridyl)-4-piperidinyl]amino}-6-oxo-2-piperazineacetic acid as well as a salt thereof.

20. A method for producing a compound according to claim 1 or a salt thereof comprising:

reacting a compound represented by Formula (II) $RSO_2Q$ wherein Q is a leaving group and other symbols are defined as described in claim 1 or a salt thereof with a compound represented by Formula (III):

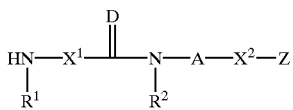

(III)

wherein the symbols are defined as described in claim 1 or a salt thereof.

21. A pharmaceutical composition comprising a compound according to claim 1 or a salt thereof.

22. A method for inhibiting blood coagulation in mammals comprising administering an effective amount of a compound according to claim 1 or a salt thereof to said mammals.

23. A method for inhibiting an activated coagulation factor X in mammals comprising administering an effective amount of a compound according to claim 1 or a salt thereof to said mammals.

24. A method for preventing and treating cardiac infarction, cerebral thrombosis or deep vein thrombosis in mammals comprising administering an effective amount of a compound according to claim 1 or a salt thereof to said mammals.

* * * * *